US007705141B2

(12) United States Patent
Nakamura et al.

(10) Patent No.: US 7,705,141 B2
(45) Date of Patent: Apr. 27, 2010

(54) GENES AND POLYPEPTIDES RELATING TO HUMAN COLON CANCERS

(75) Inventors: Yusuke Nakamura, Yokohama (JP); Yoichi Furukawa, Kawasaki (JP); Hideaki Tahara, Meguro-ku (JP); Takuya Tsunoda, Minato-ku (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 12/180,204

(22) Filed: Jul. 25, 2008

(65) Prior Publication Data

US 2009/0012032 A1 Jan. 8, 2009

Related U.S. Application Data

(60) Division of application No. 10/916,064, filed on Aug. 10, 2004, now Pat. No. 7,425,612, which is a continuation-in-part of application No. PCT/JP03/07006, filed on Jun. 3, 2003.

(60) Provisional application No. 60/451,013, filed on Feb. 28, 2003, provisional application No. 60/415,209, filed on Sep. 30, 2002, provisional application No. 60/386,985, filed on Jun. 6, 2002.

(51) Int. Cl.
*C07H 21/04* (2006.01)
(52) U.S. Cl. ...................... 536/23.5; 536/23.1
(58) Field of Classification Search ........................ None
See application file for complete search history.

(56) References Cited

U.S. PATENT DOCUMENTS

2003/0228584 A1   12/2003   Tang et al.

FOREIGN PATENT DOCUMENTS

| EP | 1 321 475 A1 | 6/2003 |
|---|---|---|
| WO | WO 00/50588 A2 | 8/2000 |
| WO | WO 01/22920 A2 | 4/2001 |
| WO | WO 01/54472 A2 | 8/2001 |
| WO | WO 01/55202 A1 | 8/2001 |
| WO | WO 01/60860 * | 8/2001 |
| WO | WO 01/66689 * | 9/2001 |
| WO | WO 01/66689 A2 | 9/2001 |
| WO | WO 01/66689 A3 | 9/2001 |
| WO | WO 01/75067 A2 | 10/2001 |
| WO | WO 01/75067 A3 | 10/2001 |

OTHER PUBLICATIONS

Boehringer Mannheim Biochemicals, 1994 Catalog, p. 93.*
Alexander-Miller, Martha A. et al.; "Selective expansion of high- or low-avidity cytotoxic T lymphocytes and efficacy for adoptive immunotherapy"; *Proc. Natl. Acad. Sci. USA* 93:4102-7107; Apr. 1996.
Altieri, Dario C. and Carlo Marchisio; "Survivin Apoptosis: An Interloper Between Cell Death and Cell Proliferation in Cancer"; *Laboratory Investigation* 79(11):1327-1333; Nov. 1999.
Anderson, Mads Hald et al.; "Identification of a Cytotoxic T Lymphocyte Response to the Apoptosis Inhibitor Protein Survivin in Cancer Patients"; *Cancer Research* 61:869-872; Feb. 1, 2000.
Artavanis-Tsakonas, Spyros et al.; "The *Notch* Locus and the Cell Biology of Neuroblast Segregation"; *Annu. Rev. Cell Biol.* 7:427-452; 1991; Annual Reviews Inc.
Bednarek, Maria A. et al.; "The minimum peptide epitope from the influenza virus matrix protein: Extra and intracellular loading of HLA-A2" *The Journal of Immunology* 147(12):4047-4053; Dec. 15, 1991.
Bienz, Mariann and Hans Clevers; "Linking Colorectal Cancer to Wnt Signaling"; *Cell* 103:311-320; Oct. 13, 2000; Cell Press.
Boon, Thierry; "Tumor Antigens Recognized by Cytolytic T lymphocytes: Present Perspectives for Specific Immunotherapy"; *Int. J. Cancer* 54:177-180; 1993; Wily-Liss, Inc.
Boon, Thierry and Pierre van der Bruggen; "Human Tumor Antigens Recognized by T Lymphocytes"; *J. Exp. Med.* 183:725-729; Mar. 1996.
Boon, Thierry, "Toward a Genetic Analysis of Tumor Rejection Antigens," *Adv. Can. Res.*, 58:177-210; 1992.
Bowie, James et al., "Deciphering the Message in Protein Sequences: Tolerance to Amino Acid Substitutions," *Science*, 247:1306-1310; Mar. 16, 1990.
Brichard, Vincent et al.; "The Tyrosinase Gene Codes for an Antigen Recognized by Autologous Cytolytic T Lymphocytes on HLA-A2 Melanomas"; *J. Exp. Med.* 178:489-495; Aug. 1993.
Butterfield, Lisa H. et al.; "Generation of Human T-cell Responses to an HLA-A2.1-resticted Peptide Epitope Derived from α-Fetoprotein"; *Cancer Research* 59:3134-3142; Jul. 1, 1999.
Celis, Esteban, "Getting peptide vaccines to work: just a matter of quality control?," *J. Clinical Investigation*, 110(12):1765-1798; Dec. 2002.
Chaux, Pascal et al., "Estimation of the Frequencies of Anti-Mage-3 Cytolytic T-Lymphocyte Precursors in Blood From Individuals Without Cancer," *Int. J. Cancer*, 77:538-542; 1998.
Chen, Yao-Tseng et al.; "A testicular antigen aberrantly expressed in human cancers detected by autologous antibody screening"; *Proc. Natl. Acad. Sci. U.S.A.* 94:1914-1918; Mar. 1997.
Clay, Timothy M. et al.; "Changes in the Fine Specificity of gp100$_{(209-217)}$-Reactive T Cells in Patients Following Vaccination with a Peptide Modified at an HLA-A2.1 Anchor Residue"; *The Journal of Immunology* 162;1749-1755; 1999.
Date, Y. et al.; "DNA typing of the HLA-A gene: population study and identification of four new alleles in Japanese"; *Tissue Antigens* 47:93-101; 1996.
Dionne, Sara O. et al.; "Functional characterization of CTL against gp100 altered peptide ligands". *Cancer Immunol. Immunother* 52:199-206; 2003.

(Continued)

*Primary Examiner*—Laura B Goddard
(74) *Attorney, Agent, or Firm*—Townsend and Townsend and Crew LLP

(57) ABSTRACT

The present application provides novel human genes RNF43 whose expression is markedly elevated in colorectal cancers, as well as CXADRL1 and GCUD1 whose expression is markedly elevated in gastric cancers compared to corresponding non-cancerous tissues. The genes and polypeptides encoded by the genes can be used, for example, in the diagnosis of a cell proliferative disease, and as target molecules for developing drugs against the disease.

8 Claims, 46 Drawing Sheets

OTHER PUBLICATIONS

Dionne, Sara O. et al.; "Her-2/*neu* altered peptide ligand-induced CTL responses: implications for peptides with increased HLA affinity and T-cell-receptor interaction"; *Cancer Immunol Immunother* 53:307-314; 2004.

Dyall, Ruben et al.; "Heteroclitic Immunization Induces Tumor Immunity". *J. Exp. Med.* 188(9):1553-1561; Nov. 2, 1998; The Rockefeller University Press.

Fechner, H. et al.; "Expression of Coxsackie adenovirus receptor and alpha$_v$-integrin does not correlate with adenovector targeting in vivo indicating anatomical vector barriers"; *Gene Therapy* 6:1520-1535; 1999; Stockton Press.

Fujie, Tatsuo et al.; "A *MAGE*-1-encoded HLA-A24-binding synthetic peptide induces specific anti-tumor cytotoxic T lymphocytes"; *Int. J. Cancer* 80:169-172; 1999; Wiley-Liss, Inc.

Fujita, Manabu et al.; "Up-Regulation of the Ectodermal-Neural Cortex 1 (*ENC1*) Gene, a Downstream Target of the β-Catenin/T-Cell Factor Complex, in Colorectal Carcinomas"; *Cancer Research* 61:7722-7726; Nov. 1, 2001.

Harris, Curtis C.; "Structure and Function of the p53 Tumor Suppressor Gene: Clues for Rational Cancer Therapeutic Strategies"; *Journal of the National Cancer Institute* 88(20):1442-1455; Oct. 16, 1996.

Hasegawa, Suguru et al.; "Genome-Wide Analysis of Gene Expression in Intestinal-Type Gastric Cancers Using a Complementary DNA Microarray Representing 23,040 Genes"; *Cancer Research* 62:7012-7017; Dec. 1, 2002.

He, Tong-Chuan et al.; "PPARδ Is an APC-Regulated Target of Nonsteroidal Anti-inflammatory Drugs"; *Cell* 99:335-345: Oct. 29, 1999; Cell Press.

Hu, Xueyou et al.; "Enhancement of Cytolytic T Lymphocyte Precursor Frequency in Melanoma Patients following Immunization with the MAGE-1 Peptide Loaded Antigen Presenting Cell-based Vaccine". *Cancer Research* 56:2479-2483; Jun. 1, 1996.

Imanishi, Tadashi et al.; "Allele and haplotype frequencies for HLA and complement loci in various ethnic groups"; *Proceedings of the Eleventh International Histocompatibility Workshop and Conference*; pp. 1065-1220; 1992; Oxford University Press.

Irvine, Kari R. et al.; "Recombinant virus vaccination against "self" antigens using anchor-fixed immunogens"; *Cancer Research* 59:2536-2540; Jun. 1, 19999.

Kawakami, Yutaka et al.; "Identification of the immunodominant peptides of the MART-1 human melanoma antigen recognized by the majority of HLA-A2-restricted tumor infiltrating lymphocytes". *The Journal of Experimental Medicine* 180:347-352; Jul. 1994.

Kawakami, T., et al.; Database; UniProt; Accession No. Q9NXDO; Oct. 10, 2001.

Kawano, Kouichiro et al.; "Identification of a new endoplasmic reticulum-resident protein recognized by HLA-A24-restricted tumor-infiltrating lymphocytes of lung cancer"; *Cancer Research* 60:3550-3558; Jul. 1, 2000.

Keogh, Elissa et al.; "Identification of new epitopes from four different tumor-associated antigens: Recognition of naturally processed epitopes correlates with HLA-A*0201-binding affinity"; *The Journal of Immunology* 167:787-796; 2001.

Kikuchi, Megumi et al.; "Identification of a SART-1-derived peptide capable of inducing HLA-A24-restricted and tumor-specific cytotoxic T lymphocytes"; *Int. J. Cancer* 81:459-466; 1999.

Kirkin, Alexei et al., "Melanoma-associated antigens recognized by cytotoxic T lymphocytes," *APMIS*, 106: 665-679; 1998.

Kitahara, Osamu et al.; "Alterations of gene expression during colorectal carcinogenesis revealed by cDNA microarrays after laser-capture microdissection of tumor tissues and normal epithelia"; *Cancer Research* 61:3544-3549; May 1, 2001.

Kondo, Akihiro et al.; "Prominent roles of secondary anchor residues in peptide binding to HLA-A24 human class I molecules"; *The Journal of Immunology* 155:4307-4312; 1995.

Kubo, Ralph T. et al.; "Definition of specific peptide motifs for four major HLA-A alleles". *Journal of Immunology* 152:3913-3924; 1994.

Lee, Kang-Hun et al., "Increased Vaccine-Specific T Cell Frequency After Peptide-Based VAccination Correlates with Increased Susceptibility to In Vitro Stimulation But Does Not Lead to Tumor Regression," *J. Immunol.*, 163:6292-6300 (1999).

Lin, Yu-Min et al.; "Identification of *AF17* as a downstream gene of the β-catenin/T-cell factor pathway and its involvement in colorectal carcinogenesis"; *Cancer Research* 61:6345-6349; Sep. 1, 2001.

Lin, Yu Min et al.; "Molecular diagnosis of colorectal tumors by expression profiles of 50 genes expressed differentially in adenomas and carcinomas"; *Oncogene* 21:4210-4128; 2002.

Mammalian Gene Collection (MGC) Program Team; "Generation and initial analysis of more than 15,000 full-length human and mouse cDNA sequences". *PNAS* 99(26):16899-16903; Dec. 24, 2002.

McCright, Brent et al.; "Defects in development of the kidney, heart and eye vasculature in mice homozygous for a hypomorphic *Notch2* mutation"; *Development* 128:491-502; 2001; The Company of Biologists Limited; Great Britain.

Mukherji, Bijay et al.; "Induction of antigen-specific cytolytic T cell in situ in human melanoma by immunization with synthetic peptide-pulsed autologous antigen presenting cells"; *Proc. Natl. Acad. Sci. U.S.A.* 92:8078-8082; Aug. 1995.

Muller, Daniel et al.; "A single amino acid substitution in an MHC class I molecule allows heteroclitic recognition by lymphocytic choriomeningitis virus-specific cytotoxic T lymphocytes" *The Journal of Immunology* 147(2):1392-1397; Aug. 15, 1991.

Nagase, Takahiro, et al.; "Prediction of the Coding Sequences of Unidentified Human Genes. V. The Coding Sequences of 40 New Genes (KIAA0161-KIAA0200) Deduced by Analysis of cDNA Clones From Human Cell Line KG-1"; *DNA Research Institute*; Feb. 29, 1996; pp. 17-24; vol. 3, No. 1.

Nagorsen, Dirk et al.; "Natural T-cell response against MHC class I epitopes of epithelial cell adhesion molecule, her-2/*neu*, and carcinoembryonic antigen in patients with colorectal cancer"; *Cancer Research* 60:4850-4854; Sep. 1, 2000.

Nishizaka, Sinya et al.; "A new tumor-rejection antigen recognized by cytotoxic T lymphocytes infiltrating into a lung adenocarcinoma"; *Cancer Research* 60:4830-4837; Sep. 1, 2000.

Nukaya, Ikuei et al.; "Identification of HLA-A24 epitope peptides of carcinoembryonic antigen which induce tumor-reactive cytotoxic T lymphocyte"; *Int. J. Cancer* 80:92-97; 1999.

Oiso, Masatake et al.; "A newly identified *MAGE*-3-derived epitope recognized by HLA-A24-restricted cytotoxic T lymphocytes"; *Int. J. Cancer* 81:387-394; 1999.

Okabe, Hiroshi et al.; "Genome-wide analysis of gene expression in human hepatocellular carcinomas using cDNA microarray: identification of genes involved in viral carcinogenesis and tumor progression". *Cancer Research* 61:2129-2137; Mar. 1, 2001.

Ono, Kenji et al.; "Identification by cDNA microarray of genes involved in ovarian carcinogenesis". *Cancer Research* 60:55007-5011; Sep. 15, 2000.

Perrais, Michaël et al.; "Aberrant expression of human mucin gene *MUC5B* in gastric carcinoma and cancer cells: Identification and regulation of a distal promoter"; *The Journal of Biological Chemistry*; May 4, 2001; pp. 15386-15396; vol. 376, No. 18; The American Society for Biochemistry and Molecular Biology, Inc; USA.

Rosenberg, Steven A. et al.; "Immunologic and therapeutic evaluation of a synthetic peptide vaccine for the treatment of patients with metastatic melanoma"; *Nature Medicine* 4(3):321-327; Mar. 1998.

Sette, Alessandro et al.; "The relationship between class I binding affinity and immunogenicity of potential cytotoxic T cell epitopes"; *The Journal of Immunology* 153:5586-5592; 1994.

Shichijo, Shigeki et al.; "A gene encoding antigenic peptides of human squamous cell carcinoma recognized by cytotoxic T lymphocytes"; *J. Exp. Med.* 187(3):277-288; Feb. 2, 1998.

Shimizu, Kiyoshi et al.; "Binding of Delta1, Jagged1, and Jagged2 to Notch2 rapidly induces cleavage, nuclear translocation, and hyperphosphorylation of Notch2". *Molecular and Cellular Biology* 20(18):6913-6922; Sep. 2000.

Slansky, Jill E. et al.; "Enhanced antigen-specific antitumor immunity with altered peptide ligands that stabilize the MHC-Peptide-TCR complex"; *Immunity* 13:529-538; Oct. 2000.

Sloan-Lancaster, Joanne and Paul M. Allen; "Altered peptide ligand-induced partial T cell activation: Molecular mechanisms and role in T cell biology"; *Annu. Rev. Immunol.* 14:1-27; 1996.

Smith, M.H. et al.; "Baculoviral expressed HLA class I heavy chains used to screen a synthetic peptide library for Allele-Specific peptide binding motifs"; *Molecular Immunology* 35:1033-1043; 1998.

Suzu, Shinya et al.; "Molecular cloning of a novel immunoglobulin superfamily gene preferentially expressed by brain and testis"; *Biochemical and Biophysical Research Communications* 296:1215-1221; 2002.

Tamura, Mayumi et al.; "Identification of cyclophilin B-derived peptides capable of inducing histocompatibility leukocyte antigen-A2-restricted and tumor-specific cytotoxic T lymphocytes"; *Jpn. J. Cancer Res.* 92:762-767; Jul. 2001.

Tanaka, Fumiaki et al.; "Induction of antitumor cytotoxic T lymphocytes with a MAGE-3-encoded synthetic peptide presented by human leukocytes antigen-A24"; *Cancer Research* 57:4465-4468; Oct. 15, 1997.

Tanaka, H. et al.; "Mapping the HLA-A24-restricted T-cell epitope peptide from a tumour-associated antigen HER2/neu: possible immunotherapy for colorectal carcinomas"; *British Journal of Cancer* 84(1):94-99; 2001.

Tourdot, Sophie et al.; "Chimeric peptides: a new approach to enhancing the immunogenicity of peptides with low MHC class I affinity: Application in antiviral vaccination"; *The Journal of Immunology* 159:2391-2398; 1997.

Trojan, Andreas et al.; "Generation of cytotoxic T lymphocytes against native and altered peptides of human leukocyte antigen-A*0201 restricted epitopes from the human epithelial cell adhesion molecule"; *Cancer Research* 61:4761-4765; Jun. 15, 2001.

Tsai, Van et al.; "Identification of subdominant CTL epitopes of the GP100 melanoma-associated tumor antigen by primary in vitro immunization with peptide-pulsed dendritic cells"; *The Journal of Immunology* 158:1796-1802; 1997.

Uchida, N. et al.; "Development of cancer vaccines in the post-genome era (translation)"; *Journal of Japan Surgical Society* 104:99 (Abstract SY7-2); 2003 (In Japanese).

Umano, Y. et al.; "Generation of cytotoxic T cell responses to an HLA-A24 restricted epitope peptide derived from wild-type *p53*"; *British Journal of Cancer* 84(8):1052-1057; 2001.

van der Bruggen, P. et al.; "A gene encoding an antigen recognized by cytolytic T lymphocytes on a human melanoma"; *Science* 254(5038):1643-1647; Dec. 1991.

van der Burgh, Sjoerd H. et al.; "Immunogenicity of peptides bound to MHC class I molecules depends on the MHC-peptide complex stability"; *The Journal of Immunology* 156:3308-3314; 1996.

Vierboom, Michel P.M. et al.; "Peptide vaccination with an anchor-replaced CTL epitope protects against human papillomavirus type 16-induced tumors expressing the wild-type epitope"; *Journal of Immunotherapy* 21(6):399-408; 1998.

Vissers, Joost L. M. et al.; "The renal cell carcinoma-associated antigen G250 encodes a human leukocyte antigen (HLA)-A2.1-restricted epitope recognized by cytotoxic T lymphocytes"; *Cancer Research* 59;5554-5559; Nov. 1, 1999.

Watanabe, Takeshi et al.; "Identification and characterization of a novel gene *CXADRL1* whose expression is frequently up-regulated in differentiated-type of gastric cancer (translation)"; *Proceedings of the Sixty-First Annual Meeting of the Japanese Cancer Association* 93(supp):77 (Abstract 2027); Oct. 1-3, 2002, Tokyo (in Japanese).

Watanabe, Takeshi et al.; "Functional analysis of *CXADRL1* frequently up-regulated in intestinal-type gastric cancer (translation)"; *Proceedings of the Sixty-Second Annual Meeting of the Japanese Cancer Association* p. 247 (Abstract 3152-OA); Sep. 25-27, 2003, Nagoya (In Japanese).

Weinmaster, Gerry; "Notch signal transduction: a real Rip and more". *Current Opinion in Genetics and Development* 10:363-369; 2000.

Williams, F. et al.; "Develoment of PCR-SSOP for the identification of HLA-A*02 subtypes and determination of HLA-A*02 frequencies within different ethnic populations"; *Tissue Antigens*; 49:129-133; 1997.

Yagyu, Ryuichiro et al.; "Identification and characterization of a novel gene *RNF-43* whose expression is frequently up-regulated in colon cancer (translation)"; *Proceedings of the Sixty-First Annual Meeting of the Japanese Cancer Association* 93(supp):251 (Abstract 2729); Oct. 1-3, 2002, Tokyo (In Japanese).

Yang, Sixun et al.; "Antimelanoma activity of CTL generated from peripheral blood mononuclear cells after stimulation with autologous dendritic cells pulsed with melanoma gp100 peptide G209-2M is correlated to TCR avidity"; *The Journal of Immunology* 169:531-539; 2002.

GENESEQ Accession No. ABB10359; from PCT Publication WO200154474 A2, claim 11, Seq Id No. 667; GenBank Oct. 4, 2007.

GENESEQ Accession No. AAU18038; from PCT Publication WO200155315 A2, claim 11, Seq Id No. 183; GenBank Aug. 23, 2005.

National Institutes of Health, Mammalian Gene Collection (MGC); "602722273F1 NIH_MGC_97 *Homo sapies* cDNA clone IMAGE:4839066 5', mRNA sequence"; May 16, 2001; EMBL Accession No. BG772497.

Katari, M. et al.; "Whole Genome Shotgun Reads from *Brassica oleracia* (2002b)"; Mar. 1, 2002; EMBL Accession No. BH745972.1.

National Institutes of Health, Mammalian Gene Collection (MGC); "603080292F1 NIH_MGC_119 *Homo sapiens* cDNA clone IMAGE:5171782 5' mRNA sequence"; Oct. 8, 2001; EMBL Accession No. BI830026.

Zaremba et al.; "Identification of an enhancer agonist cytotoxic T lymphocyte peptide from human carcinoembryonic antigen"; 1997; *Cancer Res.*; vol. 57, pp. 4750-4757.

GenPept Accession No. BAA91085; "unnamed protein product [*Homo sapiens*]" Version BAA91085.1, Sep. 2006.

* cited by examiner a b a mock     pcDNAmyc /His-CXADRL1 b

CXADRL1

GAPDH mock   #2   #5   #6   #7 c (p<0.05)

(p<0.05)

A

B mock    psiH1-CXADRL7

C pAS2 -CXADRL1 +pACT2-AIP1        pAS2(mock) +pACT2 -AIP1 a mock  pcDNAmyc/His-RNF43

← 85.5kDa b

Anti-myc          DAPI          Merge a pcDNA-RNF43   mock   pcDNA- antisense a b ($p<0.05$)

A  Semi-quantitative RT-PCR

B

C  MTT assay

A

B

C

A

B 1        2

SEQUENCE LISTING

<160> NUMBER OF SEQ ID NOS: 199

<210> SEQ ID NO 1
<211> LENGTH: 3423
<212> TYPE: DNA
<213> ORGANISM: Homo sapiens
<220> FEATURE:
<221> NAME/KEY: CDS
<222> LOCATION: (238)..(1533)
<223> OTHER INFORMATION:

<400> SEQUENCE: 1

```
gctggcgagc ccggaacgcc tctggtcaca gctcagcgtc cgcggagccg ggcggcgctg     60
gagctgcact tggctcgtct gtgggtctga cagtcccagc tctgcgcggg gaacagcggc    120
ccggagctgg gtgtgggagg accaggctgc ccaagagcg cggagactca cgcccgctcc     180
tctcctgttg cgaccgggag ccgggtagga ggcaggcgcg ctccctgcgg ccccggg       237
```

| | | | | | | | | | | | | | | | | |
|---|---|---|---|---|---|---|---|---|---|---|---|---|---|---|---|---|
| atg | act | tct | cag | cgt | tcc | cct | ctg | gcg | cct | ttg | ctg | ctc | ctc | tct | ctg | 285 |
| Met | Thr | Ser | Gln | Arg | Ser | Pro | Leu | Ala | Pro | Leu | Leu | Leu | Leu | Ser | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | ggt | gtt | gca | gca | tcc | ctg | gaa | gtg | tca | gag | agc | cct | ggg | agt | atc | 333 |
| His | Gly | Val | Ala | Ala | Ser | Leu | Glu | Val | Ser | Glu | Ser | Pro | Gly | Ser | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| cag | gtg | gcc | cgg | ggt | cag | cca | gca | gtc | ctg | ccc | tgc | act | ttc | act | acc | 381 |
| Gln | Val | Ala | Arg | Gly | Gln | Pro | Ala | Val | Leu | Pro | Cys | Thr | Phe | Thr | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| agc | gct | gcc | ctc | att | aac | ctc | aat | gtc | att | tgg | atg | gtc | act | cct | ctc | 429 |
| Ser | Ala | Ala | Leu | Ile | Asn | Leu | Asn | Val | Ile | Trp | Met | Val | Thr | Pro | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| tcc | aat | gcc | aac | caa | cct | gaa | cag | gtc | atc | ctg | tat | cag | ggt | gga | cag | 477 |
| Ser | Asn | Ala | Asn | Gln | Pro | Glu | Gln | Val | Ile | Leu | Tyr | Gln | Gly | Gly | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | ttt | gat | ggt | gcc | ccc | cgg | ttc | cac | ggt | agg | gta | gga | ttt | aca | ggc | 525 |
| Met | Phe | Asp | Gly | Ala | Pro | Arg | Phe | His | Gly | Arg | Val | Gly | Phe | Thr | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | atg | cca | gct | acc | aat | gtc | tct | atc | ttc | att | aat | aac | act | cag | tta | 573 |
| Thr | Met | Pro | Ala | Thr | Asn | Val | Ser | Ile | Phe | Ile | Asn | Asn | Thr | Gln | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | gac | act | ggc | acc | tac | cag | tgc | ctg | gtc | aac | aac | ctt | cca | gac | ata | 621 |
| Ser | Asp | Thr | Gly | Thr | Tyr | Gln | Cys | Leu | Val | Asn | Asn | Leu | Pro | Asp | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| ggg | ggc | agg | aac | att | ggg | gtc | acc | ggt | ctc | aca | gtg | tta | gtt | ccc | cct | 669 |
| Gly | Gly | Arg | Asn | Ile | Gly | Val | Thr | Gly | Leu | Thr | Val | Leu | Val | Pro | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| tct | gcc | cca | cac | tgc | caa | atc | caa | gga | tcc | cag | gat | att | ggc | agc | gat | 717 |
| Ser | Ala | Pro | His | Cys | Gln | Ile | Gln | Gly | Ser | Gln | Asp | Ile | Gly | Ser | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | atc | cta | ctc | tgt | agc | tca | gag | gaa | ggc | att | cct | cga | cca | act | tac | 765 |
| Val | Ile | Leu | Leu | Cys | Ser | Ser | Glu | Glu | Gly | Ile | Pro | Arg | Pro | Thr | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ctt | tgg | gag | aag | tta | gac | aat | acc | ctc | aaa | cta | cct | cca | aca | gct | act | 813 |
| Leu | Trp | Glu | Lys | Leu | Asp | Asn | Thr | Leu | Lys | Leu | Pro | Pro | Thr | Ala | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | gac | cag | gtc | cag | gga | aca | gtc | acc | atc | cgg | aac | atc | agt | gcc | ctg | 861 |
| Gln | Asp | Gln | Val | Gln | Gly | Thr | Val | Thr | Ile | Arg | Asn | Ile | Ser | Ala | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| tct | tca | ggt | ttg | tac | cag | tgc | gtg | gct | tct | aat | gct | att | gga | acc | agc | 909 |
| Ser | Ser | Gly | Leu | Tyr | Gln | Cys | Val | Ala | Ser | Asn | Ala | Ile | Gly | Thr | Ser | |
| | 210 | | | | | 215 | | | | | 220 | | | | | |

```
acc tgt ctt ctg gat ctc cag gtt att tca ccc cag ccc agg aac att        957
Thr Cys Leu Leu Asp Leu Gln Val Ile Ser Pro Gln Pro Arg Asn Ile
225                 230                 235                 240 gga cta ata gct gga gcc att ggc act ggt gca gtt att atc att ttt       1005
Gly Leu Ile Ala Gly Ala Ile Gly Thr Gly Ala Val Ile Ile Ile Phe
                245                 250                 255 tgc att gca cta att tta ggg gca ttc ttt tac tgg aga agc aaa aat       1053
Cys Ile Ala Leu Ile Leu Gly Ala Phe Phe Tyr Trp Arg Ser Lys Asn
            260                 265                 270 aaa gag gag gaa gaa gaa gaa att cct aat gaa ata aga gag gat gat       1101
Lys Glu Glu Glu Glu Glu Glu Ile Pro Asn Glu Ile Arg Glu Asp Asp
        275                 280                 285 ctt cca ccc aag tgt tct tct gcc aaa gca ttt cac act gag att tcc       1149
Leu Pro Pro Lys Cys Ser Ser Ala Lys Ala Phe His Thr Glu Ile Ser
    290                 295                 300 tcc tcg gac aac aac aca cta acc tct tcc aat gcc tac aac agt cga       1197
Ser Ser Asp Asn Asn Thr Leu Thr Ser Ser Asn Ala Tyr Asn Ser Arg
305                 310                 315                 320 tac tgg agc aac aat cca aaa gtt cat aga aac aca gat tca gtc agc       1245
Tyr Trp Ser Asn Asn Pro Lys Val His Arg Asn Thr Asp Ser Val Ser
                325                 330                 335 cac ttc agt gac ttg ggc caa tct ttc tct ttc cac tca ggc aat gcc       1293
His Phe Ser Asp Leu Gly Gln Ser Phe Ser Phe His Ser Gly Asn Ala
            340                 345                 350 aac ata cca tcc att tat gct aat ggg acc cat ctg gtc ccg ggt caa       1341
Asn Ile Pro Ser Ile Tyr Ala Asn Gly Thr His Leu Val Pro Gly Gln
        355                 360                 365 cat aag act ctg gta gtg aca gcc aac aga ggg tca tca cca cag gtg       1389
His Lys Thr Leu Val Val Thr Ala Asn Arg Gly Ser Ser Pro Gln Val
    370                 375                 380 atg tcc agg agc aat ggc tca gtc agt agg gag cct cgg cct cca cac       1437
Met Ser Arg Ser Asn Gly Ser Val Ser Arg Glu Pro Arg Pro Pro His
385                 390                 395                 400 act cat tcc tac acc atc agc cac gca aca ctg gaa cga att ggt gca       1485
Thr His Ser Tyr Thr Ile Ser His Ala Thr Leu Glu Arg Ile Gly Ala
                405                 410                 415 gta cct gtc atg gta cca gcc cag agt cgg gcc ggg tcc ttg gta tag      1533
Val Pro Val Met Val Pro Ala Gln Ser Arg Ala Gly Ser Leu Val
            420                 425                 430 gacatgagga aatgttgtgt tcagaaatga ataaatggaa tgccctcata caaggggag     1593 ggtggggtgg ggagtgctgg gaaagaaaca cttccttata attatattag taaaatgcac    1653
aaagaagaag gcagtgctgt tacttggcca ctaagatgtg taaaatggac tgaaatgctc    1713
catcatgaag acttgcttcc ccaccaaaga tgtcctggga ttctgctgga tctcaaagat    1773
gtgccaagcc aaggaaaaag atacaagagc agaatagtac ttaaaatcca aactgccgcc    1833
cagatgggct tgttcttcat gcctaactta ataattttta agagattaaa gtgccagatg    1893
gagtttaaat attgaaatta ttttaaaagg taggtgtctt taagaaaata acaagcaacc    1953
ctgtgatatg ttccgtctct cccaattccc tcgttatata gagggcttaa tggtataaat    2013
ggttaatatt ggtcccaaca gggctgactc ttctatcata taatcaaaac tttttacatg    2073
agcaaaattc agtaagaaat gggggaagac aaaggaaacg tctttgagaa gccccttcat    2133
atttatttat ttatctcttc ctgaaccatg aatttcatat gtggaatatt gctatattga    2193
cagattcttg cctgtctgtg ttattctagg atctgttaca ggtccatggc aattactgtt    2253
tattttttcc tggaaaaata ttttttttata aaggcttttt ttttttttttt aaatacatga  2313
```

-continued

```
gaggcattgg gctaagaaag aaaagactgt tgtataatac cttgttcaat ggttgtattt    2373
agtgagctca tagaggtcca tcatatcatg accgagctag gttgtgtggg caggaaggta    2433
gggctaaggg gttgtagcct tgctgggcag cctctcagag caaggttgtt cagatctccc    2493
ttgctattac agtaggttac tattaatgag ggcagcacct gatgcctttt gtactgaggt    2553
atgtaacttt ctccttattt gacaagtaga agttaactta cttgtcaggg agggcagacg    2613 ttttttttgtt ctgtttcgtt tttcaaaata atgcttttg caaaagaggt aagactgaga    2673
ctaaaggtgt tatcttctgg tgtgctcctg gaagtgtcta ccctacattt gtgtcagctc    2733
agggttgcag tgttgcccag atgcatttta catcactgta aagagattac ttttgtggtt    2793
actacctggc ttggctggcc ttgcggttca ccagattaat ttacaaactc ccccacttta    2853
ttttgtgcta tgtagatctg gccatacttg cattagtgac tgtcttgcct taaccacact    2913
taagcaaccc acaaatttct tctcagattt gtttcctaga ttacttatga tactcatccc    2973
atgtctcaat aagagtgtct tttctttctg gatgtgttct cttactccct cttaccacca    3033 tacttttgc tctcttctcc tgcaagcgta gtcttcacag ggagtggctt cctgacattt    3093
ttttcagtta tgtgaatgaa tggaaaccaa cagctgctgc aaacactgtt tttccaagaa    3153
ggctacactc agaacctaac cattgccaac catttcagta ttgataaaaa gctgaattta    3213
ctttagcatt acttattttt ttttccattt gatggttctt actttgtaaa aatttaaata    3273
aatgaatgtc tatacttttt ataaagaaaa gtgaaaatac catgacactg aaaagatgat    3333
gctatcagat gctgtttaga aagcatttat cttgcatttc tttattcttt ctaattatct    3393
aaaattcaat aaaattttat tcatataaaa                                    3423
```

<210> SEQ ID NO 2
<211> LENGTH: 431
<212> TYPE: PRT
<213> ORGANISM: Homo sapiens

<400> SEQUENCE: 2

```
Met Thr Ser Gln Arg Ser Pro Leu Ala Pro Leu Leu Leu Ser Leu
 1               5                  10                  15

His Gly Val Ala Ala Ser Leu Glu Val Ser Glu Ser Pro Gly Ser Ile
                20                  25                  30

Gln Val Ala Arg Gly Gln Pro Ala Val Leu Pro Cys Thr Phe Thr Thr
            35                  40                  45

Ser Ala Ala Leu Ile Asn Leu Asn Val Ile Trp Met Val Thr Pro Leu
        50                  55                  60

Ser Asn Ala Asn Gln Pro Glu Gln Val Ile Leu Tyr Gln Gly Gly Gln
    65                  70                  75                  80

Met Phe Asp Gly Ala Pro Arg Phe His Gly Arg Val Gly Phe Thr Gly
                85                  90                  95

Thr Met Pro Ala Thr Asn Val Ser Ile Phe Ile Asn Asn Thr Gln Leu
                100                 105                 110

Ser Asp Thr Gly Thr Tyr Gln Cys Leu Val Asn Asn Leu Pro Asp Ile
            115                 120                 125

Gly Gly Arg Asn Ile Gly Val Thr Gly Leu Thr Val Leu Val Pro Pro
        130                 135                 140

Ser Ala Pro His Cys Gln Ile Gln Gly Ser Gln Asp Ile Gly Ser Asp
    145                 150                 155                 160

Val Ile Leu Leu Cys Ser Ser Glu Glu Gly Ile Pro Arg Pro Thr Tyr
                165                 170                 175
```

```
Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
            195                 200                 205

Ser Ser Gly Leu Tyr Gln Cys Val Ala Ser Asn Ala Ile Gly Thr Ser
            210                 215                 220

Thr Cys Leu Leu Asp Leu Gln Val Ile Ser Pro Gln Pro Arg Asn Ile
225                 230                 235                 240

Gly Leu Ile Ala Gly Ala Ile Gly Thr Gly Ala Val Ile Ile Ile Phe
                    245                 250                 255

Cys Ile Ala Leu Ile Leu Gly Ala Phe Phe Tyr Trp Arg Ser Lys Asn
                260                 265                 270

Lys Glu Glu Glu Glu Glu Ile Pro Asn Glu Ile Arg Glu Asp Asp
            275                 280                 285

Leu Pro Pro Lys Cys Ser Ser Ala Lys Ala Phe His Thr Glu Ile Ser
    290                 295                 300

Ser Ser Asp Asn Asn Thr Leu Thr Ser Ser Asn Ala Tyr Asn Ser Arg
305                 310                 315                 320

Tyr Trp Ser Asn Asn Pro Lys Val His Arg Asn Thr Asp Ser Val Ser
                    325                 330                 335

His Phe Ser Asp Leu Gly Gln Ser Phe Ser Phe His Ser Gly Asn Ala
                340                 345                 350

Asn Ile Pro Ser Ile Tyr Ala Asn Gly Thr His Leu Val Pro Gly Gln
            355                 360                 365

His Lys Thr Leu Val Val Thr Ala Asn Arg Gly Ser Ser Pro Gln Val
    370                 375                 380

Met Ser Arg Ser Asn Gly Ser Val Ser Arg Glu Pro Arg Pro Pro His
385                 390                 395                 400

Thr His Ser Tyr Thr Ile Ser His Ala Thr Leu Glu Arg Ile Gly Ala
                    405                 410                 415

Val Pro Val Met Val Pro Ala Gln Ser Arg Ala Gly Ser Leu Val
                420                 425                 430

<210> SEQ ID NO 3
<211> LENGTH: 4987
<212> TYPE: DNA
<213> ORGANISM: Homo sapiens
<220> FEATURE:
<221> NAME/KEY: CDS
<222> LOCATION: (60)..(1304)
<223> OTHER INFORMATION:

<400> SEQUENCE: 3
gcggccgcag cctcagcacc gcagagcgga gagcggagcc cggagcccgc cgccccagg       59 atg gct gca gct cct cca agt tac tgt ttt gtt gcc ttc cct cca cgt      107
Met Ala Ala Ala Pro Pro Ser Tyr Cys Phe Val Ala Phe Pro Pro Arg
1               5                   10                  15 gct aag gat ggt ctg gtg gta ttt ggg aaa aat tca gcc cgg ccc aga      155
Ala Lys Asp Gly Leu Val Val Phe Gly Lys Asn Ser Ala Arg Pro Arg
            20                  25                  30 gat gaa gtg caa gag gtt gtg tat ttc tcg gct gct gat cac gaa ccg      203
Asp Glu Val Gln Glu Val Val Tyr Phe Ser Ala Ala Asp His Glu Pro
        35                  40                  45 gag agc aag gtt gag tgc act tac att tca atc gac caa gtt cca agg      251
Glu Ser Lys Val Glu Cys Thr Tyr Ile Ser Ile Asp Gln Val Pro Arg
    50                  55                  60 acc tat gcc ata atg ata agc aga ccc gcc tgg ctc tgg gga gca gaa      299
```

```
Thr Tyr Ala Ile Met Ile Ser Arg Pro Ala Trp Leu Trp Gly Ala Glu
 65              70                  75                  80 atg gga gcc aat gaa cat gga gtg tgc ata gcc aat gaa gcc atc aac    347
Met Gly Ala Asn Glu His Gly Val Cys Ile Ala Asn Glu Ala Ile Asn
                    85                  90                  95 acc aga gag cca gct gcc gag ata gaa gcc ttg ctg ggg atg gat ctg    395
Thr Arg Glu Pro Ala Ala Glu Ile Glu Ala Leu Leu Gly Met Asp Leu
                100                 105                 110 gtc agg ctt ggt tta gaa aga ggg gaa aca gct aaa gaa gcc tta gat    443
Val Arg Leu Gly Leu Glu Arg Gly Glu Thr Ala Lys Glu Ala Leu Asp
            115                 120                 125 gtc att gtc tcc ttg ttg gaa gaa cat gga caa ggt ggg aat tac ttt    491
Val Ile Val Ser Leu Leu Glu Glu His Gly Gln Gly Gly Asn Tyr Phe
        130                 135                 140 gaa gat gca aac tcc tgc cac agc ttc caa agt gca tat ctg att gtg    539
Glu Asp Ala Asn Ser Cys His Ser Phe Gln Ser Ala Tyr Leu Ile Val
145                 150                 155                 160 gat cgt gat gaa gcc tgg gtg ctc gag acc ata ggg aag tac tgg gct    587
Asp Arg Asp Glu Ala Trp Val Leu Glu Thr Ile Gly Lys Tyr Trp Ala
                165                 170                 175 gcc gag aaa gtc aca gag gga gtg agg tgc att tgc agt cag ctt tcg    635
Ala Glu Lys Val Thr Glu Gly Val Arg Cys Ile Cys Ser Gln Leu Ser
                180                 185                 190 ctc acc act aag atg gat gca gag cat ccg gaa ctc agg agt tac gct    683
Leu Thr Thr Lys Met Asp Ala Glu His Pro Glu Leu Arg Ser Tyr Ala
            195                 200                 205 cag agc caa ggt tgg tgg acg gga gag ggc gag ttc aat ttt tcc gaa    731
Gln Ser Gln Gly Trp Trp Thr Gly Glu Gly Glu Phe Asn Phe Ser Glu
        210                 215                 220 gtc ttt tct cca gtt gag gat cat cta gac tgc ggt gct ggc aaa gac    779
Val Phe Ser Pro Val Glu Asp His Leu Asp Cys Gly Ala Gly Lys Asp
225                 230                 235                 240 agc tta gaa aaa caa gaa gaa agc atc aca gtg cag act atg atg aac    827
Ser Leu Glu Lys Gln Glu Glu Ser Ile Thr Val Gln Thr Met Met Asn
                245                 250                 255 acc tta cgg gac aaa gcc agc gga gtg tgc ata gac tct gag ttt ttc    875
Thr Leu Arg Asp Lys Ala Ser Gly Val Cys Ile Asp Ser Glu Phe Phe
                260                 265                 270 ctc acc aca gcc agt gga gtg tct gtc ctg ccg cag aat aga agc tct    923
Leu Thr Thr Ala Ser Gly Val Ser Val Leu Pro Gln Asn Arg Ser Ser
            275                 280                 285 ccg tgc att cac tac ttc act gga acc cct gat cct tcc agg tcc ata    971
Pro Cys Ile His Tyr Phe Thr Gly Thr Pro Asp Pro Ser Arg Ser Ile
        290                 295                 300 ttc aag cct ttc atc ttt gtt gat gac gta aaa ctt gtc ccc aaa aca   1019
Phe Lys Pro Phe Ile Phe Val Asp Asp Val Lys Leu Val Pro Lys Thr
305                 310                 315                 320 cag tct ccc tgt ttt ggg gat gac gac cct gcc aaa aag gag cct cgg   1067
Gln Ser Pro Cys Phe Gly Asp Asp Asp Pro Ala Lys Lys Glu Pro Arg
                325                 330                 335 ttc cag gag aaa cca gac cgc cgg cat gag ctg tac aaa gcc cac gag   1115
Phe Gln Glu Lys Pro Asp Arg Arg His Glu Leu Tyr Lys Ala His Glu
                340                 345                 350 tgg gca cgt gcc atc atc gaa agt gac cag gag caa ggt cgc aag ctg   1163
Trp Ala Arg Ala Ile Ile Glu Ser Asp Gln Glu Gln Gly Arg Lys Leu
            355                 360                 365 agg agc acc atg ctg gag ctg gag aag caa ggc ctg gaa gcc atg gaa   1211
Arg Ser Thr Met Leu Glu Leu Glu Lys Gln Gly Leu Glu Ala Met Glu
        370                 375                 380
```

-continued

```
gaa atc ctg acc agc tcc gag cca ctg gac cct gcg aa gtg ggg gac      1259
Glu Ile Leu Thr Ser Ser Glu Pro Leu Asp Pro Ala Glu Val Gly Asp
385                 390                 395                 400 ctt ttc tat gac tgt gtt gac acg gag att aag ttc ttt aag tga          1304
Leu Phe Tyr Asp Cys Val Asp Thr Glu Ile Lys Phe Phe Lys
                405                 410 agtaagcgtt ccctttcccc ttcttattta agacttccca ccttactaaa ttaccagcaa    1364
aacaaaccac tctcctgttt gagtaaaatg agaaagttaa tatgtggcct ccttttctga    1424
agccagatca aactgttacc ttgtgttcca ccttgaatct cacagcgtcc ccttctgcaa    1484
tgtaggtctc cttcctgtgc agtgtaacat gtatcccgtt gcctgttgtt cggttgtgtg    1544
actaattgtg gattttaagc tgctattatt gtatttcagt ggcaatggac acattagcct    1604
tttacaagag gactagagtt catcaagcct tgaaggcag gcttcacagt gccgagttgg     1664
cgggaaaagc aaattctttt gaagtcttag tctttccctc agtagcggtt tctttcaggt    1724
taacaagagg catttgtgca cacacacagg gctcttgtgt gtgttgtcaa ggggaccctc    1784
cgtggcctcc cgtgagtgca tgcctgtagt gcacagtgtc tctacaggtg tcttctgggg    1844
ggcagaacca attggaagga agaaagggac ccctctccag tcctggctcc ttcctacatc    1904
ctgggctcct gaagaagctg tcttcccatt ttccatgcgc tgtgcttatg tgtggtggac    1964
tgcagagctg cttccactta caggagagct gataatttgt tagctggaac ctattcactt    2024
ccgagattca gacatagcca tgctggtggc cttctgaatc actgcatgga tgtcccagga    2084
ggcagctctc cccacacagc agcacagcca tcacaggatt cctgtgtag aaatgattcc     2144
cagtctagtt accaacagct agtctaggag taattgaatg gccctatggc acagttccac    2204
ccacagagta gtgaatctct cagccaagga gggaaagaaa aggaagaact cttgactatt    2264
tagattctag ttaaatatct ggaatcctag cagtcactac attatctcag cagagagact    2324
ttaattaaac tgatttgttt ccaatgtcgg gttcacttaa aggatttgac ttaccaccag    2384
agcatagaaa agcatgcaag gaagaccaga tgggcttagc attgggaaga cagagggcaa    2444
ggaggtgata gatggatata gaagcatttc tctgcaggat accagttcag gccccaccat    2504
tcctgccaag gccattacat cccacaaacc caaatacaaa gcagctgact tccctggatc    2564
ttccccccac tcctcacacc tcacatgtcc caggagctgc cttcattcag gcgggtagct    2624
gcactgggca tggggtggtg gtgggagctt accgccacct attcaagctc tcagctactc    2684
ctgaaacggg cagagatgat gaacagaagt gtatgtaaat acagcagcta gtgggagagc    2744
accagttggg cctaatcctg cctcatcatt cttggcagga atctgcaaat ggaaacattg    2804
tgagtatcag caatctggga agtgacaggg ttaataactc cttcccagaa gctgtatcat    2864
gagattttga ggggaccgag ccctgttaca tggatgtgaa cagtgaggat cagaggtttt    2924
atcagaacac attcttttt tctaccaact ctccagagcg tgagtatagg agtgccatga    2984
gctttttagt cagcagtttt gtaaactctg tatataaaat cattaaccac acattgtggg    3044
tgatgggaag acgatttcag ctgacagagt taatggcaac caataatggt ggcctgtagc    3104
tgctaagagc ttcacgcagg tttggcctgg gctttcactg ttggtgaatt tagagtgtcc    3164
ttttaggtgg ggcggctatt ctaaaagtgt cttctatca ctgttaaggg gggggaaag     3224
tgaggttcga ggatgacgta ggtaactctc ccctcccaag tccatgttcc aagtggctat    3284
gtaaagcaag atgatacaga aagctgctct aaaatctcac tgagtgattt caccttcgcc    3344
tactatgaaa tgtctcatca gacctgacat gtctgagata accaaggtga ttcaggattt    3404
gatcaaaaga agtctagtaa gaattaatta cacagaagcc tcctttcatt tctatgggcc    3464
```

```
aaacaaaggc catggataac cctacccgct ttatgtcatt acccattggg aaacacaatg    3524
gctacttctg ttagggtaca ttgaccttgg tcaagcatct taaagaaggc aaccctaatt    3584
gagagctgtc ttggctaata ctctgcacca caattgtgat gtcctagtcc taccactaga    3644
gggcatggta cagcctggca aaagttaaaa ggggtgtggc agctcccatc aggtctggag    3704
gtggtctata agcacagttg acagttgtgc attgggatgg gtggagaaag acgacaagag    3764
agcagagaat ctgctgatgt ggctgcgctt actttta gtg actttatgta cttatattaa    3824
cagctggaaa taggttgttg ggttttgagc aggctgttat agtgaggaat gttcattttt    3884
aaatgttcct aacagatttt gcttttgaaa aatgcttgtt acatgaataa tttgtggacc    3944
agggattgct tttctgaagg cagtataggg aacatgaata ttcaagatga aatacaaaaa    4004
ttatgtttaa gggtcatagt gtataagtag cttcctagga aacccttttgt gtatcttttc    4064 agactggggt gggggctgag catgcttgtg cagaaagaag ccatagccag aaaggacaga    4124
atctctcccc cactcccttg ccccataacc aaacataagc tagctagtct tgtctaatag    4184
atgggattta ctataggtga agatagcccct catattcaag acagaagct ctggcaggag    4244 taaattagca aagcagaaat agtacccttt cattcttgga ggtgctttga aattttaggt    4304
agaatataat cgaaattatg gaggttcctt agtgctcaat aatataagac ctggtgttat    4364
tagaacgagt ctttcttata aactaacaga gcaggtatat gcctgttaga ccttagctgt    4424
ggggttcctt tactattggg tgaatcatta ggtataaaaa ataatcatca accaggcaaa    4484
ttactttgct tcctagctga tgtcatccca cattggtaca ggtgttattc agtactgggt    4544
ggttcagcag ggaagccggg tgggaccagt gtgtctgtca tgaaaccact aactgcattc    4604
ctgactgaag agccatctgt catttattgg ggaaggtctt cagttgagct ctcagcctta    4664
ggaaggaagc acgtggagga gggacggagg aggttccctt gctgggcatg cttcgtagag    4724
ggccaggagc agcaggtcat gtgcacatgc cgttgcagca caagcttatg cttcccgtag    4784
ccgtggcttt tcattctgca cagtcccagg tcccagctcc cctcttatgg tttctgtcat    4844
aatgtgcttt atctgattga ctccaaacat cccgaaatgt cacctgcaga tttctcgtgg    4904
gaaccaatat gtacatgttt gcaattatgc tgtgagaatt taaatgtgtt agatggaaaa    4964
tgctattggc agggaataat aat                                           4987
```

<210> SEQ ID NO 4
<211> LENGTH: 414
<212> TYPE: PRT
<213> ORGANISM: Homo sapiens

<400> SEQUENCE: 4

```
Met Ala Ala Ala Pro Pro Ser Tyr Cys Phe Val Ala Phe Pro Pro Arg
1               5                   10                  15

Ala Lys Asp Gly Leu Val Val Phe Gly Lys Asn Ser Ala Arg Pro Arg
            20                  25                  30

Asp Glu Val Gln Glu Val Tyr Phe Ser Ala Ala Asp His Glu Pro
        35                  40                  45

Glu Ser Lys Val Glu Cys Thr Tyr Ile Ser Ile Asp Gln Val Pro Arg
    50                  55                  60

Thr Tyr Ala Ile Met Ile Ser Arg Pro Ala Trp Leu Trp Gly Ala Glu
65                  70                  75                  80

Met Gly Ala Asn Glu His Gly Val Cys Ile Ala Asn Glu Ala Ile Asn
                85                  90                  95
```

-continued

```
Thr Arg Glu Pro Ala Ala Glu Ile Glu Ala Leu Leu Gly Met Asp Leu
                100                 105                 110
Val Arg Leu Gly Leu Glu Arg Gly Glu Thr Ala Lys Glu Ala Leu Asp
            115                 120                 125
Val Ile Val Ser Leu Leu Glu Glu His Gly Gln Gly Gly Asn Tyr Phe
        130                 135                 140
Glu Asp Ala Asn Ser Cys His Ser Phe Gln Ser Ala Tyr Leu Ile Val
145                 150                 155                 160
Asp Arg Asp Glu Ala Trp Val Leu Glu Thr Ile Gly Lys Tyr Trp Ala
                165                 170                 175
Ala Glu Lys Val Thr Glu Gly Val Arg Cys Ile Cys Ser Gln Leu Ser
            180                 185                 190
Leu Thr Thr Lys Met Asp Ala Glu His Pro Glu Leu Arg Ser Tyr Ala
        195                 200                 205
Gln Ser Gln Gly Trp Trp Thr Gly Glu Gly Glu Phe Asn Phe Ser Glu
    210                 215                 220
Val Phe Ser Pro Val Glu Asp His Leu Asp Cys Gly Ala Gly Lys Asp
225                 230                 235                 240
Ser Leu Glu Lys Gln Glu Glu Ser Ile Thr Val Gln Thr Met Met Asn
                245                 250                 255
Thr Leu Arg Asp Lys Ala Ser Gly Val Cys Ile Asp Ser Glu Phe Phe
            260                 265                 270
Leu Thr Thr Ala Ser Gly Val Ser Val Leu Pro Gln Asn Arg Ser Ser
        275                 280                 285
Pro Cys Ile His Tyr Phe Thr Gly Thr Pro Asp Pro Ser Arg Ser Ile
    290                 295                 300
Phe Lys Pro Phe Ile Phe Val Asp Asp Val Lys Leu Val Pro Lys Thr
305                 310                 315                 320
Gln Ser Pro Cys Phe Gly Asp Asp Pro Ala Lys Lys Glu Pro Arg
                325                 330                 335
Phe Gln Glu Lys Pro Asp Arg Arg His Glu Leu Tyr Lys Ala His Glu
            340                 345                 350
Trp Ala Arg Ala Ile Ile Glu Ser Asp Gln Glu Gln Gly Arg Lys Leu
        355                 360                 365
Arg Ser Thr Met Leu Glu Leu Glu Lys Gln Gly Leu Glu Ala Met Glu
    370                 375                 380
Glu Ile Leu Thr Ser Ser Glu Pro Leu Asp Pro Ala Glu Val Gly Asp
385                 390                 395                 400
Leu Phe Tyr Asp Cys Val Asp Thr Glu Ile Lys Phe Phe Lys
                405                 410
```

<210> SEQ ID NO 5
<211> LENGTH: 5345
<212> TYPE: DNA
<213> ORGANISM: Homo sapiens
<220> FEATURE:
<221> NAME/KEY: CDS
<222> LOCATION: (489)..(2840)
<223> OTHER INFORMATION:

<400> SEQUENCE: 5

| | | |
|---|---|---|
| gtacttggtt aagcagttga aaccttttt gagcaggatc tgtaaaagca taattgaatt | 60 |
| tgtttcaccc ccgtggattc cagtgggccc gacagcgcaa cagtgcctgg caacttgatg | 120 |
| catatggaag agcaatgcca agtgatctga cataatacaa attcacgaag tgacatttta | 180 |
| tcacaagcaa agttggaaat tccaaagaga agtggtgaga tctttactag tcacagtgaa | 240 |

-continued

```
gatgggagaa aatgacatac ctgcagcaga tgtgggctga aaatatcctc ttctctgccc      300
aatcaggaat gctacctgtt tttgggaata aactttagag aaaggaaggg ccaaaactac      360
gacttggctt tctgaaacgg aagcataaat gttcttttcc tccatttgtc tggatctgag      420
aacctgcatt tggtattagc tagtggaagc agtatgtatg gttgaagtgc attgctgcag      480 ctggtagc atg agt ggt ggc cac cag ctg cag ctg gct gcc ctc tgg ccc      530
         Met Ser Gly Gly His Gln Leu Gln Leu Ala Ala Leu Trp Pro
           1               5                  10 tgg ctg ctg atg gct acc ctg cag gca ggc ttt gga cgc aca gga ctg      578
Trp Leu Leu Met Ala Thr Leu Gln Ala Gly Phe Gly Arg Thr Gly Leu
 15              20              25                  30 gta ctg gca gca gcg gtg gag tct gaa aga tca gca gaa cag aaa gct      626
Val Leu Ala Ala Ala Val Glu Ser Glu Arg Ser Ala Glu Gln Lys Ala
             35                  40                  45 att atc aga gtg atc ccc ttg aaa atg gac ccc aca gga aaa ctg aat      674
Ile Ile Arg Val Ile Pro Leu Lys Met Asp Pro Thr Gly Lys Leu Asn
                 50                  55                  60 ctc act ttg gaa ggt gtg ttt gct ggt gtt gct gaa ata act cca gca      722
Leu Thr Leu Glu Gly Val Phe Ala Gly Val Ala Glu Ile Thr Pro Ala
 65                  70                  75 gaa gga aaa tta atg cag tcc cac ccg ctg tac ctg tgc aat gcc agt      770
Glu Gly Lys Leu Met Gln Ser His Pro Leu Tyr Leu Cys Asn Ala Ser
             80                  85                  90 gat gac gac aat ctg gag cct gga ttc atc agc atc gtc aag ctg gag      818
Asp Asp Asp Asn Leu Glu Pro Gly Phe Ile Ser Ile Val Lys Leu Glu
 95                  100                 105                 110 agt cct cga cgg gcc ccc cgc ccc tgc ctg tca ctg gct agc aag gct      866
Ser Pro Arg Arg Ala Pro Arg Pro Cys Leu Ser Leu Ala Ser Lys Ala
                 115                 120                 125 cgg atg gcg ggt gag cga gga gcc agt gct gtc ctc ttt gac atc act      914
Arg Met Ala Gly Glu Arg Gly Ala Ser Ala Val Leu Phe Asp Ile Thr
             130                 135                 140 gag gat cga gct gct gct gag cag ctg cag cag ccg ctg ggg ctg acc      962
Glu Asp Arg Ala Ala Ala Glu Gln Leu Gln Gln Pro Leu Gly Leu Thr
145                 150                 155 tgg cca gtg gtg ttg atc tgg ggt aat gac gct gag aag ctg atg gag      1010
Trp Pro Val Val Leu Ile Trp Gly Asn Asp Ala Glu Lys Leu Met Glu
160                 165                 170 ttt gtg tac aag aac caa aag gcc cat gtg agg att gag ctg aag gag      1058
Phe Val Tyr Lys Asn Gln Lys Ala His Val Arg Ile Glu Leu Lys Glu
175                 180                 185                 190 ccc ccg gcc tgg cca gat tat gat gtg tgg atc cta atg aca gtg gtg      1106
Pro Pro Ala Trp Pro Asp Tyr Asp Val Trp Ile Leu Met Thr Val Val
                 195                 200                 205 ggc acc atc ttt gtg atc atc ctg gct tcg gtg ctg cgc atc cgg tgc      1154
Gly Thr Ile Phe Val Ile Ile Leu Ala Ser Val Leu Arg Ile Arg Cys
             210                 215                 220 cgc ccc cgc cac agc agg ccg gat ccg ctt cag cag aga aca gcc tgg      1202
Arg Pro Arg His Ser Arg Pro Asp Pro Leu Gln Gln Arg Thr Ala Trp
                 225                 230                 235 gcc atc agc cag ctg gcc acc agg agg tac cag gcc agc tgc agg cag      1250
Ala Ile Ser Gln Leu Ala Thr Arg Arg Tyr Gln Ala Ser Cys Arg Gln
240                 245                 250 gcc cgg ggt gag tgg cca gac tca ggg agc agc tgc agc tca gcc cct      1298
Ala Arg Gly Glu Trp Pro Asp Ser Gly Ser Ser Cys Ser Ser Ala Pro
255                 260                 265                 270 gtg tgt gcc atc tgt ctg gag gag ttc tct gag ggg cag gag cta cgg      1346
Val Cys Ala Ile Cys Leu Glu Glu Phe Ser Glu Gly Gln Glu Leu Arg
```

```
                275             280             285
gtc att tcc tgc ctc cat gag ttc cat cgt aac tgt gtg gac ccc tgg    1394
Val Ile Ser Cys Leu His Glu Phe His Arg Asn Cys Val Asp Pro Trp
            290             295             300 tta cat cag cat cgg act tgc ccc ctc tgc gtg ttc aac atc aca gag    1442
Leu His Gln His Arg Thr Cys Pro Leu Cys Val Phe Asn Ile Thr Glu
        305             310             315 gga gat tca ttt tcc cag tcc ctg gga ccc tct cga tct tac caa gaa    1490
Gly Asp Ser Phe Ser Gln Ser Leu Gly Pro Ser Arg Ser Tyr Gln Glu
    320             325             330 cca ggt cga aga ctc cac ctc att cgc cag cat ccc ggc cat gcc cac    1538
Pro Gly Arg Arg Leu His Leu Ile Arg Gln His Pro Gly His Ala His
335             340             345             350 tac cac ctc cct gct gcc tac ctg ttg ggc cct tcc cgg agt gca gtg    1586
Tyr His Leu Pro Ala Ala Tyr Leu Leu Gly Pro Ser Arg Ser Ala Val
            355             360             365 gct cgg ccc cca cgg cct ggt ccc ttc ctg cca tcc cag gag cca ggc    1634
Ala Arg Pro Pro Arg Pro Gly Pro Phe Leu Pro Ser Gln Glu Pro Gly
        370             375             380 atg ggc cct cgg cat cac cgc ttc ccc aga gct gca cat ccc cgg gct    1682
Met Gly Pro Arg His His Arg Phe Pro Arg Ala Ala His Pro Arg Ala
    385             390             395 cca gga gag cag cag cgc ctg gca gga gcc cag cac ccc tat gca caa    1730
Pro Gly Glu Gln Gln Arg Leu Ala Gly Ala Gln His Pro Tyr Ala Gln
400             405             410 ggc tgg gga atg agc cac ctc caa tcc acc tca cag cac cct gct gct    1778
Gly Trp Gly Met Ser His Leu Gln Ser Thr Ser Gln His Pro Ala Ala
415             420             425             430 tgc cca gtg ccc cta cgc cgg gcc agg ccc cct gac agc agt gga tct    1826
Cys Pro Val Pro Leu Arg Arg Ala Arg Pro Pro Asp Ser Ser Gly Ser
            435             440             445 gga gaa agc tat tgc aca gaa cgc agt ggg tac ctg gca gat ggg cca    1874
Gly Glu Ser Tyr Cys Thr Glu Arg Ser Gly Tyr Leu Ala Asp Gly Pro
        450             455             460 gcc agt gac tcc agc tca ggg ccc tgt cat ggc tct tcc agt gac tct    1922
Ala Ser Asp Ser Ser Ser Gly Pro Cys His Gly Ser Ser Ser Asp Ser
    465             470             475 gtg gtc aac tgc acg gac atc agc cta cag ggg gtc cat ggc agc agt    1970
Val Val Asn Cys Thr Asp Ile Ser Leu Gln Gly Val His Gly Ser Ser
480             485             490 tct act ttc tgc agc tcc cta agc agt gac ttt gac ccc cta gtg tac    2018
Ser Thr Phe Cys Ser Ser Leu Ser Ser Asp Phe Asp Pro Leu Val Tyr
495             500             505             510 tgc agc cct aaa ggg gat ccc cag cga gtg gac atg cag cct agt gtg    2066
Cys Ser Pro Lys Gly Asp Pro Gln Arg Val Asp Met Gln Pro Ser Val
            515             520             525 acc tct cgg cct cgt tcc ttg gac tcg gtg gtg ccc aca ggg gaa acc    2114
Thr Ser Arg Pro Arg Ser Leu Asp Ser Val Val Pro Thr Gly Glu Thr
        530             535             540 cag gtt tcc agc cat gtc cac tac cac cgc cac cgg cac cac cac tac    2162
Gln Val Ser Ser His Val His Tyr His Arg His Arg His His His Tyr
    545             550             555 aaa aag cgg ttc cag tgg cat ggc agg aag cct ggc cca gaa acc gga    2210
Lys Lys Arg Phe Gln Trp His Gly Arg Lys Pro Gly Pro Glu Thr Gly
560             565             570 gtc ccc cag tcc agg cct cct att cct cgg aca cag ccc cag cca gag    2258
Val Pro Gln Ser Arg Pro Pro Ile Pro Arg Thr Gln Pro Gln Pro Glu
575             580             585             590 cca cct tct cct gat cag caa gtc acc gga tcc aac tca gca gcc cct    2306
Pro Pro Ser Pro Asp Gln Gln Val Thr Gly Ser Asn Ser Ala Ala Pro
```

```
                                -continued

Pro Pro Ser Pro Asp Gln Gln Val Thr Gly Ser Asn Ser Ala Ala Pro
            595                 600                 605 tcg ggg cgg ctc tct aac cca cag tgc ccc agg gcc ctc cct gag cca      2354
Ser Gly Arg Leu Ser Asn Pro Gln Cys Pro Arg Ala Leu Pro Glu Pro
                610                 615                 620 gcc cct ggc cca gtt gac gcc tcc agc atc tgc ccc agt acc agc agt      2402
Ala Pro Gly Pro Val Asp Ala Ser Ser Ile Cys Pro Ser Thr Ser Ser
            625                 630                 635 ctg ttc aac ttg caa aaa tcc agc ctc tct gcc cga cac cca cag agg      2450
Leu Phe Asn Leu Gln Lys Ser Ser Leu Ser Ala Arg His Pro Gln Arg
            640                 645                 650 aaa agg cgg ggg ggt ccc tcc gag ccc acc cct ggc tct cgg ccc cag      2498
Lys Arg Arg Gly Gly Pro Ser Glu Pro Thr Pro Gly Ser Arg Pro Gln
655                 660                 665                 670 gat gca act gtg cac cca gct tgc cag att ttt ccc cat tac acc ccc      2546
Asp Ala Thr Val His Pro Ala Cys Gln Ile Phe Pro His Tyr Thr Pro
                675                 680                 685 agt gtg gca tat cct tgg tcc cca gag gca cac ccc ttg atc tgt gga      2594
Ser Val Ala Tyr Pro Trp Ser Pro Glu Ala His Pro Leu Ile Cys Gly
            690                 695                 700 cct cca ggc ctg gac aag agg ctg cta cca gaa acc cca ggc ccc tgt      2642
Pro Pro Gly Leu Asp Lys Arg Leu Leu Pro Glu Thr Pro Gly Pro Cys
            705                 710                 715 tac tca aat tca cag cca gtg tgg ttg tgc ctg act cct cgc cag ccc      2690
Tyr Ser Asn Ser Gln Pro Val Trp Leu Cys Leu Thr Pro Arg Gln Pro
            720                 725                 730 ctg gaa cca cat cca cct ggg gag ggg cct tct gaa tgg agt tct gac      2738
Leu Glu Pro His Pro Pro Gly Glu Gly Pro Ser Glu Trp Ser Ser Asp
735                 740                 745                 750 acc gca gag ggc agg cca tgc cct tat ccg cac tgc cag gtg ctg tcg      2786
Thr Ala Glu Gly Arg Pro Cys Pro Tyr Pro His Cys Gln Val Leu Ser
                755                 760                 765 gcc cag cct ggc tca gag gag gaa ctc gag gag ctg tgt gaa cag gct      2834
Ala Gln Pro Gly Ser Glu Glu Glu Leu Glu Glu Leu Cys Glu Gln Ala
            770                 775                 780 gtg tga gatgttcagg cctagctcca accaagagtg tgctccagat gtgtttgggc      2890
Val cctacctggc acagtcct gctcctggga aggaaagga ccacagcaaa caccattctt       2950
tttgccgtac ttcctagaag cactggaaga ggactggtga tggtggaggg tgagagggtg    3010
ccgtttcctg ctccagctcc agaccttgtc tgcagaaaac atctgcagtg cagcaaatcc    3070
atgtccagcc aggcaaccag ctgctgcctg tggcgtgtgt gggctggatc ccttgaaggc    3130 tgagttttg agggcagaaa gctagctatg ggtagccagg tgttacaaag gtgctgctcc     3190
ttctccaacc cctacttggt ttccctcacc ccaagcctca tgttcatacc agccagtggg    3250
ttcagcagaa cgcatgacac cttatcacct ccctccttgg gtgagctctg aacaccagct    3310
ttggcccctc cacagtaagg ctgctacatc aggggcaacc ctggctctat cattttcctt    3370
ttttgccaaa aggaccagta gcataggtga gccctgagca ctaaaaggag gggtccctga    3430
agctttccca ctatagtgtg gagttctgtc cctgaggtgg gtacagcagc cttggttcct    3490
ctgggggttg agaataagaa tagtggggag ggaaaaactc ctccttgaag atttcctgtc    3550
tcagagtccc agagaggtag aaaggaggaa tttctgctgg actttatctg ggcagaggaa    3610
ggatggaatg aagtagaaa aggcagaatt acagctgagc ggggacaaca aagagttctt     3670
ctctgggaaa agttttgtct tagagcaagg atggaaaatg gggacaacaa aggaaaagca    3730
aagtgtgacc cttgggtttg acagcccag aggcccagct ccccagtata agccatacag     3790
```

-continued

```
gccagggacc cacaggagag tggattagag cacaagtctg gcctcactga gtggacaaga    3850
gctgatgggc tcatcaggg tgacattcac cccagggcag cctgaccact cttggcccct    3910
caggcattat cccatttgga atgtgaatgt ggtggcaaag tgggcagagg accccacctg    3970 ggaaccttt tccctcagtt agtggggaga ctagcaccta ggtacccaca tgggtattta    4030
tatctgaacc agacagacgc ttgaatcagg cactatgtta agaaatatat ttatttgcta    4090
atatatttat ccacaaacag gcactatgtt aagaaatata tttatttgct aatatattta    4150
tccacaaatg tggtctggtc ttgtggtttt gttctgtcgt gactgtcact cagggtaaca    4210
acgtcatctc tttctacatc aagagaagta aattatttat gttatcagag gctaggctcc    4270
gattcatgaa aggatagggt agagtagagg gcttggcaat aagaactggt ttgtaagccc    4330
ctaaaagtgt ggcttagtga gatcagggaa ggagaaagca tgactggatt cttactgtgc    4390
ttcagtcatt attattatac tgttcacttc acacattatc atacttcagt gactcagacc    4450
ttgggcaaat actctgtgcc tcgcttttc agtccataaa atgggcctac ttaatagttg    4510
ttgcaggact tacatgagat aatagagtgt agaaaatatg ttccaaagtg gaaagttta    4570 ttcatgtgat agaaaacatc caaacctgtc acagagccca tctgaacaca gcatgggacc    4630
gccaacaaga agaaagcccg cccggaagca gctcaatcag gaggctgggc tggaatgaca    4690
gcgcagcggg gcctgaaact atttatatcc caaagctcct ctcagataaa cacaaatgac    4750
tgcgttctgc ctgcactcgg gctattgcga ggacagagag ctggtgctcc attggcgtga    4810
agtctccagg gccagaaggg gcctttgtcg cttcctcaca aggcacaagt tcccttctg    4870 cttccccgag aaaggtttgg taggggtggt ggtttagtgc ctatagaaca aggcatttcg    4930
cttcctagac ggtgaaatga aagggaaaaa aaggacacct aatctcctac aaatggtctt    4990
tagtaaagga accgtgtcta agcgctaaga actgcgcaaa gtataaatta tcagccggaa    5050
cgagcaaaca gacggagttt taaaagataa atacgcattt ttttccgccg tagctcccag    5110
gccagcattc ctgtgggaag caagtggaaa ccctatagcg ctctcgcagt taggaaggag    5170
gggtggggct gtcgctggat ttcttctcgg tctctgcaga gacaatccag agggagacag    5230
tggattcact gcccccaatg cttctaaaac ggggagacaa aacaaaaaaa aacaaacttc    5290
cgggttacca tcgggaaca ggaccgacgc ccagggccac cagccccctc gtgcc          5345
```

<210> SEQ ID NO 6
<211> LENGTH: 783
<212> TYPE: PRT
<213> ORGANISM: Homo sapiens

<400> SEQUENCE: 6

```
Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
                20                  25                  30

Ala Ala Ala Val Glu Ser Glu Arg Ser Ala Glu Gln Lys Ala Ile Ile
            35                  40                  45

Arg Val Ile Pro Leu Lys Met Asp Pro Thr Gly Lys Leu Asn Leu Thr
        50                  55                  60

Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                85                  90                  95
```

-continued

```
Asp Asn Leu Glu Pro Gly Phe Ile Ser Ile Val Lys Leu Glu Ser Pro
            100                 105                 110
Arg Arg Ala Pro Arg Pro Cys Leu Ser Leu Ala Ser Lys Ala Arg Met
            115                 120                 125
Ala Gly Glu Arg Gly Ala Ser Ala Val Leu Phe Asp Ile Thr Glu Asp
            130                 135             140
Arg Ala Ala Glu Gln Leu Gln Gln Pro Leu Gly Leu Thr Trp Pro
145             150                 155                 160
Val Val Leu Ile Trp Gly Asn Asp Ala Glu Lys Leu Met Glu Phe Val
                165                 170                 175
Tyr Lys Asn Gln Lys Ala His Val Arg Ile Glu Leu Lys Glu Pro Pro
            180                 185                 190
Ala Trp Pro Asp Tyr Asp Val Trp Ile Leu Met Thr Val Val Gly Thr
            195                 200                 205
Ile Phe Val Ile Ile Leu Ala Ser Val Leu Arg Ile Arg Cys Arg Pro
        210                 215                 220
Arg His Ser Arg Pro Asp Pro Leu Gln Gln Arg Thr Ala Trp Ala Ile
225             230                 235                 240
Ser Gln Leu Ala Thr Arg Arg Tyr Gln Ala Ser Cys Arg Gln Ala Arg
                245                 250                 255
Gly Glu Trp Pro Asp Ser Gly Ser Ser Cys Ser Ser Ala Pro Val Cys
            260                 265                 270
Ala Ile Cys Leu Glu Glu Phe Ser Glu Gly Gln Glu Leu Arg Val Ile
        275                 280                 285
Ser Cys Leu His Glu Phe His Arg Asn Cys Val Asp Pro Trp Leu His
    290                 295                 300
Gln His Arg Thr Cys Pro Leu Cys Val Phe Asn Ile Thr Glu Gly Asp
305             310                 315                 320
Ser Phe Ser Gln Ser Leu Gly Pro Ser Arg Ser Tyr Gln Glu Pro Gly
                325                 330                 335
Arg Arg Leu His Leu Ile Arg Gln His Pro Gly His Ala His Tyr His
            340                 345                 350
Leu Pro Ala Ala Tyr Leu Leu Gly Pro Ser Arg Ser Ala Val Ala Arg
            355                 360                 365
Pro Pro Arg Pro Gly Pro Phe Leu Pro Ser Gln Glu Pro Gly Met Gly
        370                 375                 380
Pro Arg His His Arg Phe Pro Arg Ala Ala His Pro Arg Ala Pro Gly
385             390                 395                 400
Glu Gln Gln Arg Leu Ala Gly Ala Gln His Pro Tyr Ala Gln Gly Trp
                405                 410                 415
Gly Met Ser His Leu Gln Ser Thr Ser Gln His Pro Ala Ala Cys Pro
            420                 425                 430
Val Pro Leu Arg Arg Ala Arg Pro Asp Ser Ser Gly Ser Gly Glu
            435                 440                 445
Ser Tyr Cys Thr Glu Arg Ser Gly Tyr Leu Ala Asp Gly Pro Ala Ser
    450                 455                 460
Asp Ser Ser Ser Gly Pro Cys His Gly Ser Ser Asp Ser Val Val
465             470                 475                 480
Asn Cys Thr Asp Ile Ser Leu Gln Gly Val His Gly Ser Ser Ser Thr
                485                 490                 495
Phe Cys Ser Ser Leu Ser Ser Asp Phe Asp Pro Leu Val Tyr Cys Ser
            500                 505                 510
Pro Lys Gly Asp Pro Gln Arg Val Asp Met Gln Pro Ser Val Thr Ser
```

-continued

```
                515                 520                 525
Arg Pro Arg Ser Leu Asp Ser Val Val Pro Thr Gly Glu Thr Gln Val
        530                 535                 540

Ser Ser His Val His Tyr His Arg His Arg His His His Tyr Lys Lys
545                 550                 555                 560

Arg Phe Gln Trp His Gly Arg Lys Pro Gly Pro Glu Thr Gly Val Pro
                565                 570                 575

Gln Ser Arg Pro Pro Ile Pro Arg Thr Gln Pro Gln Pro Glu Pro Pro
        580                 585                 590

Ser Pro Asp Gln Gln Val Thr Gly Ser Asn Ser Ala Ala Pro Ser Gly
                595                 600                 605

Arg Leu Ser Asn Pro Gln Cys Pro Arg Ala Leu Pro Glu Pro Ala Pro
        610                 615                 620

Gly Pro Val Asp Ala Ser Ser Ile Cys Pro Ser Thr Ser Ser Leu Phe
625                 630                 635                 640

Asn Leu Gln Lys Ser Ser Leu Ser Ala Arg His Pro Gln Arg Lys Arg
                645                 650                 655

Arg Gly Gly Pro Ser Glu Pro Thr Pro Gly Ser Arg Pro Gln Asp Ala
        660                 665                 670

Thr Val His Pro Ala Cys Gln Ile Phe Pro His Tyr Thr Pro Ser Val
        675                 680                 685

Ala Tyr Pro Trp Ser Pro Glu Ala His Pro Leu Ile Cys Gly Pro Pro
        690                 695                 700

Gly Leu Asp Lys Arg Leu Leu Pro Glu Thr Pro Gly Pro Cys Tyr Ser
705                 710                 715                 720

Asn Ser Gln Pro Val Trp Leu Cys Leu Thr Pro Arg Gln Pro Leu Glu
                725                 730                 735

Pro His Pro Pro Gly Glu Gly Pro Ser Glu Trp Ser Ser Asp Thr Ala
                740                 745                 750

Glu Gly Arg Pro Cys Pro Tyr Pro His Cys Gln Val Leu Ser Ala Gln
        755                 760                 765

Pro Gly Ser Glu Glu Glu Leu Glu Leu Cys Glu Gln Ala Val
770                 775                 780

<210> SEQ ID NO 7
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 7
acaacagcct caagatcatc ag                                            22

<210> SEQ ID NO 8
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 8
ggtccaccac tgacacgttg                                               20

<210> SEQ ID NO 9
<211> LENGTH: 22
<212> TYPE: DNA
<213> ORGANISM: Artificial
```

```
<220> FEATURE:
<223> OTHER INFORMATION: an artificially synthesized primer sequence

<400> SEQUENCE: 9
agctgagaca tttgttctct tg                                              22

<210> SEQ ID NO 10
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 10
tataaaccag ctgagtccag ag                                              22

<210> SEQ ID NO 11
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 11
ttcccgatat caacatctac cag                                             23

<210> SEQ ID NO 12
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 12
agtgtgtgac ctcaataagg cat                                             23

<210> SEQ ID NO 13
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 13
caggctttgg acgcacagga ctggtac                                         27

<210> SEQ ID NO 14
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 14
ctttgtgatc atcctggctt cggtgct                                         27

<210> SEQ ID NO 15
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 15
ggttgagatt taagttctca aa                                              22
```

<210> SEQ ID NO 16
<211> LENGTH: 41
<212> TYPE: DNA
<213> ORGANISM: Artificial
<220> FEATURE:
<223> OTHER INFORMATION: an artificially synthesized primer sequence

<400> SEQUENCE: 16
agttaagctt gccgggatga cttctcagcg ttcccctctg g                41

<210> SEQ ID NO 17
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 17
atctcgagta ccaaggaccc ggcccgactc tg                          32

<210> SEQ ID NO 18
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 18
gcggatccag gatggctgct gcagctcctc caag                        34

<210> SEQ ID NO 19
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 19
tagaattctt aaagaactta atctccgtgt caacac                      36

<210> SEQ ID NO 20
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 20
tgcagatctg cagctggtag catgagtggt g                           31

<210> SEQ ID NO 21
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 21
gaggagctgt gtgaacaggc tgtgtgagat gt                          32

<210> SEQ ID NO 22
<211> LENGTH: 16
<212> TYPE: DNA
<213> ORGANISM: Artificial
<220> FEATURE:
<223> OTHER INFORMATION: an artificially synthesized S-oligonucleotide

```
<400> SEQUENCE: 22
tctgcacggt gagtag                                                    16

<210> SEQ ID NO 23
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 23
ctactcaccg tgcaga                                                    16

<210> SEQ ID NO 24
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 24
ttctgtaggt gttgca                                                    16

<210> SEQ ID NO 25
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 25
tgcaacacct acagaa                                                    16

<210> SEQ ID NO 26
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 26
cttttcagga tggctg                                                    16

<210> SEQ ID NO 27
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 27
cagccatcct gaaaag                                                    16

<210> SEQ ID NO 28
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 28
aggttgaggt aagccg                                                    16

<210> SEQ ID NO 29
```

```
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 29
cggcttacct caacct                                                  16

<210> SEQ ID NO 30
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 30
tggtagcatg agtggt                                                  16

<210> SEQ ID NO 31
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 31
accactcatg ctacca                                                  16

<210> SEQ ID NO 32
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 32
tggtagccaa gtgcaggtta ta                                           22

<210> SEQ ID NO 33
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 33
ccaaagggtt tctgcagttt ca                                           22

<210> SEQ ID NO 34
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 34
tgcggatcca gagcagattg tactgagagt                                   30

<210> SEQ ID NO 35
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 35
```

```
ctctatctcg agtgaggcgg aaagaacca                                       29
```

<210> SEQ ID NO 36
<211> LENGTH: 47
<212> TYPE: DNA
<213> ORGANISM: Artificial
<220> FEATURE:
<223> OTHER INFORMATION: an artificially synthesized primer sequence

<400> SEQUENCE: 36

```
tttaagcttg aagaccattt ttggaaaaaa aaaaaaaaa aaaaaac                    47
```

<210> SEQ ID NO 37
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 37

```
tttaagcttg aagacatggg aaagagtggt ctca                                 34
```

<210> SEQ ID NO 38
<211> LENGTH: 51
<212> TYPE: DNA
<213> ORGANISM: Artificial
<220> FEATURE:
<223> OTHER INFORMATION: an artificially synthesized oligonucleotide
      sequence

<400> SEQUENCE: 38

```
caccgaagca gcacgacttc ttcttcaaga gagaagaagt cgtgctgctt c              51
```

<210> SEQ ID NO 39
<211> LENGTH: 51
<212> TYPE: DNA
<213> ORGANISM: Artificial
<220> FEATURE:
<223> OTHER INFORMATION: an artificially synthesized oligonucleotide
      sequence

<400> SEQUENCE: 39

```
aaaagaagca gcacgacttc ttctctcttg aagaagaagt cgtgctgctt c              51
```

<210> SEQ ID NO 40
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 40

```
tcccgtcacc ggatccaact cagttcaaga gactgagttg gatccggtga c              51
```

<210> SEQ ID NO 41
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 41

```
aaaagtcacc ggatccaact cagtctcttg aactgagttg gatccggtga c              51
```

```
<210> SEQ ID NO 42
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 42
tcccgctatt gcacagaacg cagttcaaga gactgcgttc tgtgcaatag c          51

<210> SEQ ID NO 43
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 43
aaaagctatt gcacagaacg cagtctcttg aactgcgttc tgtgcaatag c          51

<210> SEQ ID NO 44
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 44
tccccagaaa gctgttatca gagttcaaga gactctgata acagctttct g          51

<210> SEQ ID NO 45
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 45
aaaacagaaa gctgttatca gagtctcttg aactctgata acagctttct g          51

<210> SEQ ID NO 46
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 46
tccctgagcc acctccaatc cacttcaaga gagtggattg gaggtggctc a          51

<210> SEQ ID NO 47
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 47
aaaatgagcc acctccaatc cactctcttg aagtggattg gaggtggctc a          51
```

<210> SEQ ID NO 48
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 48
tcccctgcac ggacatcagc ctattcaaga gataggctga tgtccgtgca g         51

<210> SEQ ID NO 49
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 49
aaaactgcac ggacatcagc ctatctcttg aataggctga tgtccgtgca g         51

<210> SEQ ID NO 50
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 50
tcccgtgtca gagagccctg ggattcaaga gatcccaggg ctctctgaca c         51

<210> SEQ ID NO 51
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 51
aaaagtgtca gagagccctg ggatctcttg aatcccaggg ctctctgaca c         51

<210> SEQ ID NO 52
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 52 tcccctcaa tgtcatttgg atgttcaaga gacatccaaa tgcaattgag g          51

<210> SEQ ID NO 53
<211> LENGTH: 51
<212> TYPE: DNA
<213> ORGANISM: Artificial
<220> FEATURE:
<223> OTHER INFORMATION: an artificially synthesized oligonucleotide for siRNA

<400> SEQUENCE: 53
aaaacctcaa tgtcatttgg atgtctcttg aacatccaaa tgcaattgag g         51

<210> SEQ ID NO 54

```
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 54
tccctgtcat ttggatggtc actttcaaga gaagtgacca tccaaatgac a           51

<210> SEQ ID NO 55
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 55
aaaatgtcat ttggatggtc acttctcttg aaagtgacca tccaaatgac a           51

<210> SEQ ID NO 56
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 56
tccctgccaa ccaacctgaa cagttcaaga gactgttcag gttggttggc a           51

<210> SEQ ID NO 57
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 57
aaaatgccaa ccaacctgaa cagtctcttg aactgttcag gttggttggc a           51

<210> SEQ ID NO 58
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 58
tcccccaacc tgaacaggtc atcttcaaga gagatgacct gttcaggttg g           51

<210> SEQ ID NO 59
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 59
aaaaccaacc tgaacaggtc atctctcttg aagatgacct gttcaggttg g           51

<210> SEQ ID NO 60
<211> LENGTH: 51
```

```
<212> TYPE: DNA
<213> ORGANISM: Artificial
<220> FEATURE:
<223> OTHER INFORMATION: an artificially synthesized oligonucleotide for
      siRNA

<400> SEQUENCE: 60 tcccctgaa caggtcatcc tgtttcaaga gaacaggatg acctgttcag g                 51

<210> SEQ ID NO 61
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 61
aaaacctgaa caggtcatcc tgttctcttg aaacaggatg acctgttcag g                51

<210> SEQ ID NO 62
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 62
tccccaggtc atcctgtatc aggttcaaga gacctgatac aggatgacct g                51

<210> SEQ ID NO 63
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 63
aaaacaggtc atcctgtatc aggtctcttg aacctgatac aggatgacct g                51

<210> SEQ ID NO 64
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 64
gaagatctgc agcggtggag tctgaaag                                          28

<210> SEQ ID NO 65
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 65
ggaattcgga ctgggaaaat gaatctccct c                                      31

<210> SEQ ID NO 66
<211> LENGTH: 26
<212> TYPE: DNA
<213> ORGANISM: Artificial
<220> FEATURE:
```

<223> OTHER INFORMATION: an artificially synthesized primer sequence

<400> SEQUENCE: 66
ggagatctcc tgatcagcaa gtcacc                                      26

<210> SEQ ID NO 67
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 67
ggaattccac agcctgttca cacagctcct c                                31

<210> SEQ ID NO 68
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 68
gcggatccag gatggctgca gctcctccaa g                                31

<210> SEQ ID NO 69
<211> LENGTH: 38
<212> TYPE: DNA
<213> ORGANISM: Artificial
<220> FEATURE:
<223> OTHER INFORMATION: an artificially synthesized primer sequence

<400> SEQUENCE: 69
ctgaattcac ttaaagaact taatctccgt gtcaacac                         38

<210> SEQ ID NO 70
<211> LENGTH: 10
<212> TYPE: DNA
<213> ORGANISM: Homo sapiens

<400> SEQUENCE: 70
cccgggatga                                                        10

<210> SEQ ID NO 71
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 71

Ser Tyr Gln Glu Pro Gly Arg Arg Leu
1               5

<210> SEQ ID NO 72
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 72

His Tyr His Leu Pro Ala Ala Tyr Leu
1               5

<210> SEQ ID NO 73
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 73

Leu Phe Asn Leu Gln Lys Ser Ser Leu
1               5

<210> SEQ ID NO 74
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 74

Gly Phe Gly Arg Thr Gly Leu Val Leu
1               5

<210> SEQ ID NO 75
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 75

Arg Tyr Gln Ala Ser Cys Arg Gln Ala
1               5

<210> SEQ ID NO 76
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 76

Arg Ala Pro Gly Glu Gln Gln Arg Leu
1               5

<210> SEQ ID NO 77
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 77

Arg Ala Pro Arg Pro Cys Leu Ser Leu
1               5

<210> SEQ ID NO 78
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 78

Arg Pro Pro Arg Pro Gly Pro Phe Leu
1               5

<210> SEQ ID NO 79

```
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 79

Lys Ala Val Ile Arg Val Ile Pro Leu
1               5

<210> SEQ ID NO 80
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 80

Asn Ser Gln Pro Val Trp Leu Cys Leu
1               5

<210> SEQ ID NO 81
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 81

Ser Tyr Cys Thr Glu Arg Ser Gly Tyr Leu
1               5                   10

<210> SEQ ID NO 82
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 82

His Tyr His Leu Pro Ala Ala Tyr Leu Leu
1               5                   10

<210> SEQ ID NO 83
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 83

Cys Tyr Ser Asn Ser Gln Pro Val Trp Leu
1               5                   10

<210> SEQ ID NO 84
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 84

Ile Phe Val Ile Ile Leu Ala Ser Val Leu
1               5                   10

<210> SEQ ID NO 85
<211> LENGTH: 10
```

```
<212> TYPE: PRT
<213> ORGANISM: Artificial
<220> FEATURE:
<223> OTHER INFORMATION: an artificially synthesized peptide sequence

<400> SEQUENCE: 85

Val Phe Asn Ile Thr Glu Gly Asp Ser Phe
1               5                   10

<210> SEQ ID NO 86
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 86

Thr Phe Cys Ser Ser Leu Ser Ser Asp Phe
1               5                   10

<210> SEQ ID NO 87
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 87

Lys Leu Met Gln Ser His Pro Leu Tyr Leu
1               5                   10

<210> SEQ ID NO 88
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 88

Lys Met Asp Pro Thr Gly Lys Leu Asn Leu
1               5                   10

<210> SEQ ID NO 89
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 89

His Tyr Thr Pro Ser Val Ala Tyr Pro Trp
1               5                   10

<210> SEQ ID NO 90
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 90

Gly Gln Glu Leu Arg Val Ile Ser Cys Leu
1               5                   10

<210> SEQ ID NO 91
<211> LENGTH: 9
<212> TYPE: PRT
```

```
<213> ORGANISM: Artificial
<220> FEATURE:
<223> OTHER INFORMATION: an artificially synthesized peptide sequence

<400> SEQUENCE: 91

Asn Phe Gln Pro Val Trp Leu Cys Leu
1               5

<210> SEQ ID NO 92
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 92

Asn Tyr Gln Pro Val Trp Leu Cys Leu
1               5

<210> SEQ ID NO 93
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 93

Lys Leu Asn Leu Thr Leu Glu Gly Val
1               5

<210> SEQ ID NO 94
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 94

Gln Leu Ala Ala Leu Trp Pro Trp Leu
1               5

<210> SEQ ID NO 95
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 95

Leu Met Gln Ser His Pro Leu Tyr Leu
1               5

<210> SEQ ID NO 96
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 96

Leu Leu Gly Pro Ser Arg Ser Ala Val
1               5

<210> SEQ ID NO 97
<211> LENGTH: 9
<212> TYPE: PRT
<213> ORGANISM: Artificial
```

```
<220> FEATURE:
<223> OTHER INFORMATION: an artificially synthesized peptide sequence

<400> SEQUENCE: 97

Ala Leu Trp Pro Trp Leu Leu Met Ala
1               5

<210> SEQ ID NO 98
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 98

Trp Leu Leu Met Ala Thr Leu Gln Ala
1               5

<210> SEQ ID NO 99
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 99

Trp Ile Leu Met Thr Val Val Gly Thr
1               5

<210> SEQ ID NO 100
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 100

Lys Leu Met Glu Phe Val Tyr Lys Asn
1               5

<210> SEQ ID NO 101
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 101

Asn Leu Thr Leu Glu Gly Val Phe Ala
1               5

<210> SEQ ID NO 102
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 102

Gly Leu Thr Trp Pro Val Val Leu Ile
1               5

<210> SEQ ID NO 103
<211> LENGTH: 10
<212> TYPE: PRT
<213> ORGANISM: Artificial
<220> FEATURE:
```

-continued

<223> OTHER INFORMATION: an artificially synthesized peptide sequence

<400> SEQUENCE: 103

Tyr Leu Leu Gly Pro Ser Arg Ser Ala Val
1               5                   10

<210> SEQ ID NO 104
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 104

Leu Met Thr Val Val Gly Thr Ile Phe Val
1               5                   10

<210> SEQ ID NO 105
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 105

Cys Leu His Glu Phe His Arg Asn Cys Val
1               5                   10

<210> SEQ ID NO 106
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 106

Ser Leu Ser Ser Asp Phe Asp Pro Leu Val
1               5                   10

<210> SEQ ID NO 107
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 107

Gln Leu Ala Ala Ile Trp Pro Trp Leu Leu
1               5                   10

<210> SEQ ID NO 108
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 108

Ala Leu Trp Pro Trp Leu Leu Met Ala Thr
1               5                   10

<210> SEQ ID NO 109
<211> LENGTH: 10
<212> TYPE: PRT
<213> ORGANISM: Artificial
<220> FEATURE:
<223> OTHER INFORMATION: an artificially synthesized peptide sequence

```
<400> SEQUENCE: 109

Leu Gln Leu Ala Ala Leu Trp Pro Trp Leu
1               5                   10

<210> SEQ ID NO 110
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 110

Trp Leu Cys Leu Thr Pro Arg Gln Pro Leu
1               5                   10

<210> SEQ ID NO 111
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 111

Trp Leu His Gln His Arg Thr Cys Pro Leu
1               5                   10

<210> SEQ ID NO 112
<211> LENGTH: 20
<212> TYPE: DNA
<213> ORGANISM: Artificial
<220> FEATURE:
<223> OTHER INFORMATION: an artificially synthesized target sequence for
      siRNA

<400> SEQUENCE: 112
gtcaccggat ccaactcagt                                          20

<210> SEQ ID NO 113
<211> LENGTH: 20
<212> TYPE: DNA
<213> ORGANISM: Artificial
<220> FEATURE:
<223> OTHER INFORMATION: an artificially synthesized target sequence for
      siRNA

<400> SEQUENCE: 113
gctattgcac agaacgcagt                                          20

<210> SEQ ID NO 114
<211> LENGTH: 20
<212> TYPE: DNA
<213> ORGANISM: Artificial
<220> FEATURE:
<223> OTHER INFORMATION: an artificially synthesized target sequence for
      siRNA

<400> SEQUENCE: 114
caggtcatcc tgtatcaggt                                          20

<210> SEQ ID NO 115
<211> LENGTH: 9
<212> TYPE: PRT
<213> ORGANISM: Artificial
<220> FEATURE:
<223> OTHER INFORMATION: an artificially synthesized peptide sequence
```

<400> SEQUENCE: 115

Tyr Leu Trp Glu Lys Leu Asp Asn Thr
1               5

<210> SEQ ID NO 116
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 116

Leu Leu Leu Leu Ser Leu His Gly Val
1               5

<210> SEQ ID NO 117
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 117

Ile Asn Leu Asn Val Ile Trp Met Val
1               5

<210> SEQ ID NO 118
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 118

Trp Met Val Thr Pro Leu Ser Asn Ala
1               5

<210> SEQ ID NO 119
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 119

Cys Leu Val Asn Asn Leu Pro Asp Ile
1               5

<210> SEQ ID NO 120
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 120

Ser Leu His Gly Val Ala Ala Ser Leu
1               5

<210> SEQ ID NO 121
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 121

```
Val Ile Ile Ile Phe Cys Ile Ala Leu
1               5

<210> SEQ ID NO 122
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 122

Leu Ile Asn Leu Asn Val Ile Trp Met
1               5

<210> SEQ ID NO 123
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 123

Ala Val Leu Pro Cys Thr Phe Thr Thr
1               5

<210> SEQ ID NO 124
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 124

Ala Leu Ser Ser Gly Leu Tyr Gln Cys
1               5

<210> SEQ ID NO 125
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 125

Val Met Ser Arg Ser Asn Gly Ser Val
1               5

<210> SEQ ID NO 126
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 126

Ser Ile Phe Ile Asn Asn Thr Gln Leu
1               5

<210> SEQ ID NO 127
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 127
```

```
Lys Val His Arg Asn Thr Asp Ser Val
1               5
```

<210> SEQ ID NO 128
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 128

```
Arg Ile Gly Ala Val Pro Val Met Val
1               5
```

<210> SEQ ID NO 129
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 129

```
Asn Ile Gly Val Thr Gly Leu Thr Val
1               5
```

<210> SEQ ID NO 130
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 130

```
Ser Ile Tyr Ala Asn Gly Thr His Leu
1               5
```

<210> SEQ ID NO 131
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 131

```
Leu Leu Cys Ser Ser Glu Glu Gly Ile
1               5
```

<210> SEQ ID NO 132
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 132

```
Leu Leu Ser Leu His Gly Val Ala Ala
1               5
```

<210> SEQ ID NO 133
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 133

```
Ile Ile Phe Cys Ile Ala Leu Ile Leu
```

```
<210> SEQ ID NO 134
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 134

Thr Met Pro Ala Thr Asn Val Ser Ile
1               5

<210> SEQ ID NO 135
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 135

Tyr Leu Trp Glu Lys Leu Asp Asn Thr Leu
1               5                   10

<210> SEQ ID NO 136
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 136

Leu Ile Asn Leu Asn Val Ile Trp Met Val
1               5                   10

<210> SEQ ID NO 137
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 137

Ala Leu Ser Ser Gly Leu Tyr Gln Cys Val
1               5                   10

<210> SEQ ID NO 138
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 138

Ala Leu Ile Asn Leu Asn Val Ile Trp Met
1               5                   10

<210> SEQ ID NO 139
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 139

Ile Leu Leu Cys Ser Ser Glu Glu Gly Ile
1               5                   10
```

```
<210> SEQ ID NO 140
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 140

Val Leu Pro Cys Thr Phe Thr Thr Ser Ala
1               5                   10

<210> SEQ ID NO 141
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 141

Leu Leu Leu Ser Leu His Gly Val Ala Ala
1               5                   10

<210> SEQ ID NO 142
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 142

Ser Ile Tyr Ala Asn Gly Thr His Leu Val
1               5                   10

<210> SEQ ID NO 143
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 143

Gln Leu Ser Asp Thr Gly Thr Tyr Gln Cys
1               5                   10

<210> SEQ ID NO 144
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 144

Gly Leu Tyr Gln Cys Val Ala Ser Asn Ala
1               5                   10

<210> SEQ ID NO 145
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 145

Pro Leu Leu Leu Leu Ser Leu His Gly Val
1               5                   10
```

-continued

<210> SEQ ID NO 146
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 146

Ile Gln Val Ala Arg Gly Gln Pro Ala Val
1               5                   10

<210> SEQ ID NO 147
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 147

Phe Ile Asn Asn Thr Gln Leu Ser Asp Thr
1               5                   10

<210> SEQ ID NO 148
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 148

Leu Val Pro Gly Gln His Lys Thr Leu Val
1               5                   10

<210> SEQ ID NO 149
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 149

Asn Leu Pro Asp Ile Gly Gly Arg Asn Ile
1               5                   10

<210> SEQ ID NO 150
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 150

Val Leu Val Pro Pro Ser Ala Pro His Cys
1               5                   10

<210> SEQ ID NO 151
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 151

Ala Val Ile Ile Ile Phe Cys Ile Ala Leu
1               5                   10

```
<210> SEQ ID NO 152
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 152

Val Ile Ile Ile Phe Cys Ile Ala Leu Ile
1               5                   10

<210> SEQ ID NO 153
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 153

Ile Leu Gly Ala Phe Phe Tyr Trp Arg Ser
1               5                   10

<210> SEQ ID NO 154
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 154

Gly Leu Thr Val Leu Val Pro Pro Ser Ala
1               5                   10

<210> SEQ ID NO 155
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 155

Ser Ile Phe Lys Pro Phe Ile Phe Val
1               5

<210> SEQ ID NO 156
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 156

Trp Leu Trp Gly Ala Glu Met Gly Ala
1               5

<210> SEQ ID NO 157
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 157

Ile Met Ile Ser Arg Pro Ala Trp Leu
1               5

<210> SEQ ID NO 158
```

```
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 158

Leu Leu Gly Met Asp Leu Val Arg Leu
1               5

<210> SEQ ID NO 159
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 159

Phe Ile Phe Val Asp Asp Val Lys Leu
1               5

<210> SEQ ID NO 160
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 160

Val Cys Ile Asp Ser Glu Phe Phe Leu
1               5

<210> SEQ ID NO 161
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 161

Lys Pro Phe Ile Phe Val Asp Asp Val
1               5

<210> SEQ ID NO 162
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 162

Ile Val Asp Arg Asp Glu Ala Trp Val
1               5

<210> SEQ ID NO 163
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 163

Thr Leu Arg Asp Lys Ala Ser Gly Val
1               5

<210> SEQ ID NO 164
<211> LENGTH: 9
```

```
<212> TYPE: PRT
<213> ORGANISM: Artificial
<220> FEATURE:
<223> OTHER INFORMATION: an artificially synthesized peptide sequence

<400> SEQUENCE: 164

Lys Met Asp Ala Glu His Pro Glu Leu
1               5

<210> SEQ ID NO 165
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 165

Ala Leu Asp Val Ile Val Ser Leu Leu
1               5

<210> SEQ ID NO 166
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 166

Tyr Ala Gln Ser Gln Gly Trp Trp Thr
1               5

<210> SEQ ID NO 167
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 167

Lys Leu Arg Ser Thr Met Leu Glu Leu
1               5

<210> SEQ ID NO 168
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 168

Tyr Leu Ile Val Asp Arg Asp Glu Ala
1               5

<210> SEQ ID NO 169
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 169

Ala Ala Pro Pro Ser Tyr Cys Phe Val
1               5

<210> SEQ ID NO 170
<211> LENGTH: 9
<212> TYPE: PRT
```

```
<213> ORGANISM: Artificial
<220> FEATURE:
<223> OTHER INFORMATION: an artificially synthesized peptide sequence

<400> SEQUENCE: 170

Gly Met Asp Leu Val Arg Leu Gly Leu
1               5

<210> SEQ ID NO 171
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 171

Lys Val Thr Glu Gly Val Arg Cys Ile
1               5

<210> SEQ ID NO 172
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 172

Cys Ile Asp Ser Glu Phe Phe Leu Thr
1               5

<210> SEQ ID NO 173
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 173

Thr Val Gln Thr Met Met Asn Thr Leu
1               5

<210> SEQ ID NO 174
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 174

Glu Met Gly Ala Asn Glu His Gly Val
1               5

<210> SEQ ID NO 175
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 175

Phe Ile Phe Val Asp Asp Val Lys Leu Val
1               5                   10

<210> SEQ ID NO 176
<211> LENGTH: 10
<212> TYPE: PRT
<213> ORGANISM: Artificial
```

```
<220> FEATURE:
<223> OTHER INFORMATION: an artificially synthesized peptide sequence

<400> SEQUENCE: 176

Leu Ile Val Asp Arg Asp Glu Ala Trp Val
1               5                   10

<210> SEQ ID NO 177
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 177

Phe Leu Thr Thr Ala Ser Gly Val Ser Val
1               5                   10

<210> SEQ ID NO 178
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 178

Thr Met Leu Glu Leu Glu Lys Gln Gly Leu
1               5                   10

<210> SEQ ID NO 179
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 179

Ala Leu Leu Gly Met Asp Leu Val Arg Leu
1               5                   10

<210> SEQ ID NO 180
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 180

Ala Ile Met Ile Ser Arg Pro Ala Trp Leu
1               5                   10

<210> SEQ ID NO 181
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 181

Gly Val Cys Ile Asp Ser Glu Phe Phe Leu
1               5                   10

<210> SEQ ID NO 182
<211> LENGTH: 10
<212> TYPE: PRT
<213> ORGANISM: Artificial
<220> FEATURE:
```

<223> OTHER INFORMATION: an artificially synthesized peptide sequence

<400> SEQUENCE: 182

Lys Leu Val Pro Lys Thr Gln Ser Pro Cys
1               5                   10

<210> SEQ ID NO 183
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 183

Phe Asn Phe Ser Glu Val Phe Ser Pro Val
1               5                   10

<210> SEQ ID NO 184
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 184

Tyr Ile Ser Ile Asp Gln Val Pro Arg Thr
1               5                   10

<210> SEQ ID NO 185
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 185

Gly Glu Gly Glu Phe Asn Phe Ser Glu Val
1               5                   10

<210> SEQ ID NO 186
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 186

Trp Ala Ala Glu Lys Val Thr Glu Gly Val
1               5                   10

<210> SEQ ID NO 187
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 187

Val Leu Pro Gln Asn Arg Ser Ser Pro Cys
1               5                   10

<210> SEQ ID NO 188
<211> LENGTH: 10
<212> TYPE: PRT
<213> ORGANISM: Artificial
<220> FEATURE:
<223> OTHER INFORMATION: an artificially synthesized peptide sequence

```
<400> SEQUENCE: 188

Ala Ala Ala Pro Pro Ser Tyr Cys Phe Val
1               5                   10

<210> SEQ ID NO 189
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 189

Thr Met Met Asn Thr Leu Arg Asp Lys Ala
1               5                   10

<210> SEQ ID NO 190
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 190

Glu Val Gly Asp Leu Phe Tyr Asp Cys Val
1               5                   10

<210> SEQ ID NO 191
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 191

Ala Glu Met Gly Ala Asn Glu His Gly Val
1               5                   10

<210> SEQ ID NO 192
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 192

Gly Leu Val Val Phe Gly Lys Asn Ser Ala
1               5                   10

<210> SEQ ID NO 193
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 193

Gln Leu Ser Leu Thr Thr Lys Met Asp Ala
1               5                   10

<210> SEQ ID NO 194
<211> LENGTH: 10
<212> TYPE: PRT
<213> ORGANISM: Artificial
<220> FEATURE:
<223> OTHER INFORMATION: an artificially synthesized peptide sequence
```

```
<400> SEQUENCE: 194

Arg Ser Ile Phe Lys Pro Phe Ile Phe Val
1               5                   10

<210> SEQ ID NO 195
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 195

Ala Leu Ser Ser Gly Leu Tyr Gln Val
1               5

<210> SEQ ID NO 196
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 196

Ala Leu Ser Ser Gly Leu Tyr Gln Leu
1               5

<210> SEQ ID NO 197
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 197

Lys Leu Asp Ala Glu His Pro Glu Leu
1               5

<210> SEQ ID NO 198
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 198

Lys Met Asp Ala Glu His Pro Glu Val
1               5

<210> SEQ ID NO 199
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 199

Lys Leu Asp Ala Glu His Pro Glu Val
1               5
```

GENES AND POLYPEPTIDES RELATING TO HUMAN COLON CANCERS

The present application is a divisional of U.S. Ser. No. 10/916,064, now U.S. Pat. No. 7,425,612, filed Aug. 10, 2004, which is a continuation in part of PCT/JP2003/007006, filed Jun. 3, 2003, which claims priority to U.S. Ser. No. 60/386,985, filed Jun. 6, 2002, U.S. Ser. No. 60/415,209, filed Sep. 30, 2002, and U.S. Ser No. 60/451,013, filed Feb. 28, 2003, each of which is incorporated herein by reference in its entirety.

TECHNICAL FIELD

The present invention relates to the field of biological science, more specifically to the field of cancer research. In particular, the present invention relates to novel genes, RNF43, CXADRL1, and GCUD1, involved in the proliferation mechanism of cells, as well as polypeptides encoded by the genes. The genes and polypeptides of the present invention can be used, for example, in the diagnosis of cell proliferative disease, and as target molecules for developing drugs against the disease.

BACKGROUND ART

Gastric cancers and colorectal cancers are leading causes of cancer death worldwide. In spite of recent progress in diagnostic and therapeutic strategies, prognosis of patients with advanced cancers remains very poor. Although molecular studies have revealed the involvement of alterations in tumor suppressor genes and/or oncogenes in carcinogenesis, the precise mechanisms still remain to be elucidated.

cDNA microarray technologies have enabled to obtain comprehensive profiles of gene expression in normal and malignant cells, and compare the gene expression in malignant and corresponding normal cells (Okabe et al., Cancer Res 61:2129-37 (2001); Kitahara et al., Cancer Res 61: 3544-9 (2001); Lin et al., Oncogene 21:4120-8 (2002); Hasegawa et al., Cancer Res 62:7012-7 (2002)). This approach enables to disclose the complex nature of cancer cells, and helps to understand the mechanism of carcinogenesis. Identification of genes that are deregulated in tumors can lead to more precise and accurate diagnosis of individual cancers, and to develop novel therapeutic targets (Bienz and Clevers, Cell 103:311-20 (2000)). To disclose mechanisms underlying tumors from a genome-wide point of view, and discover target molecules for diagnosis and development of novel therapeutic drugs, the present inventors have been analyzing the expression profiles of tumor cells using cDNA microarray of 23040 genes (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)).

Studies designed to reveal mechanisms of carcinogenesis have already facilitated identification of molecular targets for anti-tumor agents. For example, inhibitors of farnesyltransferase (FTIs) which were originally developed to inhibit the growth-signaling pathway related to Ras, whose activation depends on posttranslational farnesylation, has been effective in treating Ras-dependent tumors in animal models (He et al., Cell 99:335-45 (1999)). Clinical trials on human using a combination of anti-cancer drugs and anti-HER2 monoclonal antibody, trastuzumab, have been conducted to antagonize the proto-oncogene receptor HER2/neu; and have been achieving improved clinical response and overall survival of breast-cancer patients (Lin et al., Cancer Res 61:6345-9 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (Fujita et al., Cancer Res 61:7722-6 (2001)). Therefore, gene products commonly up-regulated in cancerous cells may serve as potential targets for developing novel anti-cancer agents.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the discovered TAAs are now in the stage of clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Nat'l Acad Sci USA 94: 1914-8 (1997)). On the other hand, gene products which had been demonstrated to be specifically overexpressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenbeg et al., Nature Med 4: 321-7 (1998); Mukherji et al., Proc Nat'l Acad Sci USA 92: 8078-82 (1995); Hu et al., Cancer Res 56: 2479-83 (1996)), only limited number of candidate TAAs for the treatment of adenocarcinomas, including colorectal cancer, are available. TAAs abundantly expressed in cancer cells, and at the same time which expression is restricted to cancer cells would be promising candidates as immunotherapeutic targets. Further, identification of new TAAs inducing potent and specific anti-tumor immune responses is expected to encourage clinical use of peptide vaccination strategy in various types of cancer (Boon and can der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Nat'l Acad Sci USA 94: 1914-8 (1997); Harris, J Nat'l Cancer Inst 88: 1442-5 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both of HLA-A24 and HLA-A0201 are one of the popular HLA alleles in Japanese, as well as Caucasian (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Hictocompatibility Workshop and Conference Oxford University Press, Oxford, 1065 (1992); Williams et al., Tissue Antigen 49: 129 (1997)). Thus, antigenic peptides of cancers presented by these HLAs may be especially useful for the treatment of cancers among Japanese and Caucasian. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Nat'l Acad Sci USA 93: 4102-7 (1996)).

SUMMARY OF THE INVENTION

An object of the present invention is to provide novel proteins involved in the proliferation mechanism of gastric or colorectal cancer cells and the genes encoding the proteins, as well as methods for producing and using the same in the diagnosis and treatment of gastric cancer or colorectal cancer.

To disclose the mechanism of gastric and colorectal carcinogenesis and identify novel diagnostic markers and/or drug targets for the treatment of these tumors, the present inventors analyzed the expression profiles of genes in gastric and colorectal carcinogenesis using a genome-wide cDNA microarray containing 23040 genes. From the pharmacological point of view, suppressing oncogenic signals is easier in practice than activating tumor-suppressive effects. Thus, the present inventors searched for genes that are up-regulated during gastric and colorectal carcinogenesis.

Among the transcripts that were commonly up-regulated in gastric cancers, novel human genes CXADRL1 (coxsackie and adenovirus receptor like 1) and GCUD1 (up-regulated in gastric cancer) were identified on chromosome band 3q13 and 7p14, respectively. Gene transfer of CXADRL1 or GCUD1 promoted proliferation of cells. Furthermore, reduction of CXADRL1 or GCUD1 expression by transfection of their specific antisense S-oligonucleotides or small interfering RNAs inhibited the growth of gastric cancer cells. Many anticancer drugs, such as inhibitors of DNA and/or RNA synthesis, metabolic suppressors, and DNA intercalators, are not only toxic to cancer cells but also for normally growing cells. However, agents suppressing the expression of CXADRL1 may not adversely affect other organs due to the fact that normal expression of the gene is restricted to the testis and ovary, and thus may be of great importance for treating cancer.

Furthermore, among the transcripts that were commonly up-regulated in colorectal cancers, gene RNF43 (Ring finger protein 43) assigned at chromosomal band 17pter-p13.1 was identified. In addition, yeast two-hybrid screening assay revealed that RNF43 protein associated with NOTCH2 or STRIN.

NOTCH2 is a large transmembrane receptor protein that is a component of an evolutionarily conserved intercellular signaling mechanism. NOTCH2 is a protein member of the Notch signaling pathway and is reported to be involved in glomerulogenesis in the kidney and development of heart and eye vasculature (McCright et al., Development 128: 491-502 (2001)). Three Delta/Serrate/Lag-2 (DSL) proteins, Delta1, Jaggaed1, and Jaggaed2, are reported as functional ligands for NOTCH2 (Shimizu et al., Mol Cell Biol 20: 6913-22 (2000)). The signal induced by ligand binding in the Notch signaling pathway is transmitted intracellularly by a process involving proteolysis of the receptor and nuclear translocation of the intracellular domain of the NOTCH protein (see reviews Artavanis-Tsakonas et al., Annu Rev Cell Biol 7: 427-52 (1999); Weinmaster, Curr Opin Genet Dev 10: 363-9 (2000)). Furthermore, reduction of RNF43 expression by transfection of specific antisense S-oligonucleotides or small interfering RNAs corresponding to RNF43 inhibited the growth of colorectal cancer cells. As already described above many anticancer drugs, are not only toxic to cancer cells but also for normally growing cells. However, agents suppressing the expression of RNF43 may also not adversely affect other organs due to the fact that normal expression of the gene is restricted to fetus, more specifically fetal lung and fetal kidney, and thus may be of great importance for treating cancer.

Thus, the present invention provides isolated novel genes, CXADRL1, GCUD1, and RNF43, which are candidates as diagnostic markers for cancer as well as promising potential targets for developing new strategies for diagnosis and effective anti-cancer agents. Furthermore, the present invention provides polypeptides encoded by these genes, as well as the production and the use of the same. More specifically, the present invention provides the following:

The present application provides novel human polypeptides, CXADRL1, GCUD1, and RNF43, and functional equivalents thereof, that promote cell proliferation and is up-regulated in cell proliferative diseases, such as gastric and colorectal cancers.

In a preferred embodiment, the CXADRL1 polypeptide includes a putative 431 amino acid protein with about 37% identity to CXADR (coxsackie and adenovirus receptor). CXADRL1 is encoded by the open reading frame of SEQ ID NO: 1 and contains two immunoglobin domains at codons 29-124 and 158-232, as well as a transmembrane domain at codons 246-268. The CXADRL1 polypeptide preferably includes the amino acid sequence set forth in SEQ ID NO: 2. The present application also provides an isolated protein encoded from at least a portion of the CXADRL1 polynucleotide sequence, or polynucleotide sequences at least 30%, more preferably at least 40% complementary to the sequence set forth in SEQ ID NO: 1.

On the other hand, in a preferred embodiment, the GCUD1 polypeptide includes a putative 414 amino acid protein encoded by the open reading frame of SEQ ID NO: 3. The GCUD1 polypeptide preferably includes the amino acid sequence set forth in SEQ ID NO: 4. The present application also provides an isolated protein encoded from at least a portion of the GCUD1 polynucleotide sequence, or polynucleotide sequences at least 15%, more preferably at least 25% complementary to the sequence set forth in SEQ ID NO: 3.

Furthermore, in a preferred embodiment, the RNF43 polypeptide includes a putative 783 amino acid protein encoded by the open reading frame of SEQ ID NO: 5. The RNF43 polypeptide preferably includes the amino acid sequence set forth in SEQ ID NO: 6 and contains a Ring finger motif at codons 272-312. The RNF43 polypeptide showed 38% homology to RING finger protein homolog DKFZp566H073.1 (GenBank Accession Number: T08729). The present application also provides an isolated protein encoded from at least a portion of the RNF43 polynucleotide sequence, or polynucleotide sequences at least 30%, more preferably at least 40% complementary to the sequence set forth in SEQ ID NO: 5.

The present invention further provides novel human genes, CXADRL1 and GCUD1, whose expressions are markedly elevated in a great majority of gastric cancers as compared to corresponding non-cancerous mucosae. In addition to gastric cancers, CXADRL1 and GCUD1 were also highly expressed in colorectal cancer and liver cancer. The isolated CXADRL1 gene includes a polynucleotide sequence as described in SEQ ID NO: 1. In particular, the CXADRL1 cDNA includes 3423 nucleotides that contain an open reading frame of 1296 nucleotides (SEQ ID NO: 1). The present invention further encompasses polynucleotides which hybridize to and which are at least 30%, and more preferably at least 40% complementary to the polynucleotide sequence set forth in SEQ ID NO: 1, to the extent that they encode a CXADRL1 protein or a functional equivalent thereof. Examples of such polynucleotides are degenerates and allelic mutants of SEQ ID NO: 1. On the other hand, the isolated GCUD1 gene includes a polynucleotide sequence as described in SEQ ID NO: 3. In particular, the GCUD1 cDNA includes 4987 nucleotides that contain an open reading frame of 1245 nucleotides (SEQ ID NO: 3). The present invention further encompasses polynucleotides which hybridize to and which are at least 15%, and more preferably at least 25% complementary to the polynucleotide sequence set forth in SEQ ID NO: 3, to the extent that they encode a GCUD1 protein or a functional equivalent thereof. Examples of such polynucleotides are degenerates and allelic mutants of SEQ ID NO: 3.

Furthermore, the present invention provides a novel human gene RNF43, whose expression is markedly elevated in a great majority of colorectal cancers as compared to corresponding non-cancerous mucosae. In addition to colorectal cancers, RNF43 was also highly expressed in lung cancer, gastric cancer, and liver cancer. The isolated RNF43 gene includes a polynucleotide sequence as described in SEQ ID NO: 5. In particular, the RNF43 cDNA includes 5345 nucleotides that contain an open reading frame of 2352 nucleotides (SEQ ID NO: 5). The present invention further encompasses polynucleotides which hybridize to and which are at least 30%, and more preferably at least 40% complementary to the polynucleotide sequence set forth in SEQ ID NO: 5, to the extent that they encode a RNF43 protein or a functional equivalent thereof. Examples of such polynucleotides are degenerates and allelic mutants of SEQ ID NO: 5.

As used herein, an isolated gene is a polynucleotide whose structure is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1, 3, or 5. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1, 3, or 5. In the case of an isolated polynucleotide which is longer than or equivalent in length to the reference sequence, e.g., SEQ ID NO: 1, 3, or 5, the comparison is made with the full-length of the reference sequence. When the isolated polynucleotide is shorter than the reference sequence, e.g., shorter than SEQ ID NO: 1, 3, or 5, the comparison is made to segment of the reference sequence of the same length (excluding any loop required by the homology calculation).

The present invention also provides a method of producing a protein by transfecting or transforming a host cell with a polynucleotide sequence encoding the CXADRL1, GCUD1, or RNF43 protein, and expressing the polynucleotide sequence. In addition, the present invention provides vectors comprising a nucleotide sequence encoding the CXADRL1, GCUD1, or RNF43 protein, and host cells harboring a polynucleotide encoding the CXADRL1, GCUD1, or RNF43 protein. Such vectors and host cells may be used for producing the CXADRL1, GCUD1, or RNF43 protein.

An antibody that recognizes the CXADRL1, GCUD1, or RNF43 protein is also provided by the present application. In part, an antisense polynucleotide (e.g., antisense DNA), ribozyme, and siRNA (small interfering RNA) of the CXADRL1, GCUD1, or RNF43 gene is also provided.

The present invention further provides a method for diagnosis of cell proliferative diseases that includes determining an expression level of the gene in biological sample of specimen, comparing the expression level of CXADRL1, GCUD1, or RNF43 gene with that in normal sample, and defining a high expression level of the CXADRL1, GCUD1, or RNF43 gene in the sample as having a cell proliferative disease such as cancer. The disease diagnosed by the expression level of CXADRL1 or GCUD1 is suitably a gastric, colorectal, and liver cancer; and that detected by the expression level of RNF43 is colorectal, lung, gastric, and liver cancer.

Furthermore, a method of screening for a compound for treating a cell proliferative disease is provided. The method includes the steps of contacting the CXADRL1, GCUD1, or RNF43 polypeptide with test compounds, and selecting test compounds that bind to the CXADRL1, GCUD1, or RNF43 polypeptide.

The present invention further provides a method of screening for a compound for treating a cell proliferative disease, wherein the method includes the steps of contacting the CXADRL1, GCUD1, or RNF43 polypeptide with a test compound, and selecting the test compound that suppresses the expression level or biological activity of the CXADRL1, GCUD1, or RNF43 polypeptide.

Alternatively, the present invention provides a method of screening for a compound for treating a cell proliferative disease, wherein the method includes the steps of contacting CXADRL1 and AIP1 in the presence of a test compound, and selecting the test compound that inhibits the binding of CXADRL1 and AIP1.

Furthermore, the present invention provides a method of screening for a compound for treating a cell proliferative disease, wherein the method includes the steps of contacting RNF43 and NOTCH2 or STRIN in the presence of a test compound, and selecting the test compound that inhibits the binding of RNF43 and NOTCH2 or STRIN.

The present application also provides a pharmaceutical composition for treating cell proliferative disease, such as cancer. The pharmaceutical composition may be, for example, an anti-cancer agent. The pharmaceutical composition can be described as at least a portion of the antisense S-oligonucleotides or siRNA of the CXADRL1, GCUD1, or RNF43 polynucleotide sequence shown and described in SEQ ID NO: 1, 3, or 5, respectively. A suitable antisense S-oligonucleotide has the nucleotide sequence selected from the group of SEQ ID NO: 23, 25, 27, 29, or 31. The antisense S-oligonucleotide of CXADRL1 including those having the nucleotide sequence of SEQ ID NO: 23 or 25 may be suitably used to treat gastric, colorectal and liver cancer; the antisense S-oligonucleotide of GCUD1 including those having the nucleotide sequence of SEQ ID NO: 27 or 29, suitably to treat gastric, colorectal, or liver cancer; and the antisense S-oligonucleotide of RNF43 including those having the nucleotide sequence of SEQ ID NO: 31, suitably for colorectal, lung, gastric, or liver cancer. A suitable target sequence of siRNA has the nucleotide sequences selected from the group of SEQ ID NOs: 112, 113, or 114. The target sequence of siRNA of CXADRL1 including those having the nucleotide sequence of SEQ ID NOs: 114 may be suitably used to treat gastric, colorectal, or liver cancer; and the target sequence of siRNA of RNF43 including those having the nucleotide sequence of SEQ ID NOs: 112, or 113, suitably for colorectal, lung, gastric, or liver cancer. The pharmaceutical compositions may be also those comprising the compounds selected by the present methods of screening for compounds for treating cell proliferative diseases.

The course of action of the pharmaceutical composition is desirably to inhibit growth of the cancerous cells. The pharmaceutical composition may be applied to mammals including humans and domestic mammals.

The present invention further provides methods for treating a cell proliferative disease using the pharmaceutical composition provided by the present invention.

In addition, the present invention provides method for treating or preventing cancer, which method comprises the step of administering the CXADRL1, GCUD1, or RNF43 polypeptide. It is expected that anti-tumor immunity be induced by the administration of the CXADRL1, GCUD1, or RNF43 polypeptide. Thus, the present invention also provides method for inducing anti-tumor immunity, which method comprises the step of administering the CXADRL1, GCUD1, or RNF43 polypeptide, as well as pharmaceutical composition for treating or preventing cancer comprising the CXADRL1, GCUD1, or RNF43 polypeptide.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 1a depicts the relative expression ratios (cancer/non-cancer) of A5928 in primary 14 gastric cancers examined by cDNA microarray. Its expression was up-regulated (Cy3:Cy5 intensity ratio, >2.0) in 14 of the 14 gastric cancers that passed through the cutoff filter (both Cy3 and Cy5 signals greater than 25,000). FIG. 1b depicts the relative expression ratios (cancer/non-cancer) of C8121 in primary 12 gastric cancers examined by cDNA microarray. Its expression was up-regulated (Cy3:Cy5 intensity ratio, >2.0) in 10 of the 12 gastric cancers that passed through the cutoff filter. FIG. 1c depicts the expression of CXADRL1 analyzed by semi-quantitative RT-PCR using 10 gastric cancer cases. FIG. 1d depicts the expression of GCUD1 analyzed by semi-quantitative RT-PCR using 9 gastric cancer cases. Expression of GAPDH served as an internal control for both the expression analyses of CXADRL1 and GCUD1.

FIG. 2a is a photograph depicting expression of CXADRL1 in various human tissues analyzed by multiple-tissue Northern-blot analysis. FIG. 2b depicts the predicted protein structure of CXADRL1. The CXADRL1 cDNA consists of 3,423 nucleotides with an ORF of 1,296 nucleotides and is composed of 7 exons.

FIG. 3a is a photograph depicting the result of colony formation assays of NIH3T3 cells transfected with CXADRL1. FIG. 3b depicts the expression of exogenous CXADRL1 in NIH3T3-CXADRL1 cells analyzed by semi-quantitative RT-PCR. Expression of GAPDH served as an internal control. #2, #5, #6, and #7 all indicate NIH3T3 cells transfected with CXADRL1. FIG. 3c depicts the number of NIH3T3 cells. Growth of NIH3T3-CXADRL1 cells was statistically higher than that of mock (NIH3T3-LacZ) cells in culture media containing 10% FBS ($P<0.05$).

FIG. 5A presents photographs depicting the expression of CXADRL1 and GAPDH (control) in St-4 cells transfected with mock or CXADRL1-siRNA#7. FIG. 5B depicts photographs depicting the result of Giemsa's staining of viable cells treated with control-siRNA or CXADRL1-siRNA#7. FIG. 5C depicts the result of MTT assay on cells transfected with control plasmid or plasmids expressing CXADRL1-siRNA7.

FIG. 7 is a photograph depicting the interaction of CXADRL1 with AIP1 examined by the two-hybrid system.

FIG. 24a depicts the relative expression ratios (cancer/non-cancer) of FLJ20315 in 11 primary colon cancer cases examined by cDNA microarray. Its expression was up-regulated (Cy3:Cy5 intensity ratio, >2.0) in 10 of the 11 colon cancer cases that passed through the cut-off filter (both Cy3 and Cy5 signals greater than 25,000). FIG. 24b depicts the expression of FLJ20315 analyzed by semi-quantitative RT-PCR using additional 18 colon cancer cases (T, tumor tissue; N, normal tissue). Expression of GAPDH served as an internal control.

FIG. 26a is a photograph depicting the result of Western-blot analysis of myc-tagged RNF43 protein using extracts from COS7 cells transfected with either pcDNA3.1-myc/His-RNF43 or control plasmids (mock). FIG. 26b presents photographs of the transfected cells that were stained with mouse anti-myc antibody and visualized by FITC-conjugated secondary antibody. Nuclei were counter-stained with DAPI.

FIG. 27a is a photograph depicting the result of colony formation assay of RNF43 in NIH3T3 cells. FIG. 27b presents photographs depicting the expression of RNF43 in mock (COS7-pcDNA) and COS7-RNF43 cells that was established by the transfection of COS7 cells with pcDNA-RNF43. FIG. 27c depicts the result of comparison on cell growth between COS7-RNF43 cells stably expressing exogenous RNF43 and mock cells.

FIG. 28a presents photographs depicting the expression of RNF43 in LoVo cells treated for 12 h with either control (RNF43-S1) or antisense S-oligonucleotides (RNF43-AS1) analyzed by semi-quantitative RT-PCR. FIG. 28b depicts the cell viability of LoVo cells after treatment with the control or antisense S-oligonucleotides measured by MTT assay. The MTT assay was carried out in triplicate.

FIG. 29A presents photographs depicting the effect of RNF43-siRNAs on the expression of RNF43. FIG. 29B presents photographs depicting the result of Giemsa's staining of viable cells after the treatment with control-siRNA or RNF43-siRNAs. FIG. 29C depicts the result of MTT assay on cells transfected with control plasmid or plasmids expressing RNF43-siRNAs. *, a significant difference (p<0.05) as determined by a Fisher's protected least significant difference test.

FIG. 30A is a photograph depicting the result of Western-blot analysis of Flag-tagged RNF43 protein secreted in the culture media of COS7 cells transfected with pFLAG-5CMV-RNF43 (lane 2) or mock vector (lane 1). FIG. 30B is a photograph depicting the result of Western-blot analysis of Myc-tagged RNF43 protein secreted in the culture media of COS7 cells transfected with pcDNA3.1-Myc/His-RNF43 (lane 2) or mock vector (lane 1).

FIG. 31A presents photographs depicting the morphology of NIH3T3 cells cultured in control media (1) or in conditioned media of COS7 cells transfected with mock vector (2), pcDNA3.1-Myc/His-RNF43 (3), or pFLAG-5CMV-RNF43 (4). FIG. 31B depicts the number of NIH3T3 cells cultured in the indicated media described in FIG. 31A. Data are shown as means of triplicate experiments for each group; bars, ±SE. *, significant difference when compared with control, mock (p<0.05).

FIG. 32A depicts the schematic structure of the recombinant protein RNF43-N1 and -C1. FIG. 32B is a photograph depicting the expression of Nus™-tagged RNF43-N1 protein in *E. coli* with (lane 2) or without (lane 1) 0.2 mM of IPTG. FIG. 32C is a photograph depicting the expression of Nus™-tagged RNF43-C1 protein in *E. coli* with (lane 2) or without (lane 1) 1 mM of IPTG.

FIG. 33A depicts the predicted structure and the interacting region of NOTCH2. (a) shows the predicted full-length structure of NOTCH2 protein, and (b) shows the predicted responsible region for the interaction (ECD, Extracellular domain; TM, transmembrane domain; ICD, Intracellular domain). FIG. 33B is a photograph depicting the interaction of RNF43 with NOTCH2 examined by the two-hybrid system.

FIG. 34A depicts the predicted structure and the interacting region of STRIN. (a) shows the predicted full-length structure of STRIN protein, and (b) shows the predicted responsible region for the interaction (RING, RING domain). FIG. 34B is a photograph depicting the interaction of RNF43 with STRIN examined by the two-hybrid system.

DETAILED DESCRIPTION OF THE INVENTION

Figure 1:
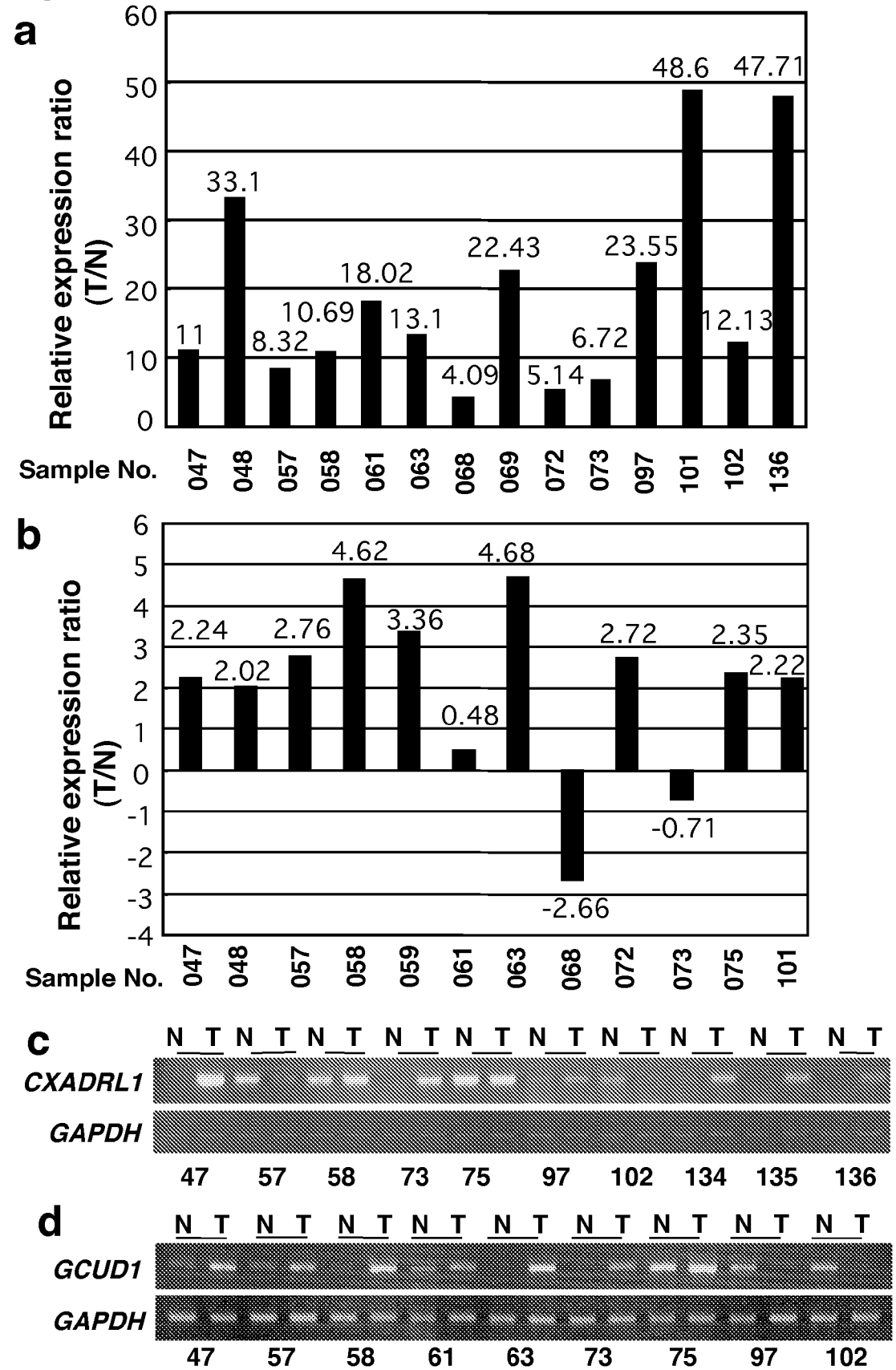
FIG. 1a to 1d depict the expression of A5928 (CXADRL1) and C8121 (GCUD1) in gastric cancers.

The words "a", "an", and "the" as used herein mean "at least one" unless otherwise specifically indicated.

The present application identifies novel human genes CXADRL1 and GCUD1 whose expression is markedly elevated in gastric cancer compared to corresponding non-cancerous tissues. The CXADRL1 cDNA consists of 3423 nucleotides that contain an open reading frame of 1296 nucleotides as set forth in SEQ ID NO: 1. The open reading frame encodes a putative 431-amino acid protein. CXADRL1 associates with atripin-1-interacting protein 1 (AIP1). AIP1 is a protein that associates with atripin-1, a gene responsible for a hereditary disease, dentatorubral-pallidoluysian atrophy. AIP1 encodes a deduced 1455-amino acid protein containing guanylate kinase-like domain, two WW domains and five PDZ domains. The mouse homolog of AIP1 was shown to interact with activin type IIA. However, the function of AIP1 remains to be resolved. The predicted amino acid sequence showed an identity of about 37% to coxsackie and adenovirus receptor (CXADR). Therefore this protein was dubbed coxsackie and adenovirus receptor like 1 (CXADRL1). On the other hand, the GCUD1 cDNA consists of 4987 nucleotides that contain an open reading frame of 1245 nucleotides as set forth in SEQ ID NO: 3. The open reading frame encodes a putative 414-amino acid protein. Since the expression of the protein was up-regulated in gastric cancer, the protein was dubbed GCUD1 (up-regulated in gastric cancer).

Furthermore, the present invention encompasses novel human gene RNF43 whose expression is markedly elevated in colorectal cancer compared to corresponding non-cancerous tissue. The RNF43 cDNA consists of 5345 nucleotides that contain an open reading frame of 2352 nucleotides as set forth in SEQ ID NO: 5. The open reading frame encodes a putative 783-amino acid protein. RNF43 associates with NOTCH2 and STRIN. NOTCH2 is reported as a large transmembrane receptor protein that is a component of an evolutionarily conserved intercellular signaling mechanism. NOTCH2 is a protein member of the Notch signaling pathway and is reported to be involved in glomerulogenesis in the kidney and development of heart and eye vasculature. Furthermore, three Delta/Serrate/Lag-2 (DSL) proteins, Delta1, Jaggaed1, and Jaggaed2, are reported as functional ligands for NOTCH2. STRIN encodes a putative protein that shares 79% identity with mouse Trif. The function of STRIN or Trif remains to be clarified.

Consistently, exogenous expression of CXADRL1, GCUD1, or RNF43 into cells conferred increased cell growth, while suppression of its expression with antisense S-oligonucleotides or small interfering RNA (siRNA) resulted in significant growth-inhibition of cancerous cells. These findings suggest that CXADRL1, GCUD1, and RNF43 render oncogenic activities to cancer cells, and that inhibition of the activity of these proteins could be a promising strategy for the treatment of cancer.

The present invention encompasses novel human gene CXADRL1, including a polynucleotide sequence as described in SEQ ID NO: 1, as well as degenerates and mutants thereof, to the extent that they encode a CXADRL1 protein, including the amino acid sequence set forth in SEQ ID NO: 2 or its functional equivalent. Examples of polypeptides functionally equivalent to CXADRL1 include, for example, homologous proteins of other organisms corresponding to the human CXADRL1 protein, as well as mutants of human CXADRL1 proteins.

The present invention also encompasses novel human gene GCUD1, including a polynucleotide sequence as described in SEQ ID NO: 3, as well as degenerates and mutants thereof, to the extent that they encode a GCUD1 protein, including the amino acid sequence set forth in SEQ ID NO: 4 or its functional equivalent. Examples of polypeptides functionally equivalent to GCUD1 include, for example, homologous proteins of other organisms corresponding to the human GCUD1 protein, as well as mutants of human GCUD1 proteins.

Furthermore, the present invention encompasses novel human gene RNF43, including a polynucleotide sequence as described in SEQ ID NO: 5, as well as degenerates and mutants thereof, to the extent that they encode a RNF43 protein, including the amino acid sequence set forth in SEQ ID NO: 6 or its functional equivalent. Examples of polypeptides functionally equivalent to RNF43 include, for example, homologous proteins of other organisms corresponding to the human RNF43 protein, as well as mutants of human RNF43 proteins.

In the present invention, the phrase "functionally equivalent" means that the subject polypeptide has activities to promote cell proliferation like CXADRL1, GCUD1, or RNF43 protein and to confer oncogenic activity to cancer cells. Whether the subject polypeptide has a cell proliferation activity or not can be judged by introducing the DNA encoding the subject polypeptide into a cell expressing the respective polypeptide, and detecting promotion of proliferation of the cells or increase in colony forming activity. Such cells include, for example, NIH3T3 cells for CXADRL1 and GCUD1; and NIH3T3 cells, SW480 cells, and COS7 cells for RNF43. Alternatively, whether the subject polypeptide is functionally equivalent to CXADRL1 may be judged by detecting its binding ability to AIP1. Furthermore, whether the subject polypeptide is functionally equivalent to RNF43 may be judged by detecting its binding ability to NOTCH2 or STRIN.

Methods for preparing polypeptides functionally equivalent to a given protein are well known by a person skilled in the art and include known methods of introducing mutations into the protein. For example, one skilled in the art can prepare polypeptides functionally equivalent to the human CXADRL1, GCUD1, or RNF43 protein by introducing an appropriate mutation in the amino acid sequence of either of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92 (1985); Kunkel, Methods Enzymol 85: 2763-6 (1988)). Amino acid mutations can occur in nature, too. The polypeptide of the present invention includes proteins having the amino acid sequences of the human CXADRL1, GCUD1, or RNF43 protein in which one or more amino acids are mutated, provided the resulting mutated polypeptides are functionally equivalent to the human CXADRL1, GCUD1, or RNF43 protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of human CXADRL1, GCUD1, or RNF43 protein is a fusion protein containing the human CXADRL1, GCUD1, or RNF43 protein. Fusion proteins are, fusions of the human CXADRL1, GCUD1, or RNF43 protein and other peptides or proteins, and are included in the present invention. Fusion proteins can be made by techniques well known to a person skilled in the art, such as by linking the DNA encoding the human CXADRL1, GCUD1, or RNF43 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human CXADRL1, GCUD1, or RNF43 protein (i.e., SEQ ID NO: 1, 3, or 5), and isolate functionally equivalent polypeptides to the human CXADRL1, GCUD1, or RNF43 protein from the isolated DNA. The polypeptides of the present invention include those that are encoded by DNA that hybridize with a whole or part of the DNA sequence encoding the human CXADRL1, GCUD1, or RNF43 protein and are functionally equivalent to the human CXADRL1, GCUD1, or RNF43 protein. These polypeptides include mammal homologues corresponding to the protein derived from human (for example, a polypeptide encoded by a monkey, rat, rabbit or bovine gene). In isolating a cDNA highly homologous to the DNA encoding the human CXADRL1 protein from animals, it is particularly preferable to use tissues from testis or ovary. Alternatively, in isolating a cDNA highly homologous to the DNA encoding the human GCUD1 from animals, it is particularly preferable to use tissues from testis, ovary, or brain. Further, in isolating a cDNA highly homologous to the DNA encoding the human RNF43 protein from animals, it is particularly preferable to use tissue from fetal lung or fetal kidney.

The condition of hybridization for isolating a DNA encoding a polypeptide functionally equivalent to the human CXADRL1, GCUD1, or RNF43 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors in addition to temperature and salt concentration, such as length of the probe and GC content of the probe, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human CXADRL1, GCUD1, or RNF43 protein, using a primer synthesized based on the sequence information of the protein encoding DNA (SEQ ID NO: 1, 3, or 5).

Polypeptides that are functionally equivalent to the human CXADRL1, GCUD1, or RNF43 protein encoded by the DNA isolated through the above hybridization techniques or gene amplification techniques, normally have a high homology to the amino acid sequence of the human CXADRL1, GCUD1, or RNF43 protein. "High homology" typically refers to a homology of 40% or higher, preferably 60% or higher, more preferably 80% or higher, even more preferably 95% or higher. The homology of a polypeptide can be determined by following the algorithm in "Wilbur and Lipman, Proc Natl Acad Sci USA 80: 726-30 (1983)".

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human CXADRL1, GCUD1, or RNF43 protein of the present invention, it is within the scope of the present invention.

The polypeptides of the present invention can be prepared as recombinant proteins or natural proteins, by methods well known to those skilled in the art. A recombinant protein can be prepared by inserting a DNA, which encodes the polypeptide of the present invention (for example, the DNA comprising the nucleotide sequence of SEQ ID NO: 1, 3, or 5), into an appropriate expression vector, introducing the vector into an appropriate host cell, obtaining the extract, and purifying the polypeptide by subjecting the extract to chromatography, for example, ion exchange chromatography, reverse phase chromatography, gel filtration, or affinity chromatography utilizing a column to which antibodies against the protein of the present invention is fixed, or by combining more than one of the aforementioned columns.

Also when the polypeptide of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines, or FLAG, it can be detected and purified using antibodies to c-myc, His, or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the CXADRL1, GCUD1, or RNF43 protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, screening for accelerators or inhibitors of the polypeptide of the present invention, and as a tumor-associated antigen (TAA).

A partial peptide of the invention can be produced by genetic engineering, by known methods of peptide synthesis, or by digesting the polypeptide of the invention with an appropriate peptidase. For peptide synthesis, for example, solid phase synthesis or liquid phase synthesis may be used.

Furthermore, the present invention provides polynucleotides encoding the polypeptide of the present invention. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention include a DNA comprising a given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 1, 3, or 5) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 1, 3, or 5), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue, or organ (e.g., testis or ovary for CXADRL1; testis, ovary, or brain for GCUD1; and fetal lung, or fetal kidney for RNF43) in which the object polypeptide of the invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyavsky et al., Nucleic Acids Res 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA, or TAG).

Specifically, the polynucleotide of the present invention encompasses the DNA comprising the nucleotide sequence of SEQ ID NO: 1, 3, or 5.

Furthermore, the present invention provides a polynucleotide that hybridizes under stringent conditions with a polynucleotide having a nucleotide sequence of SEQ ID NO: 1, 3, or 5, and encodes a polypeptide functionally equivalent to the CXADRL1, GCUD1, or RNF43 protein of the invention described above. One skilled in the art may appropriately choose a stringent condition. For example, low stringent condition can be used. More preferably, high stringent condition can be used. These conditions are the same as those described above. The hybridizing DNA above is preferably a cDNA or a chromosomal DNA.

The present invention also provides a vector into which a polynucleotide of the present invention is inserted. A vector of the present invention is useful to keep a polynucleotide, especially a DNA, of the present invention in host cell, to express the polypeptide of the present invention, or to administer the polynucleotide of the present invention for gene therapy.

When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol, or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce the protein of the present invention, an expression vector is particularly useful. For example, an expression vector to be expressed in E. coli should have the above characteristics to be amplified in E. coli. When E. coli, such as JM109, DH5α, HB101, or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter, or the like, that can efficiently express the desired gene in E. coli. In that respect, pGEX-5X-1 (Pharmacia), "QIAexpress system" (Qiagen), pEGFP, and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the E. coli is the pelB signal sequence (Lei et al., J Bacteriol 169: 4379-83 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Mizushima et al., Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01), and expression vectors derived from Bacillus subtilis (e.g., pPL608, pKTH50) can be used for producing the polypeptide of the present invention.

In order to express the vector in animal cells, such as CHO, COS, or NIH3T3 cells, the vector should have a promoter necessary for expression in such cells, for example, the SV40 promoter (Mulligan et al., Nature 277: 108-14 (1979)), the MMLV-LTR promoter, the EF1α promoter (Mizushima et al., Nucleic Acids Res 18: 5322 (1990)), the CMV promoter, and the like; and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to stably express a gene and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells, and purified as a substantially pure homogeneous polypeptide. The phrase "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides highly purified polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and so on.

The present invention provides an antibody that binds to the polypeptide of the invention. The antibody of the invention can be used in any form, such as monoclonal or polyclonal antibodies, and includes antiserum obtained by immunizing an animal such as rabbit with the polypeptide of the invention, all classes of polyclonal and monoclonal antibodies, human antibodies, and humanized antibodies produced by genetic recombination.

A polypeptide of the invention used as an antigen to obtain an antibody may be derived from any animal species, but preferably is derived from a mammal such as human, mouse, or rat, more preferably from human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention. More specifically, a polypeptide of CXADRL1 encompassing the codons from 235 to 276, from 493 to 537, or from 70 to 111 can be used as partial peptides for producing antibodies against CXADRL1 of the present invention.

Alternatively, for the production of antibodies against the polypeptide of the present invention, peptides comprising any one of following amino acid sequences may be used:

RNF43; SEQ ID No: 80, 97, or 108;
CXADRL1; SEQ ID No: 124; and
GCUD1; SEQ ID No: 164.

Herein, an antibody is defined as a protein that reacts with either the full-length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates, or a chemically synthesized polypeptide may be used as the antigen.

Any mammalian animal may be immunized with the antigen, but preferably the compatibility with parental cells used for cell fusion is taken into account. In general, animals of Rodentia, Lagomorpha, or Primates are used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion.

The immune cells used for cell fusion are preferably obtained from spleen. Other preferred parental cells to be fused with the above immunocyte include, for example, myeloma cells of mammals, and more preferably myeloma cells having an acquired property that enables selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells, or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography, or an affinity column to which the polypeptide of the present invention is coupled. The antibody of the present invention can be used not only for purification and detection of the polypeptide of the present invention, but also is a candidate for agonists and antagonists of the polypeptide of the present invention. In addition, this antibody can be applied to antibody treatment for diseases related to the polypeptide of the present invention. When the obtained antibody is administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells, or their lysates. Antibody producing cells are then collected from the animals and fused with myeloma cells to obtain hybridoma, from which human antibodies against the polypeptide can be prepared (see WO92-03918, WO93-02227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, F(ab')$_2$, Fv, or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention further provides such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared using known technology.

Antibodies obtained as above may be purified to homogeneity. For example, the separation and purification of the antibody can be performed according to separation and purification methods used for general proteins. For example, the antibody may be separated and isolated by appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC, and FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

The present invention also provides a polynucleotide which hybridizes with the polynucleotide encoding human CXADRL1, GCUD1, or RNF43 protein (SEQ ID NO: 1, 3, or 5) or the complementary strand thereof, and which comprises at least 15 nucleotides. The polynucleotide of the present invention is preferably a polynucleotide which specifically hybridizes with the DNA encoding the polypeptide of the present invention. The phrase "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

The present invention includes an antisense oligonucleotide that hybridizes with any site within the nucleotide sequence of SEQ ID NO: 1, 3, or 5. This antisense oligonucleotide is preferably against at least 15 continuous nucleotides of the nucleotide sequence of SEQ ID NO: 1, 3, or 5. The above-mentioned antisense oligonucleotide, which contains an initiation codon in the above-mentioned at least 15 continuous nucleotides, is even more preferred. More specifically, such antisense oligonucleotides include those comprising the nucleotide sequence of SEQ ID NO: 23 or 25 for suppressing the expression of CXADRL1; SEQ ID NO: 27, or 29 for GCUD1; and SEQ ID NO: 31 for RNF43.

Derivatives or modified products of antisense oligonucleotides can be used as antisense oligonucleotides. Examples of such modified products include lower alkyl phosphonate modifications, such as methyl-phosphonate-type or ethyl-phosphonate-type, phosphorothioate modifications and phosphoroamidate modifications.

The phrase "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 1, 3, or 5.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the polypeptide of the invention as stated in a later example or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA, and inhibiting the expression of the polypeptide of the invention, thereby resulting in the inhibition of the polypeptide's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops, and freeze-dried agents by adding excipients, isotonic agents, solubilizers, stabilizers, preservatives, pain-killers, and such. These can be prepared following usual methods.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin, or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The present invention also includes small interfering RNAs (siRNA) comprising a combination of a sense strand nucleic acid and an antisense strand nucleic acid of the nucleotide sequence of SEQ ID NO: 1, 3, or 5.

The term "siRNA" refers to a double-stranded RNA molecule which prevents translation of a target mRNA. Standard techniques are used for introducing siRNA into cells, including those wherein DNA is used as the template to transcribe RNA. The siRNA comprises a sense nucleic acid sequence and an antisense nucleic acid sequence of the polynucleotide encoding human CXADRL1, GCUD1, or RNF43 protein (SEQ ID NO: 1, 3, or 5). The siRNA is constructed such that a single transcript (double-stranded RNA) has both the sense and complementary antisense sequences from a target gene, e.g., a hairpin.

The method is used to alter gene expression of a cell, i.e., up-regulate the expression of CXADRL1, GCUD1, or RNF43, e.g., as a result of malignant transformation of the cells. Binding of the siRNA to CXADRL1, GCUD1, or RNF43 transcript in the target cell results in a reduction of protein production by the cell. The length of the oligonucleotide is at least 10 nucleotides and may be as long as the naturally occurring transcript. Preferably, the oligonucleotide is 19-25 nucleotides in length. Most preferably, the oligonucleotide is less than 75, 50, or 25 nucleotides in length. Examples of CXADRL1, GCUD1, or RNF43 siRNA oligonucleotides which inhibit the expression in mammalian cells include oligonucleotides containing any of SEQ ID NO: 112-114. These sequences are target sequence of the following siRNA sequences respectively.

SEQ ID NO: 112, (RNF43);
SEQ ID NO: 113, (RNF43); and
SEQ ID NO: 114, (CXADRL1).

The nucleotide sequence of siRNAs may be designed using an siRNA design computer program available from the Ambion website. Nucleotide sequences for the siRNA are selected by the computer program based on the following protocol:

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: ncbi.nlm.nih.gov/BLAST/.
3. Select qualifying target sequences for synthesis. At Ambion, preferably several target sequences can be selected along the length of the gene for evaluation.

The antisense oligonucleotide or siRNA of the invention inhibit the expression of the polypeptide of the invention and is thereby useful for suppressing the biological activity of the polypeptide of the invention. Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as cancer.

Moreover, the present invention provides a method for diagnosing a cell proliferative disease using the expression level of the polypeptides of the present invention as a diagnostic marker.

This diagnosing method comprises the steps of: (a) detecting the expression level of the CXADRL1, GCUD1, or RNF43 gene of the present invention; and (b) relating an elevation of the expression level to cell proliferative disease, such as cancer.

The expression levels of the CXADRL1, GCUD1, or RNF43 gene in a particular specimen can be estimated by quantifying mRNA corresponding to or protein encoded by the CXADRL1, GCUD1, or RNF43 gene. Quantification methods for mRNA are known to those skilled in the art. For example, the levels of mRNAs corresponding to the CXADRL1, GCUD1, or RNF43 gene can be estimated by Northern blotting or RT-PCR. Since the full-length nucleotide sequences of the CXADRL1, GCUD1, or RNF43 genes are shown in SEQ ID NO: 1, 3, or 5, anyone skilled in the art can design the nucleotide sequences for probes or primers to quantify the CXADRL1, GCUD1, or RNF43 gene.

Also the expression level of the CXADRL1, GCUD1, or RNF43 gene can be analyzed based on the activity or quantity of protein encoded by the gene. A method for determining the quantity of the CXADRL1, GCUD1, or RNF43 protein is shown below. For example, immunoassay method is useful for the determination of the proteins in biological materials. Any biological materials can be used for the determination of the protein or it's activity. For example, blood sample is analyzed for estimation of the protein encoded by a serum marker. On the other hand, a suitable method can be selected for the determination of the activity of a protein encoded by the CXADRL1, GCUD1, or RNF43 gene according to the activity of each protein to be analyzed.

Expression levels of the CXADRL1, GCUD1, or RNF43 gene in a specimen (test sample) are estimated and compared with those in a normal sample. When such a comparison shows that the expression level of the target gene is higher than those in the normal sample, the subject is judged to be affected with a cell proliferative disease. The expression level of CXADRL1, GCUD1, or RNF43 gene in the specimens from the normal sample and subject may be determined at the same time. Alternatively, normal ranges of the expression levels can be determined by a statistical method based on the results obtained by analyzing the expression level of the gene in specimens previously collected from a control group. A result obtained by comparing the sample of a subject is compared with the normal range; when the result does not fall within the normal range, the subject is judged to be affected with the cell proliferative disease. In the present invention, the cell proliferative disease to be diagnosed is preferably cancer. More preferably, when the expression level of the CXADRL1, or GCUD1 gene is estimated and compared with those in a normal sample, the cell proliferative disease to be diagnosed is gastric, colorectal, or liver cancer; and when the RNF43 gene is estimated for its expression level, then the disease to be diagnosed is colorectal, lung, gastric, or liver cancer.

In the present invention, a diagnostic agent for diagnosing cell proliferative disease, such as cancer including gastric, colorectal, lung, and liver cancers, is also provided. The diagnostic agent of the present invention comprises a compound that binds to a polynucleotide or a polypeptide of the present invention. Preferably, an oligonucleotide that hybridizes to the polynucleotide of the present invention, or an antibody that binds to the polypeptide of the present invention may be used as such a compound.

Moreover, the present invention provides a method of screening for a compound for treating a cell proliferative disease using the polypeptide of the present invention. An embodiment of this screening method comprises the steps of: (a) contacting a test compound with a polypeptide of the present invention, (b) detecting the binding activity between the polypeptide of the present invention and the test compound, and (c) selecting a compound that binds to the polypeptide of the present invention.

The polypeptide of the present invention to be used for screening may be a recombinant polypeptide or a protein derived from nature, or a partial peptide thereof. Any test compound, for example, cell extracts, cell culture supernatant, products of fermenting microorganism, extracts from marine organism, plant extracts, purified or crude proteins, peptides, non-peptide compounds, synthetic micromolecular compounds, and natural compounds, can be used. The polypeptide of the present invention to be contacted with a test compound can be, for example, a purified polypeptide, a soluble protein, a form bound to a carrier, or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-1α promoter (Kim et al., Gene 91: 217-23 (1990)), the CAG promoter (Niwa et al., Gene 108: 193-9 (1991)), the RSV LTR promoter (Cullen, Methods in Enzymology 152: 684-704 (1987)) the SRα promoter (Takebe et al., Mol Cell Biol 8: 466-72 (1988)), the CMV immediate early promoter (Seed and Aruffo, Proc Natl Acad Sci USA 84: 3365-9 (1987)), the SV40 late promoter (Gheysen and Fiers, J Mol Appl Genet. 1: 385-94 (1982)), the Adenovirus late promoter (Kaufman et al., Mol Cell Biol 9: 946-58 (1989)), the HSV TK promoter, and so on. The introduction of the gene into animal cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard, Cell 76: 1025-37 (1994); Lamb et al., Nature Genetics 5: 22-30 (1993): Rabindran et al., Science 259: 230-4 (1993)), and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP), and so on by the use of its multiple cloning sites are commercially available.

A fusion protein prepared by introducing only small epitopes consisting of several to a dozen amino acids so as not to change the property of the polypeptide of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the polypeptide of the present invention (Experimental Medicine 13: 85-90 (1995)).

In immunoprecipitation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, tissues such as testis and ovary for screening proteins binding to CXADRL1; testis, ovary, and brain for screening proteins binding to GCUD1; and fetal lung, and fetal kidney for those binding to RNF43), or cultured cells expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope, fluorescence, and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene, and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized polypeptide of the present invention is exposed to synthetic chemical compounds, or natural substance banks, or a random phage peptide display library, and the methods of screening using high-throughput based on combinatorial chemistry techniques (Wrighton et al., Science 273: 458-63 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

Alternatively, the screening method of the present invention may comprise the following steps:
a) contacting a candidate compound with a cell into which a vector comprising the transcriptional regulatory region of one or more marker genes and a reporter gene that is expressed under the control of the transcriptional regulatory region has been introduced, wherein the one or more marker genes are selected from the group consisting of CXADRL1, GCUD1, and RNF43,
b) measuring the expression level or activity of said reporter gene; and
c) selecting a compound that reduces the expression level or activity of said reporter gene as compared to a control.

Suitable reporter genes and host cells are well known in the art. The reporter construct required for the screening can be prepared using the transcriptional regulatory region of a marker gene. When the transcriptional regulatory region of a marker gene is known, a reporter construct can be prepared based on the previous sequence information. When the transcriptional regulatory region of a marker gene is unidentified, a nucleotide segment containing the transcriptional regulatory region can be isolated from a genome library based on the nucleotide sequence information of the marker gene.

A compound isolated by the screening is a candidate for drugs which promote or inhibit the activity of the polypeptide of the present invention, for treating or preventing diseases attributed to, for example, cell proliferative diseases, such as cancer. A compound in which a part of the structure of the compound obtained by the present screening method having the activity of binding to the polypeptide of the present invention converted by addition, deletion, insertion, and/or replacement, is included in the compounds obtained by the screening method of the present invention.

In a further embodiment, the present invention provides methods for screening candidate agents which are potential targets in the treatment of cell proliferative disease. As discussed in detail above, by controlling the expression levels of the CXADRL1, GCUD1, or RNF43, one can control the onset and progression of either gastric cancer, or colorectal, lung, gastric, or liver cancer. Thus, candidate agents, which are potential targets in the treatment of cell proliferative disease, can be identified through screenings that use the expression levels and activities of CXADRL1, GCUD1, or RNF43 as indices. In the context of the present invention, such screening may comprise, for example, the following steps:

a) contacting a candidate compound with a cell expressing the CXADRL1, GCUD1, or RNF43; and
b) selecting a compound that reduces the expression level of CXADRL1, GCUD1, or RNF43 in comparison with the expression level detected in the absence of the test compound.

Cells expressing at least one of the CXADRL1, GCUD1, or RNF43 include, for example, cell lines established from gastric, colorectal, lung, or liver cancers; such cells can be used for the above screening of the present invention. The expression level can be estimated by methods well known to one skilled in the art. In the method of screening, a compound that reduces the expression level of at least one of CXADRL1, GCUD1, or RNF43 can be selected as candidate agents.

In another embodiment of the method for screening a compound for treating a cell proliferative disease of the present invention, the method utilizes biological activity of the polypeptide of the present invention as an index. Since the CXADRL1, GCUD1, and RNF43 proteins of the present invention have the activity of promoting cell proliferation, a compound which promotes or inhibits this activity of one of these proteins of the present invention can be screened using this activity as an index. This screening method includes the steps of: (a) contacting a test compound with the polypeptide of the present invention; (b) detecting the biological activity of the polypeptide of step (a); and (c) selecting a compound that suppresses the biological activity of the polypeptide in comparison with the biological activity detected in the absence of the test compound.

Any polypeptides can be used for screening so long as they comprise the biological activity of the CXADRL1, GCUD1, or RNF43 protein. Such biological activity includes cell-proliferating activity of the human CXADRL1, GCUD1, or RNF43 protein, and the activity of RNF43 to bind to NOTCH2 or STRIN. For example, a human CXADRL1, GCUD1, or RNF43 protein can be used and polypeptides functionally equivalent to these proteins can also be used. Such polypeptides may be endogenously or exogenously expressed by cells.

Any test compounds, for example, cell extracts, cell culture supernatants, products of fermenting microorganism, extracts of marine organism, plant extracts, purified or crude proteins, peptides, non-peptide compounds, synthetic micromolecular compounds, and natural compounds, can be used.

The compound isolated by this screening is a candidate for agonists or antagonists of the polypeptide of the present invention. The term "agonist" refers to molecules that activate the function of the polypeptide of the present invention by binding thereto. Likewise, the term "antagonist" refers to molecules that inhibit the function of the polypeptide of the present invention by binding thereto. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

The compound isolated by the above screenings is a candidate for drugs which inhibit the activity of the polypeptide of the present invention and can be applied to the treatment of diseases associated with the polypeptide of the present invention, for example, cell proliferative diseases including cancer. More particularly, when the biological activity of CXADRL1 or GCUD1 protein is used as the index, compounds screened by the present method serve as a candidate for drugs for the treatment of gastric, colorectal, or liver cancer. On the other hand, when the biological activity of RNF43 protein is used as the index, compounds screened by the present method serve as a candidate for drugs for the treatment of colorectal, lung, gastric, or liver cancer.

Moreover, when the compound isolated by the above screenings is a polypeptide, and a part of the structure of the compound inhibiting the activity of CXADRL1, GCUD1, or RNF43 protein is converted by addition, deletion, insertion, and/or replacement are also included in the compounds obtainable by the screening method of the present invention.

In a further embodiment of the method for screening a compound for treating a cell proliferative disease of the present invention, the method utilizes the binding ability of RNF43 to NOTCH2 or STRIN. The RNF43 protein of the present invention was revealed to associated with NOTCH2 and STRIN. These findings suggest that the RNF43 protein of the present invention exerts the function of cell proliferation via its binding to molecules, such as NOTCH2 and STRIN. Thus, it is expected that the inhibition of the binding between the RNF43 protein and NOTCH2 or STRIN leads to the suppression of cell proliferation, and compounds inhibiting the binding serve as pharmaceuticals for treating cell proliferative disease such as cancer. Preferably, the cell proliferative disease treated by the compound screened by the present method is colorectal, lung, gastric, or liver cancer.

This screening method includes the steps of: (a) contacting a polypeptide of the present invention with NOTCH2 or STRIN in the presence of a test compound; (b) detecting the binding between the polypeptide and NOTCH2 or STRIN; and (c) selecting the compound that inhibits the binding between the polypeptide and NOTCH2 or STRIN.

The RNF43 polypeptide of the present invention, and NOTCH2 or STRIN to be used for the screening may be a recombinant polypeptide or a protein derived from nature, or may also be a partial peptide thereof so long as it retains the binding ability to each other. The RNF43 polypeptide, NOTCH2 or STRIN to be used in the screening can be, for example, a purified polypeptide, a soluble protein, a form bound to a carrier, or a fusion protein fused with other polypeptides.

Any test compound, for example, cell extracts, cell culture supernatants, products of fermenting microorganism, extracts from marine organism, plant extracts, purified or crude proteins, peptides, non-peptide compounds, synthetic micromolecular compounds, and natural compounds, can be used.

As a method of screening for compounds that inhibit the binding between the RNF43 protein and NOTCH2 or STRIN, many methods well known by one skilled in the art can be used. Such a screening can be carried out as an in vitro assay system, for example, in acellular system. More specifically, first, either the RNF43 polypeptide, or NOTCH2 or STRIN is bound to a support, and the other protein is added together with a test sample thereto. Next, the mixture is incubated, washed, and the other protein bound to the support is detected and/or measured.

In the same way, a compound interfering the association of CXADRL1 and AIP1 can be isolated by the present invention. It is expected that the inhibition of the binding between the CXADRL1 and AIP1 leads to the suppression of cell proliferation, and compounds inhibiting the binding serve as pharmaceuticals for treating cell proliferative disease such as cancer.

Examples of supports that may be used for binding proteins include insoluble polysaccharides, such as agarose, cellulose, and dextran; and synthetic resins, such as polyacrylamide, polystyrene, and silicon; preferably commercial available beads and plates (e.g., multi-well plates, biosensor chip, etc.) prepared from the above materials may be used. When using beads, they may be filled into a column.

The binding of a protein to a support may be conducted according to routine methods, such as chemical bonding, and physical adsorption. Alternatively, a protein may be bound to a support via antibodies specifically recognizing the protein. Moreover, binding of a protein to a support can be also conducted by means of avidin and biotin binding.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia). Therefore, it is possible to evaluate the binding between the RNF43 polypeptide and NOTCH2 or STRIN using a biosensor such as BIAcore.

Alternatively, either the RNF43 polypeptide, or NOTCH2 or STRIN, may be labeled, and the label of the bound protein may be used to detect or measure the bound protein. Specifically, after pre-labeling one of the proteins, the labeled protein is contacted with the other protein in the presence of a test compound, and then, bound proteins are detected or measured according to the label after washing.

Labeling substances such as radioisotope (e.g., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine), and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, the binding of the RNF43 polypeptide and NOTCH2 or STRIN can be also detected or measured using antibodies to the RNF43 polypeptide and NOTCH2 or STRIN. For example, after contacting the RNF43 polypeptide immobilized on a support with a test compound and NOTCH2 or STRIN, the mixture is incubated and washed, and detection or measurement can be conducted using an antibody against NOTCH2 or STRIN. Alternatively, NOTCH2 or STRIN may be immobilized on a support, and an antibody against RNF43 may be used as the antibody.

In case of using an antibody in the present screening, the antibody is preferably labeled with one of the labeling substances mentioned above, and detected or measured based on the labeling substance. Alternatively, the antibody against the RNF43 polypeptide, NOTCH2, or STRIN, may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, the RNF43 polypeptide of the invention is fused to the SRF-binding region or GAL4-binding region and expressed in yeast cells. The NOTCH2 or STRIN binding to the RNF43 polypeptide of the invention is fused to the VP16 or GAL4 transcriptional activation region and also expressed in the yeast cells in the existence of a test compound. When the test compound does not inhibit the binding between the RNF43 polypeptide and NOTCH2 or STRIN, the binding of the two activates a reporter gene, making positive clones detectable.

As a reporter gene, for example, Ade2 gene, lacZ gene, CAT gene, luciferase gene, and such can be used besides HIS3 gene.

The compound isolated by the screening is a candidate for drugs which inhibit the activity of the RNF43 protein of the present invention and can be applied to the treatment of diseases associated with the RNF43 protein, for example, cell proliferative diseases such as cancer, more particularly colorectal, lung, gastric, or liver cancer. Moreover, when the compound isolated by the screening is a polypeptide, and a part of the structure of the compound inhibiting the binding between the RNF43 protein and NOTCH2 or STRIN is converted by addition, deletion, substitution, and/or insertion are also included in the compounds obtainable by the screening method of the present invention.

When administrating the compound isolated by the methods of the invention as a pharmaceutical for humans and other mammals, such as mice, rats, guinea-pigs, rabbits, chicken, cats, dogs, sheep, pigs, cattle, monkeys, baboons, and chimpanzees, for treating a cell proliferative disease (e.g., cancer) the isolated compound can be directly administered or can be formulated into a dosage form using known pharmaceutical preparation methods. For example, as needed, the drugs can be taken orally, as sugarcoated tablets, capsules, elixirs and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum, and arabic gum; excipients such as crystalline cellulose; swelling agents such as corn starch, gelatin, and alginic acid; lubricants such as magnesium stearate; sweeteners such as sucrose, lactose, and saccharin; flavoring agents such as peppermint, Gaultheria adenothrix oil, and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol; polyalcohols, such as propylene glycol and polyethylene glycol; and non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizer and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections, and also as intranasal, transbronchial, intramuscular, or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms, and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Moreover, the present invention provides a method for treating or preventing a cell proliferative disease, such as cancer, using an antibody against the polypeptide of the present invention. According to the method, a pharmaceutically effective amount of an antibody against the polypeptide of the present invention is administered. Since the expression of the CXADRL1, GCUD1, and RNF43 protein are up-regulated in cancer cells, and the suppression of the expression of these proteins leads to the decrease in cell proliferating activity, it is expected that cell proliferative diseases can be treated or prevented by binding the antibody and these proteins. Thus, an antibody against the polypeptide of the present invention are administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Alternatively, an antibody binding to a cell surface marker specific for tumor cells can be used as a tool for drug delivery. For example, the antibody conjugated with a cytotoxic agent is administered at a dosage sufficient to injure tumor cells.

The present invention also relates to a method of inducing anti-tumor immunity comprising the step of administering CXADRL1, GCUD1, or RNF43 protein, an immunologically active fragment thereof, or a polynucleotide encoding the protein or fragments thereof. The CXADRL1, GCUD1, or RNF43 protein, or the immunologically active fragments thereof are useful as vaccines against cell proliferative diseases. In some cases the proteins or fragments thereof may be administered in a form bound to the T cell recepor (TCR) or presented by an antigen presenting cell (APC), such as macrophage, dendritic cell (DC), or B-cells. Due to the strong antigen presenting ability of DC, the use of DC is most preferable among the APCs.

In the present invention, vaccine against cell proliferative disease refers to a substance that has the function to induce anti-tumor immunity upon inoculation into animals. According to the present invention, polypeptides comprising the amino acid sequence of SEQ ID NO: 80, 97, or 108 were suggested to be HLA-A24 or HLA-A*0201 restricted epitope peptides that may induce potent and specific immune response against colorectal, lung, gastric, or liver cancer cells expressing RNF43. According to the present invention, polypeptides comprising the amino acid sequence of SEQ ID NO:124 was suggested to be HLA-A*0201 restricted epitopes peptides that may induce potent and specific immune response against colorectal, gastric, or liver cancer cells expressing CXADRL1. According to the present invention, polypeptides comprising the amino acid sequence of SEQ ID NO: 164 was suggested to be HLA-A*0201 restricted epitopes peptides that may induce potent and specific immune response against colorectal, gastric, or liver cancer cells expressing GCUD1. Thus, the present invention also encompasses method of inducing anti-tumor immunity using polypeptides comprising the amino acid sequence of SEQ ID NO: 80, 97, 108, 124 or 164.

Furthermore, the present invention revealed that modification of anchor residues increases the binding affinity of epitope peptides to HLAs. Therefore, polypeptides administered for treating or preventing cancer, or inducing anti-tumor immunity according to the present invention includes epitope peptides wherein the anchor residues are modified. Herein, the phrase "anchor residue(s)" refers to amino acid residues of the epitope that binds to the HLA class I peptide-binding cleft, but that does not contact with TCR; more specifically, positions two and nine of an epitope peptide is considered to be such anchor residues. According to the HLA-A2 antigen motif previously reported by Smith et al. (Smith et al., Mol Immunol 35: 1033-43 (1998)), leucine (Leu) and isoleucine (Iso) have proven to be an optimal anchor residue at position 2 that enhance the binding affinity of the peptide for the HLA-A*0201 molecule. Similarly, valine (Val) at position 9 is also preferred for nonamer peptides. Thus, nonamer peptides wherein the amino acid at position two is Leu or Ile, or the amino acid at position nine is Leu, Ile, or Val are preferred examples as the polypeptide to be administered according to the present invention. Particularly preferable examples of such nonamer peptides include those having the amino acid sequence of SEQ ID NOs: 195-198. However, the present invention is not restricted to these examples and any modification may be introduced into the polypeptides used for the present invention.

In general, anti-tumor immunity includes immune responses such as follows:
induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing cytotoxic T cells. Activity of CTL against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DC, peripheral blood mononuclear cells (PBMCs) may also be used as the APC. The induction of CTL is reported that it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of cell proliferating diseases, such as gastric, colorectal, lung, and liver cancers. Therapy against cancer or prevention of the onset of cancer includes any of the steps, such as inhibition of the growth of cancerous cells, involution of cancer, and suppression of occurrence of cancer. Decrease in mortality of individuals having cancer, decrease of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum, and such, but are not limited thereto. Furthermore, the vaccine of this invention may be combined appropriately with a pharmaceutically acceptable carrier. Examples of such carriers are sterilized water, physiological saline, phosphate buffer, culture fluid, and such. Furthermore, the vaccine may contain as necessary, stabilizers, suspensions, preservatives, surfactants, and such. The vaccine is administered systemically or locally. Vaccine administration may be performed by single administration, or boosted by multiple administrations.

When using APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of the polypeptide of the present invention is provided. The pharmaceutical composition may be used for raising anti-tumor immunity. The normal expression of CXADRL1, restricted to testis and ovary; normal expression of GCUD1 is restricted to testis, ovary, and brain; and normal expression of RNF43 is restricted to fetus, more specifically to fetal lung and kidney. Therefore, suppression of these genes may not adversely affect other organs. Thus, the CXADRL1 and GCUD1 polypeptides are preferable for treating cell proliferative disease, especially gastric, colorectal, or liver cancer; and RNF43 polypeptide is preferable for treating cell proliferative disease, especially colorectal, lung, gastric, and liver cancers.

Furthermore, since peptide fragments of RNF43 comprising the amino acid sequences of SEQ ID NO: 80, 97, and 108, respectively, were revealed to induce immune response against RNF43, polypeptides comprising the amino acid sequence of SEQ ID NO: 80, 97, or 108 are preferable examples of polypeptides that can be used in a pharmaceutical composition for treating or preventing cell proliferative disease, especially colorectal, lung, gastric, and liver cancers.

Furthermore, since peptide fragments of CXADRL1 comprising the amino acid sequences of SEQ ID NO: 124, was revealed to induce immune response against CXADRL1, polypeptide comprising the amino acid sequence of SEQ ID NO: 124 is a preferable example of polypeptide that can be used in a pharmaceutical composition for treating or preventing cell proliferative disease, especially colorectal, lung, gastric, and liver cancers. Moreover, anchor-modified polypeptides of the polypeptide comprising the amino acid sequence of SEQ ID NO: 124 were revealed to exhibit increased binding affinity to HLA-A*0201 molecules, activate a certain portion of TCR repertoire recognizing the naturally processed wild-type epitope peptide presented by tumor cells, and elicit native peptide specific CTSs more frequently and abundantly than the wild-type peptide. Thus, such anchor-modified polypeptides are preferable examples of polypeptide that can be used in a pharmaceutical composition for treating or preventing the cell proliferative diseases. Example of these anchor-modified polypeptides includes those having the amino acid sequences of SEQ ID NOs: 195 and 196.

Furthermore, since peptide fragment of GCUD1 comprising the amino acid sequences of SEQ ID NO: 164 was revealed to induce immune response against GCUD1, polypeptide comprising the amino acid sequence of SEQ ID NO: 164 is a preferable example of polypeptide that can be used in a pharmaceutical composition for treating or preventing cell proliferative disease, especially colorectal, lung, gastric, and liver cancers. Moreover, anchor-modified polypeptide of the polypeptides comprising the amino acid sequence of SEQ ID NO: 164 were revealed to exhibit increased binding affinity to HLA-A*0201 molecules, activate a certain portion of TCR repertoire recognizing the naturally processed wild-type epitope peptide presented by tumor cells, and elicit native peptide specific CTSs more frequently and abundantly than the wild-type peptide. Thus, such anchor-modified polypeptides are preferable examples of polypeptide that can be used in a pharmaceutical composition for treating or preventing the cell proliferative diseases. Example of these anchor-modified polypeptides includes those having the amino acid sequences of SEQ ID NOs: 197 and 198.

In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications, and publications cited herein are incorporated by reference.

BEST MODE FOR CARRYING OUT THE INVENTION

The present invention is illustrated in details by following Examples, but is not restricted to these Examples.

1. Materials and Methods (1) Patients and Tissue Specimens

All gastric and colorectal cancer tissues, as well as corresponding non-cancerous tissues were obtained with informed consent from surgical specimens of patients who underwent surgery.

(2) Genome-wide cDNA Microarray

In-house genome-wide cDNA microarray comprising 23040 genes were used in this study. DNase I treated total RNA extracted from microdissected tissue was amplified with Ampliscribe T7 Transcription Kit (Epicentre Technologies) and labeled during reverse transcription with Cy-dye (Amersham) (RNA from non-cancerous tissue with Cy5 and RNA from tumor with Cy3). Hybridization, washing, and detection were carried out as described previously (Ono et al., Cancer Res. 60: 5007-11 (2000)), and fluorescence intensity of Cy5 and Cy3 for each target spot was measured using Array Vision software (Amersham Pharmacia). After subtraction of background signal, duplicate values were averaged for each spot. Then, all fluorescence intensities on a slide were normalized to adjust the mean Cy5 and Cy3 intensity of 52 housekeeping genes for each slide. Genes with intensities below 25,000 fluorescence units for both Cy3 and Cy5 were excluded from further investigation, and those with Cy3/Cy5 signal ratios >2.0 were selected for further evaluation.

(3) Cell Lines

Human embryonic kidney 293 (HEK293) were obtained from TaKaRa. COS7 cell, NIH3T3 cell, human cervical cancer cell line HeLa, human gastric cancer cell lines MKN-1 and MKN-28, human hepatoma cell line Alexander, and human colon cancer cell lines, LoVo, HCT116, DLD-1 and SW480, were obtained from the American Type Culture Collection (ATCC, Rockville, Md.). Human hepatoma cell line SNU475 and human colon cancer cell lines, SNUC4 and SNUC5, were obtained from the Korea cell-line bank. All cells were grown in monolayers in appropriate media: Dulbecco's modified Eagle's medium for COS7, NIH3T3, HEK293, and Alexander; RPMI1640 for MKN-1, MKN-28, SNU475, SNUC4, DLD-1 and SNUC5; McCoy's 5A medium for HCT116; Leibovitz's L-15 for SW480; HAM's F-12 for LoVo; and Eagle's minimum essential medium for HeLa (Life Technologies, Grand Island, N.Y.). All media were supplemented with 10% fetal bovine serum and 1% antibiotic/antimycotic solution (Sigma). A human gastric cancer cell line St-4 was kindly provided by Dr. Tsuruo of Cancer Institute in Japan. St-4 cells were grown in monolayers in RPMI 1640 supplemented with 10% fetal bovine serum and 1% antibiotic/antimycotic solution (Sigma). T2 cells (HLA-A*0201) and EHM (HLA-A3/3), human B-lymphoblastoid cell lines, were generous gifts from Prof. Shiku (Univ. Mie). HT29 (colon carcinoma cell line; HLA-A24/01), WiDR (colon carcinoma cell line; HLA-A24/01), HCT116 (colon carcinoma cell line; HLA-A02/01), DLD-1 (colon carcinoma cell line; HLA-A24/01), SNU475 (hepatocellular carcinoma cell line; HLA-A*0201), MKN45 (gastric cancer cell line; HLA-A2 negative), and MKN74 (gastric cancer cell line; HLA-A2 negative) were also purchased from ATCC. TISI cells (HLA-A24/24) were generous gifts from Takara Shuzo Co, Ltd. (Otsu, Japan). RT-PCR examinations revealed strong CXADRL1 expression in SNU475 and MKN74, and strong GCUD1 expression in SNU475 and MKN45.

(4) RNA Preparation and RT-PCR

Total RNA was extracted with Qiagen RNeasy kit (Qiagen) or Trizol reagent (Life Technologies) according to the manufacturers' protocols. Ten-microgram aliquots of total RNA were reversely transcribed for single-stranded cDNAs using poly $dT_{12-18}$ primer (Amersham Pharmacia Biotech) with Superscript II reverse transcriptase (Life Technologies). Each single-stranded cDNA preparation was diluted for subsequent PCR amplification by standard RT-PCR experiments carried out in 20 μl volumes of PCR buffer (TaKaRa). Amplification was conducted under following conditions: denaturing for 4 min at 94° C., followed by 20 (for GAPDH), 35 (for CXADRL1), 30 (for GCUD1), 30 (for RNF43) cycles of 94° C. for 30 s, 56° C. for 30 s, and 72° C. for 45 s, in GeneAmp PCR system 9700 (Perkin-Elmer, Foster City, Calif.). Primer sequences were; for GAPDH: forward, 5'-ACAACAGCCT-CAAGATCATCAG (SEQ ID NO: 7) and reverse, 5'-GGTC-CACCACTGACACGTTG (SEQ ID NO: 8); for CXADRL1: forward, 5'-AGCTGAGACATTTGTTCTCTTG (SEQ ID NO: 9) and reverse: 5'-TATAAACCAG CTGAGTCCAGAG (SEQ ID NO: 10); for GCUD1 forward: 5'-TTCCCGATAT-CAACATCTACCAG (SEQ ID NO: 11) reverse: 5'-AGTGT-GTGACCTCAATAAGGCAT (SEQ ID NO: 12), for RNF43 forward; 5'-CAGGCTTTGGACGCACAGGACTGGTAC-3' (SEQ ID NO: 13) and reverse; 5'-CTTTGTGATCATCCTG-GCTTCGGTGCT-3' (SEQ ID NO: 14).

(5) Northern-blot Analysis

Human multiple-tissue blots (Clontech, Palo Alto, Calif.) were hybridized with $^{32}$P-labeled PCR products of CXADRL1, GCUD1, or RNF43. Pre-hybridization, hybridization and washing were performed according to the supplier's recommendations. The blots were autoradiographed with intensifying screens at −80° C. for 24 to 72 h.

(6) 5' Rapid Amplification of cDNA Ends (5' RACE)

5' RACE experiments were carried out using Marathon cDNA amplification kit (Clontech) according to the manufacturer's instructions. For the amplification of the 5' part of CXADRL1, gene-specific reverse primers (5'-GGT-TGAGATTTAAGTTCTCAAA-3' (SEQ ID NO: 15)) and the AP-1 primer supplied with the kit were used. The cDNA template was synthesized from human testis mRNA (Clontech). The PCR products were cloned using TA cloning kit (Invitrogen) and their sequences were determined with ABI PRISM 3700 DNA sequencer (Applied Biosystems).

(7) Construction of Plasmids Expressing CXADRL1, GCUD1, and FLJ20315

The entire coding regions of CXADRL1, GCUD1, and RNF43 were amplified by RT-PCR using gene specific primer sets; for CXADRL1, 5'-AGTTAAGCTTGCCGGGAT-GACTTCTCAGCGTTCCCCTCTGG-3' (SEQ ID NO: 16) and 5'-ATCTCGAGTACCAAGGACCCGGC-CCGACTCTG-3' (SEQ ID NO: 17); for GCUD1 5'-GCG-GATCCAGGATGGCTGCTGCAGCTCCTCCAAG-3' (SEQ ID NO: 18) and 5'-TAGAATTCTTAAAGAACT-TAATCTCCGTGTCAACAC-3' (SEQ ID NO: 19); and for RNF43, 5'-TGCAGATCTGCAGCTGGTAGCATGAGTG-GTG-3' (SEQ ID NO: 20) and 5'-GAGGAGCTGTGTGAA-CAGGCTGTGTGAGATGT-3' (SEQ ID NO: 21). The PCR products were cloned into appropriate cloning site of either pcDNA3.1 (Invitrogen), or pcDNA3.1myc/His (Invitrogen) vector.

(8) Immunoblotting

Cells transfected with pcDNA3.1myc/His-CXADRL1, pcDNA3.1myc/His-GCUD1, pcDNA3.1 myc/His-RNF43, or pcDNA3.1myc/His-LacZ were washed twice with PBS and harvested in lysis buffer (150 mM NaCl, 1% Triton X-100, 50 mM Tris-HCl pH 7.4, 1 mM DTT, and 1X complete Protease Inhibitor Cocktail (Boehringer)). Following homogenization, the cells were centrifuged at 10,000×g for 30 min, the supernatant were standardized for protein concentration by the Bradford assay (Bio-Rad). Proteins were separated by 10% SDS-PAGE and immunoblotted with mouse anti-myc (SANTA CRUZ) antibody. HRP-conjugated goat anti-mouse IgG (Amersham) served as the secondary antibody for the ECL Detection System (Amersham).

(9) Immunohistochemical Staining

Cells transfected with pcDNA3.1myc/His-CXADRL1, pcDNA3.1myc/His-GCUD1, pcDNA3.1myc/His-RNF43, or pcDNA3.1myc/His-LacZ were fixed with PBS containing 4% paraformaldehyde for 15 min, then made permeable with PBS containing 0.1% Triton X-100 for 2.5 min at RT. Subsequently the cells were covered with 2% BSA in PBS for 24 h at 4° C. to block non-specific hybridization. Mouse anti-myc monoclonal antibody (Sigma) at 1:1000 dilution was used as the primary antibody, and the reaction was visualized after incubation with Rhodamine-conjugated anti-mouse secondary antibody (Leinco and ICN). Nuclei were counter-stained with 4',6'-diamidine-2'-phenylindole dihydrochloride (DAPI). Fluorescent images were obtained under an ECLIPSE E800 microscope.

(10) Colony Formation Assay

Cells transfected with plasmids expressing each gene or control plasmids were incubated with an appropriate concentration of geneticin for 10 to 21 days. The cells were fixed with 100% methanol and stained by Giemsa solution. All experiments were carried out in duplicate.

(11) Establishment of Cells Over-expressing CXADRL1 or RNF43

NIH3T3, COS7, and LoVo cells transfected with either pcDNA3.1myc/His-CXADRL1, pcDNA3.1myc/His-RNF43, pcDNA3.1myc/His-LacZ, or control plasmids, respectively, were maintained in media containing appropriate concentration of geneticin. Two weeks after the transfection, surviving single colonies were selected, and expression of each gene was examined by semi-quantitative RT-PCR.

(12) Examination on the Effect of Anti-sense Oligonucleotides on Cell Growth

Cells plated onto 10-cm dishes ($2\times10^5$ cells/dish) were transfected either with plasmid, or synthetic S-oligonucleotides of CXADRL1, GCUD1, or RNF43 using LIPOFEC-TIN Reagent (GIBCO BRL). Then the cells were cultured with the addition of an appropriate concentration of geneticin for six to twelve days. The cells were then fixed with 100% methanol and stained by Giemsa solution. Sequences of the S-oligonucleotides were as follows:

```
CXADRL1-S4,
5'-TCTGCACGGTGAGTAG-3';      (SEQ ID NO: 22)

CXADRL1-AS4,
5'-CTACTCACCGTGCAGA-3';      (SEQ ID NO: 23)

CXADRL1-S5,
5'-TTCTGTAGGTGTTGCA-3';      SEQ ID NO: 24)
```

-continued

```
CXADRL1-AS5,
5'-TGCAACACCTACAGAA-3';           (SEQ ID NO: 25)

GCUD1-S5,
5'-CTTTTCAGGATGGCTG-3';           (SEQ ID NO: 26)

GCUD1-AS5,
5'-CAGCCATCCTGAAAAG-3';           (SEQ ID NO: 27)

GCUD1-S8,
5'-AGGTTGAGGTAAGCCG-3';           (SEQ ID NO: 28)

GCUD1-AS8,
5'-CGGCTTACCTCAACCT-3';           (SEQ ID NO: 29)

RNF43-S1,
5'-TGGTAGCATGAGTGGT-3';           (SEQ ID NO: 30)
and

RNF43-AS1,
5'-ACCACTCATGCTACCA-3'.           (SEQ ID NO: 31)
```

(13) 3-(4,5-dimethylthiazol-2-yl)-2,5-diphenyltetrazolium bromide (MTT) assay

Cells plated at a density of $5\times10^5$ cells/100 mm dish were transfected in triplicate with sense or antisense S-oligonucleotides designated to suppress the expression of CXADRL1, GCUD1, or RNF43. Seventy-two hours after transfection, the medium was replaced with fresh medium containing 500 μg/ml of MTT (3-(4,5-dimethylthiazol-2-yl)-2,5-diphenyl tetrazolium bromide) (Sigma) and the plates were incubated for four hours at 37° C. Subsequently, the cells were lysed by the addition of 1 ml of 0.01 N HCl/10% SDS and the absorbance of lysates was measured with ELISA plate reader at a test wavelength of 570 nm (reference, 630 nm). The cell viability was represented by the absorbance compared to that of control cells.

(14) Construction of psiH1BX3.0

Since H1RNA gene was reported to be transcribed by RNA polymerase III, which produce short transcripts with uridines at the 3' end, a genomic fragment of H1RNA gene containing its promoter region was amplified by PCR using a set of primers [5'-TGGTAGCCAAGTGCAGGTTATA-3' (SEQ ID NO: 32), and 5'-CCAAAGGGTTTCTGCAGTTTCA-3' (SEQ ID NO: 33)] and human placental DNA as a template. The products were purified and cloned into pCR2.0 plasmid vector using TA cloning kit (Invitrogen) according to the supplier's protocol. The BamHI and XhoI fragment containing the H1RNA gene was purified and cloned into pcDNA3.1 (+) plasmid at the nucleotide position from 1257 to 56, which plasmid was amplified by PCR with a set of primers, 5'-TGCGGATCCAGAGCAGATTGTACTGAGAGT-3' (SEQ ID NO: 34) and 5'-CTCTATCTCGAGTGAGGCG-GAAAGAACCA-3' (SEQ ID NO: 35), and then digested with BamHI and XhoI. The ligated DNA was used as a template for PCR with primers, 5'-TTTAAGCTTGAAGAC-CATTTTTGGAAAAAAAAAAAAAAAAAAAAAAAAAC-3' (SEQ ID NO: 36) and 5'-TTTAAGCTTGAAGACATGG-GAAAGAGTGGTCTCA-3' (SEQ ID NO: 37). The product was digested with HindIII, and subsequently self-ligated to produce psiH1BX3.0 vector plasmid. As the control, psiH1BX-EGFP was prepared by cloning double-stranded oligonucleotides of 5'-CACCGAAGCAGCACGACTTCT-TCTTCAAGAGAAGAAGTCGTGCTGCTTC-3' (SEQ ID NO: 38) and 5'-AAAAGAAGCAGCACGACTTCT-TCTCTCTTGAAGAAGAAGTCGTGCTGCTTC-3' (SEQ ID NO: 39) into the BbsI site of the psiH1BX vector.

(15) Examination on the Gene Silencing Effect of RNF43, or CXADRL1-siRNAs

A plasmid expressing either RNF43-siRNA or CXA-DRL1-siRNA was prepared by cloning double-stranded oligonucleotides into psiH1BX3.0 vector. Oligonucleotides used as RNF43 siRNAs were: 5'-TCCCGTCACCGGATC-CAACTCAGTTCAAGAGACTGAGTTG-GATCCGGTGAC-3' (SEQ ID NO: 40) and 5'-AAAAGT-CACCGGATCCAACTCAGTCTCTTGAACTGAGTTG GATCCGGTGAC-3' (SEQ ID NO: 41) as siRNA16-4; 5'-TCCCGCTATTGCACAGAACGCAGTTCAA-GAGACTGCGTTCTGTGCAATAGC-3' (SEQ ID NO: 42) and 5'-AAAAGCTATTGCACAGAACGCAGTCTCT-TGAACTGCGTTCTGTGCAATAGC-3' (SEQ ID NO: 43) as siRNA1834; 5'-TCCCCAGAAAGCTGTTATCAGAGT-TCAAGAGACTCTGATAACAGCTTTCTG-3' (SEQ ID NO: 44) and 5'-AAAACAGAAAGCTGTTATCA-GAGTCTCTTGAACTCTGATAACAGCTTTCTG-3' (SEQ ID NO: 45) as siRNA1; 5'-TCCCTGAGCCACCTCCAATC-CACTTCAAGAGAGTGGATTGGAGGTGGCTCA-3' (SEQ ID NO: 46) and 5'-AAAATGAGCCACCTCCAATC-CACTCTCTTGAAGTGGATTGGAGGTGGCTCA-3' (SEQ ID NO: 47) as siRNA14; 5'-TCCCCTGCACGGACAT-CAGCCTATTCAAGAGATAGGCTGATGTCCGTGCAG-3' (SEQ ID NO: 48) and 5'-AAAACTGCACGGACAT-CAGCCTATCTCTTGAATAGGCTGATGTCCGTGCAG-3' (SEQ ID NO: 49) as siRNA15. Oligonucleotides used as CXADRL1-siRNAs were: 5'-TCCCGTGTCAGAGAGC-CCTGGGATTCAAGAGATCCCAGGGCTCTCTGACAC-3' (SEQ ID NO: 50) and 5'-AAAAGTGTCAGAGAGC-CCTGGGATCTCTTGAATCCCAGGGC TCTCTGACAC-3' (SEQ ID NO: 51) as siRNA#1; 5'-TCCCCCTCAATGTCATTTGGAT GTTCAAGAGA-CATCCAAATGCAATTGAGG-3' (SEQ ID NO: 52) and 5'-AAAACCT CAATGTCATTTGGATGTCTCTTGAA-CATCCAAATGCAATTGAGG-3' (SEQ ID NO: 53) as siRNA#2; 5'-TCCCTGTCATTTGGATGGTCACTTTCAA-GAGAAGTGACCATCCA AATGACA-3' (SEQ ID NO: 54) and 5'-AAAATGTCATTTGGATGGTCACTTCTCTTG AAAGTGACCATCCAAATGACA-3' (SEQ ID NO: 55) as siRNA#3; 5'-TCCCTGCCAA CCAACCTGAACAGT-TCAAGAGACTGTTCAGGTTGGTTGGCA-3' (SEQ ID NO: 56) and 5'-AAAATGCCAACCAACCTGAA-CAGTCTCTTGAACTGTTCAGGTTGGTTGGCA-3' (SEQ ID NO: 57) as siRNA#4; 5'-TCCCCCAACCTGAA-CAGGTCATCTTCAAGAG AGATGACCTGTTCAGGT-TGG-3' (SEQ ID NO: 58) and 5'-AAAACCAACCTGAACA GGTCATCTCTCTTGAAGATGACCTGTTCAGGTTGG-3' (SEQ ID NO: 59) as siRNA#5; 5'-TCCCCCTGAACAG-GTCATCCTGTTTCAAGAGAACAGGAT-GACCTGTTCAGG-3' (SEQ ID NO: 60) and 5'-AAAACCTGAACAGGTCATCCTGTTCTCT-TGAAACAGGA TGACCTGTTCAGG-3' (SEQ ID NO: 61) as siRNA#6; and 5'-TCCCCAGGTCATCCT GTATCAGGT-TCAAGAGACCTGATACAGGATGACCTG-3' (SEQ ID NO: 62) and 5'-A AAACAGGTCATCCTGTATCAG-GTCTCTTGAACCTGATACAGGATGACCTG-3' (SEQ ID NO: 63) as CXADRL-siRNA#7. psiH1BX-RNF43, psiH1BX-CXADRL1, or psiH1 BX-mock plasmids were transfected into SNUC4 or St-4 cells using FuGENE6 reagent (Roche) according to the supplier's recommendations. Total RNA was extracted from the cells 48 hours after the transfection.

(16) Construction of Recombinant Amino- and Carboxyl-terminal Regions of RNF43 Protein The amino- and carboxyl-terminal regions of RNF43 was amplified by RT-PCR using following sets of primers:

5'-GAAGATCTGCAGCGGTGGAGTCTGAAAG-3' (SEQ ID NO: 64) and 5'-GGAATTCGGACTGGGAAAAT-GAATCTCCCTC-3' (SEQ ID NO: 65) for the amino-terminal region; and 5'-GGAGATCTCCTGATCAGCAAGT-CACC-3' (SEQ ID NO: 66) and 5'-GGAATTCCACAGCCTGTTCACACAGCTCCTC-3' (SEQ ID NO: 67) for the carboxyl-terminal region. The products were digested with BamHI-EcoRI and cloned into the BamHI-EcoRI site of pET-43.1a(+) vector (Novagen). The plasmids were transfected into E. coli BL21trxB(DE3)pLysS cells (Stratagene). Recombinant RNF43 protein was extracted from cells cultured at 25° C. for 16 h after the addition of 0.2 mM IPTG

(17) Yeast Two-hybrid Experiment

Yeast two-hybrid assay was performed using MATCH-MAKER GAL4 Two-Hybrid System 3 (Clontech) according to the manufacturer's protocols. The entire coding sequence of RNF43 was cloned into the EcoR I-BamH I site of pAS2-1 vector as a bait for screening human-testis cDNA library (Clontech). To confirm the interaction in yeast, pAS2-RNF43 was used as bait vector, pACT2-NOTCH2 and pACT2-STRIN as prey vector.

Furthermore, the cytoplasmic region of CXADRL1 was cloned into the EcoRI site of pAS2-1 vector as a bait for screening human testis cDNA library (Clontech). To confirm interaction in yeast, pAS2-CXADRL1 was used as the bait vector, and pACT2-AIP1 as the prey vector.

(18) Preparation of CXADRL Specific Antibody

Anti-CXADRL antisera were prepared by immunization with synthetic polypeptides of CXADRL1 encompassing codons from 235 to 276 for Ab-1, from 493 to 537 for Ab-2, or from 70 to 111 for Ab-3. Sera were purified using recombinant His-tagged CXADRL1 protein prepared in E. coli transfected with pET-CXADRL plasmid. Protein extracted from cells expressing Flag-tagged CXADRL1 was further separated by 10% SDS-PAGE and immunoblotted with either anti-CXADRL1 sera or anti-Flag antibody. HRP-conjugated goat anti-rabbit IgG or HRP-conjugated sheep anti-mouse IgG antibody served as the secondary antibody, respectively, for ECL Detection System (Amersham Pharmacia Biotech, Piscataway, N.J.). Immunoblotting with anti-CXADRL antisera showed a 50 kD band of FLAG-tagged CXADRL1, which pattern was identical to that detected with anti-FLAG antibody.

(19) Preparation of Recombinant GCUD1 Protein

To generate an antibody specific against GCUD1, recombinant GCUD1 protein was prepared. The entire coding region of GCUD1 was amplified by RT-PCR with a set of primers, 5'-GCGGATCCAGGATGGCTGCAGCTCCTC-CAAG-3' (SEQ ID NO: 68) and 5'-CTGAATTCACTTAAA-GAACTTAATCTCCGTGTCAACAC-3' (SEQ ID NO: 69). The product was purified, digested with BamH1 and EcoR1, and cloned into an appropriate cloning site of pGEX6P-2. The resulting plasmid was dubbed pGEX-GCUD1. pGEX-GCUD1 plasmid was transformed into E. coli DH10B. The production of the recombinant protein was induced by the addition of IPTG, and the protein was purified with Glutathione Sepharose™ 4B (Amersham Pharmacia) according to the manufacturers' protocols.

(20) Preparation of GCUD1 Specific Antibody

Polyclonal antibody against GCUD1 was purified from the serum. Proteins from cells transfected with plasmids expressing Flag-tagged GCUD1 were separated by 10% SDS-PAGE and immunoblotted with anti-GCUD1 or anti-Flag antibody. HRP-conjugated goat anti-rabbit IgG (Santa Cruz Biotechnology, Santa Cruz, Calif.) or HRP-conjugated anti-Flag antibody served as the secondary antibody, respectively, for ECL Detection System (Amersham Pharmacia Biotech, Piscataway, N.J.). Immunoblotting with the anti-GCUD1 antibody showed a 47 kD band of FLAG-tagged GCUD1, which pattern was identical to that detected with the anti-FLAG antibody.

(21) Statistical Analysis

The data were subjected to analysis of variance (ANOVA) and the Scheffé's F test.

(22) Preparation of Peptides

9mer and 10 mer peptides of RNF43, CXADRL1, or GCUD1 that bind to HLA-A24 or HLA-A*0201 molecule were predicted with the aid of binding prediction software. These peptides were synthesized by Mimotopes, San Diego, LA according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80° C.

(23) In Vitro CTL Induction

Monocyte-derived dendritic cells (DCs) were used as antigen-presenting cells (APCs) to induce CTL responses against peptides presented on HLA. DCs were generated in vitro as described elsewhere (Nukaya et al., Int J Cancer 80: 92-7 (1999); Tsai et al., J Immunol 158: 1796-802 (1997)). Specifically, peripheral blood mononuclear cells (PBMCs) were isolated from a healthy volunteer with HLA-A*0201 or HLA-A24 using Ficoll-Plaque (Pharmacia) solution, and monocyte fraction of PBMCs were separated by adherence to a plastic tissue culture flask (Becton Dickinson). This monocyte fraction was cultured for seven days in AIM-V medium (Invitrogen) containing 2% heat-inactivated autologous serum (AS), 1000 U/ml of GM-CSF (provided by Kirin Brewery Company), and 1000 U/ml of IL-4 (Genzyme) to obtain DCs fraction. Candidate peptides were pulsed onto this DC enriched cell population at the concentration of 20 µg/ml, in the presence of 3 µg/ml of P2-microglobulin for 4 h at 20° C. in AIM-V. These peptide-pulsed antigen presenting cells were then irradiated (5500 rad) and mixed at a 1:20 ratio with autologous CD8+ T cells, obtained by positive selection with Dynabeads M-450 CD8 (Dynal) and Detachabead (Dynal). These cultures were set up in 48-well plates (Corning); each well contained $1.5 \times 10^4$ peptide-pulsed antigen presenting cells, $3 \times 10^5$ CD8+ T cells and 10 ng/ml of IL-7 (Genzyme) in 0.5 ml of AIM-V with 2% AS. Three days later, these cultures were supplemented with IL-2 (CHIRON) to a final concentration of 20 IU/ml. On day 7 and 14, the T cells were further restimulated with the autologous peptide-pulsed antigen presenting cells which were prepared each time in the same manner as described above. Lymphoid cells in the culture on day 21 were harvested and tested for cytotoxicity against peptide-pulsed TISI or T2 cells.

(24) CTL Expansion

Cultured lymphoid cells with proved significant cytotoxicity against peptide-pulsed TISI or T2 were further expanded in culture using a method similar to that described by Riddell, et al. (Walter et al., N Engl J Med 333:1038-1044, 1995; Riddell et al., Nature Med. 2:216-23 (1996)). $5 \times 10^4$ of lymphoid cells were resuspended in 25 ml of AIM-V supplemented with 5% AS containing $25 \times 10^6$ irradiated (3300 rads) PBMC, $5 \times 10^6$ irradiated (8000 rads) EHM cells, and 40 ng/ml of anti-CD3 monoclonal antibody (Pharmingen). One day after initiating the cultures, 120 IU/ml of IL-2 were added to the cultures. The cultures comprised fresh AIM-V supplemented with 5% AS and 30 IU/ml of IL-2 on days 5, 8 and 11.

(25) Establishment of CTL Clones

Some of the lymphoid cells with potent cytotoxicity were used to obtain CTL clones. The cell suspensions were diluted to densities of 0.3, 1, and 3 CTLs/lymphoid cells per well in 96 round-bottom microtiter plate (Nalge Nunc International). These cells were cultured in 150 µl/well of AIM-V supplemented with 5% AS containing $7 \times 10^4$ cells/well of allogenic PBMCs, $1 \times 10^4$ cells/well of EHM, 30 ng/ml of anti-CD3 antibody, and 125 U/ml of IL-2. 10 days later, 50 µl/well of IL-2 was added to the medium to a final concentration of 125 U/ml. Cytotoxic activity of cultured CTLs was tested on day 14, and CTL clones were expanded using the same method as described above.

(26) Cytotoxicity Assay

Target cells were labeled with 100 µCi of $Na_2{}^{51}CrO_4$ (Perkin Elmer Life Sciences) for 1 h at 37° C. in a $CO_2$ incubator. When peptide-pulsed targets were used, target cells were incubated with the addition of 20 µg/ml of the peptide for 16 h at 37° C. before the labeling with $Na_2{}^{51}CrO_4$. Target cells were rinsed and mixed with effectors at a final volume of 0.2 ml in round-bottom microtiter plates. The plates were centrifuged (4 minutes at 800×g) to increase cell-to-cell contact and placed in a $CO_2$ incubator at 37° C. After 4 h of incubation, 0.1 ml of the supernatant was collected from each well and the radioactivity was determined with a gamma counter. In case of evaluating cytotoxicity against target cells that endogenously express RNF43, CXADRL1, or GCUD1, the cytolytic activity was tested in the presence of a 30-fold excess of unlabeled K562 cells to reduce any non-specific lysis due to NK-like effectors. Antigen specificity was confirmed by the cold target inhibition assay, which utilized unlabeled TISI or T2 cells that were pulsed with peptide (20 µg/ml for 16 h at 37° C.) to compete for the recognition of $^{51}$Cr-labeled HT29 or SNU475 cells. The MHC restriction was examined by blocking assay, measuring the inhibition of the cytotoxicity with anti-HLA-class I (W6/32) antibody and anti-HLA-class II antibody, or anti-CD4 antibody and anti-CD8 antibody (DAKO).

The percentage of specific cytotoxicity was determined by calculating the percentage of specific $^{51}$Cr-release by the following formula: {(cpm of the test sample release–cpm of the spontaneous release)/(cpm of the maximum release–cpm of the spontaneous release)}×100. Spontaneous release was determined by incubating the target cells alone in the absence of effectors, and the maximum release was obtained by incubating the targets with 1N HCl. All determinants were done in duplicate, and the standard errors of the means were consistently below 10% of the value of the mean.

2. Results (1) Identification of Two Novel Human Genes, CXADRL1 and GCUD1, Commonly up-Regulated in Gastric Cancers By means of a genome-wide cDNA microarray containing 23040 genes, expression profiles of 20 gastric cancers were compared with corresponding non-cancerous mucosae. Among commonly up-regulated genes detected in the microarray analysis, a gene with an in-house accession number of A5928 corresponding to an EST, Hs.6658 of UniGene cluster, was found to be over-expressed in a range between 4.09 and 48.60 (FIG. 1a). Since an open reading frame of this gene encoded a protein approximately 37% identical to that of CXADR (coxsackie and adenovirus receptor), this gene was dubbed CXADRL1 (coxsackie and adenovirus receptor like 1). CXADRL1 was also up-regulated in 6 of 6 colorectal cancer cases and 12 out of 20 HCC cases. Furthermore, a gene with an in-house accession number of C8121, corresponding to KIAA0913 gene product (Hs.75137) of UniGene cluster was also focused due to its significantly enhanced expression in nine of twelve gastric cancer tissues compared with the corresponding non-cancerous gastric mucosae by microarray (FIG. 1b). This gene with the in-house accession number C8121 was dubbed GCUD1 (up-regulated in gastric cancer). GCUD1 was also up-regulated in 5 of 6 colorectal cancer cases, 1 out of 6 HCC cases, 1 out of 14 lung cancer (squamous cell carcinoma) cases, 1 out of 13 testicular seminomas cases. To clarify the results of the cDNA microarray, expression of these transcripts in gastric cancers was examined by semi-quantitative RT-PCR to confirm an increased expression of CXADRL1 in all of the 10 tumors (FIG. 1c) and elevated expression of GCUD1 in seven of nine cancers (FIG. 1d).

(2) Isolation and Structure of a Novel Gene CXADRL1

Figure 2:
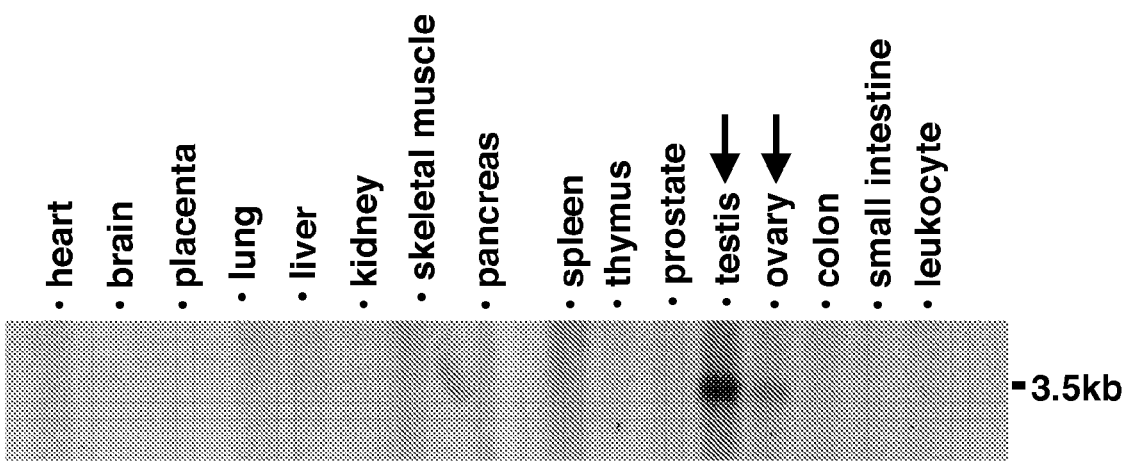
FIGS. 2a and 2b depict the expression of CXADRL1 in various human tissues and the predicted protein structure and protein motifs of CXADRL1.
Figure 2:
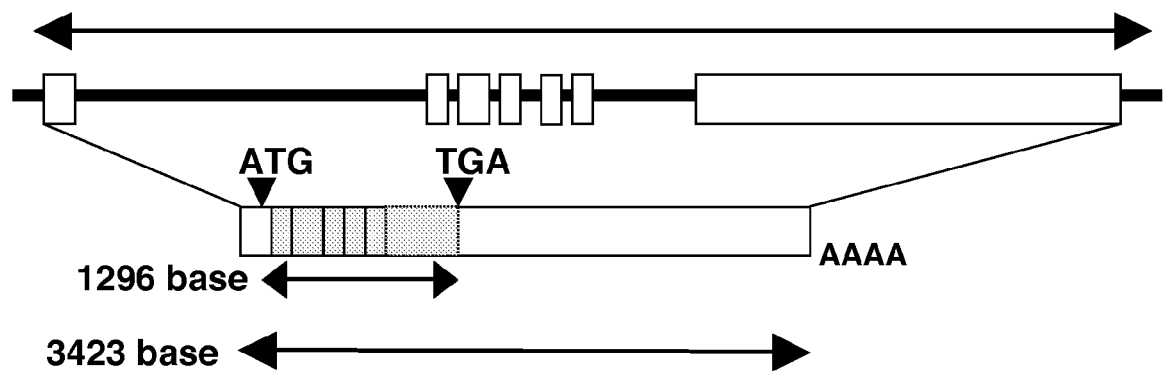

Multiple-tissue Northern-blot analysis using a PCR product of CXADRL1 as a probe revealed the expression of a 3.5-kb transcript in testis and ovary (FIG. 2a). Since A5928 was smaller than the gene detected on the Northern-blot, 5'RACE experiments were carried out to determine the entire coding sequence of the CXADRL1 gene. The putative full-length cDNA consisted of 3423 nucleotides, with an open reading frame of 1296 nucleotides (SEQ ID NO: 1) encoding a 431-amino-acid protein (SEQ ID NO: 2) (GenBank Accession number: AB071618). The first ATG was flanked by a sequence (CCCGGGATGA) (SEQ ID NO: 70) that was consistent with the consensus sequence for the initiation of translation in eukaryotes, with an in-frame stop codon upstream. Using the BLAST program to search for homologies in the NCBI (the National Center for Biotechnology Information) databases, a genomic sequence with the GenBank accession number AC068984 was identified, which sequence had been assigned to chromosomal band 3q13. Comparison of the cDNA and the genomic sequence revealed that CXADRL1 consisted of 7 exons (FIG. 2b).

A search for protein motifs using the Simple Modular Architecture Research Tool (SMART) revealed that the predicted protein contained two immunoglobin domains (codons 29-124 and 158-232) and a transmembrane domain (codons 246-268), suggesting that CXADRL1 might belong to the immunoglobin super family.

(3) Effect of CXADRL1 on Cell Growth

Figure 3:
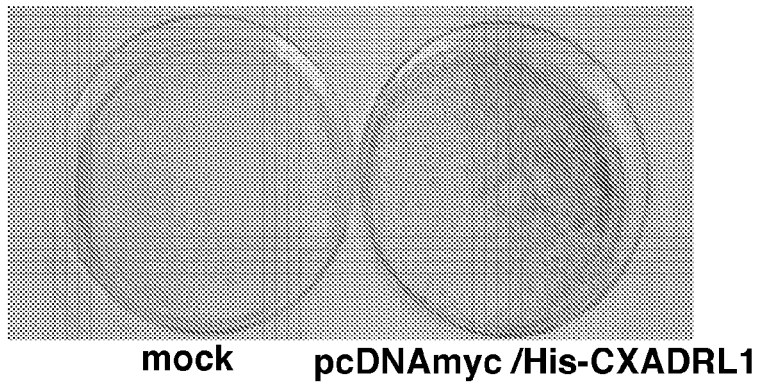
FIG. 3a to 3c depict the growth-promoting effect of CXADRL1.
Figure 3:
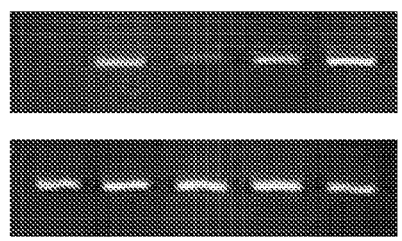
Figure 3:
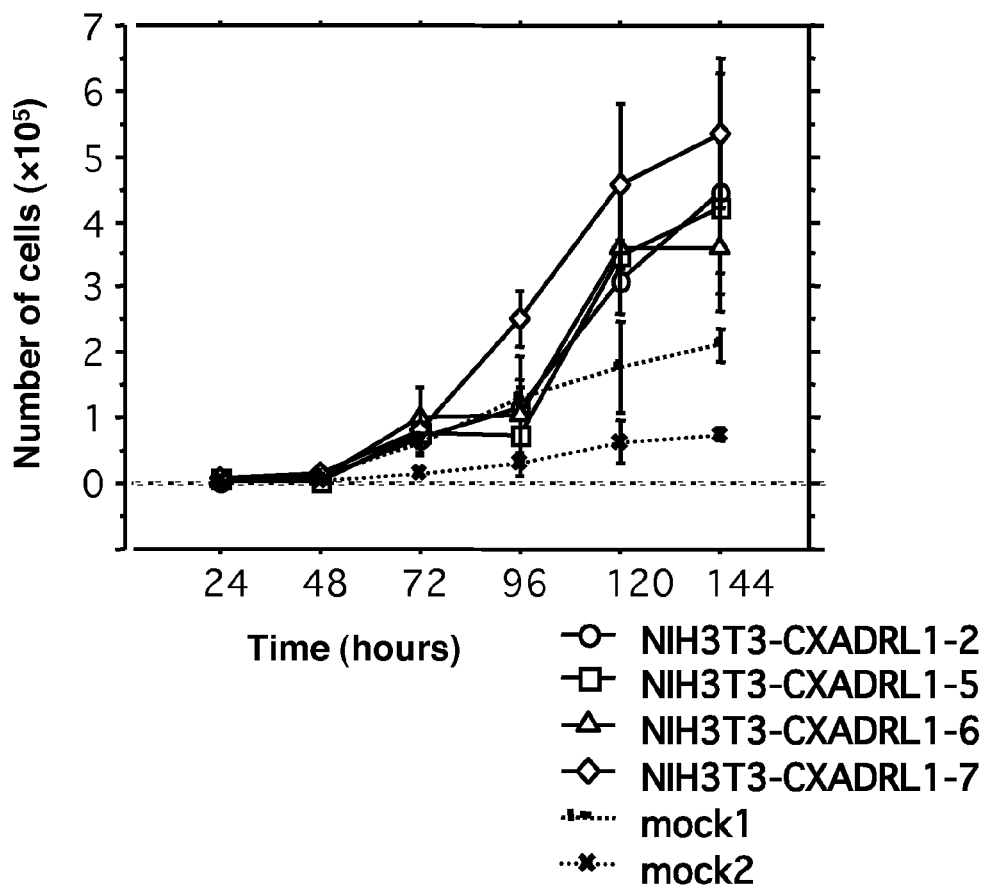

A colony-formation assay was performed by transfecting NIH3T3 cells with a plasmid expressing CXADRL1 (pcDNA3.1myc/His-CXADRL1). Cells transfected with pcDNA3.1 myc/His-CXADRL1 produced markedly more colonies than mock-transfected cells (FIG. 3a). To further investigate this growth-promoting effect of CXADRL1, NIH3T3 cells that stably expressed exogenous CXADRL1 were established (FIG. 3b). The growth rate of NIH3T3-CXADRL1 cells was significantly higher than that of parental NIH3T3 cells in culture media containing 10% FBS (FIG. 3c).

Figure 4:
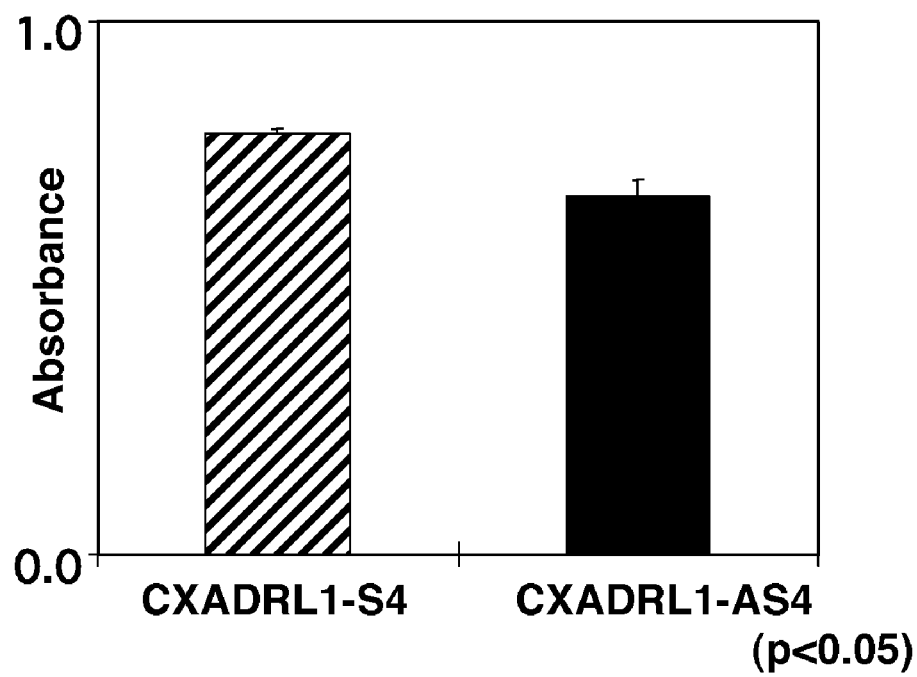
FIG. 4 depicts the growth-inhibitory effect of antisense S-oligonucleotides designated to suppress CXADRL1 in MKN-1 cells. CXADRL1-AS4 and CXADRL1-AS5 were demonstrated to suppress the growth of MKN-1 cells.
Figure 4:
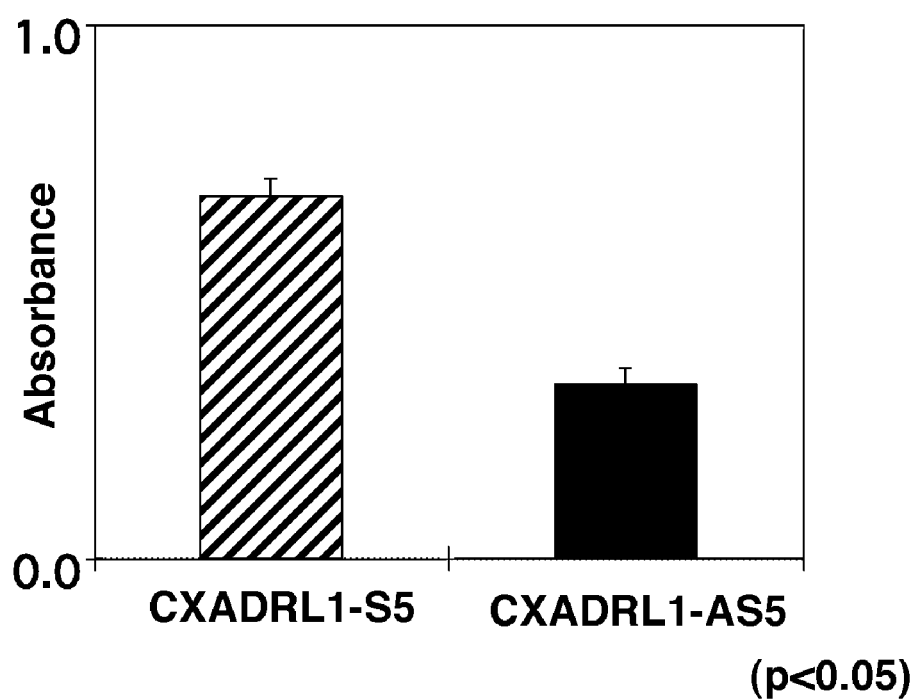

(4) Suppression of CXADRL1 Expression in Human Gastric Cancer Cells by Antisense S-oligonucleotides Six pairs of control and antisense S-oligonucleotides corresponding to CXADRL1 were transfected into MKN-1 gastric cancer cells, which had shown the highest level of CXADRL1 expression among the examined six gastric cancer cell lines. Six days after transfection, viability of transfected cells was measured by MTT assay. Viable cells transfected with antisense S-oligonucleotides (CXADRL1-AS4 or -AS5) were markedly fewer than those transfected with control S-oligonucleotides (CXADRL1-S4 or -S5) (FIG. 4). Consistent results were obtained in three independent experiments.

Figure 5:
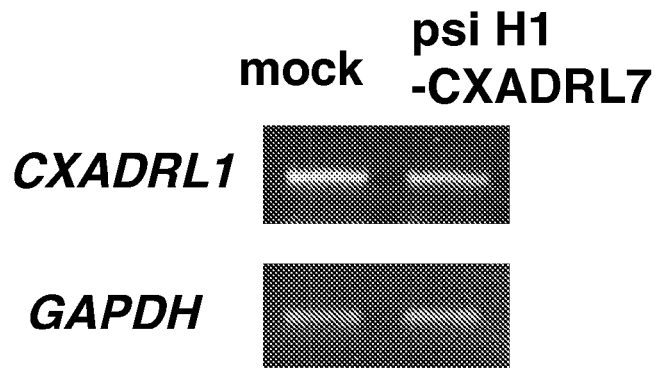
FIG. 5A to 5C depict the growth suppressive effect of CXADRL1-siRNA on St-4 cells.
Figure 5:
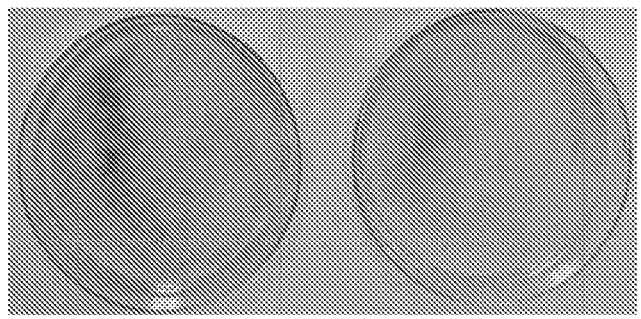
Figure 5:
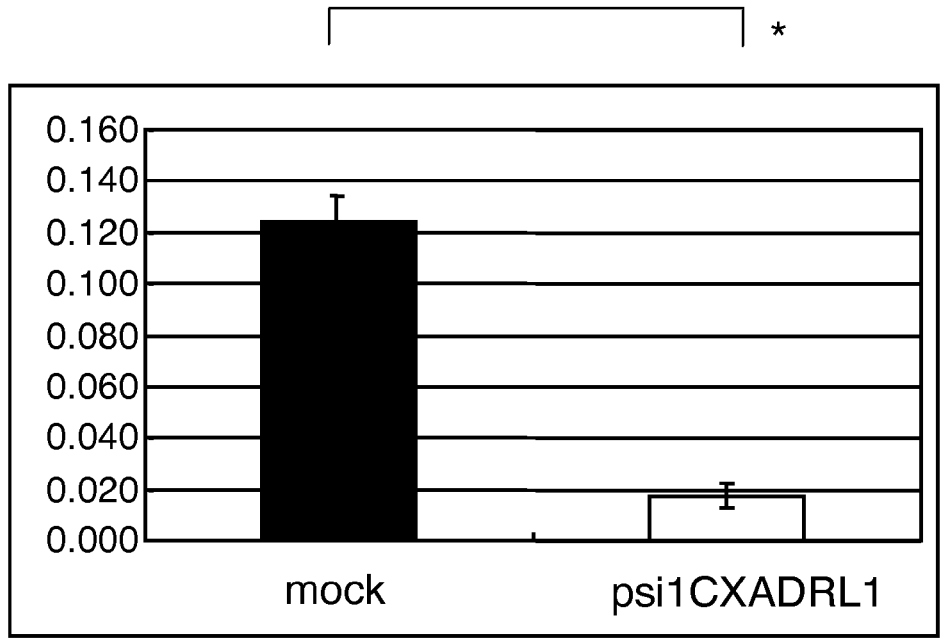

(5) Construction of Plasmids Expressing CXADRL1 siRNAs and their Effect on the Growth of Gastric Cancer Cells Plasmids expressing various CXADRL1-siRNA were constructed and examined for their effect on CXADRL1 expression. Among the constructed siRNAs, psiH1BX-CXADRL7 significantly suppressed the expression of CXADRL1 in St-4 cells (FIG. 5A). To test whether the suppression of CXADRL1 may result in growth suppression of colon cancer cells, St-4 cells were transfected with psiH1BX-CXADRL7 or mock vector. The number of viable cells transfected with psiH1BX-CXADRL7 was fewer than the number of viable control cells (FIGS. 5B and 5C).

(6) Preparation of Anti-CXADRL1 Antibody

Figure 6:
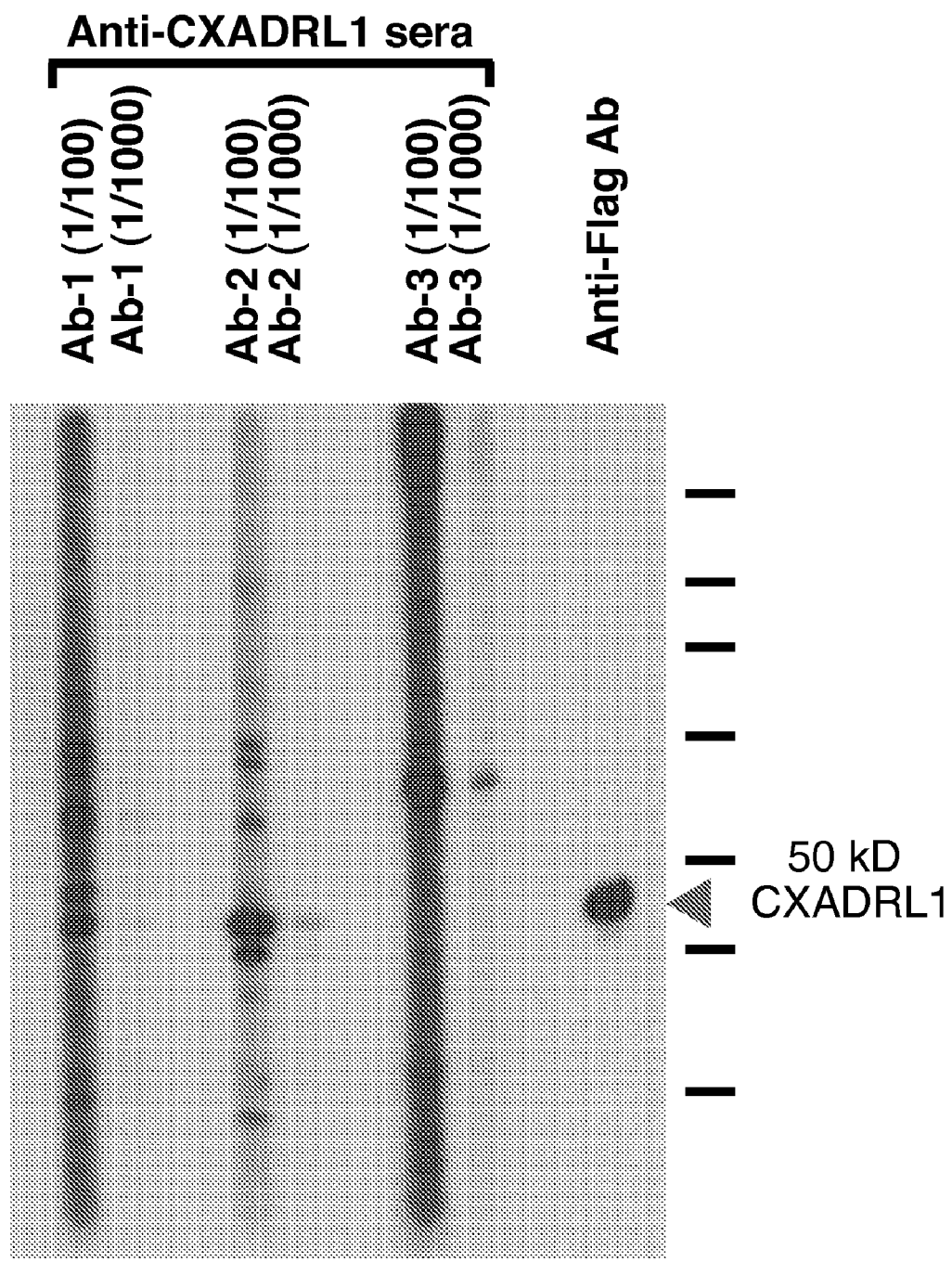
FIG. 6 depicts a photograph demonstrating the result of immunoblot analysis of cells expressing exogenous Flag-tagged CXADRL1 protein with anti-CXADRL1 antiserum or anti-Flag antibody.

To examine the expression and explore the function of CXADRL1, antiserum against CXADRL1 was prepared. Immunoblotting with anti-CXADRL1 detected a 50 kD band of FLAG-tagged CXADRL1, which was almost identical by size to that detected with anti-FLAG antibody (FIG. 6).

Figure 7:
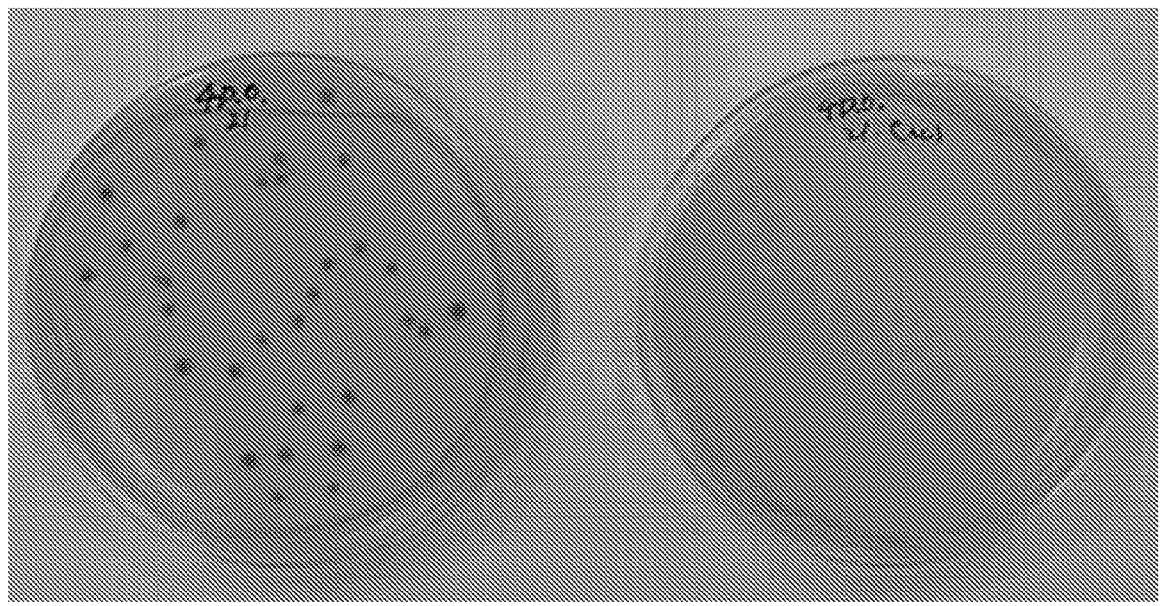
FIG. 7 depicts the interaction between CXADRL1 and AIP1 examined by yeast two-hybrid system.

(7) Identification of CXADRL1-interacting Protein by Yeast Two-hybrid Screening System To clarify the function of CXADRL1, CXADRL1-interacting proteins were searched using yeast two-hybrid screening system. Among the positive clones identified, C-terminal region of nuclear AIP1 (atriphin interacting protein 1) interacted with CXADRL1 in the yeast cells that were simultaneously transformed with pAS2.1-CXADRL1 and pACT2-AIP1 (FIG. 7). The positive clones contained codons between 808 and 1008, indicating that the responsible region for the interaction with AIP1 is within this region.

(8) Prediction of Candidate Peptides for CTLs Derived from CXADRL1

Table 1 shows the candidate peptides (SEQ ID NOs: 115-154) in order of high binding affinity. Forty peptides in total were selected and examined as described below.

TABLE 1

Prediction of candidate peptides derived from CXADRL1

| Rank | sequence | Score | Position |
|---|---|---|---|
| HLA-A*0201 9 mer | | | |
| 1 | YLWEKLDNT | 1314.7 | 176 |
| 2 | LLLLSLHGV | 1006.2 | 11 |
| 3 | INLNVIWMV | 49.262 | 53 |
| 4 | WMVTPLSNA | 37.961 | 59 |
| 5 | CLVNNLPDI | 23.995 | 120 |
| 6 | SLHGVAASL | 21.362 | 15 |
| 7 | VIIIFCIAL | 18.975 | 252 |
| 8 | LINLNVIWM | 14.69 | 52 |
| 9 | AVLPCTFTT | 13.993 | 40 |
| 10 | ALSSGLYQC | 11.426 | 207 |
| 11 | VMSRSNGSV | 11.101 | 384 |
| 12 | SIFINNTQL | 10.868 | 104 |
| 13 | KVHRNTDSV | 10.437 | 327 |
| 14 | RIGAVPVMV | 9.563 | 413 |
| 15 | NIGVTGLTV | 9.563 | 132 |
| 16 | SIYANGTHL | 9.399 | 356 |
| 17 | LLCSSEEGI | 8.691 | 163 |
| 18 | LLSLHGVAA | 8.446 | 13 |
| 19 | IIFCIALIL | 7.575 | 254 |
| 20 | TMPATNVSI | 7.535 | 97 |
| HLA-A*0201 10 mer | | | |
| 1 | YLWEkLDNTL | 3344 | 176 |
| 2 | LINLnVIWMV | 280.45 | 52 |
| 3 | ALSSgLYQCV | 104.33 | 207 |
| 4 | ALININVIWM | 62.845 | 51 |
| 5 | ILLCsSEEGI | 32.155 | 162 |
| 6 | VLPCtFTTSA | 32.093 | 41 |
| 7 | LLLSIHGVAA | 31.249 | 12 |
| 8 | SIYAnGTHLV | 30.603 | 356 |
| 9 | QLSDtGTYQC | 20.369 | 111 |
| 10 | GLYQcVASNA | 15.898 | 211 |
| 11 | PLLLISLHGV | 13.022 | 10 |
| 12 | IQVArGQPAV | 11.988 | 32 |
| 13 | FINNtQLSDT | 10.841 | 106 |
| 14 | LVPGqHKTLV | 10.346 | 364 |
| 15 | NLPDiGGRNI | 8.555 | 124 |
| 16 | VLVPpSAPHC | 8.446 | 140 |
| 17 | AVIIiFCIAL | 7.103 | 251 |
| 18 | VIIIfCIALI | 5.609 | 252 |
| 19 | ILGAfFYWRS | 5.416 | 261 |
| 20 | GLTVIVPPSA | 4.968 | 137 |

Figure 8:
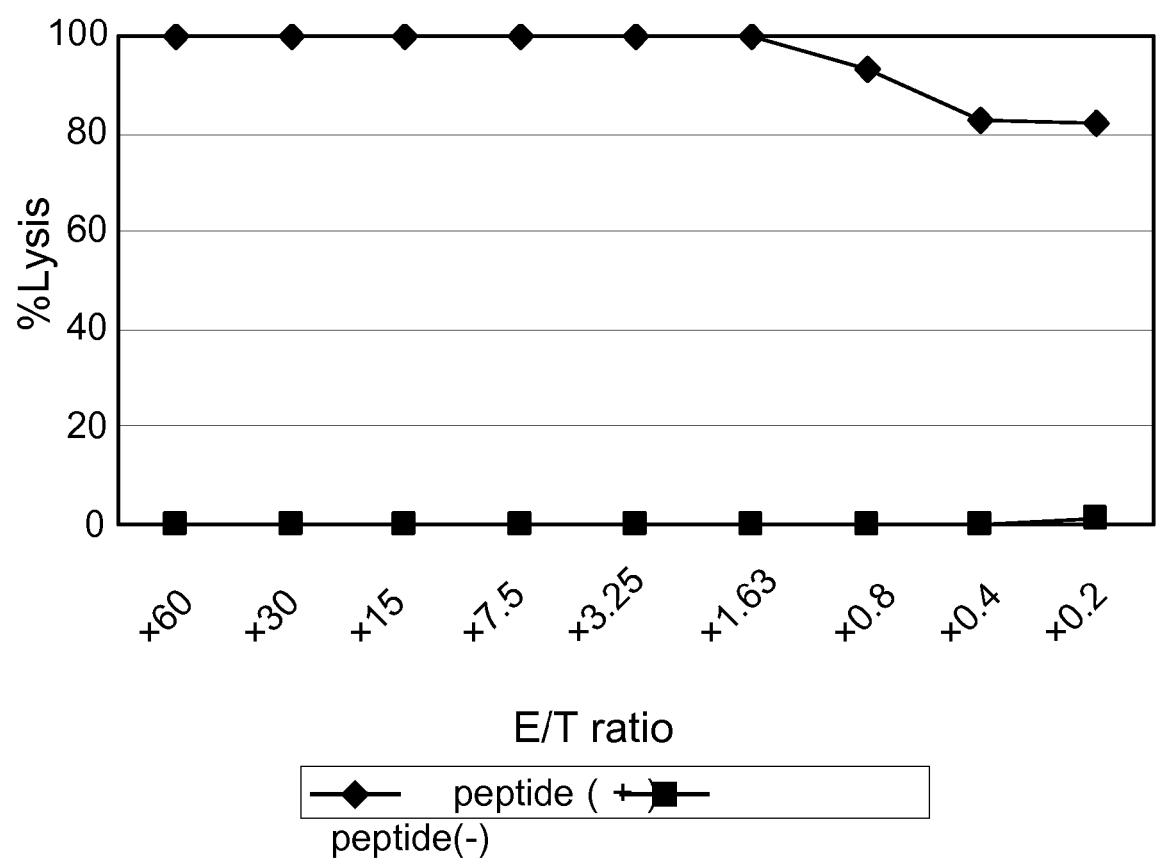
FIG. 8 depicts the peptide specific cytotoxicity of CTL line raised by CXADRL1-207 stimulation. The CTL line showed high cytotoxic activity on target cells (T2) pulsed with CXADRL1-207, whereas no significant cytotoxic activity was detected on the same target cells (T2) pulsed without peptides.

(9) Stimulation of T Cells and Establishment of CTL Clones Using Candidate Peptides Lymphoid cells were cultured using these candidate peptides derived from CXADRL1 in the manner described in "Materials and Methods". Resulting lymphoid cells showing detectable cytotoxic activity were expanded, and CTL clones were established. CTL clones were propagated from the CTL lines described above using the limiting dilution methods. A CTL clone induced with CXADRL1-207 (ALSSGLYQC) (SEQ ID NO: 124) showed higher cytotoxic activities against the target pulsed with peptides than to the targets not pulsed with any peptide. Cytotoxic activity of this CTL clone is shown in FIG. 8. This CTL clone had very potent cytotoxic activity against the peptide-pulsed target without showing any cytotoxic activity against the non-pulsed target.

Figure 9:
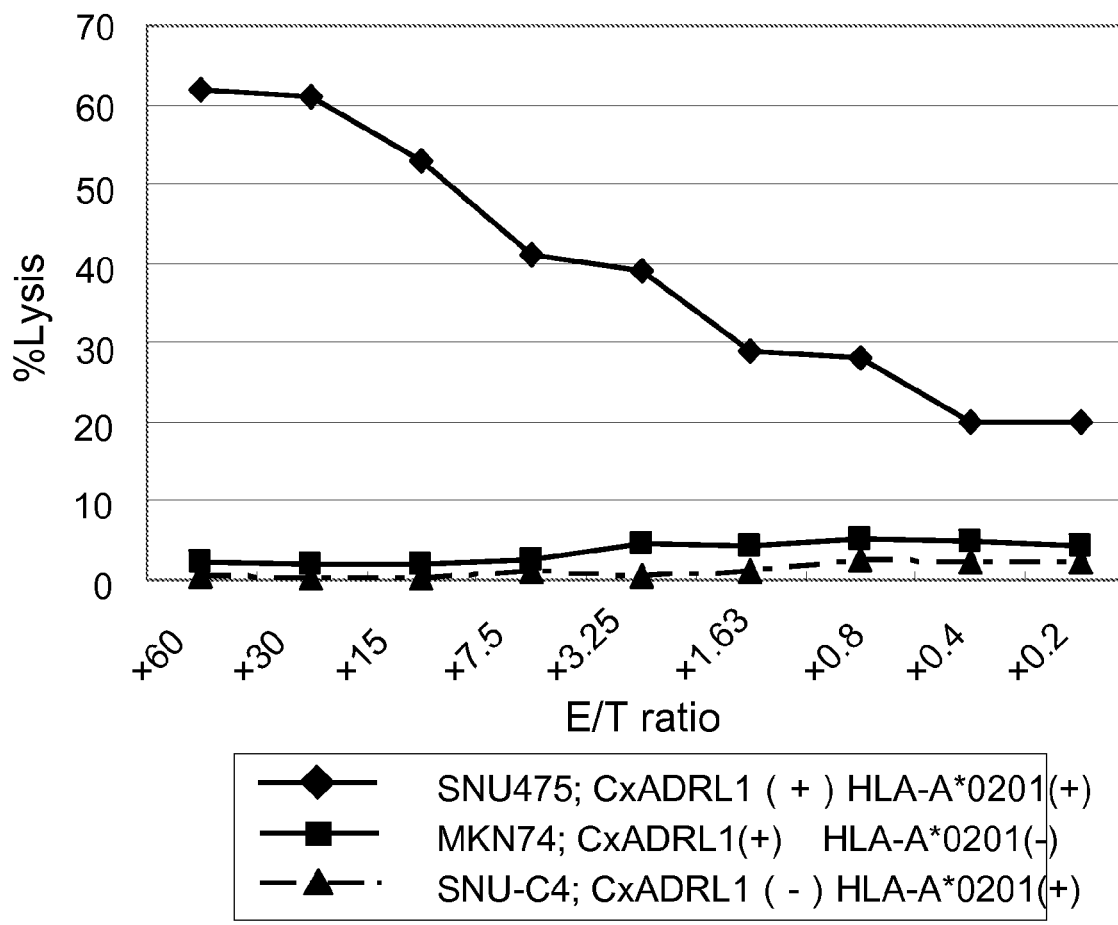
FIG. 9 depicts the cytotoxic activity of CXADRL1-207 CTL Clone on SNU475, MKN74, and SNU-C4. CXADRL1-207 CTL Clone showed high cytotoxic activity on SNU475 that expresses both CXADRL1 and HLA-A*0201. On the other hand, CXADRL1-207 CTL Clone showed no significant cytotoxic activity on MKN74, which expresses CXADRL1 but not HLA-A*0201. Furthermore, this CTL Clone did not show significant cytotoxic activity on SNU-C4, which expresses HLA-A*0201 but not CXADRL1.

(10) Cytotoxic Activity Against Tumor Cell Lines Endogenously Expressing CXADRL1 as a Target The CTL clones raised against predicted peptides were examined for their ability to recognize and kill tumor cells endogenously expressing CXADRL1. FIG. 9 shows the results of CTL Clone 75 raised against CXADRL1-207 (ALSSGLYQC) (SEQ ID NO: 124). CTL Clone 75 showed potent cytotoxic activity against SNU475 that expresses CXADRL1 and HLA-A*0201, however, not against MKN74 that expresses CXADRL1 but not HLA-A*0201, and SNU-C4 that expresses HLA-A*0201 but not CXADRL1.

(11) Specificity of the Established CTLs

Figure 10:
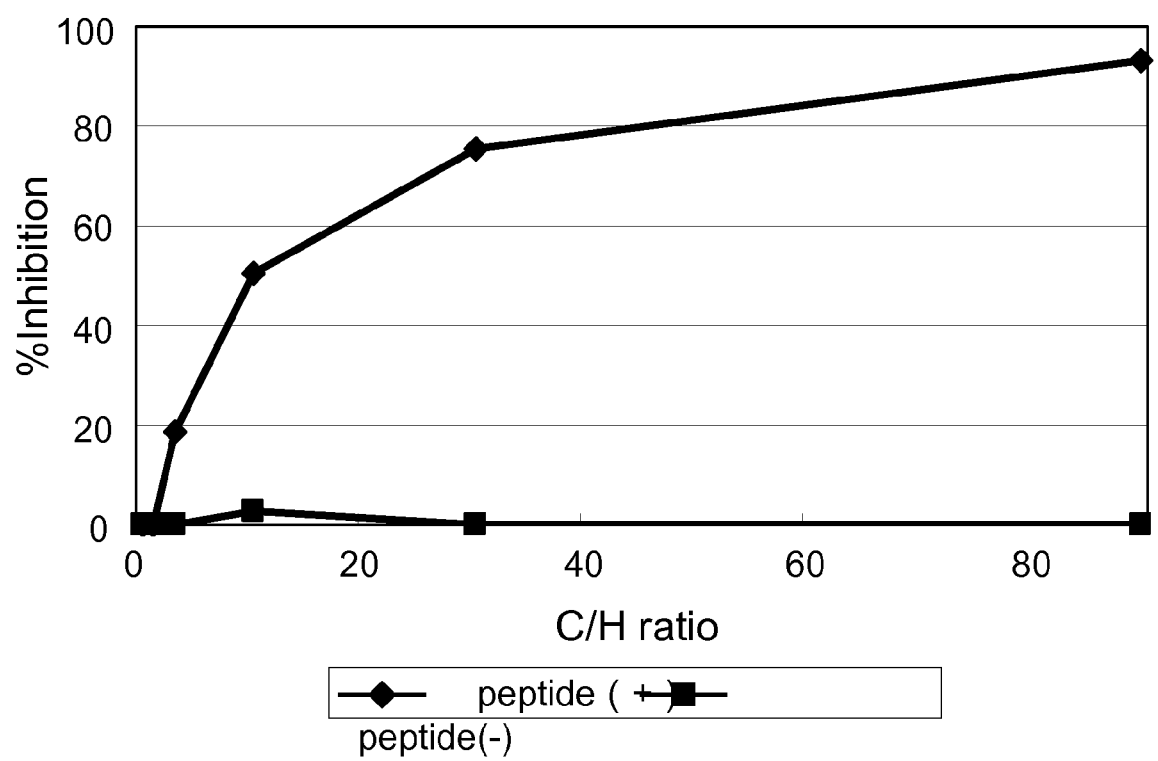
FIG. 10 depicts the result of the cold target inhibition assay. CXADRL1-207 CTL Clone specifically recognizes CXADRL1-207 in an HLA-A*0201 restricted manner. SNU475 labeled with $Na_2^{51}CrO_4$ was prepared as a hot target, while CXADRL1-207 peptide-pulsed T2 (Peptide+) was used as a cold target (Inhibitors). E/T ratio was fixed to 20. The cytotoxic activity on SNU475 was inhibited by the addition of T2 pulsed with the identical peptide, while almost no inhibition by the addition of T2 without peptide pulse.

Cold target inhibition assay was performed to confirm the specificity of CXADRL1-207 CTL Clone. SNU475 cells labeled with $^{51}$Cr were used as a hot target, while T2 cells pulsed with CXADRL1-207 (SEQ ID NO: 124) were used without 5 Cr labeling as a cold target. Specific cell lysis against SNU475 cells was significantly inhibited, when T2 pulsed with CXADRL1-207 (SEQ ID NO: 124) was added in the assay at various ratios (FIG. 10). The results are indicated as the percentage of specific lysis at an E/T ratio of 20.

Figure 11:
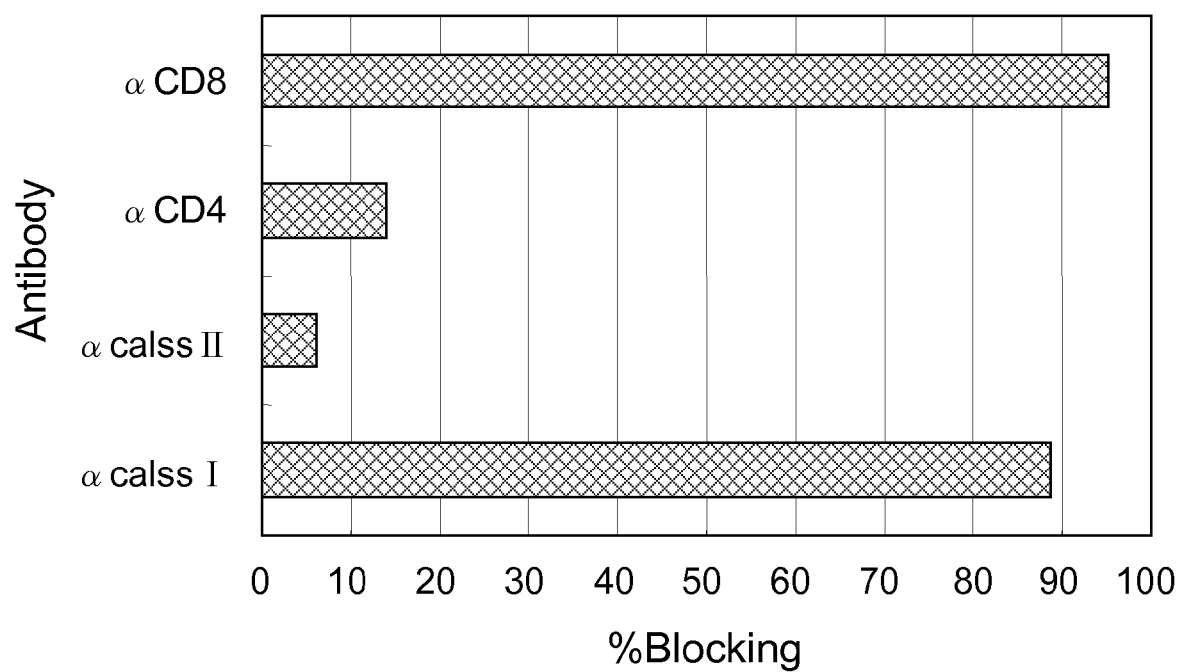
FIG. 11 depicts the result of the blocking assay showing the effect of antibodies raised against HLA-Class I, HLA-Class II, CD4, and CD8 on the cytotoxic activity of CXADRL1-207 CTL Clone. CXADRL1-207 CTL Clone showed cytotoxic activity in HLA-Class I and CD8 restricted manner. To examine the characteristics of CTL clone raised with CXADRL1 peptide, antibodies against HLA-Class I, HLA-Class II, CD4, and CD8 were tested for their ability to inhibit the cytotoxic activity. The horizontal axis reveals % inhibition of the cytotoxicity. The cytotoxicity of CTL clone on SNU475 targets was significantly reduced when anti-class I and CD8 antibodies were used. This result indicates that the CTL clone recognizes the CXADRL1 derived peptide in a HLA-Class I and CD8 dependant manner.

In the interest of clone CXADRL1-207 CTL, to examine its characteristics, antibodies against HLA-Class I, HLA-Class II, CD4, and CD8 were tested for their capacity to inhibit its cytotoxic activity. The cytotoxicity of the CTL clone against SNU475 cells was significantly inhibited when anti-HLA-Class I antibody and anti-CD8 antibody were used (FIG. 11), indicating that the CTL clone recognizes the CXADRL1 derived peptide in an HLA-Class I and CD8 dependent manner.

(12) Induction of CTLs by Anchor-modified Peptides (CXADRL1)

The newly defined epitope, CXADRL1-9mer-207 (SEQ ID NO: 124) had a relatively low binding score. Thus, to increase the binding with MHC class I molecule, altered peptides were developed from the CXADRL1-9mer-207.

HLA-A*0201 allele-binding peptides frequently are nonamers. Position two and nine of the peptides are considered to be primary anchor residues that bind to the HLA class I peptide-binding cleft alone but do not contact with TCR. According to the HLA-A2 antigen motif previously reported by Smith et al. (Smith et al., Mol Immunol 35: 1033-43 (1998)), leucine (Leu) and isoleucine (Iso) have proven to be an optimal anchor residue at position 2 that enhance the binding affinity of the peptide for the HLA-A*0201 molecule. Similarly, valine (Val) at position 9 is also preferred for nonamer peptides. Based on these knowledge, two anchor-modified altered peptides of CXADRL1-9mer-207 with amino acid substitutions to contain the optimal HLA-A*0201 allele-binding amino acids as anchor residues to increase the binding affinity to HLA-A*0201 molecules were designed and synthesized.

TABLE 2

Anchor modified altered peptides; modification of IGSF11CXADRL1-9mer-207 peptide with increased binding affinity for HLA-A*0201 molecule

| Peptide | Amino Acid Sequence | Binding Score* | SEQ ID NO |
|---|---|---|---|
| wild-type | ALSSGLYQC | 11.4 | 124 |
| anchor-modified-1 | ALSSGLYQV | 49.0 | 195 |
| anchor-modified-2 | ALSSGLYQL | 159.8 | 196 |

*The binding score of these altered peptides were calculated by the BIMAS's epitope prediction algorithm.

Figure 12:
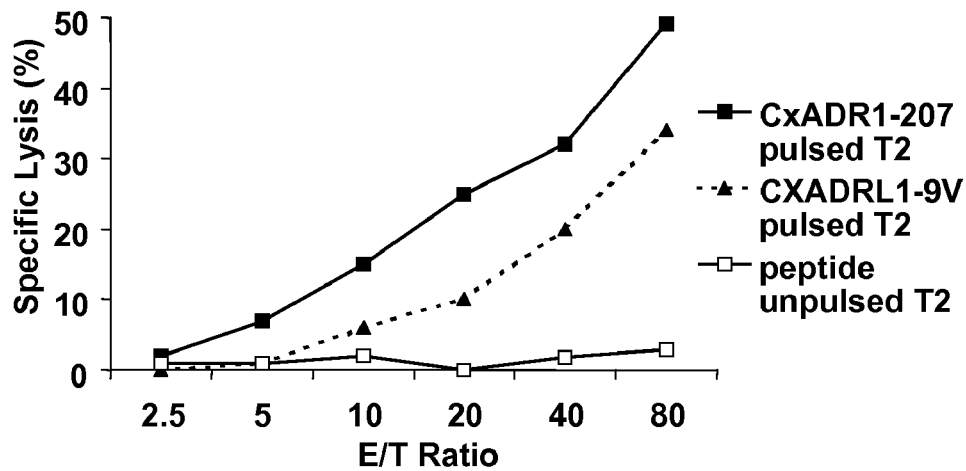
FIG. 12 depicts the cytotoxic activities of CTLs induced with anchor modified peptide CXADRL1-9V. The cytotoxic activities of CXADRL1-9V induced CTL line 5 (A) and CTL clone 69 (B) against peptide pulsed T2 cells (HLA-A*0201 positive cell line) and tumor cell lines were examined by 4h $^{51}$Cr release assay. Both the CTL line 5 and CTL clone 69 recognized not only CXADRL1-9V but also the parental peptide CXADRL1-9mer-207, equally or more sharply at a low E/T ratio in the CTL clone 69, and killed SNU475 cells expressing naturally processed wild-type peptide CXADRL1-9mer-207 on the HLA-A*0201 molecule (C).
Figure 12:
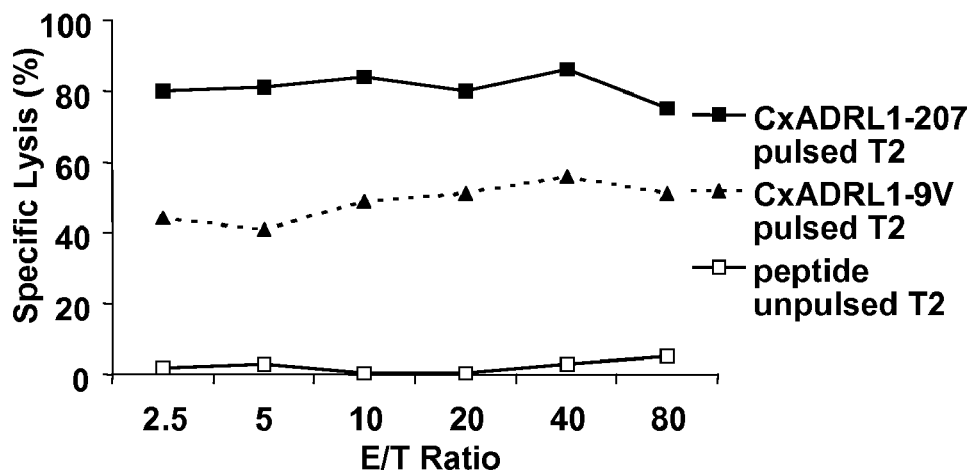
Figure 12:
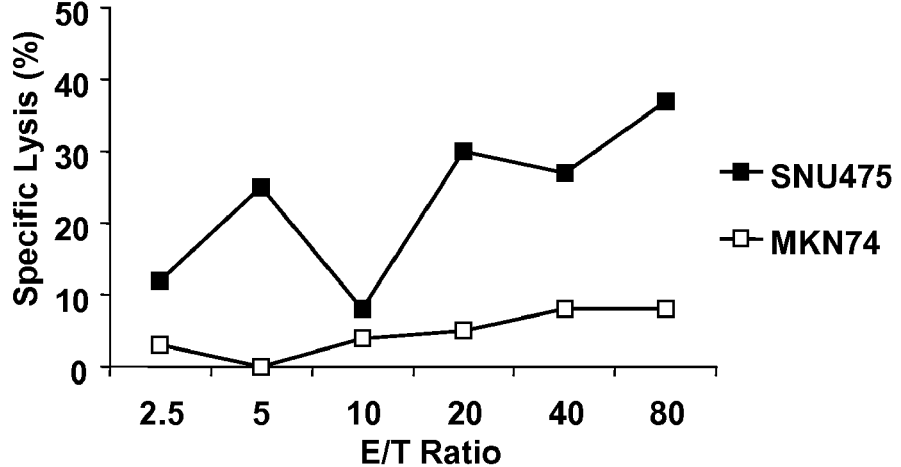

The binding score of these peptides were calculated using BIMAS's epitope prediction algorithm as previously described, and both of the altered peptides showed higher HLA-A*0201-binding scores compared to the wild-type CXADRL1 peptide. These anchor-modified peptides were tested for their ability to elicit CTLs, and moreover, whether the induced CTLs recognize not only the altered peptide but also the parental CXADRL1-9mer-207 peptide on T2. After CTL induction with CXADRL1-9V (SEQ ID NO:195) and CXADRL1-9L (SEQ ID NO:196), CTL line 5 and CTL clone 69 were obtained by the stimulation with CXADRL1-9V peptide shown in FIGS. 12A 12B. These CTLs cross-reacted with the wild-type CXADRL1-9mer-207 peptide on T2 cells, and also killed tumor cell line SNU475 that endogenously express naturally processed CXADRL1 derived peptide, as measured by $^{51}$Cr release assay shown in FIG. 2C.

Several published studies have shown the utility of such altered peptides. Peptides having high affinity for an MHC class I molecule are presented on the cell surfaces for a longer time than those with low affinity. Therefore, peptides with increased affinity for MHC class I molecule have been considered to have increased potential to induce T-cell-mediated immune responses (Keogh et al., J Immunol 167: 787-96 (2001); Tourdot et al., J Immunol 159: 2391-8 (1997); Sette et al., J Immunol 153: 5586-92 (1994)). The binding score calculated by the BIMAS's prediction software of CXADRL1-9mer-207 (SEQ ID NO:124) was 11.4, relatively low compared to viral antigens or other TAAs (Bendnarek et al., J Immunol 147: 4047-53 (1991); Sette et al, J Immunol 153: 5586-92 (1994)). To increase immunogenicity of the native epitope peptide, altered peptides were designed and synthesized that have the anchor residue at position 2 or 9 replaced with optimized amino acids for HLA-A*0201 (Vierboom et al., J Immunother 21: 399-408 (1998); Irvine et al., Cancer Res 59: 2536-40 (1999); Dyall et al., J Exp Med 188: 1553-61 (1998); Muller et al., J Immunol 147: 1329-97 (1991)). CTLs raised against CXADRL1-9V (SEQ ID NO:195) with a binding score of 49 responded not only to the CXADRL1-9V peptide but also to the parental peptide CXADRL1-9mer-207 on T2 cells. Furthermore, these CTLs induced by the GCUD1-9V peptide also recognized the native peptide naturally processed by tumor cell. However, many recent studies indicate that increased affinity for MHC class I does not necessarily correlate with increased peptide immunogenicity or an ability to stimulate CTL (Clay et al., J Immunol 162: 1749-55 (1999); Dionne et al., Cancer Immuno Immunother 52: 199-206 (2003); Slansky et al., Immunity, 13: 529-38 (2000); Sloan-Lancaster et al., Annu Rev Immunol 14: 1-27 (1996); Yang et al., J Immunol 169: 531-9 (2002); Trojan et al., Cancer Res 61: 4761-5 (2001); Dionne et al, Cancer Immuno Immunother 53: 307-14 (2004)). Alteration of peptide ligands can result in a generation of peptides with dramatically different phenotypes of the T cells and sometimes act as partial agonists or even as antagonists in course of T cell activation or TCR signal transduction. It cannot be decided whether CTLs stimulated with altered peptide work more efficiently as effectors than CTLs elicited by native peptide in vivo. However, in this experiment, an altered peptide, CXA-DRL1-9V, that activates a certain part of TCR repertoire recognizing the naturally processed wild-type epitope peptide presented by tumor cells was defined. A further important point is that this altered peptide could elicit native peptide specific CTLs more frequently and abundantly than the wild-type peptide. Native peptide specific CTLs were generated in three of the four individuals upon stimulations with this altered peptide, whereas the wild-type peptide induced CTLs in only one healthy volunteer. This improved induction of CTLs implicate some advantages in clinical application, and provides an option in clinical investigations. In other words, the potentiality of anchor-modified peptide was demonstrated.

(13) Expression and Characterization of Novel Human Gene GCUD1

Figure 13:
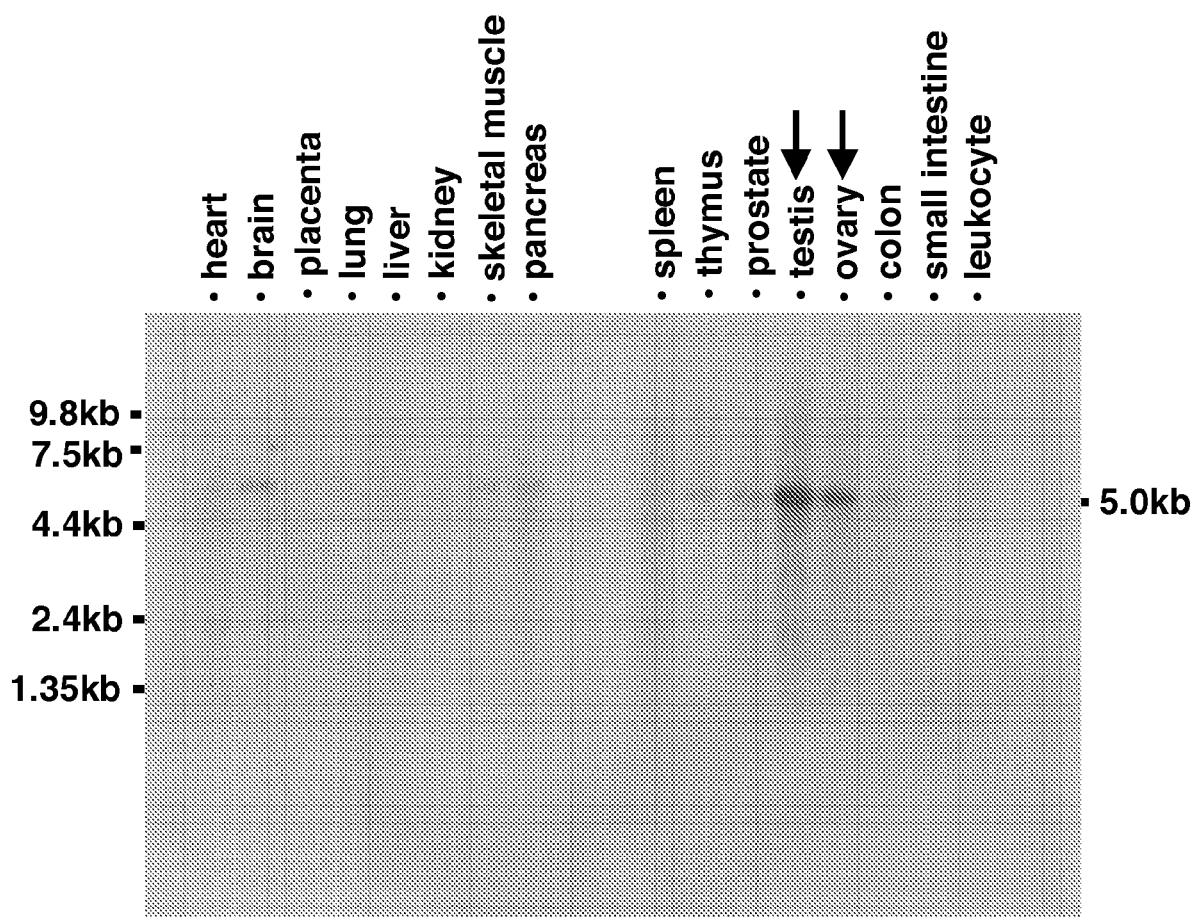
FIG. 13 is a photograph depicting the result of Northern-blot analysis of GCUD1 in various human tissues. The transcript of GCUD1 is approximately 5.0-kb by size.

Multi-tissue Northern-blot analysis using GUCD1 cDNA as a probe showed a 5.0-kb transcript that was specifically expressed in testis, ovary, and brain (FIG. 13). Although the nucleotide sequence of KIAA0913 (GenBank Accession Number: XM-014766), corresponding to GCUD1, consisted of 4987 nucleotides, RT-PCR experiments using testis, ovary, and cancer tissues revealed a transcript that consisted of 4987 nucleotides containing an open reading frame of 1245 nucleotides (SEQ ID NO: 3) (GenBank Accession Number: AB071705). Furthermore, the genomic sequence corresponding to GUCD1 was searched in genomic databases to find a draft sequence assigned to chromosomal band 7p14 (GenBank Accession Number: NT_007819). Comparison between the cDNA sequence and the genomic sequence revealed that the GUCD1 gene consisted of 8 exons.

(14) Subcellular Localization of GCUD1

Figure 14:
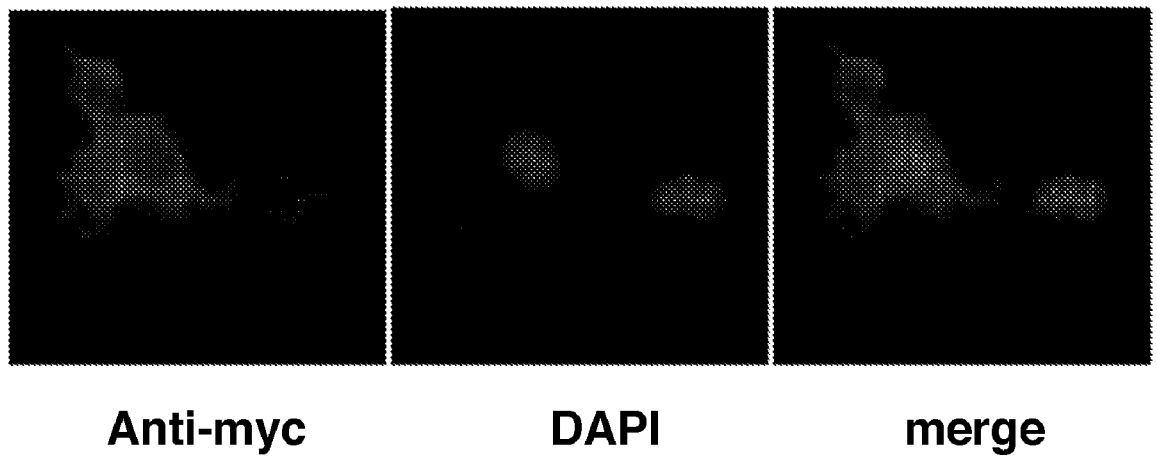
FIG. 14 shows a photograph depicting the subcellular localization of GCUD1 observed by immunocytochemistry of cells transfected with pcDNA3.1myc/His-GCUD1. cMyc-tagged GCUD1 protein expressed from the plasmid localized in the cytoplasm.

The entire coding region corresponding to GCUD1 was cloned into pcDNA3.1 myc/His vector and the construct was transiently transfected into COS7 cell. Immunocytochemical staining of the COS7 cell revealed that the tagged-GCUD1 protein was present in the cytoplasm (FIG. 14).

(15) Effect of GCUD1 on Cell Growth

Figure 15:
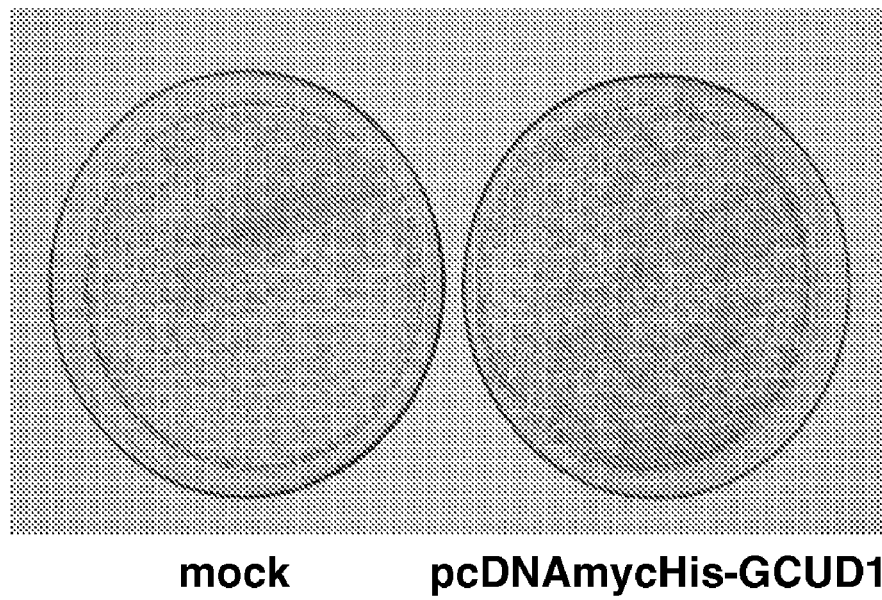
FIG. 15 is a photograph showing the growth-promoting effect of GCUD1 on NIH3T3 cells examined by colony formation assays.

To analyze the effect of GCUD1 on cell growth, a colony-formation assay was conducted by transfecting NIH3T3 cells with a plasmid expressing GCUD1 (pcDNA3.1myc/His-GCUD1). Compared with a control plasmid (pcDNA3.1myc/His-LacZ), pcDNA3.1myc/His-GCUD1 induced markedly more colonies in NIH3T3 cells (FIG. 15). This result was confirmed by three independent experiments.

(16) Growth Suppression of Gastric Cancer Cells by Antisense S-Oligonucleotides Designated to Reduce Expression of GCUD1

Figure 16:
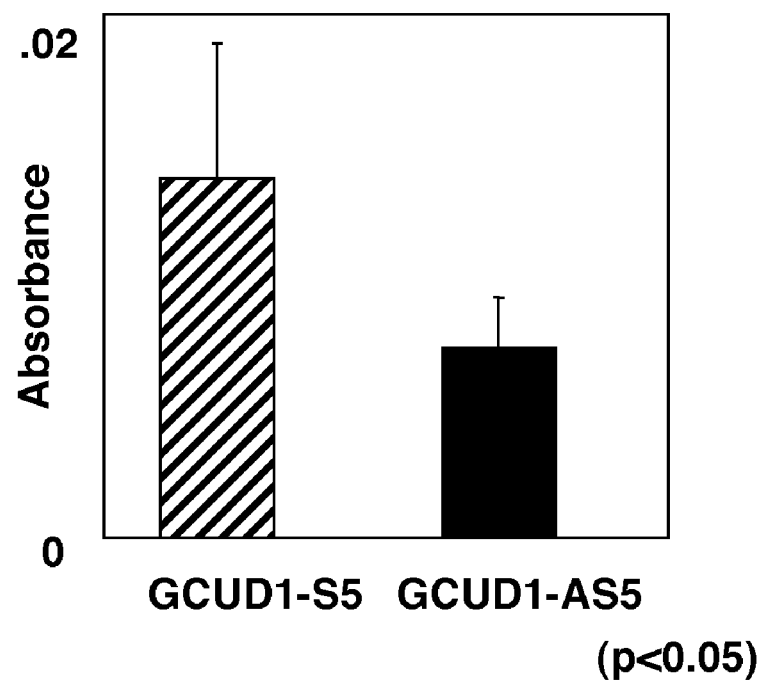
FIG. 16 depicts the growth-inhibitory effect of antisense S-oligonucleotides designated to suppress GCUD1 on MKN-28 cells. GCUD1-AS5 and GCUD1-AS8 were revealed to suppress the growth of MKN-28 cells.
Figure 16:
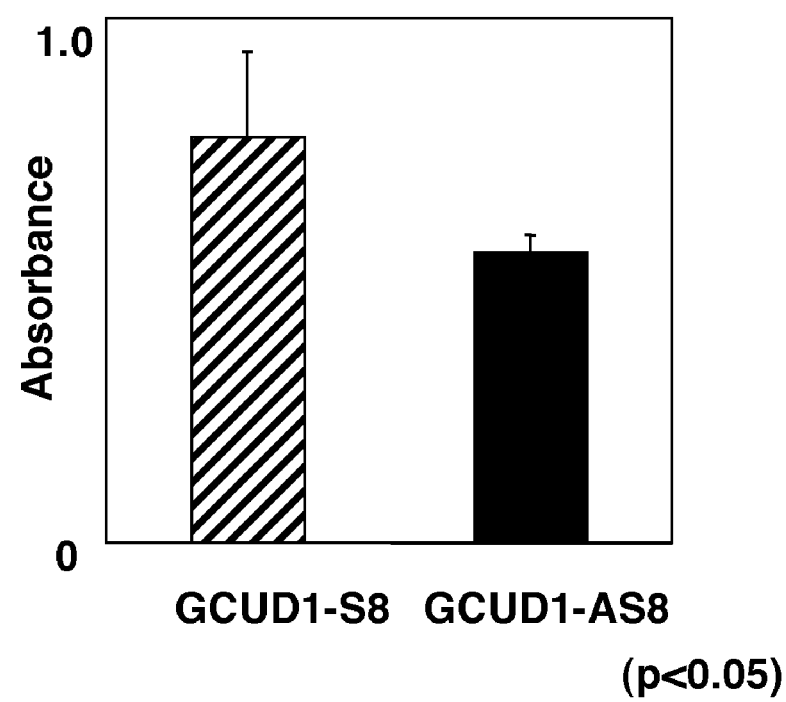

To test whether the suppression of GCUD1 may result in cell death of gastric cancer cells, various antisense S-oligonucleotides designed to suppress the expression of GCUD1 were synthesized. Six days after transfection of the respective antisense S-oligonucleotides, viability of transfected cells was measured by MTT assay. Viable cells transfected with antisense S-oligonucleotides (GCUD1-AS5 or -AS8) were markedly fewer than those transfected with control S-oligonucleotides (GCUD1-S5 or -S8) in MKN-28 cells (FIG. 16). This result was confirmed by three independent experiments. Similar result was observed with MKN-1 cells.

(17) Preparation of Anti-GCUD1 Antibody

Figure 17:
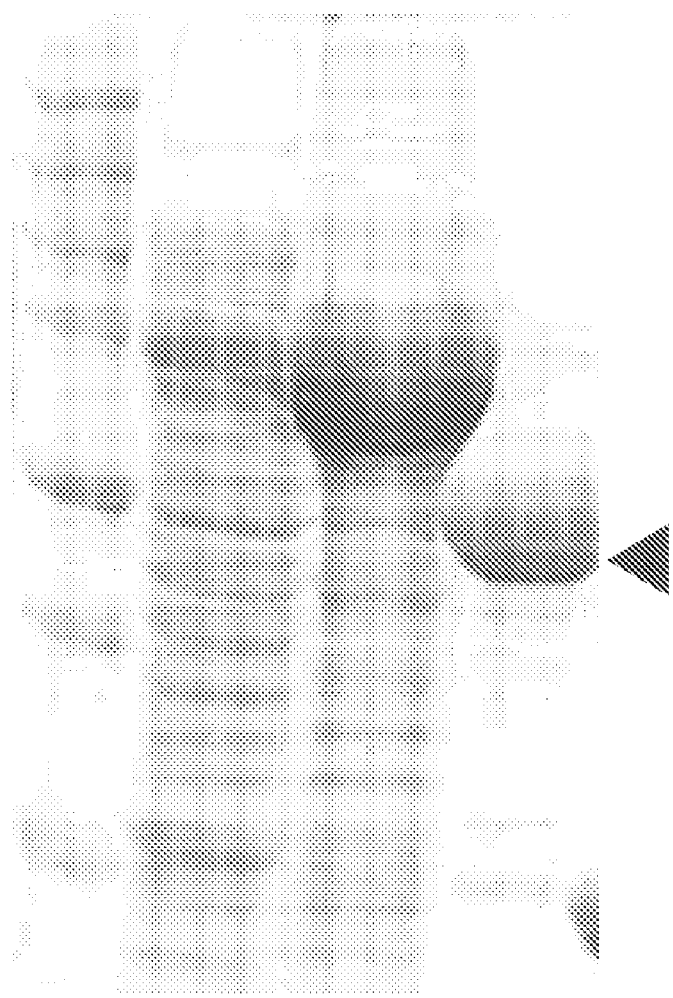
FIG. 17 depicts a photograph showing the purification of recombinant GCUD1 protein.
Figure 18:
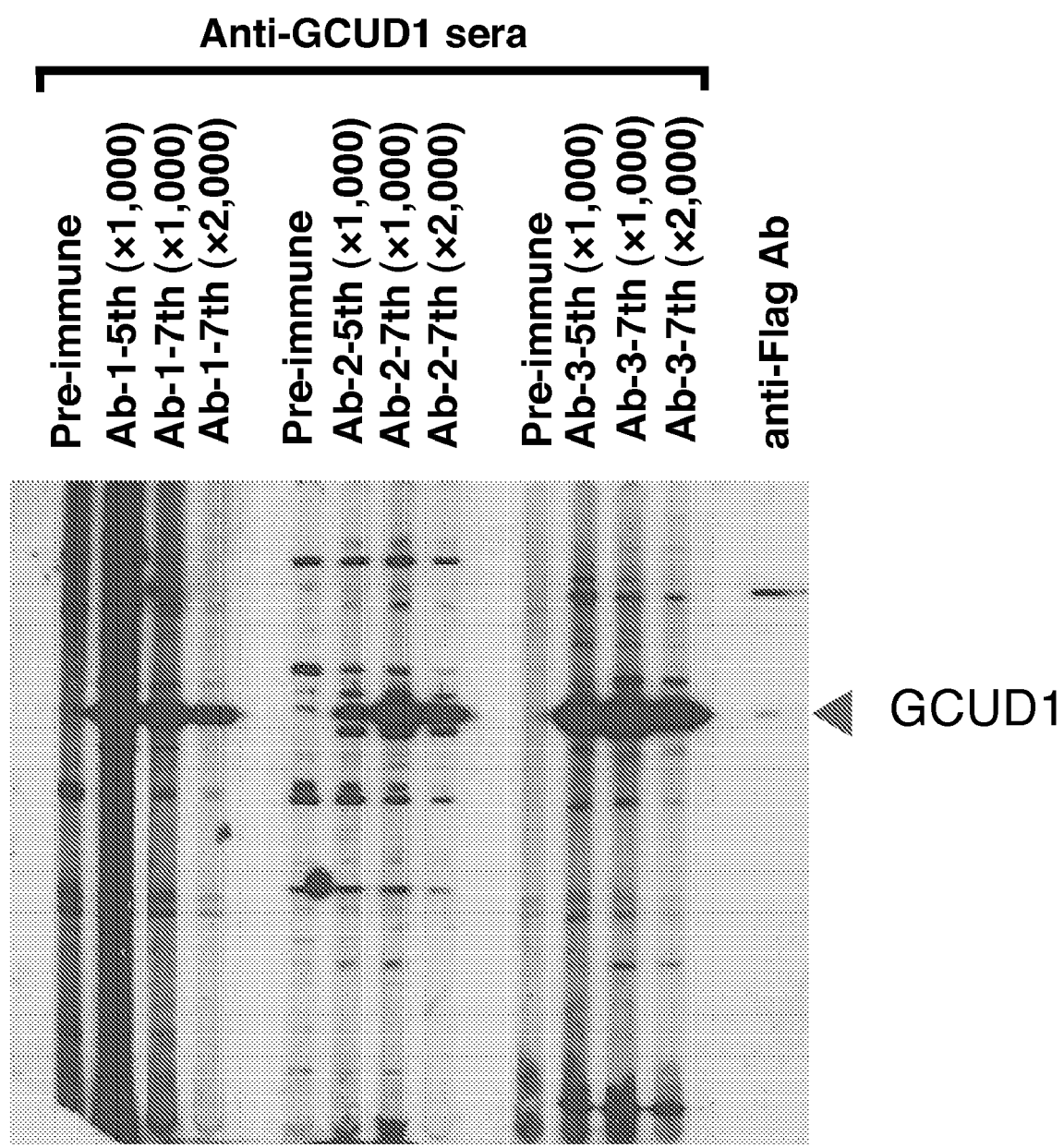
FIG. 18 depicts a photograph demonstrating the result of immunoblot analysis of cells expressing exogenous Flag-tagged GCUD1 protein with anti-GCUD1 antiserum or anti-Flag antibody.

To examine the expression and explore the function of GCUD1, antiserum against GCUD1 was prepared. Recombinant protein of GCUD1 was extracted and purified from bacterial cells expressing GST-GCUD1 fusion protein (FIG. 17). The recombinant protein was used for immunization of three rabbits. Immunoblotting with anti-GCDU1 sera but not pre-immune sera showed a 47 kD band of FLAG-tagged GCUD1, which was almost identical by size to that detected with anti-FLAG antibody (FIG. 18).

(18) Prediction of Candidate Peptides for CTLs Derived from GCUD1

Table 3 (GCUD1) shows the candidate peptides (SEQ ID NOs: 155-194) in order of high binding affinity. Forty peptides in total were selected and examined as described below.

TABLE 3

Prediction of candidate peptides derived from GCUD1

| Rank | sequence | Score | Position |
|---|---|---|---|
| HLA-A*0201 9 mer | | | |
| 1 | SIFKPFIFV | 369.77 | 303 |
| 2 | WLWGAEMGA | 189.68 | 75 |
| 3 | IMISRPAWL | 144.26 | 68 |
| 4 | LLGMDLVRL | 83.527 | 107 |
| 5 | FIFVDDVKL | 49.993 | 308 |
| 6 | VCIDSEFFL | 31.006 | 265 |
| 7 | KPFIFVDDV | 25.18 | 306 |
| 8 | IVDRDEAWV | 22.761 | 159 |
| 9 | TLRDKASGV | 21.672 | 257 |
| 10 | KMDAEHPEL | 21.6 | 196 |
| 11 | ALDVIVSLL | 19.653 | 126 |
| 12 | YAQSQGWWT | 19.639 | 207 |
| 13 | KLRSTMLEL | 13.07 | 367 |
| 14 | YLIVDRDEA | 11.198 | 157 |
| 15 | AAPPSYCFV | 7.97 | 3 |
| 16 | GMDLVRLGL | 6.171 | 109 |
| 17 | KVTEGVRCI | 6.026 | 179 |
| 18 | CIDSEFFLT | 4.517 | 266 |
| 19 | TVQTMMNTL | 4.299 | 250 |
| 20 | EMGANEHGV | 3.767 | 80 |
| HLA-A*0201 10 mer | | | |
| 1 | FIFVdDVKLV | 374.37 | 308 |
| 2 | LIVDrDEAWV | 366.61 | 158 |
| 3 | FLTTaSGVSV | 319.94 | 272 |
| 4 | TMLEIEKQGL | 234.05 | 371 |

TABLE 3-continued

Prediction of candidate peptides derived from GCUD1

| Rank | sequence | Score | Position |
|---|---|---|---|
| 5 | ALLGmDLVRL | 181.79 | 106 |
| 6 | AIMIsRPAWL | 59.775 | 67 |
| 7 | GVCIdSEFFL | 59.628 | 264 |
| 8 | KLVPkTQSPC | 17.388 | 315 |
| 9 | FNFSeVFSPV | 14.682 | 220 |
| 10 | YISIdQVPRT | 10.841 | 56 |
| 11 | GEGEfNFSEV | 10.535 | 216 |
| 12 | WAAEkVTEGV | 8.927 | 175 |
| 13 | VLPQnRSSPC | 8.446 | 281 |
| 14 | AAAPpSYCFV | 7.97 | 2 |
| 15 | TMMNtLRDKA | 6.505 | 253 |
| 16 | EVGDIFYDCV | 5.227 | 397 |
| 17 | AEMGaNEHGV | 5.004 | 79 |
| 18 | GLVVfGKNSA | 4.968 | 20 |
| 19 | QLSLtTKMDA | 4.968 | 190 |
| 20 | RSIFkPFIFV | 4.745 | 302 |

Figure 19:
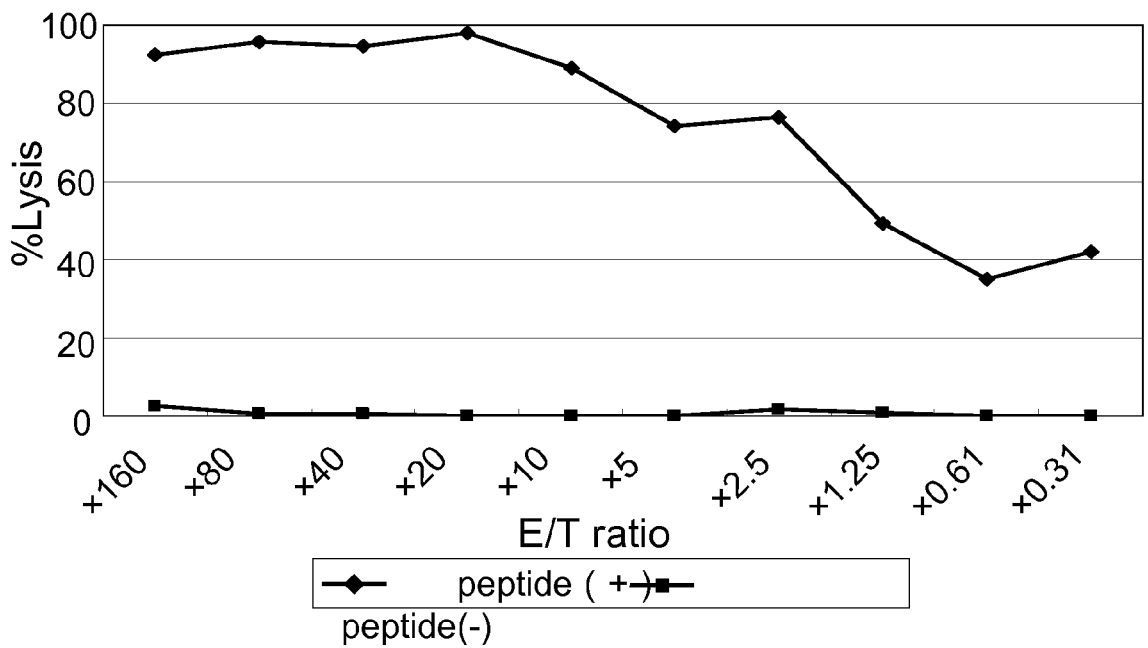
FIG. 19 depicts the peptide specific cytotoxicity of CTL line raised by GCUD1-196 or GCUD1-272 stimulation. The CTL line showed high cytotoxic activity on target cells (T2) pulsed with GCUD1-196 or GCUD1-272, whereas no significant cytotoxic activity was detected on the same target cells (T2) pulsed without peptides.
Figure 19:
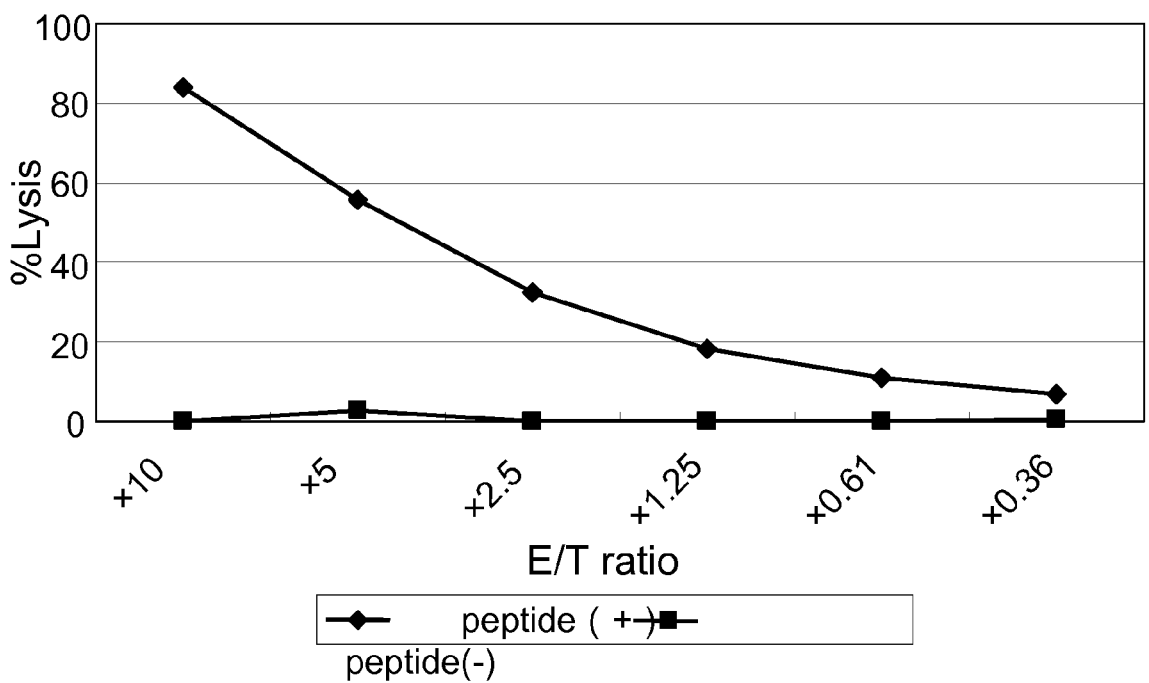

(19) Stimulation of T Cells and Establishment of CTL Clones Using Candidate Peptides Lymphoid cells were cultured using the above candidate peptides of (18) derived from GCUD1 in the manner described under the item of "Materials and Methods". Resulting lymphoid cells showing detectable cytotoxic activity were expanded, and CTL clones were established. CTL clones were propagated from the CTL lines described above using the limiting dilution methods. CTL clones induced with GCUD1-196 (KMDAEHPEL) (SEQ ID NO: 164) and GCUD1-272 (FLTTASGVSV) (SEQ ID NO: 177) showed higher cytotoxic activities against the target pulsed with peptides than the targets not pulsed with any peptide. Cytotoxic activity of these CTL clones is shown in FIG. 19. Each CTL clone had very potent cytotoxic activity against the peptide-pulsed target without showing any cytotoxic activity against the non-pulsed target.

Figure 20:
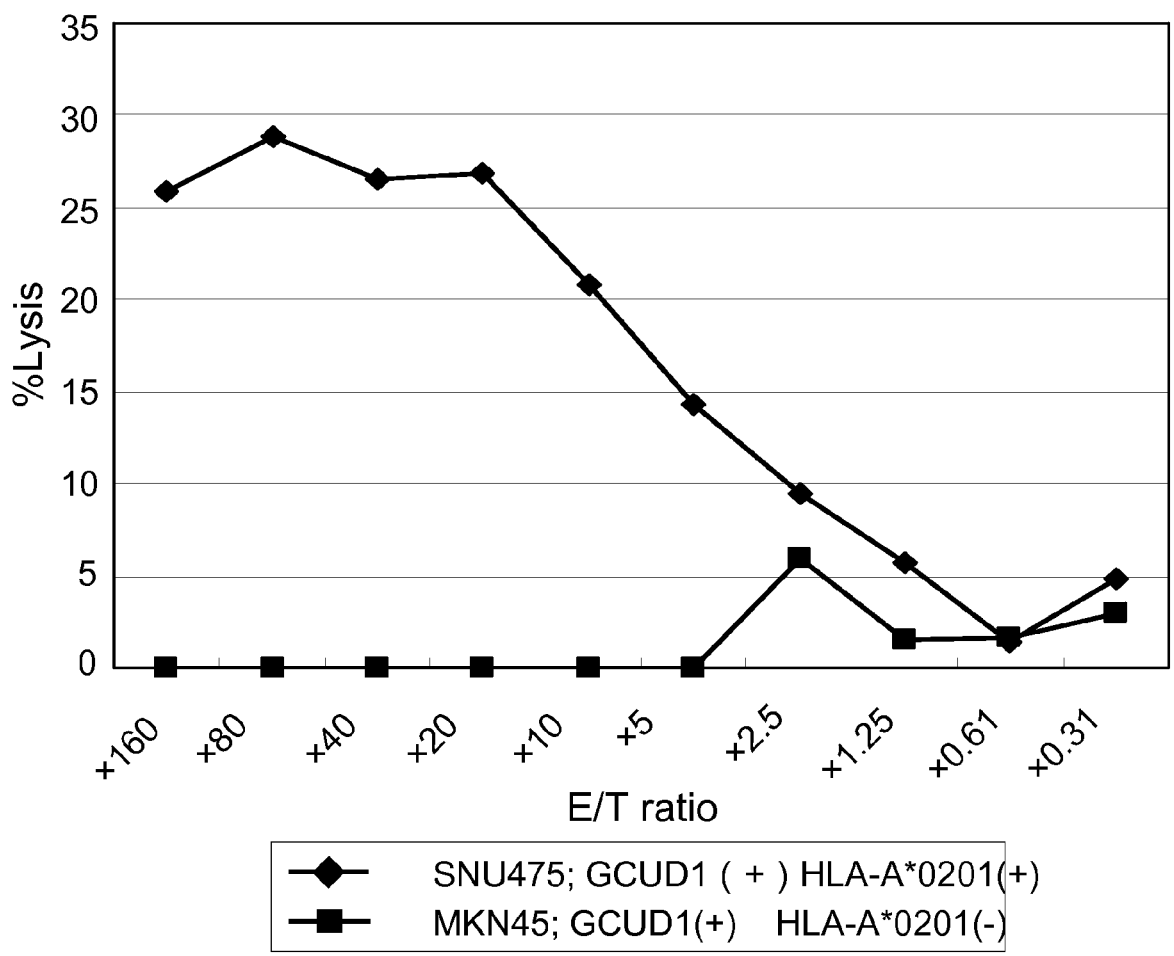
FIG. 20 depicts the cytotoxic activity of GCUD1-196 CTL Clone on SNU475 and MKN45. GCUD1-196 CTL Clone showed high cytotoxic activity on SNU475 that expresses both GCUD1 and HLA-A*0201. On the other hand, GCUD1-196 CTL Clone showed no significant cytotoxic activity on MKN45, which expresses GCUD1 but not HLA-A*0201.

(20) Cytotoxic Activity Against Tumor Cell Lines Endogenously Expressing GCUD1 as a Target The CTL clones raised against predicted peptides were examined for their ability to recognize and kill tumor cells endogenously expressing GCUD1. FIG. 20 shows the results of CTL Clone 23 raised against GCUD1-196 (SEQ ID NO: 164). CTL Clone 23 showed potent cytotoxic activity against SNU475 which expresses GCUD1 and HLA-A*0201, however, not against MKN45 that expresses GCUD1 but not HLA-A*0201.

(21) Specificity of Established CTLs

Figure 21:
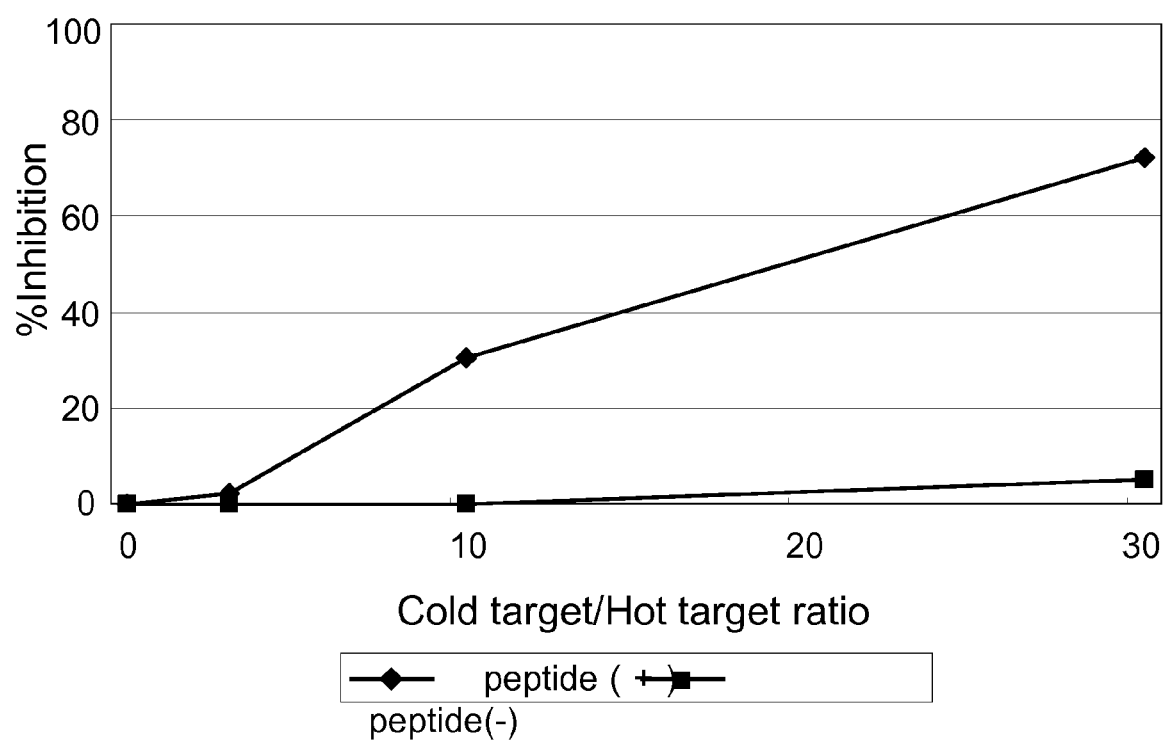
FIG. 21 depicts the result of the cold target inhibition assay. GCUD1-196 CTL Clone specifically recognizes GCUD1-196 in an HLA-A*0201 restricted manner. SNU475 labeled with Na$_2$$^{51}$CrO$_4$ was prepared as a hot target, while GCUD1-196 peptide-pulsed T2 (Peptide+) was used as a cold target (Inhibitors). E/T ratio was fixed to 20. The cytotoxic activity on SNU475 was inhibited by the addition of T2 pulsed with the identical peptide, while almost no inhibition was observed by the addition of T2 without peptide pulse.

Cold target inhibition assay was also performed to confirm the specificity of GCUD1-196 CTL Clone. SNU475 cells labeled with $^{51}$Cr were used as a hot target, while T2 cells pulsed with GCUD1-196 were used without $^{51}$Cr labeling as a cold target. Specific cell lysis against SNU475 cells was significantly inhibited, when T2 pulsed with GCUD1-196 (SEQ ID NO: 164) was added in the assay at various ratios (FIG. 21). The results are indicated as the percentage of specific lysis at an E/T ratio of 20.

Figure 22:
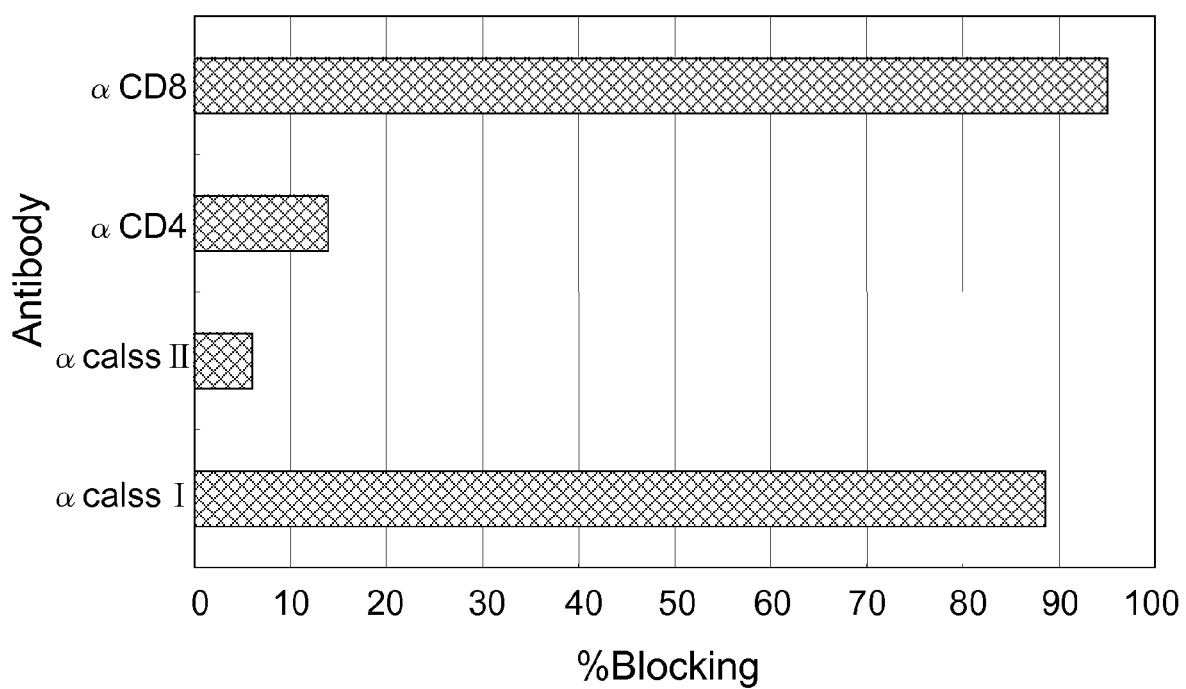
FIG. 22 depicts the result of the blocking assay showing the effect of antibodies raised against HLA-Class I, HLA-Class II, CD4, and CD8 on the cytotoxic activity of GCUD1-196 CTL Clone. GCUD1-196 CTL Clone showed cytotoxic activity in HLA-Class I and CD8 restricted manner. To examine the characteristics of CTL clone raised with GCUD1 peptide, antibodies against HLA-Class I, HLA-Class II, CD4, and CD8 were tested for their ability to inhibit the cytotoxic activity. The horizontal axis reveals % inhibition of the cytotoxicity. The cytotoxicity of CTL clone on SNU475 targets was significantly reduced when anti-class I and CD8 antibodies were used. This result indicates that the CTL clone recognizes the GCUD1 derived peptide in a HLA Class I and CD8 dependent manner.

In the interest of the GCUD1-196 (SEQ ID NO: 164) CTL clone, to examine its characteristics, antibodies against HLA-Class I, HLA-Class II, CD4, and CD8 were tested for their capacity to inhibit its cytotoxic activity. The cytotoxicity of the CTL clone against SNU475 cells was significantly inhibited by the use of anti-HLA-Class I antibody and anti-CD8 antibody (FIG. 22), indicating that the CTL clone recognizes the GCUD1 derived peptide in an HLA-Class I and CD8 dependent manner.

(22) Induction of CTLs by Anchor-modified Peptides (GCUD1)

The newly defined epitope, GCUD1-196 (SEQ ID NO:164) showed relatively low binding score. Therefore, to increase its binding ability with MHC class I molecule, altered peptides were made from the GCUD1-196 peptide.

As mentioned above, HLA-A*0201 allele-binding peptides are frequently nonamers whose amino acids at position two and nine are considered primary anchor residues that solely bind to the HLA class I peptide-binding cleft but do not contact with TCR. According to the HLA-A2 antigen motif previously reported by Smith et al. (Smith et al., Mol Immunol 35: 1033-43 (1998)), leucine (Leu) and isoleucine (Iso) have proven to be an optimal anchor residue at position 2 that enhance the binding affinity of the peptide for the HLA-A*0201 molecule. Similarly, valine (Val) at position 9 was also preferred for nonamer peptides.

Thus, two anchor-modified altered peptides of GCUD1-196 with amino acid substitutions that contain the optimal HLA-A*0201 allele-binding amino acids as anchor residues to increase the binding affinity to HLA-A*0201 molecules were designed and synthesized.

TABLE 4

Anchor modified altered peptides; modification of GCUD1-196 wild-type peptide with increased binding affinity for HLA-A*0201 molecule

| Peptide | Amino Acid Sequence | Binding Score** | SEQ ID NO |
|---|---|---|---|
| wild-type | KMDAEHPEL | 21.6 | 164 |
| anchor-modified-1 | KLDAEHPEL | 29.9 | 197 |
| anchor-modified-2 | KMDAEHPEV | 70.3 | 198 |
| anchor-modified-3 | KLDAEHPEV | 97.3 | 199 (N.S.*) |

*N.S.: Not synthesized due to its hydrophobicity of its amino acid sequence.
*Binding Score: High scores indicate high affinity to MHC class I molecules. The binding scores of these altered peptides were calculated by the BIMAS's epitope prediction algorithm.

Figure 23:
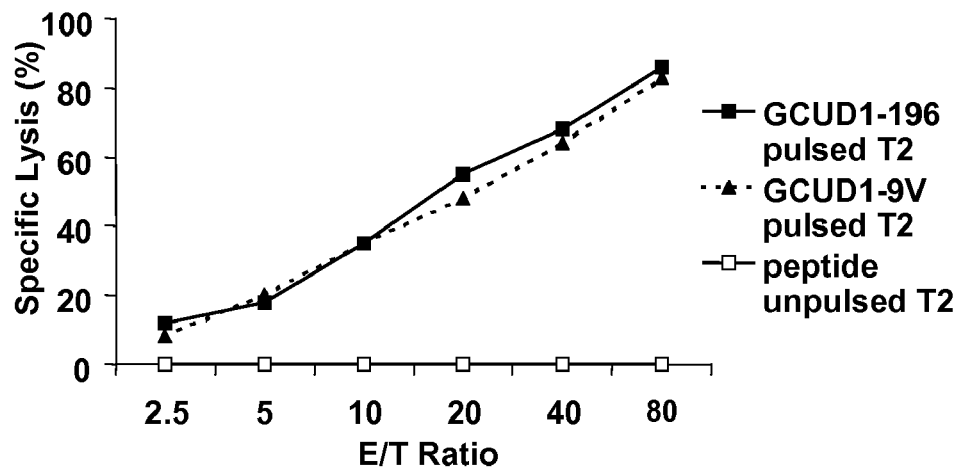
FIG. 23 depicts the cytotoxic activities of CTLs induced with anchor modified peptide GCUD1-9V. The cytotoxic activities of GCUD1-9V induced CTL line 3 (A) and CTL clone 16 (B) against peptide pulsed T2 cells (HLA-A*0201 positive cell line) and tumor cell lines were examined by 4h $^{51}$Cr release assay. Both CTL line 3 and CTL clone 16 recognized not only GCUD1-9V but also the parental peptide GCUD1-196, equally or more sharply at a low E/T ratio in CTL clone 16, and killed SNU475 cells expressing naturally processed wild-type peptide GCUD1-196 on the HLA-A*0201 molecule (C).
Figure 23:
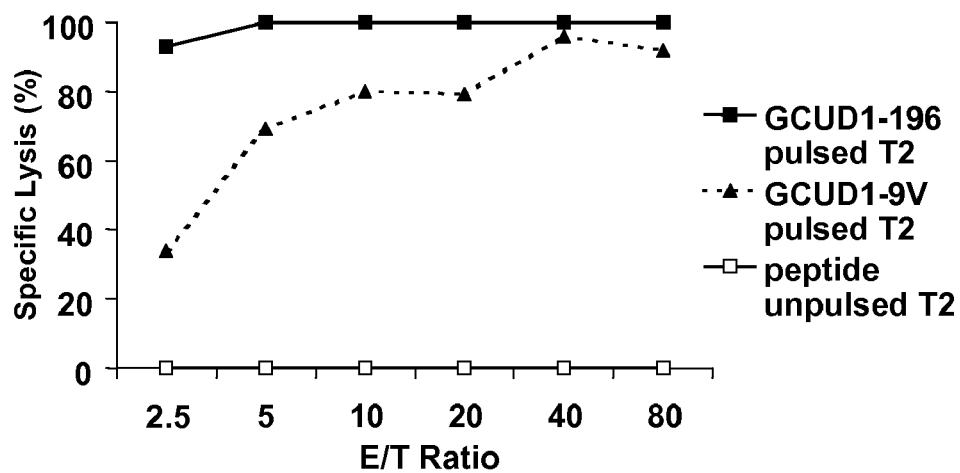
Figure 23:
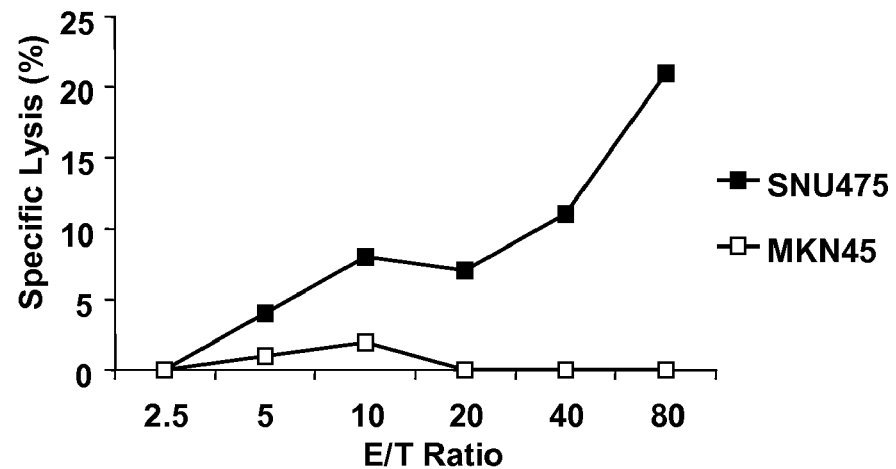

The binding score of these peptides were calculated based on the BIMAS's epitope prediction algorithm as previously described, and all three altered peptides received higher HLA-A*0201-binding scores compared to the wild-type GCUD1 peptide. These anchor-modified peptides were tested for their ability to elicit CTLs, and moreover, whether the induced CTLs recognize the parental GCUD1-196 peptide on T2 in addition to the altered peptides. After CTL induction with GCUD1-9V (SEQ ID NO:198) and GCUD1-2L (SEQ ID NO:197), CTL line 3 and CTL clone 16 were obtained via the stimulation with GCUD1-9V peptide shown in FIGS. 23A and 23B. These CTLs cross-reacted with the wild-type GCUD1-196 peptide on T2 cells, and also killed tumor cell line SNU475 that endogenously express naturally processed GCUD1-196 peptide, as measured by $^{51}$Cr release assay shown in FIG. 23C.

Notably, GCUD1-196 specific CTLs were generated in three of the four HLA-A*0201 positive individuals by GCUD1-9V peptide (SEQ ID NO:198), whereas GCUD1-196 wild-type peptide specific responses were observed in one of the four individuals when GCUD1-196 was used for the CTL induction.

The binding score of GCUD1-196 (SEQ ID NO:164) wild-type peptide calculated by the BIMAS's prediction software was 21.6, relatively low compared to those of viral antigens or other TAAs (Bendnarek et al., J Immunol 147: 4047-53 (1991); Sette et al., J Immunol 153: 5586-92 (1994)). To increase immunogenicity of this native epitope peptide, altered peptides with anchor residue modification at position 2 or 9, replacement to optimized amino acids for HLA-A*0201, were designed and synthesized (Vierboom et al., J Immunother 21: 399-408 (1998); Irvine et al., Cancer Res 59: 2536-40 (1999); Dyall et al., J Exp Med 188: 1553-61 (1998); Muller et al., J Immunol 147: 1329-97 (1991)). CTLs raised against GCUD1-9V peptide (SEQ ID NO:198) with a binding score of 70.3 responded not only to the GCUD1-9V peptide but also to the parental wild-type peptide GCUD1-196 on T2 cells. Furthermore, these CTLs induced by the GCUD1-9V peptide also recognized the native peptide naturally processed by tumor cell. However, as mentioned above, many recent studies indicated that increased affinity for MHC class I did not necessarily correlate with increased peptide immunogenicity or ability to stimulate CTL (Clay et al., J Immunol 162: 1749-55 (1999); Dionne et al., Cancer Immuno Immunother 52: 199-206 (2003); Slansky et al., Immunity 13: 529-38 (2000); Sloan-Lancaster and Allen, Annu Rev Immunol 14: 1-27 (1996); Yang et al., Immunol 169: 531-9 (2002); Trojan et al., Cancer Res, 61: 4761-5 (2001); Dionne et al., Cancer Immuno Immunother 53: 307-14 (2004)); and alteration of peptide ligands can result in a generation of peptides with dramatically different phenotypes of the T cells, and sometimes act as partial agonists or even as antagonists in course of T cell activation or TCR signal transduction. Therefore, it cannot be decided whether CTLs stimulated with altered peptide work more efficiently as effectors than CTLs elicited by native peptide in vivo. However, in this experiment, an altered peptide, GCUD1-9V, that activates a certain part of TCR repertoire recognizing the naturally processed wild-type epitope peptide presented by tumor cells was defined. More important is that this altered peptide elicited native peptide specific CTLs more frequently and abundantly than the wild-type peptide. Three of the four individuals generated the native peptide specific CTLs by stimulations with this altered peptide, whereas the wild-type peptide induced CTLs in only one healthy volunteer. This evidence may implicate some advantages in clinical application, and an option in clinical investigations was provided by the present invention. In other words, a potential anchor-modified altered peptide was provided.

The amino acid sequences of GCUD1-196 (SEQ ID NO:164) and GCUD1-9V (SEQ ID NO:198) were subjected to BLAST's homology analysis. No peptide with high homology derived from any other known molecule was detected. These results support the fact that the identified peptides are GCUD1-specific and have little chance to possess cross-reactivity against other known molecules. This also suggests the possibility of the use of these peptides in clinical applications without unwanted adverse effects.

Figure 24:
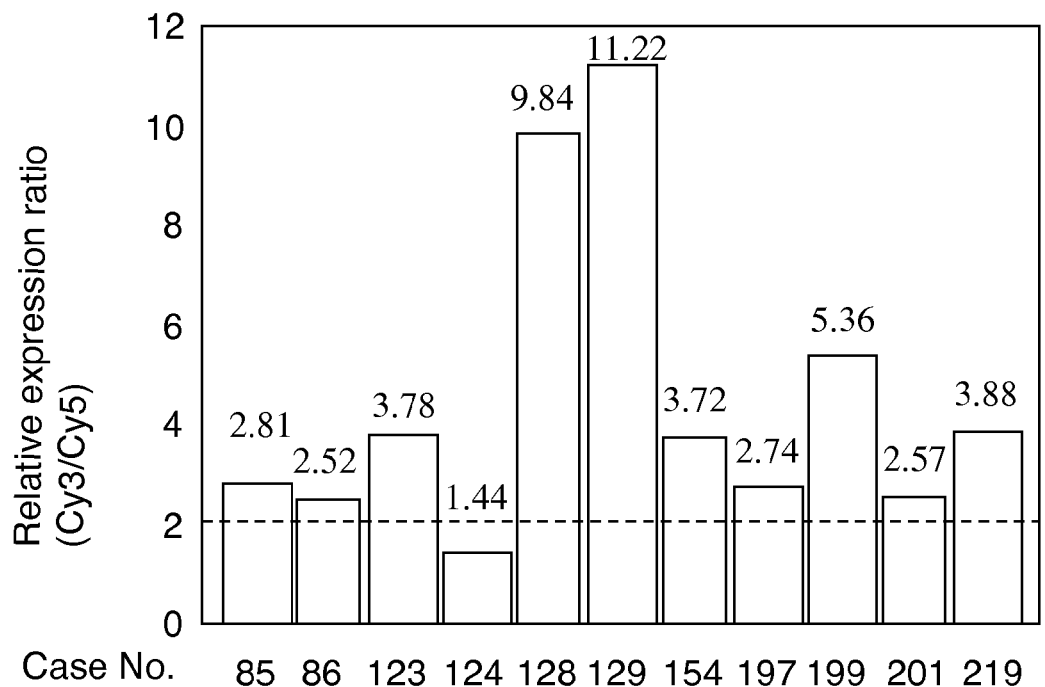
FIGS. 24a and 24b depict the expression of FLJ20315 in colon cancer.
Figure 24:
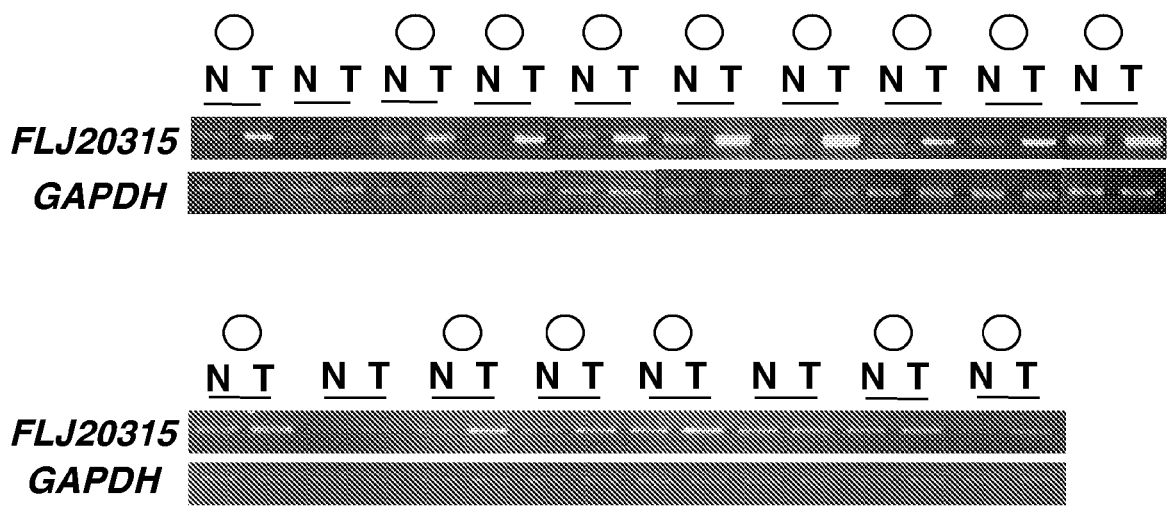

(23) Identification of Gene FLJ20315 Commonly Up-regulated in Human Colon Cancer Expression profiles of 11 colon cancer tissues were compared with non-cancerous mucosal tissues of the colon corresponding thereto using the cDNA microarray containing 23040 genes. According to this analysis, expression levels of a number of genes that were frequently elevated in cancer tissues were compared to corresponding non-cancerous tissues. Among them, a gene with an in-house accession number of B4469 corresponding to an EST (FLJ20315), Hs.18457 in UniGene cluster, was up-regulated in the cancer tissues compared to the corresponding non-cancerous mucosae at a magnification range between 1.44 and 11.22 (FIG. 24a). FLJ20315 was also up-regulated in 6 out of 18 gastric cancer cases, 12 out of 20 HCC cases, 11 out of 22 lung cancer (adenocarcinoma) cases, 2 out of 2 testicular seminomas cases and 3 out of 9 prostate cancer cases. To clarify the results of the microarray, the expression of these transcripts in additional colon cancer samples were examined by semi-quantitative RT-PCR to confirm the increase of FLJ20315 expression in 15 of the 18 tumors (FIG. 24b).

(24) Expression and Structure of RNF43

Figure 25:
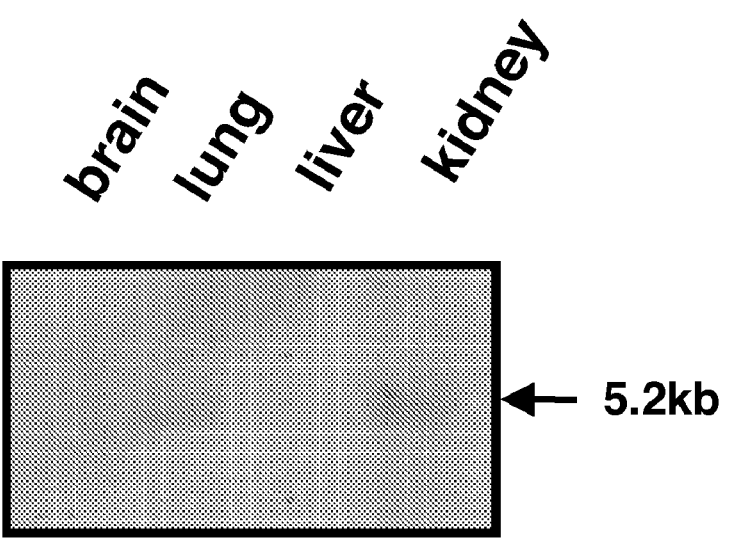
FIG. 25a depicts a photograph showing the result of fetal-tissue Northern-blot analysis of RNF43 in various human fetal tissues.
FIG. 25b depicts the predicted protein structure of RNF43.
Figure 25:
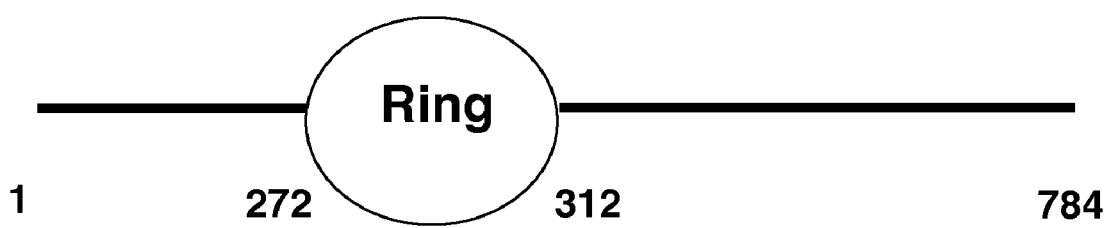

Additional homology searches of the sequence of FLJ20315 in public databases using BLAST program in National Center for Biotechnology Information identified ESTs including XM_097063, BF817142, and a genomic sequence with a GenBank Accession Number NT_010651 assigned to chromosomal band 17pter-p13.1. As a result, an assembled sequence of 5345 nucleotides containing an open reading frame of 2352 nucleotides (SEQ ID NO: 5) encoding a 783-amino-acid protein (SEQ ID NO: 6) (GenBank Accession Number: AB081837) was obtained. The gene was dubbed RNF43 (Ring finger protein 43). The first ATG was flanked by a sequence (AGCATGC) that agreed with the consensus sequence for initiation of translation in eukaryotes, and by an in-frame stop codon upstream. Comparison of the cDNA and the genomic sequence revealed that this gene consisted of 11 exons. Northern-blot analysis using human adult Multiple-Tissue Northern-blots with a PCR product of RNF43 as a probe failed to detect any band (data not shown). However, a 5.2 kb-transcript was detected to be expressed in fetal lung and fetal kidney using a human fetal tissue Northern-blot with the same PCR product as a probe (FIG. 25a). A search for protein motifs with the Simple Modular Architecture Research Tool (SMART) revealed that the predicted protein contained a Ring finger motif (codons 272-312) (FIG. 25b).

(25) Subcellular Localization of Myc-tagged RNF43 Protein

Figure 26:
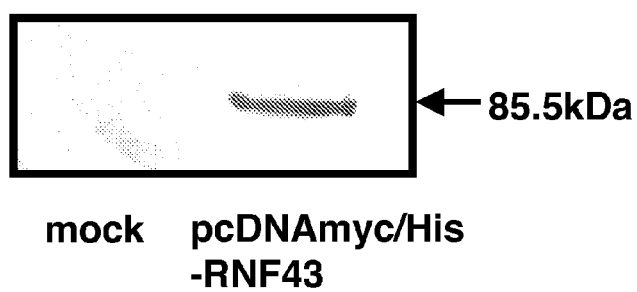
FIGS. 26a and 26b show photographs depicting the subcellular localization of myc-tagged RNF43 protein.
Figure 26:
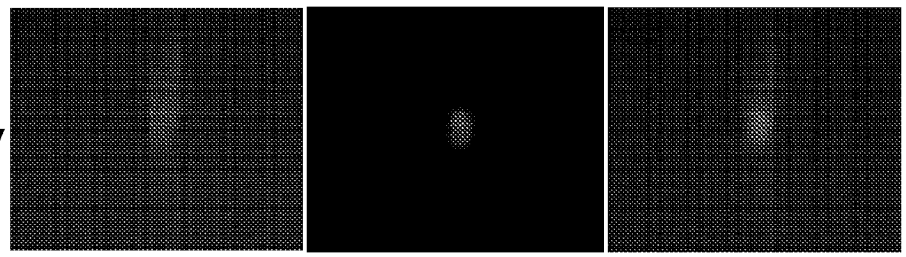
Figure 26:
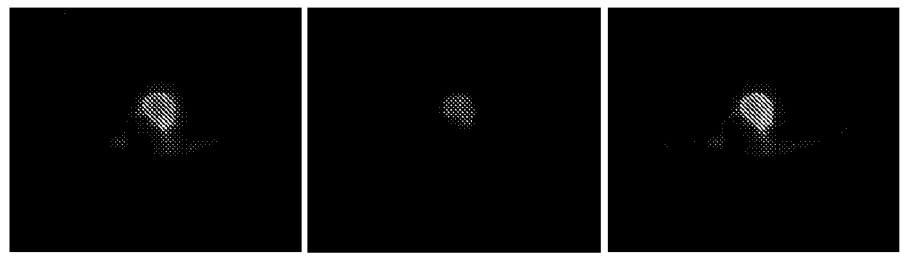

To investigate the subcellular localization of RNF43 protein, a plasmid expressing myc-tagged RNF43 protein (pDNAmyc/His-RNF43) was transiently transfected into COS7 cells. Western-blot analysis using extracts from the cells and anti-myc antibody revealed a 85.5-KDa band corresponding to the tagged protein (FIG. 26a). Subsequent immunohistochemical staining of the cells with the same antibody indicated the protein to be mainly present in the nucleus (FIG. 26b). Similar subcellular localization of RNF43 protein was observed in SW480 human colon cancer cells.

(26) Effect of RNF43 on Cell Growth

Figure 27:
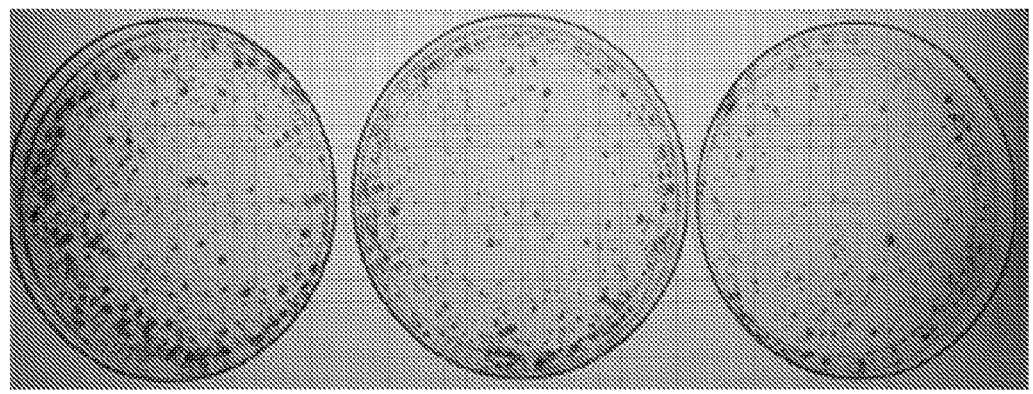
FIG. 27a to 27c depicts the effect of RNF43 on cell growth.
Figure 27:
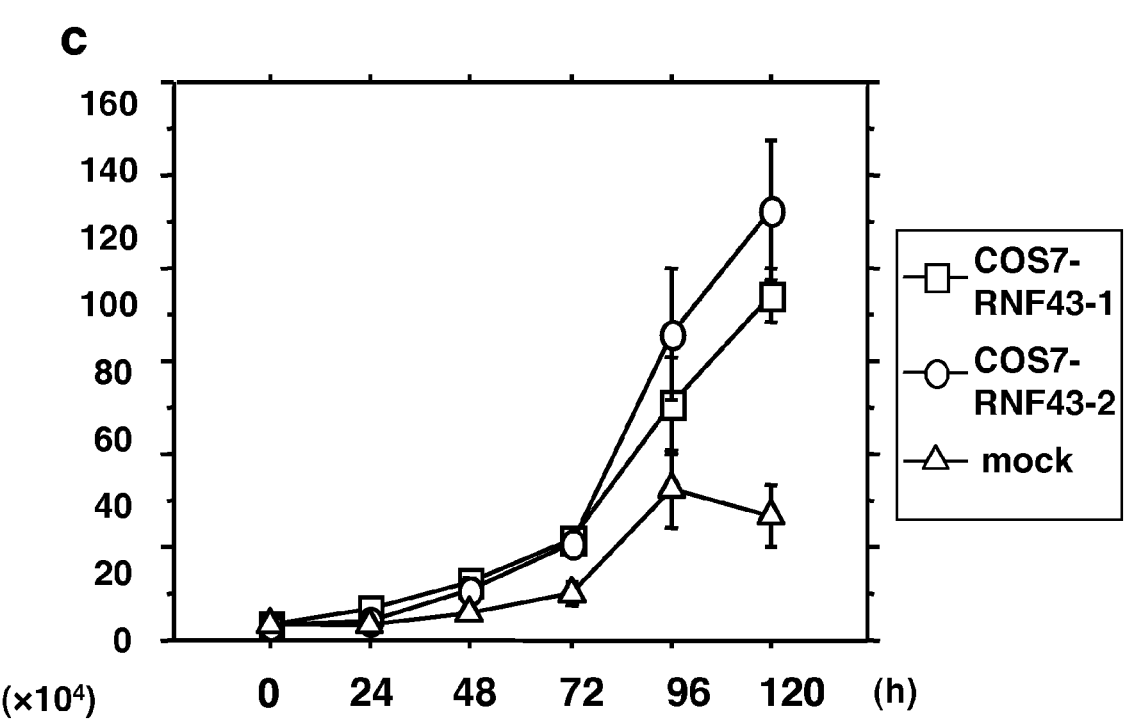

A colony-formation assay was conducted by transfecting NIH3T3 cells with a plasmid expressing RNF43 (pcDNA- RNF43). Cells transfected with pcDNA-RNF43 produced significantly more number of colonies than control cells (FIG. 27a). Increased activity of colony formation by RNF43 was also shown in SW480 cells wherein the endogenous expression of RNF43 was very low (data not shown). To further investigate this growth-promoting effect, COS7 cells that stably express exogenous RNF43 (COS7-RNF43) were established (FIG. 27b). The growth rate of COS7-RNF43 cells was significantly higher than that of COS7-mock cells in culture media containing 10% FBS (FIG. 27c).

(27) Growth Suppression of Colon Cancer Cells by Antisense S-oligonucleotides Designated to Reduce Expression of RNF43

Figure 28:
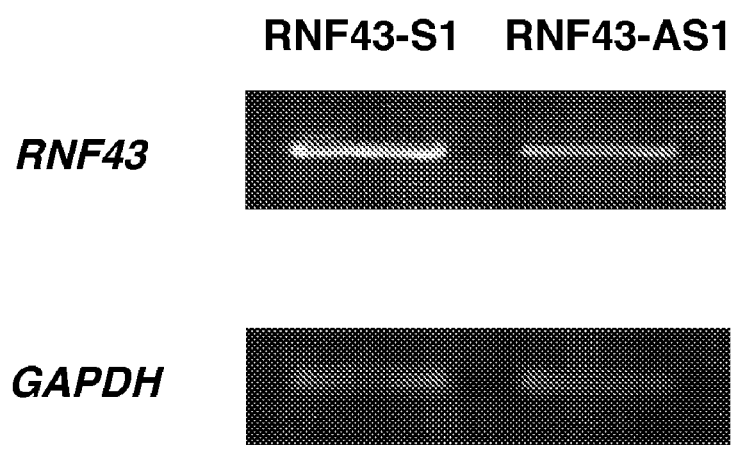
FIGS. 28a and 28b depict the growth-inhibitory effect of antisense S-oligonucleotides designed to suppress RNF43.
Figure 28:
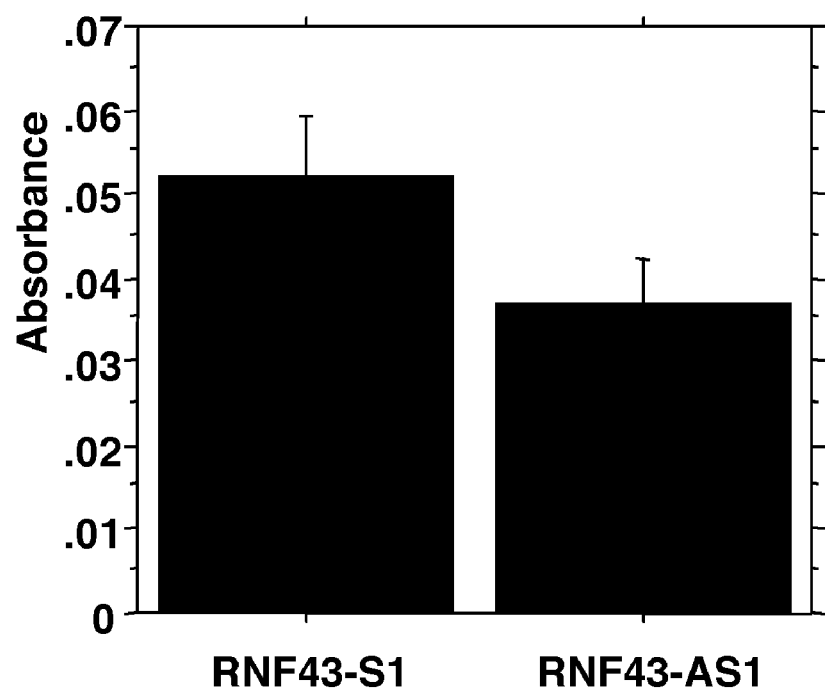

To test whether the suppression of RNF43 expression may result in growth retardation and/or cell death of colon cancer cells, five pairs of control and antisense S-oligonucleotides corresponding to RNF43 were synthesized and transfected into LoVo colon cancer cells, which show a higher level of RNF43 expression among the examined 11 colon cancer cell lines. Among the five antisense S-oligonucleotides, RNF43-AS1 significantly suppressed the expression of RNF43 compared to control S-oligonucleotides (RNF43-S1) 12 hours after transfection (FIG. 28a). Six days after transfection, number of surviving cells transfected with RNF43-AS1 was significantly fewer than those transfected with RNF43-S1 suggesting that the suppression of RNF43 expression reduced growth and/or survival of transfected cells (FIG. 28b). Consistent results were obtained in three independent experiments.

Figure 29:
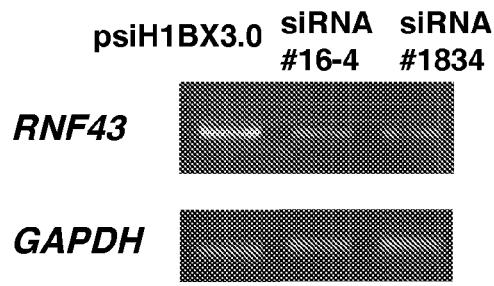
FIG. 29A to 29C depict the growth suppressive effect of RNF43-siRNAs.
Figure 29:
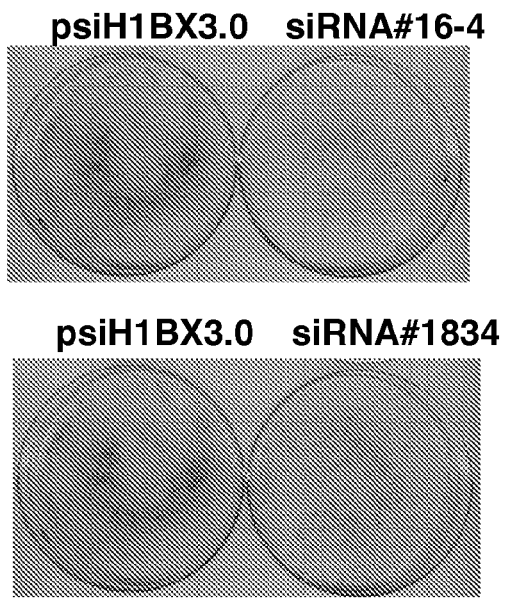
Figure 29:
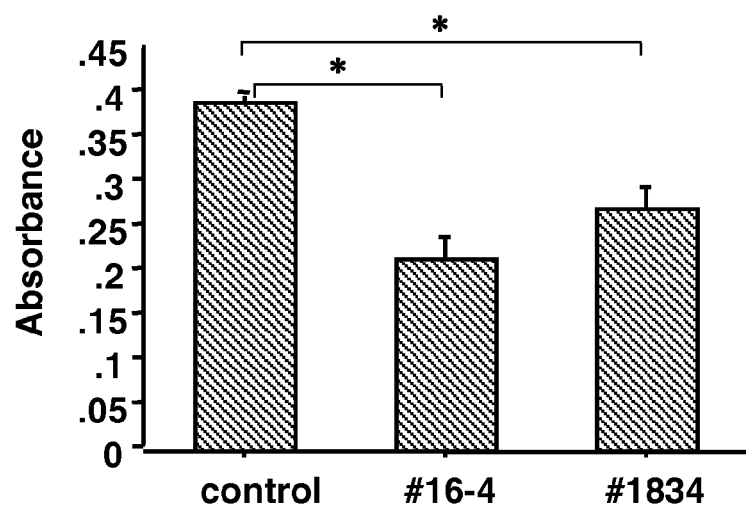

(28) Construction of Plasmids Expressing RNF43 siRNAs and their Effect on Growth of Colon Cancer Cells In mammalian cells, small interfering RNA (siRNA) composed of 20 or 21-mer double-stranded RNA (dsRNA) with 19 complementary nucleotides and 3' terminal complementary dimmers of thymidine or uridine, has been recently shown to have a gene specific gene silencing effect without inducing global changes in gene expression. Therefore, plasmids expressing various RNF43-siRNAs were constructed to examine their effect on RNF43 expression. Among the various RNF43-siRNAs, psiH1BX-RNF16-4 and psiH1BX-RNF1834 significantly suppressed the expression of RNF43 in SNUC4 cells (FIG. 29A). To test whether the suppression of RNF43 results in growth suppression of colon cancer cells, SNUC4 cells were transfected with psiH1BX-RNF16-4, psiH1BX-RNF1834 or mock vector. In line with the data of antisense S-oligonucleotides, the number of viable cells transfected with psiH1BX-RNF16-4 or psiH1BX-RNF1834 was fewer than the number of viable control cells (FIGS. 29B and 29C).

Figure 30:
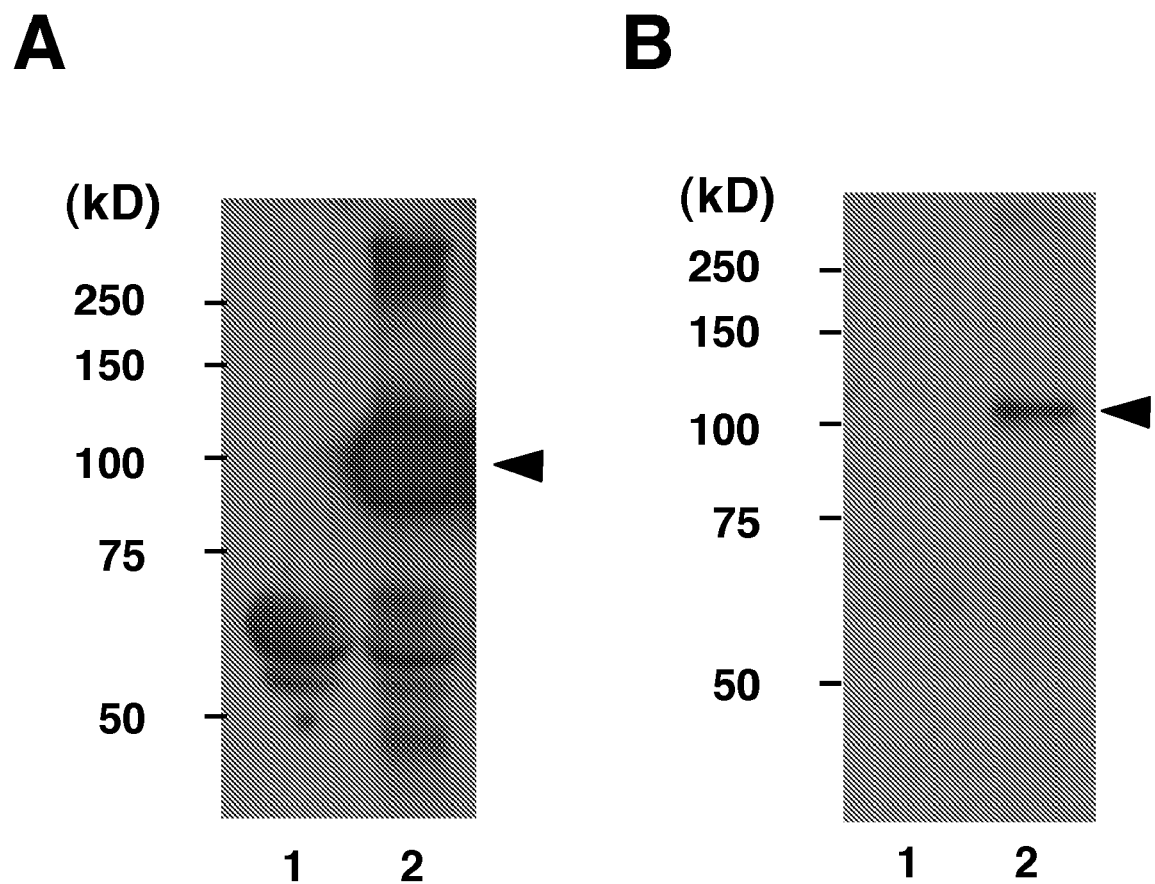
FIGS. 30A and 30B depict the expression of tagged RNF43 protein.

(29) Secretion of Flag-tagged RNF43 Protein in Culture Media of COS7 Cells with Exogenous Flag-Tagged RNF43 Protein Since a search for protein motifs with amino acid sequence of RNF43 using Simple Modular Architecture Research Tool (SMART) predicted a signal peptide and a ring finger domain, secretion of the RNF43 protein was examined. Plasmid expressing Flag-tagged RNF43 (pFLAG-RNF43) or Myc-tagged RNF43 (pcDNA3.1-Myc/His-RNF43), or mock vector was transfected into COS7 cells, and the cells were cultured in media supplemented with 0.5% of bovine calf serum for 48 h. Western-blot analysis with anti-Flag antibody or anti-Myc antibody detected secreted Flag-tagged RNF43 or Myc-tagged protein in the media containing cells transfected with pFLAG-RNF43 or pcDNA3.1-Myc/His-RNF43, respectively, but not in the media containing cells with mock vector (FIGS. 30A and 30B).

Figure 31:
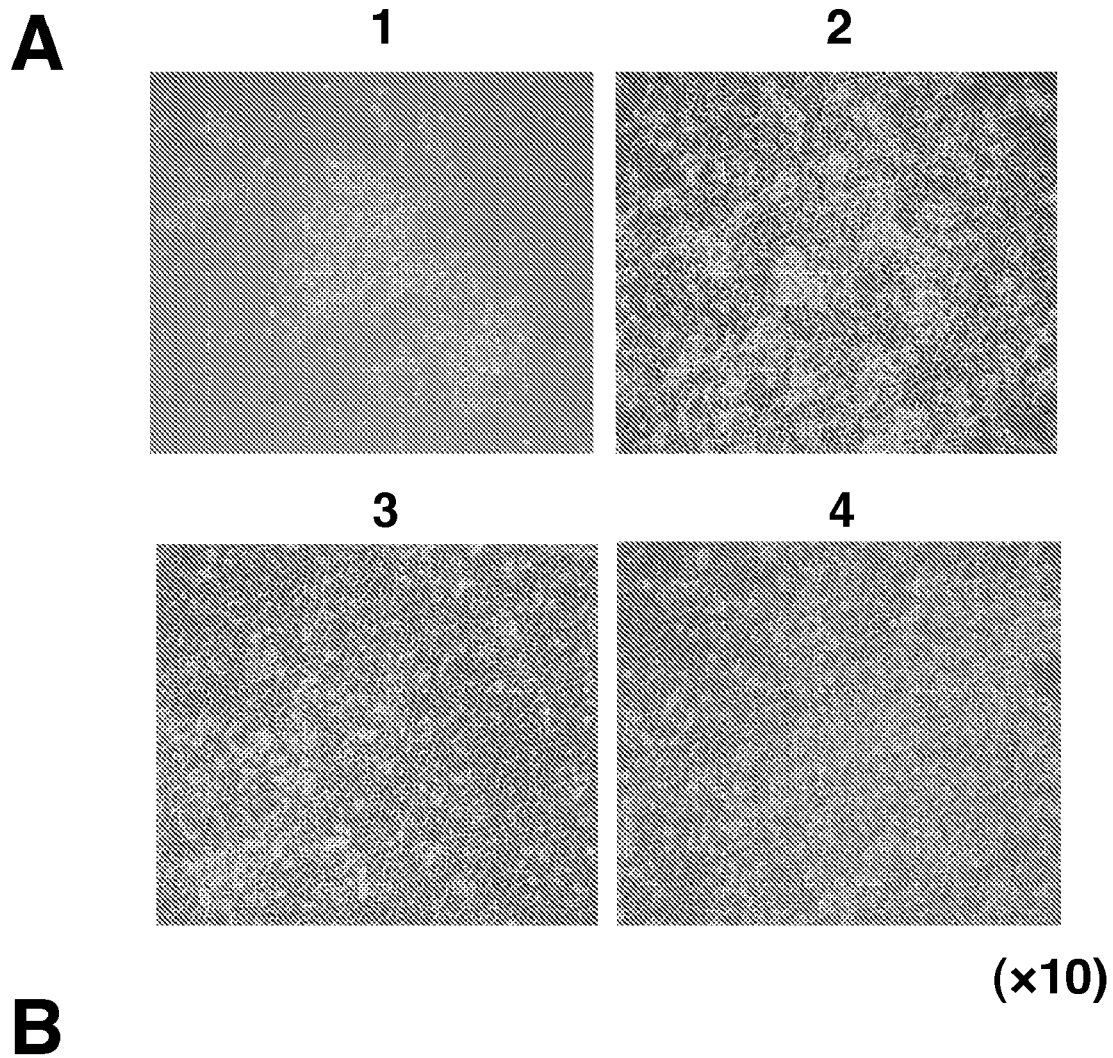
FIGS. 31A and 31B depict the growth promoting effect of conditioned media containing the Myc-tagged or Flag-tagged RNF43 protein.
Figure 31:
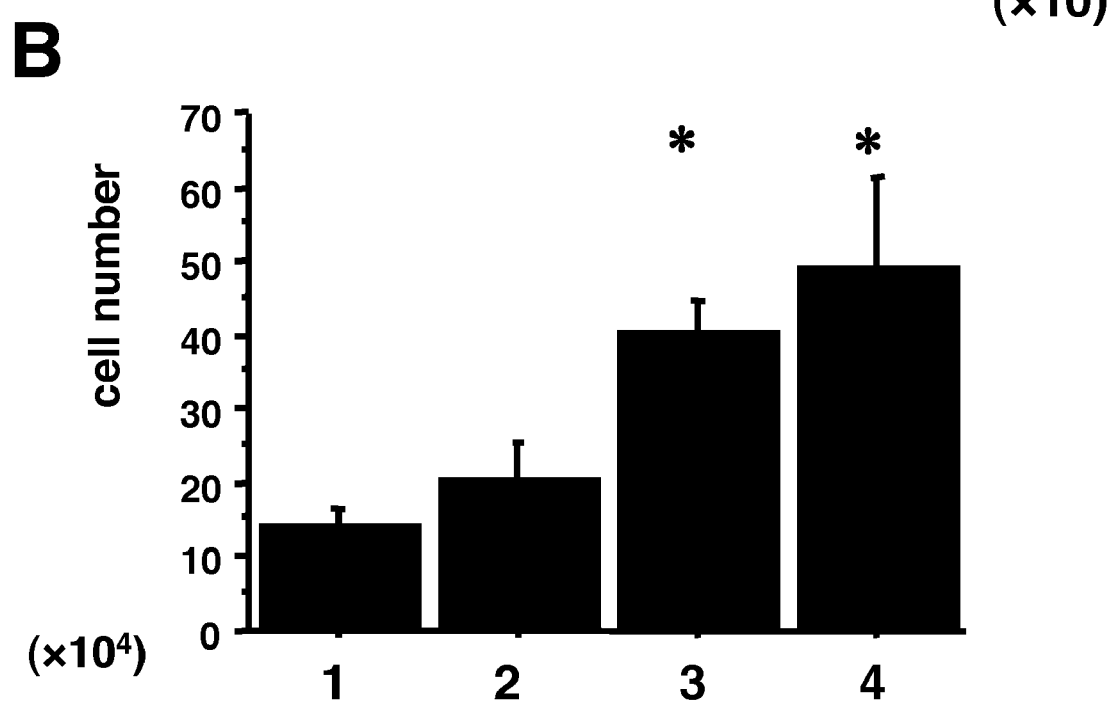

(30) Effect of Cultured Media of Cells Transfected with pFLAG-RNF43 on NIH3T3 Cells Since exogenous expression of RNF43 conferred growth promoting effect on NIH3T3 cells, secreted Flag-tagged RNF43 was examined whether it also exerts a proliferative effect on NIH3T3 cells. NIH3T3 cells were cultured without the change of media, or with conditioned media of mock-transfected cells, or cells transfected with pFlag-RNF43. As expected, NIH3T3 cells showed a significantly higher growth rate when cultured in conditioned media of cells transfected with either pFlag-RNF43 or pcDNA3.1-Myc/His-RNF43 compared to those cultured in conditioned media of non-treated cells or mock-vector transfected cells (FIGS. 31A and 31B). These data suggest that RNF43 may exert its growth promoting effect in an autocrine manner.

(31) Preparation of Recombinant Amino- and Carboxyl-terminal RNF43 Protein

Figure 32:
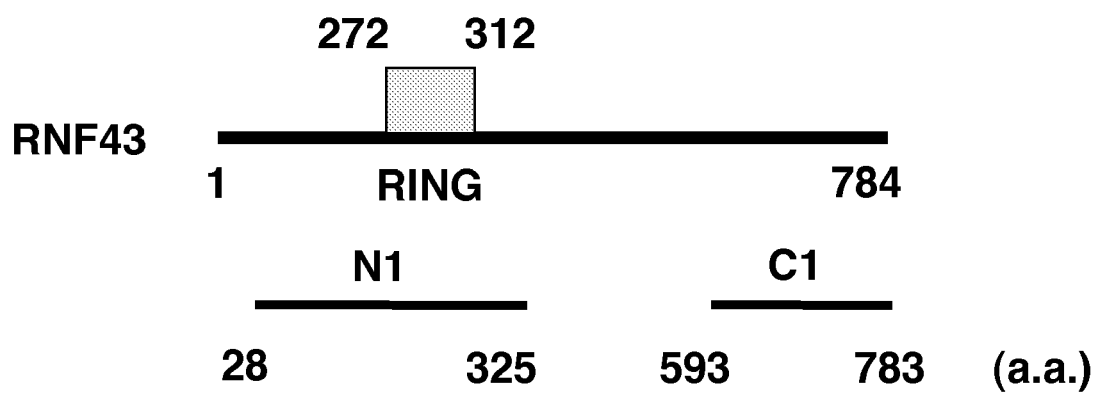
FIG. 32A to 32C depict the preparation of N-terminal (N1) and C-terminal (C1) recombinant protein of RNF43.
Figure 32:
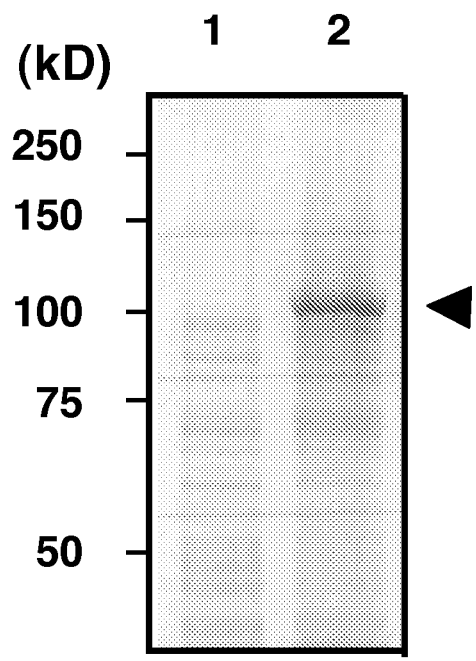
Figure 32:
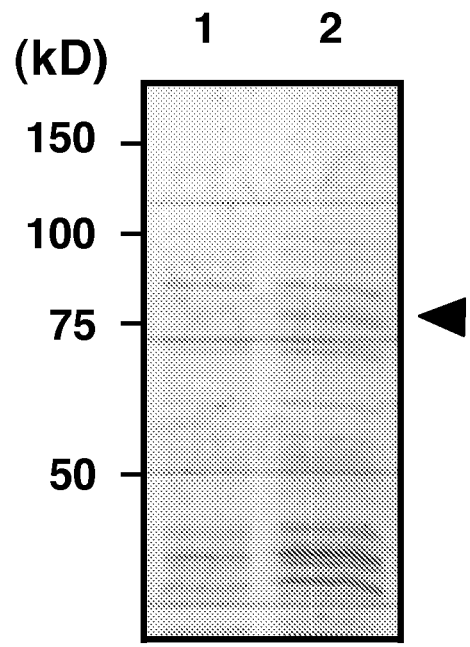

To generate a specific antibody against RNF43, a plasmid expressing Nus-tagged RNF43 protein was constructed (FIG. 32A). Upon transformation of the plasmid into E. coli BL21trxB(DE3)pLysS cell, production of a recombinant protein in the bacterial extract with the expected size was observed by SDS-PAGE (FIGS. 32B and 32C).

Figure 33:
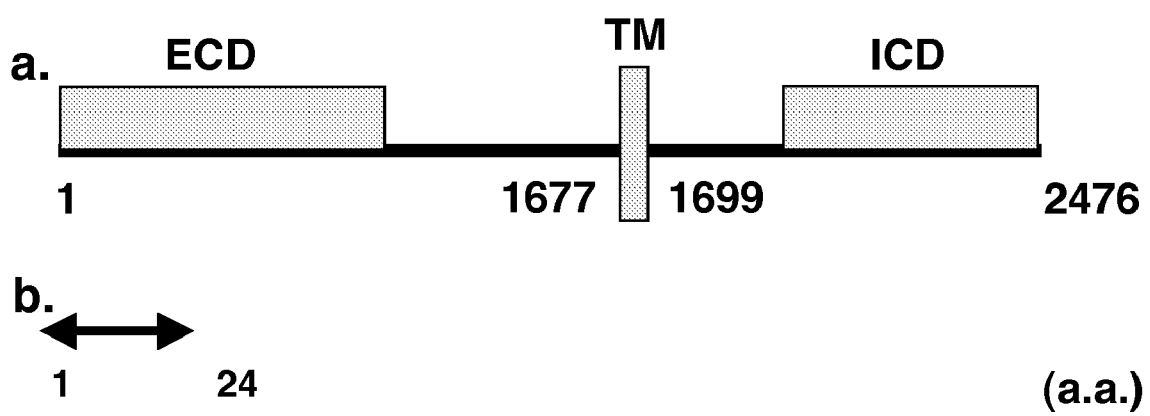
FIGS. 33A and 33B depict the interaction between RNF43 and NOTCH2 examined by yeast two-hybrid system.
Figure 33:
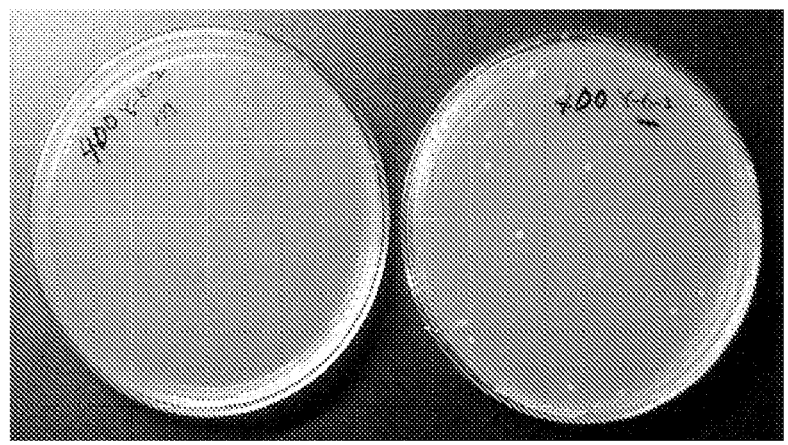
Figure 34:
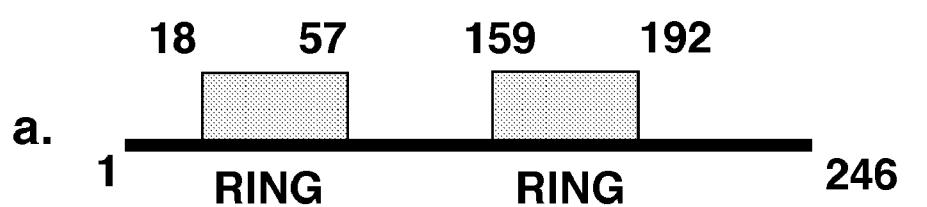
FIGS. 34A and 34B depict the interaction between RNF43 and STRIN examined by the yeast two-hybrid system.
Figure 34:
Figure 34:
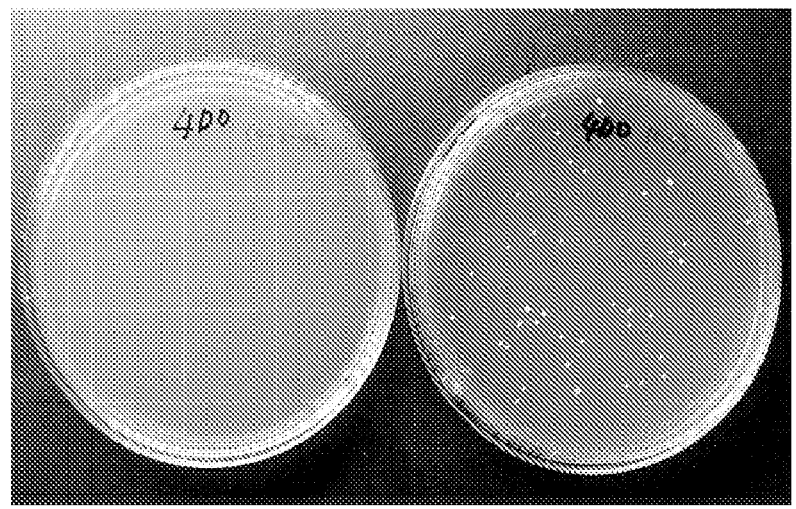

(32) Identification of RNF43-interacting Proteins by Yeast Two-hybrid Screening System To clarify the oncogenic mechanism of RNF43, RNF43-interacting proteins were searched using yeast two-hybrid screening system. Among the identified positive clones, NOTCH2 or STRIN interacted with RNF43 by simultaneous transformation of an yeast cell with pAS2.1-RNF43 and pACT2-NOTCH2 (FIG. 33B), or pAS2.1-RNF43 and pACT2-STRIN (FIG. 34B). The regions responsible for the interaction in NOTCH2 and STRIN are indicated in FIGS. 33A and 34A, respectively.

(33) Prediction of HLA-A24 Binding Peptides Derived from RNF43

The amino acid sequence of RNF43 was scanned for peptides with a length of 9 or 10 amino acids which peptides bind to HLA-A24 using the binding prediction software. Table 5 shows the predicted peptides (SEQ ID NOs: 71-90) in order of high binding affinity. Twenty peptides in total were selected and examined as described below. Table 5

| Predicted RNF43 peptides binding to HLA-A24 | | |
|---|---|---|
| Start position | AA sequence (9mers) | Binding affinity *[1] |
| RNF43-331 | SYQEPGRRL | 360 |
| RNF43-350 | HYHLPAAYL | 200 |
| RNF43-639 | LFNLQKSSL | 30 |
| RNF43-24 | GFGRTGLVL | 20 |
| RNF43-247 | RYQASCRQA | 15 |
| RNF43-397 | RAPGEQQRL | 14 |

-continued

| Predicted RNF43 peptides binding to HLA-A24 | | |
|---|---|---|
| RNF43-114 | RAPRPCLSL | 12 |
| RNF43-368 | RPPRPGPFL | 12 |
| RNF43-45 | KAVIRVLPL | 12 |
| RNF43-721 | NSQPVWLCL | 10 |

| Start position | AA sequence (10mers) | Binding affinity |
|---|---|---|
| RNF43-449 | SYCTERSGYL | 200 |
| RNF43-350 | HYHLPAAYLL | 200 |
| RNF43-718 | CYSNSQPVWL | 200 |
| RNF43-209 | IFVIILASVL | 36 |
| RNF43-313 | VFNITEGDSF | 15 |
| RNF43-496 | TFCSSLSSDF | 12 |
| RNF43-81 | KLMQSHPLYL | 12 |
| RNF43-54 | KMDPTGKLNL | 9 |

-continued

| Predicted RNF43 peptides binding to HLA-A24 | | |
|---|---|---|
| RNF43-683 | HYTPSVAYPW | 8 |
| RNF43-282 | GQELRVISCL | 4 |

In the table, start position indicates the location of amino acids from the N-terminus of RNF43.

(34) Stimulation of T Cells Using the Predicted Peptides

CTLs against these peptides derived from RNF43 were generated according to the method described in the above "Materials and Methods". Resulting CTLs showing detectable cytotoxic activity were expanded, and CTL lines were established.

The cytotoxic activities of CTL lines induced by 9 mer-peptide (SEQ ID NOs: 71-80) stimulation are shown in Table 6.

TABLE 6

Cytotoxicity of CTL lines (9mer)

| Start position | AA sequences | Binding affinity | Cytotoxicity | | | | Established CTL clones |
|---|---|---|---|---|---|---|---|
| | | | x20 | | x2 | | |
| | | | Pep(+) | Pep(-) | Pep(+) | Pep(-) | |
| RNF43-331 | SYQEPGRRL | 360.0 | 2% | 1% | 0% | 0% | |
| RNF43-350 | HYHLPAAYL | 200.0 | 26% | 17% | 5% | 4% | |
| RNF43-639 | LFNLQKSSL | 30.0 | 42% | 33% | 7% | 5% | 1 |
| RNF43-24 | GFGRTGLVL | 20.0 | 8% | 9% | 1% | 2% | |
| RNF43-247 | RYQASCRQA | 15.0 | 71% | 82% | 28% | 16% | |
| RNF43-397 | RAPGEQQRL | 14.4 | 41% | 32% | 15% | 15% | |
| RNF43-114 | RAPRPCLSL | 12.0 | 23% | 26% | 6% | 9% | |
| RNF43-368 | RPPRPGPFL | 12.0 | 1% | 0% | 0% | 0% | |
| RNF43-45 | KAVIRVIPL | 12.0 | NE | | | | |
| RNF43-721 | NSQPVWLCL | 10.0 | 68% | 0% | 26% | 0% | 13 |

NE: No establishment of CTL lines

CTL lines stimulated with RNF43-350 (HYHLPAAYL) (SEQ ID NO: 72), RNF43-639 (LFNLQKSSL) (SEQ ID NO: 73), and RNF43-721 (NSQPVWLCL) (SEQ ID NO: 80) showed higher cytotoxic activities on the target that were pulsed with peptides than on the target that was not pulsed with any of the peptides. Starting from these CTLs, one CTL clone was established with RNF43-639 and 13 CTL clones were established with RNF43-721.

Figure 35:
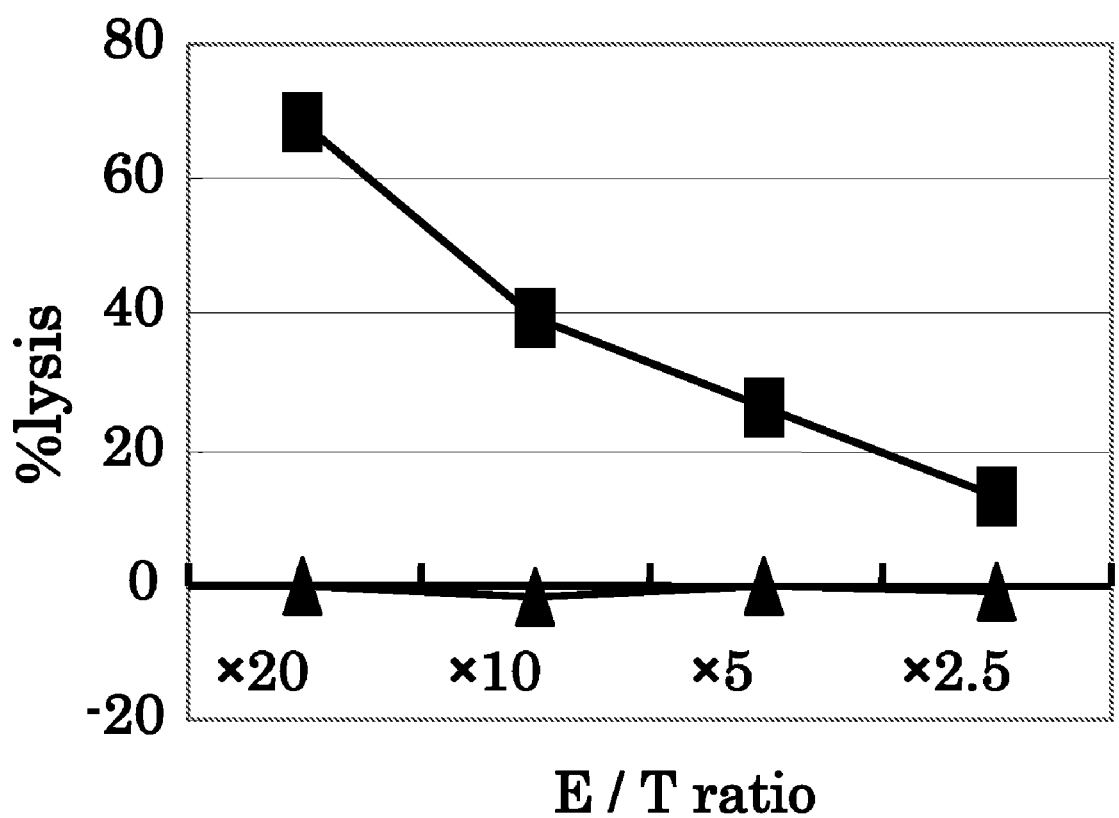
FIG. 35 depicts the peptide specific cytotoxicity of CTL line raised by RNF43-721 stimulation. The CTL line showed high cytotoxic activity on target cells (TISI) pulsed with RNF43-721 (quadrilateral line), whereas no significant cytotoxic activity was detected on the same target cells (TISI) pulsed without peptides (triangular line). CTL line was demonstrated to have a peptide specific cytotoxicity.

The CTL line stimulated with RNF43-721 showed a potent cytotoxic activity on the peptide-pulsed target without showing any significant cytotoxic activity on the target that was not pulsed with any of the peptides (FIG. 35).

The results obtained by examining the cytotoxic activity of CTL lines stimulated with the 10 mer-peptides (SEQ ID NOs: 81-90) are shown in Table 7.

showed a potent cytotoxic activity on HT29 and WiDR both expressing RNF43 and HLA-A24. On the other hand, CTL Clone 45 did not show any cytotoxic activity on either HCT116 (expressing RNF43 but not HLA-A24) or TISI (expressing HLA-A24 but not RNF43). Moreover, CTL Clone 45 did not show any cytotoxic activity on irrelevant peptide pulsed TISI and SNU-C4 that express RNF43 but little HLA-A24 (data not shown).

(37) Characterization of Established CTLs

A cold target inhibition assay was performed to confirm the specificity of RNF43-721 CTL Clone. HT29 cells labeled with $^{51}$Cr were used as a hot target, while TISI cells pulsed with RNF43-721 without $^{51}$Cr labeling were used as a cold target. When TISI pulsed with RNF43-721 was added in the

TABLE 7

Cytotoxicity of CTL lines (10mer)

| Start position | AA sequences | Binding affinity | Cytotoxicity x20 Pep(+) | x20 Pep(-) | x2 Pep(+) | x2 Pep(-) | Established CTL clones |
|---|---|---|---|---|---|---|---|
| RNF43-449 | SYCTERSGYL | 200.0 | 1% | 1% | 0% | 0% | |
| RNF43-350 | HYHLPAAYLL | 200.0 | NE | | | | |
| RNF43-718 | CYSNSQPVWL | 200.0 | NE | | | | |
| RNF43-209 | IFVLILASVL | 36.0 | Not synthesis | | | | |
| RNF43-313 | VFNLTEGDSF | 15.0 | Not synthesis | | | | |
| RNF43-496 | TFCSSLSSDF | 12.0 | 8% | 9% | 0% | 0% | |
| RNF43-81 | KLMQSHPLYL | 12.0 | 10% | 5% | 2% | -3% | |
| RNF43-54 | KMDPTGKLNL | 9.6 | 5% | 2% | 0% | -1% | |
| RNF43-683 | HYTPSVAYPW | 8.4 | 0% | 0% | 0% | -1% | |
| RNF43-282 | GQELRVISCL | 8.4 | NE | | | | |

NE: No establishment of CTL lines

CTL lines stimulated with RNF43-81 (KLMQSHPLYL) (SEQ ID NO: 87) or RNF43-54 (KMDPTGKLNL) (SEQ ID NO: 88) showed modest cytotoxic activity on the peptide-pulsed target compared with that on the target that was not pulsed with any of the peptides.

(35) Establishment of CTL Clones

Figure 36:
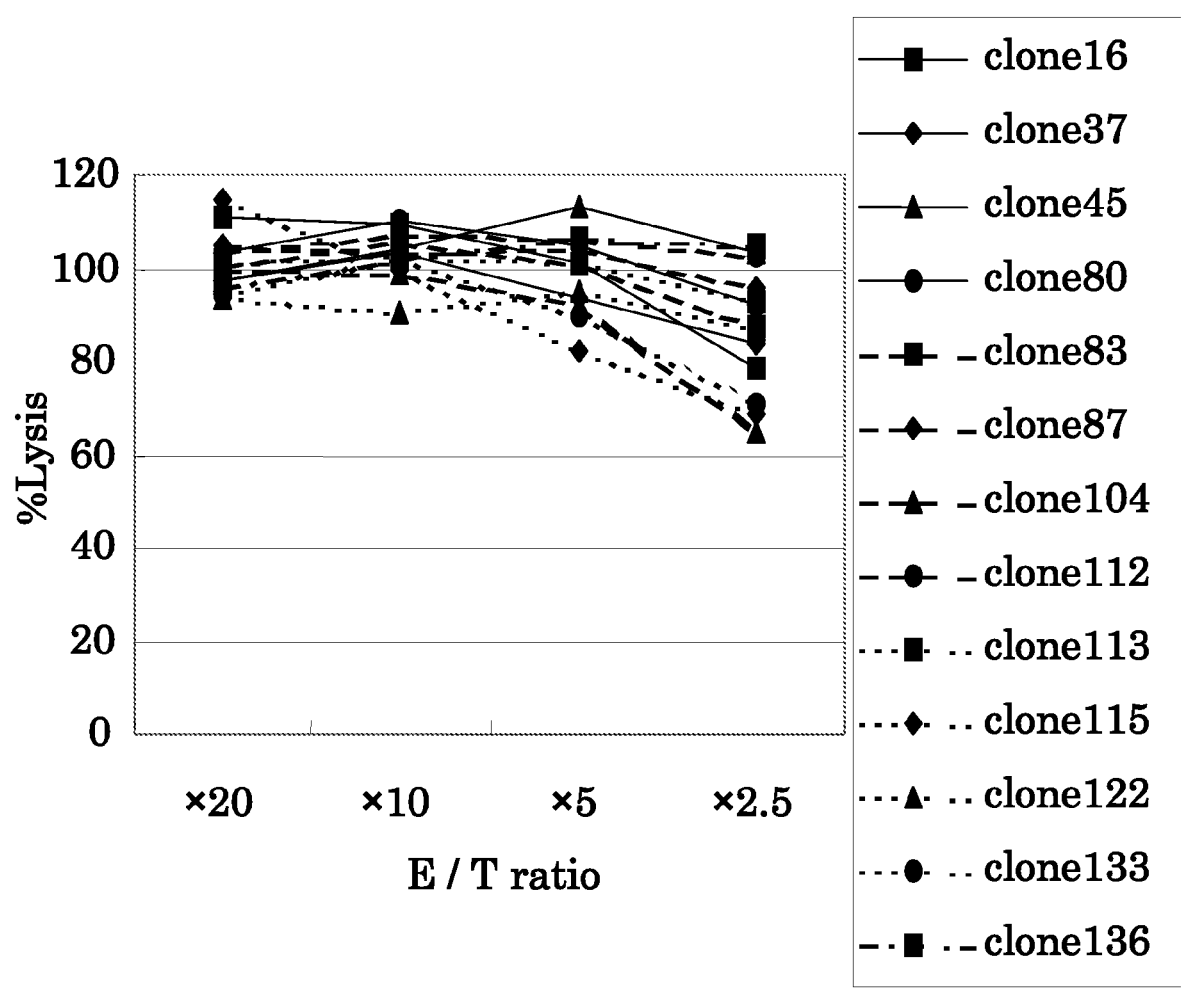
FIG. 36 depicts the peptide specific cytotoxicity of CTL clones raised by RNF43-721 stimulation. The cytotoxic activity of 13 RNF43-721 CTL clones on peptide-pulsed targets (TISI) was tested as described under the item of "Materials and Methods". The established RNF43-721 CTL clones had very potent cytotoxic activity on target cells (TISI) pulsed with the peptides without showing any significant cytotoxic activity on the same target cells (TISI) that were not pulsed with any peptides.

CTL clones were propagated from the CTL lines described above using the limiting dilution method. 13 CTL clones against RNF43-721 and 1 CTL clone against RNF43-639 were established (see Table 6 supra). The cytotoxic activity of RNF43-721 CTL clones is shown in FIG. 36. Each CTL clone had a very potent cytotoxic activity on the peptide-pulsed target without showing any cytotoxic activity on the target that was not pulsed with any of the peptides.

Figure 37:
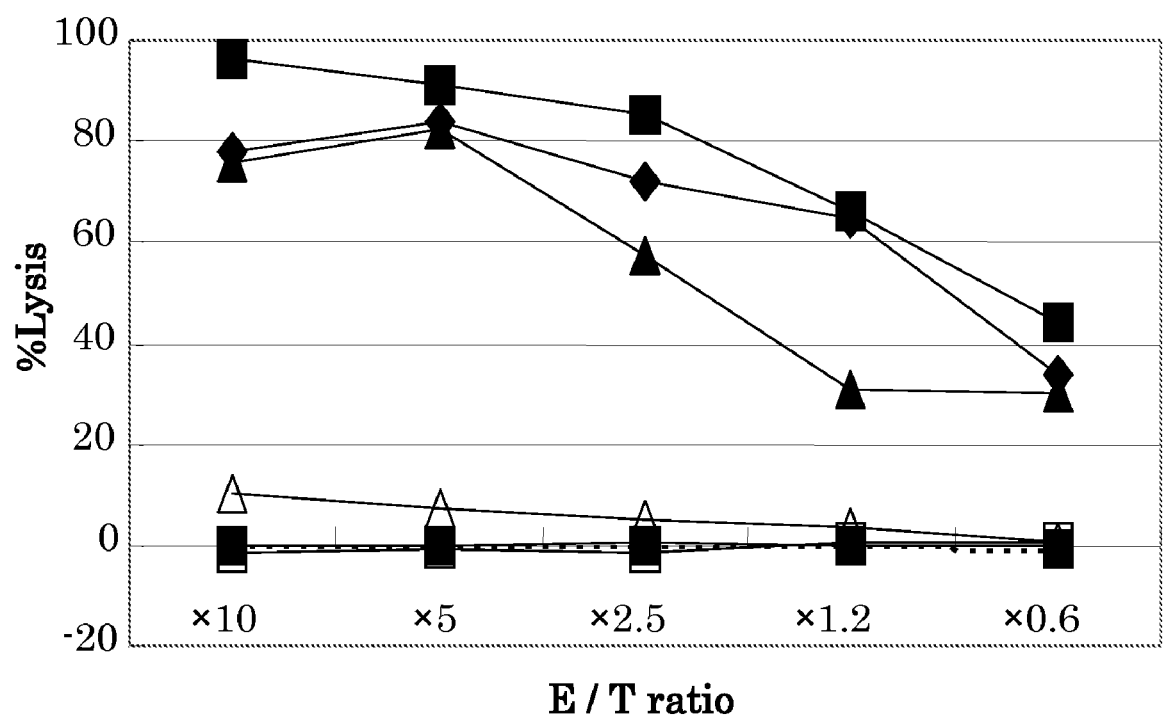
FIG. 37 depicts the cytotoxic activity of RNF43-721 CTL Clone 45 on HT29, WiDR and HCT116. RNF43-721 CTL Clone recognizes and lyses tumor cells that endogenously express RNF43 in an HLA restricted fashion. HT29, WiDR, and HCT116 all endogenously express RNF43, and RNF43-721 CTL Clone 45 served as an effector cell. TISI was used as the target that does not express RNF43. RNF43-721 CTL Clone 45 showed high cytotoxic activity on HT29 (filled triangular line) and WiDR (diamond line) that express both RNF43 and HLA-A24. On the other hand, RNF43-721 CTL Clone 45 showed no significant cytotoxic activity on HCT116 (empty triangular line), which expresses RNF43 but not HLA-A24, and TISI (empty quadrilateral line), which expresses HLA-A24 but not RNF43. Moreover, RNF43-721 CTL Clone 45 showed no cytotoxic activity on irrelevant peptide pulsed TISI (filled quadrilateral dotted line) and SNU-C4 (filled circle line) which expresses RNF43 but little HLA-A24.
Figure 38:
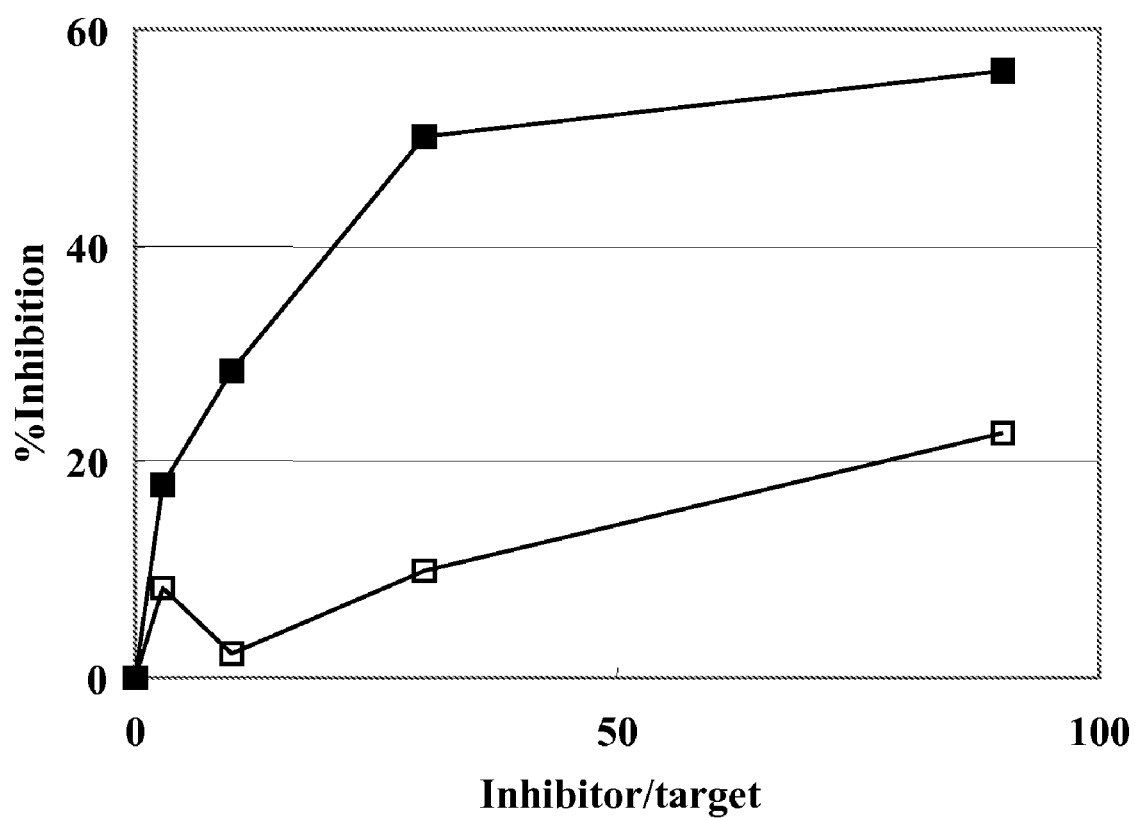
FIG. 38 depicts the result of the cold target inhibition assay. RNF43-721 CTL Clone specifically recognizes RNF 43-721 in an HLA-A24 restricted manner. HT29 labeled with $Na_2^{51}CrO_4$ was prepared as a hot target, while RNF43-721 peptide-pulsed TISI (Peptide+) was used as a cold target (Inhibitors). E/T ratio was fixed to 20. The cytotoxic activity on HT29 was inhibited by the addition of TISI pulsed with the identical peptide (filled quadrilateral line), while almost no inhibition occurred by the addition of TISI without peptide pulsing (empty quadrilateral line).
Figure 39:
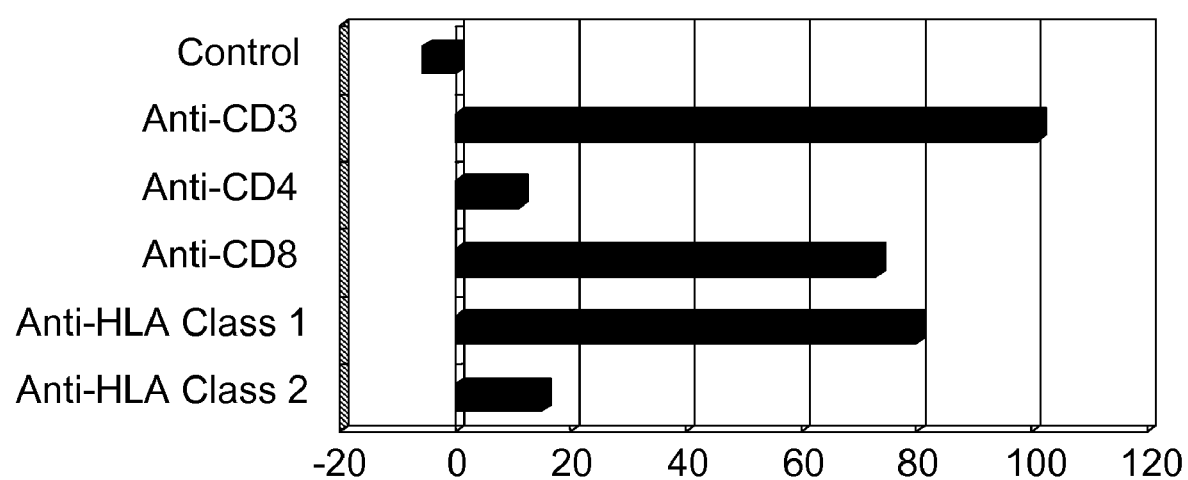
FIG. 39 depicts the result of the blocking assay showing the effect of antibodies raised against HLA-Class I, HLA-Class II, CD3, CD4, and CD8 on the cytotoxic activity of RNF43-721 CTL Clone. RNF43-721 CTL Clone showed cytotoxic activity in HLA-Class I, CD3, and CD8 restricted manner. To examine the characteristics of CTL clone raised with RNF43 peptide, antibodies against HLA-Class I, HLA-Class II, CD3, CD4, and CD8 were tested for their ability to inhibit the cytotoxic activity. The horizontal axis reveals % inhibition of the cytotoxicity. The cytotoxicity of CTL clone on WiDR targets was significantly reduced when anti-class I, CD3, and CD8 antibodies were used. This result indicates that the CTL clone recognizes the RNF43 derived peptide in an HLA Class I, CD3, and CD8 dependent manner.

(36) Cytotoxic Activity Against Colorectal Cancer Cell Lines Endogenously Expressing RNF43 as Target The CTL clones raised against predicted peptides were examined for their ability to recognize and kill tumor cells that endogenously express RNF43. FIG. 37 shows the results of CTL Clone 45 raised against RNF43-721. CTL Clone 45 assay at various ratios, specific cell lysis against the HT29 cell target was significantly inhibited, (FIG. 38). This result is indicated as the percentage of specific lysis at an E/T ratio of 20. To examine the characteristics of the CTL clone raised against RNF43 peptide, antibodies against HLA-Class I, HLA-Class I, CD3, CD4, and CD8 were tested for their ability to inhibit the cytotoxic activity of the CTL clone. The cytotoxicity of the CTL clone on the WiDR cell target was significantly inhibited when anti-HLA-Class I, CD3, and CD8 antibodies were used (FIG. 39). The result indicates that the CTL clone recognizes the RNF43 derived peptide via HLA-Class I, CD3, and CD8.

(38) Homology Analysis of RNF43-721 Peptide

The CTL clones established against RNF43-721 showed a very potent cytotoxic activity. This result may indicate that the sequence of RNF43-721 is homologous to the peptides derived from other molecules which are known to sensitize human immune system. To exclude this possibility, homology analysis of RNF43-721 was performed using BLAST. No sequence completely matching or highly homologous to RNF43-721 was found among the molecules listed in BLAST (Table 8).

TABLE 8

| Homology analysis of RNF43-721 (BLAST) | |
| --- | --- |
| Identification(9/9) | 0 |
| Identification(8/9) | 0 |
| Identification(7/9) | 0 |
| Identification(6/9) | 2 |

These results indicate that the sequence of RNF43-721 is unique and there is little possibility for the CTL clones established with RNF43-721 to raise immunologic response to other molecules.

(39) Modification of RNF43-721 to Improve the Efficacy of Epitope Presentation

To improve the efficacy of peptide presentation, RNF43-721 peptide were modified at amino acid alternations on the anchor site. The modification was expected to improve the binding affinity of the peptide to the HLA Class I molecule. Table 9 demonstrates a better binding affinity to HLA-A24 molecule of RNF43-721 with alternations of amino acids at position 2 (SEQ ID NOs: 91 and 92).

TABLE 9

Predicted binding capacities of the peptides modified from the RNF43-721 native peptide

| Sequence | Score | Rank* |
| --- | --- | --- |
| NSQPVWLCL | 10.08 | 10 |
| NFQPVWLCL | 50.40 | 3 |
| NYQPVWLCL | 504.00 | 1 |

*In HLA-A24 restricted 9mer peptides

(40) Prediction of HLA-A02 Binding Peptides Derived from RNF43

Table 10 shows candidate peptides (SEQ ID NOs: 87, and 93-111) in order of high binding affinity.

TABLE 10

RNF43:Prediction of epitope peptides (HLA-A*0201)

| No | Starting position | Sequences | Score |
| --- | --- | --- | --- |
| | | 9mer | |
| 1 | 60 | KLNLTLEGV | 274.3 |
| 2 | 8 | QLAALWPWL | 199.7 |
| 3 | 82 | LMQSHPLYL | 144.2 |
| 4 | 358 | LLGPSRSAV | 118.2 |
| 5 | 11 | ALWPWLLMA | 94.8 |
| 6 | 15 | WLLMATLQA | 84.5 |
| 7 | 200 | WILMTVVGT | 40.1 |
| 8 | 171 | KLMEFVYKN | 34.5 |
| 9 | 62 | NLTLEGVFA | 27.3 |
| 10 | 156 | GLTWPVVLI | 23.9 |
| | | 10mer | |
| 11 | 81 | KLMQSHPLYL | 1521.5 |
| 12 | 357 | YLLGPSRSAV | 1183.7 |
| 13 | 202 | LMTVVGTIFV | 469.6 |
| 14 | 290 | CLHEFHRNCV | 285.1 |
| 15 | 500 | SLSSDFDPLV | 264.2 |
| 16 | 8 | QLAAIWPWLL | 160.2 |
| 17 | 11 | ALWPWLLMAT | 142.2 |
| 18 | 7 | LQLAALWPWL | 127.3 |
| 19 | 726 | WLCLTPRQPL | 98.2 |
| 20 | 302 | WLHQHRTCPL | 98.2 |

Twenty peptides in total were selected and examined as described below.

(41) Stimulation of T Cells Using Candidate Peptides

Lymphoid cells were cultured using the candidate peptides derived from RNF43 according to the method described in the above "Materials and Methods". Resulting lymphoid cells showing detectable cytotoxic activity were expanded, and CTL lines were established. The cytotoxic activities of CTL lines induced by the stimulation using 9 mer-peptides (SEQ ID NOs: 93-102) are shown in Table 11.

TABLE 11

Cytotoxicity of CTL lines (HLA-A*0201 9mer)

| | | | Cytotoxicity(%) | | | |
| --- | --- | --- | --- | --- | --- | --- |
| | | | x20 | | x2 | |
| Start position | AA sequences | Binding affinity | Pep (+) | Pep (−) | Pep (+) | Pep (−) |
| RNF43-60 | KLNLTLEGV | 274.3 | −2.1 | 0.2 | −1.6 | 0.0 |
| RNF43-8 | QLAALWPWL | 199.7 | 3.5 | 0.0 | 0.0 | 1.0 |
| RNF43-82 | LMQSHPLYL | 144.2 | 1.7 | 1.2 | 0.0 | −0.4 |
| RNF43-358 | LLGPSRSAV | 118.2 | −0.4 | −0.7 | 0.0 | −0.8 |
| RNF43-11 | ALWPWLLMA | 94.8 | 90.2 | 1.5 | 45.4 | 1.3 |
| RNF43-15 | WLLMATLQA | 84.5 | −0.2 | 0.0 | −0.4 | −0.9 |
| RNF43-200 | WILMTVVGT | 40.1 | Not Synthesis | | | |
| RNF43-171 | KLMEFVYKN | 34.5 | 2.6 | 0.0 | 1.1 | −0.5 |

TABLE 11-continued

Cytotoxicity of CTL lines (HLA-A*0201 9mer)

| | | | Cytotoxicity(%) | | | |
|---|---|---|---|---|---|---|
| | | | x20 | | x2 | |
| Start position | AA sequences | Binding affinity | Pep (+) | Pep (−) | Pep (+) | Pep (−) |
| RNF43-62 | NLTLEGVFA | 27.3 | Not Synthesis | | | |
| RNF43-156 | GLTWPVVLI | 23.9 | −0.4 | 0.7 | −0.5 | −0.3 |

NE: No establishment of CTL lines

Figure 40A:
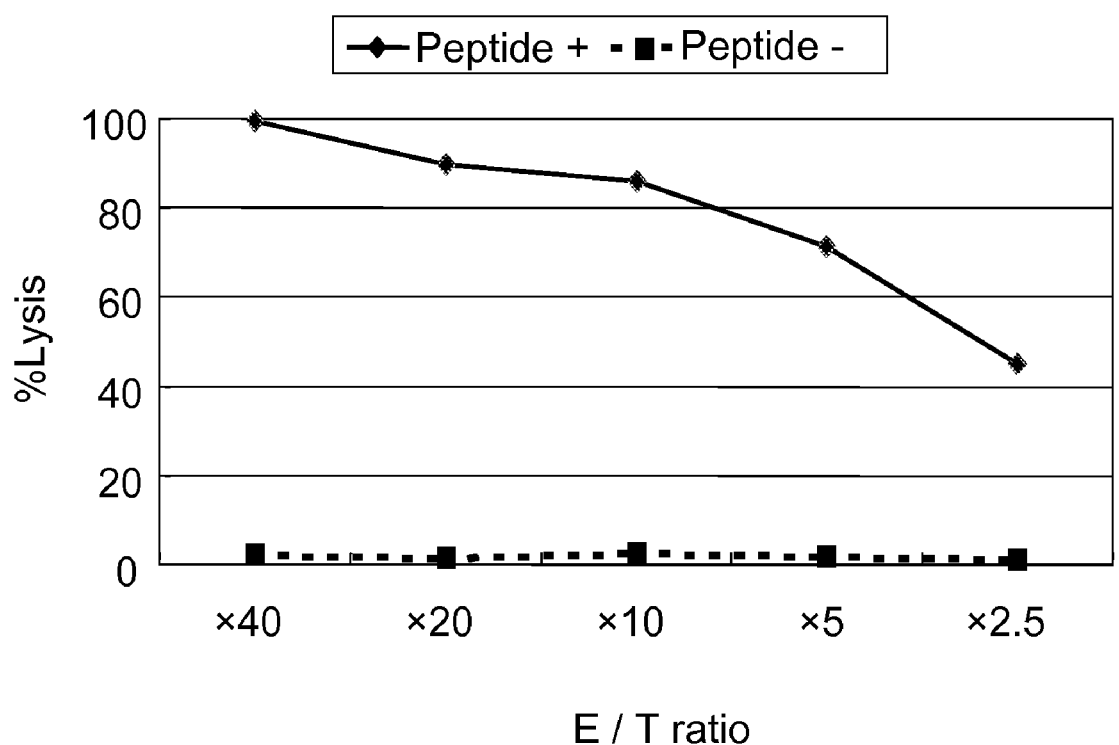
FIGS. 40A and 40B depict the peptide specific cytotoxicity of the CTL lines raised with RNF43-11-9 (A) or RNF43-11-10 (B). These CTL lines showed high cytotoxic activity on target cells (T2) pulsed with RNF43-11-9 or RNF43-11-10, whereas no significant cytotoxic activity was observed on the same target cells (T2) pulsed without peptides.

CTL lines induced with RNF43-11-9 (ALWPWLLMA) (SEQ ID NO: 97) showed higher cytotoxic activities on the target pulsed with peptides than on the target that was not pulsed with any of the peptides. Starting from these CTLs, four CTL clone were established with RNF43-11-9. The CTL line stimulated with RNF43-11-9 showed a potent cytotoxic activity on the peptide-pulsed target without showing any significant cytotoxic activity on the target that was not pulsed with any of the peptides (FIG. 40A).

The results of examination on the cytotoxic activity of CTL lines induced with the 10 mer-peptides (SEQ ID NOs: 87, and 103-111) are shown in Table 12.

TABLE 12

Cytotoxicity of CTL lines (HLA-A*0201 10mer)

| | | | Cytotoxicity(%) | | | |
|---|---|---|---|---|---|---|
| | | | x20 | | x2 | |
| Start position | AA sequences | Binding affinity | Pep (+) | Pep (−) | Pep (+) | Pep (−) |
| RNF43-81 | KLMQSHPLYL | 1521.5 | 18.0 | 27.6 | 6.3 | 8.3 |
| RNF43-357 | YLLGPSRSAV | 1183.7 | 18.2 | 15.4 | 3.7 | 3.0 |
| RNF43-202 | LMTVVGTIFV | 469.6 | Not Synthesis | | | |
| RNF43-290 | CLHEFHRNCV | 285.1 | 9.6 | 9.7 | 2.7 | 3.7 |
| RNF43-500 | SLSSDFDPLV | 264.2 | NE | | | |
| RNF43-8 | QLAAIWPWLL | 160.2 | 6.7 | 9.0 | 1.1 | 1.3 |
| RNF43-11 | ALWPWLLMAT | 142.2 | 91.5 | 27.1 | 40.5 | 4.3 |
| RNF43-7 | LQLAALWPWL | 127.3 | NE | | | |
| RNF43-726 | WLCLTPRQPL | 98.2 | NE | | | |
| RNF43-302 | WLHQHRTCPL | 98.2 | 7.4 | 6.1 | 1.5 | 2.2 |

NE: No establishment of CTL lines

Figure 40B:
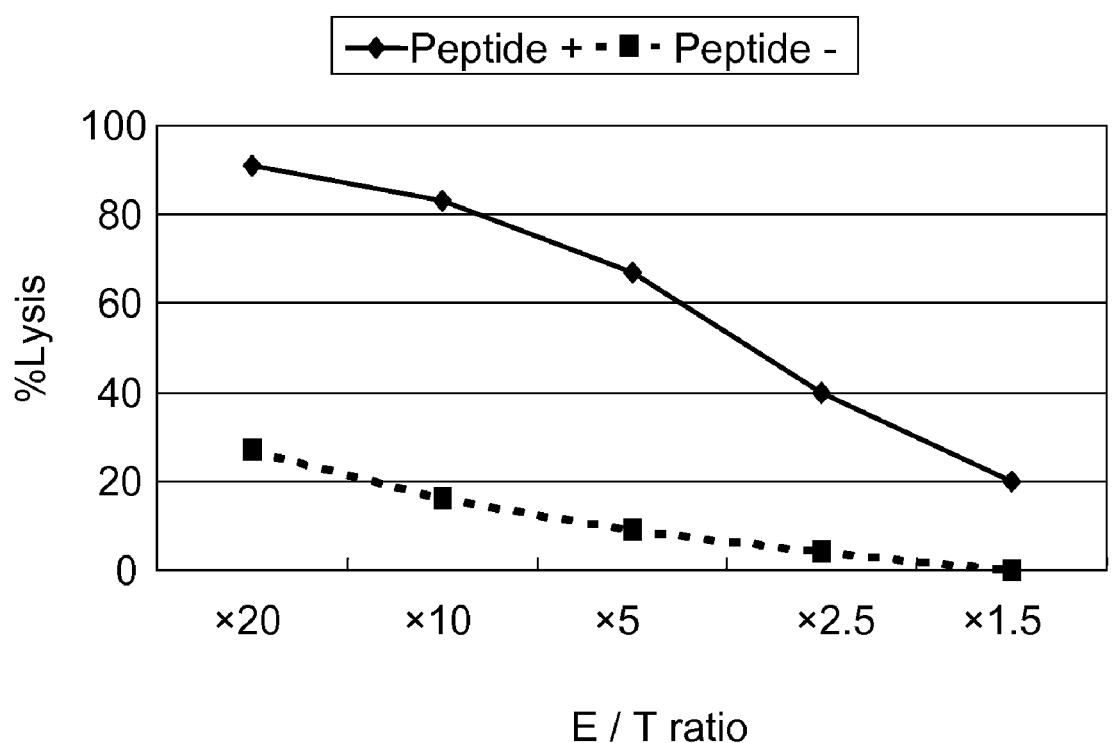

CTL lines induced with RNF43-11-10 (ALWPWLLMAT) (SEQ ID NO: 108) showed a higher cytotoxic activity on the peptide-pulsed target than on the target that was not pulsed with any of the peptides (FIG. 40B).

(42) Establishment of CTL Clones

Figure 41A:
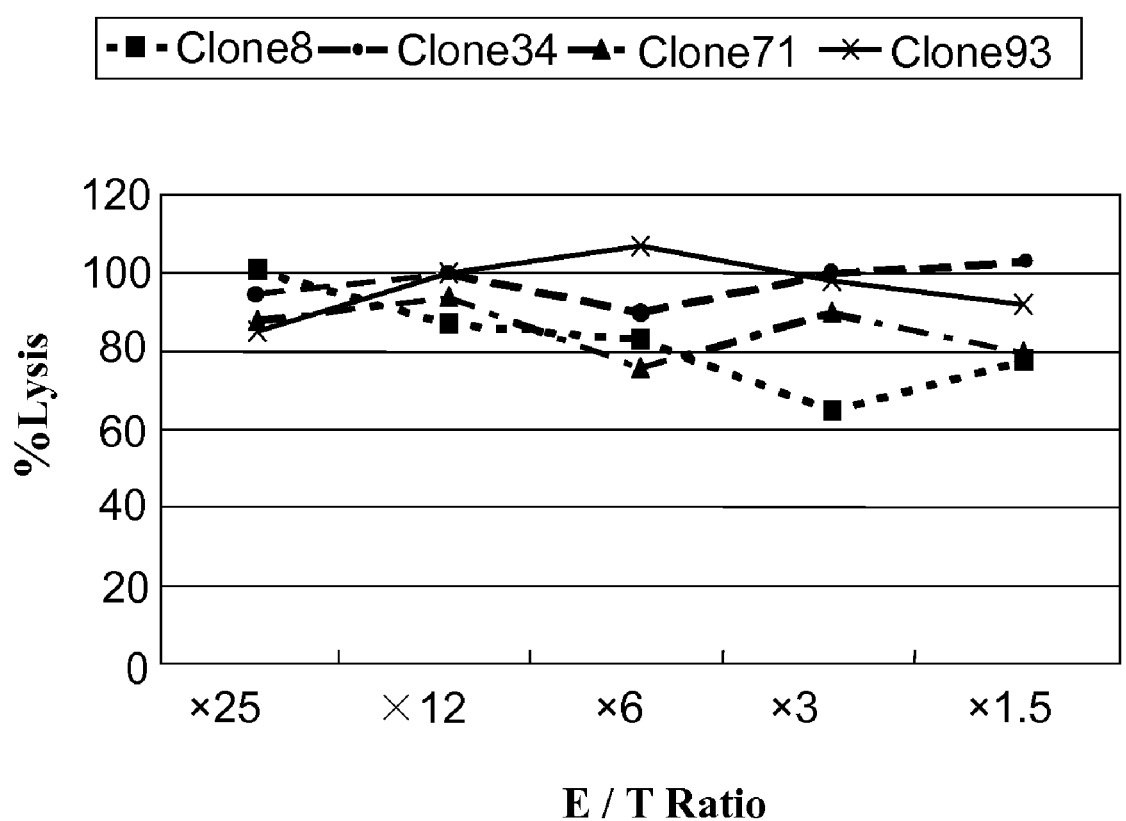
FIGS. 41A and 41B depict the peptide specific cytotoxicity of CTL clones raised by RNF43-11-9 stimulation. Cytotoxic activity of 4 RNF43-11-9 CTL clones on peptide-pulsed targets (T2) was tested as described under the item of "Materials and Methods". The established RNF43-11-9 CTL clones had very potent cytotoxic activities on target cells (T2) pulsed with the peptides without showing any significant cytotoxic activity on the same target cells (T2) that were not pulsed with any peptides.
Figure 41B:
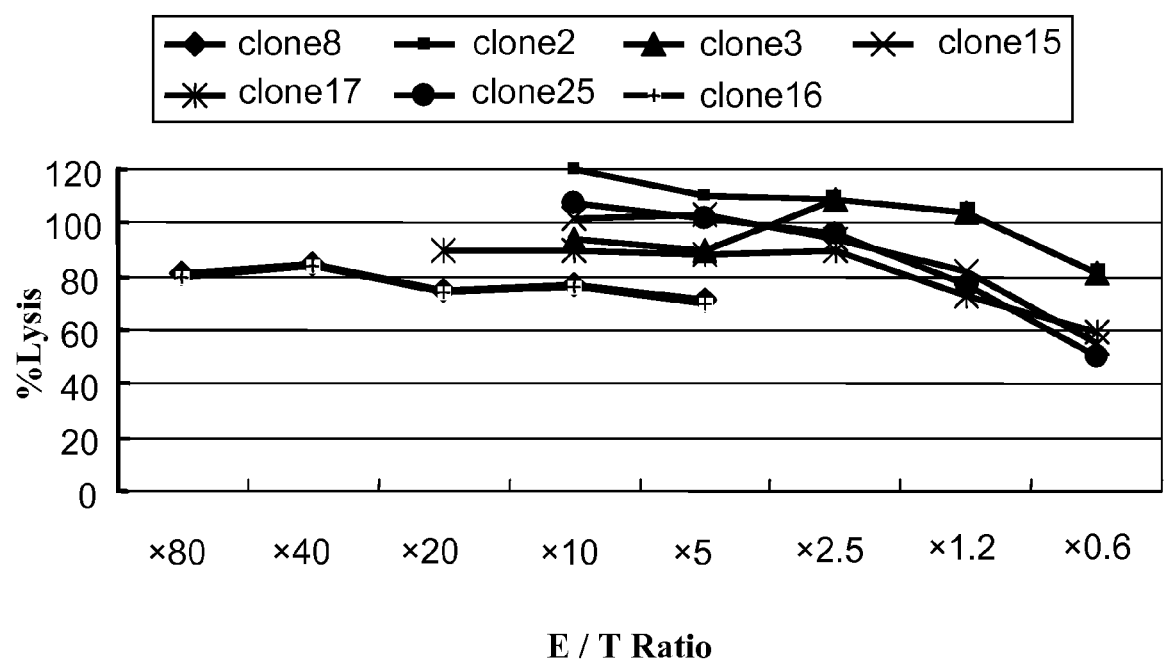

CTL clones were propagated from the CTL lines described above using the limiting dilution method. Four CTL clones against RNF43-11-9 were established (see Table 11 supra). The cytotoxic activity of RNF43 peptides-derived CTL clones is shown in FIGS. 41A and 41B. Each CTL clone had a very potent cytotoxic activity on the peptide-pulsed target without showing any cytotoxic activity on the target that was not pulsed with any of the peptides.

Figure 42A:
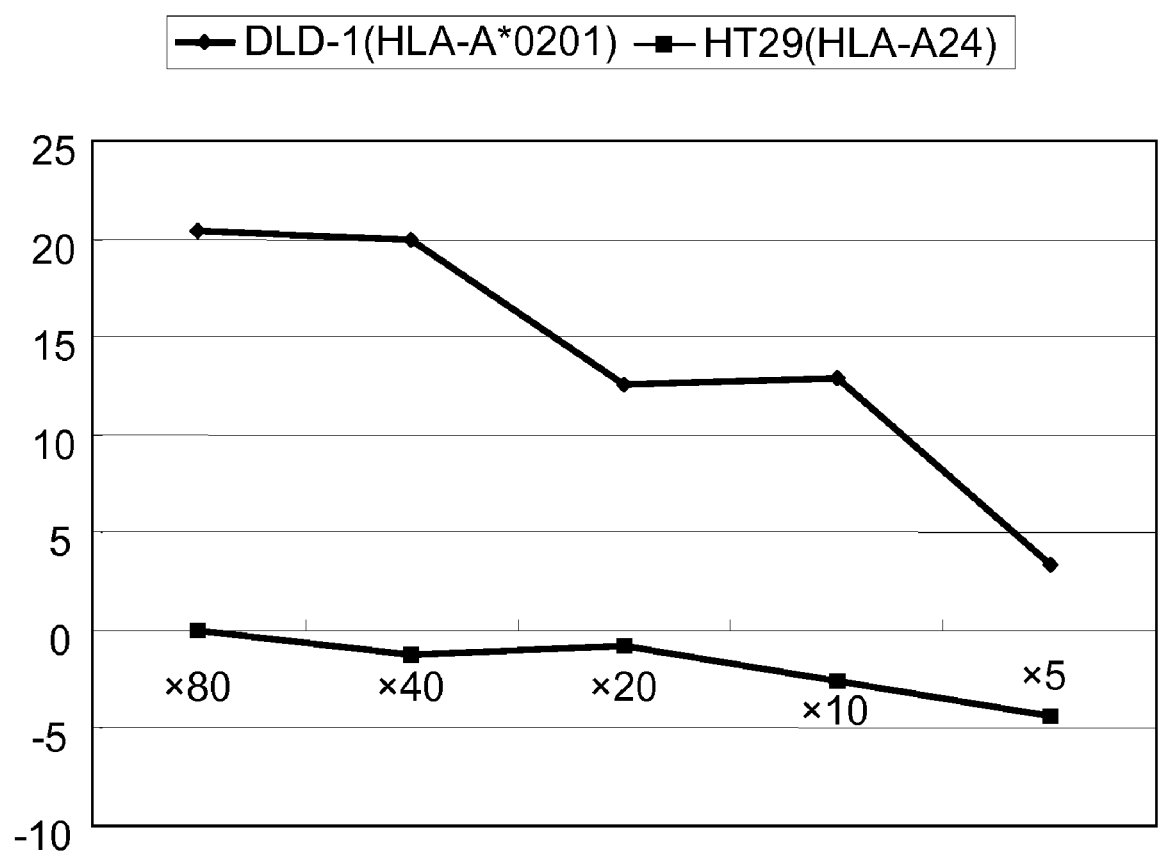
FIGS. 42A and 42B depict the cytotoxic activity of RNF43-5 CTL Clone 90 and RNF43-17 CTL Clone 25 on HT29 and DLD-1. RNF43-5 CTL Clone 90 and RNF43-17 CTL Clone 25 recognize and lyse tumor cells that endogenously express RNF43 in an HLA restricted fashion. HT29 and DLD-1 all endogenously express RNF43, and RNF43-5 CTL Clone 90 and RNF43-17 CTL Clone 25 served as an effector cell. T2 was used as the target that does not express RNF43. RNF43-5 CTL Clone 90 and RNF43-17 CTL Clone 25 showed high cytotoxic activity on DLD-1 that express both RNF43 and HLA-A*0201. On the other hand, RNF43-5 CTL Clone 90 and RNF43-17 CTL Clone 25 showed no significant cytotoxic activity on HT29, which expresses RNF43 but not HLA-A*0201.
Figure 42B:
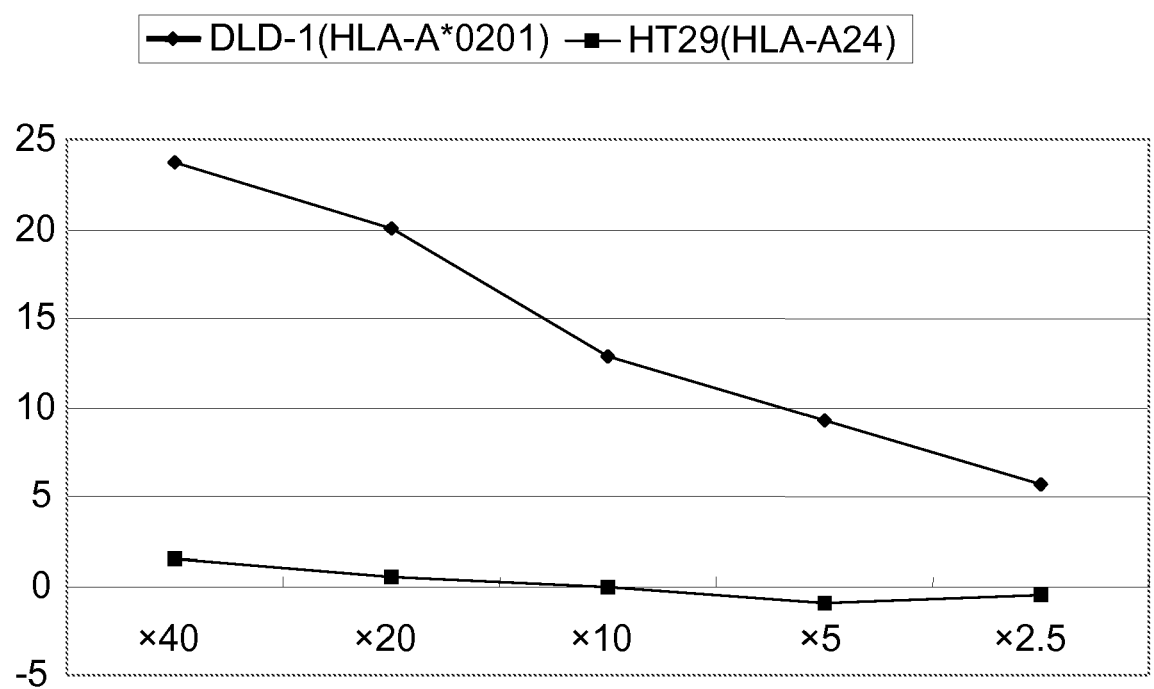

(43) Cytotoxic Activity Against Colorectal Cancer Cell Lines Endogenously Expressing RNF43 as Targets The CTL clones raised against the predicted peptides were examined for their ability to recognize and kill tumor cells that endogenously express RNF43. FIGS. 42A and 42B show the results obtained for the CTL clones raised against RNF43 derived peptides. The CTL Clones showed a potent cytotoxic activity on DLD-1 which expresses RNF43 and HLA-A*0201, but none on HT29 which expresses RNF43 but not HLA-A*0201.

(44) Specificity of CTL Clones

Figure 43:
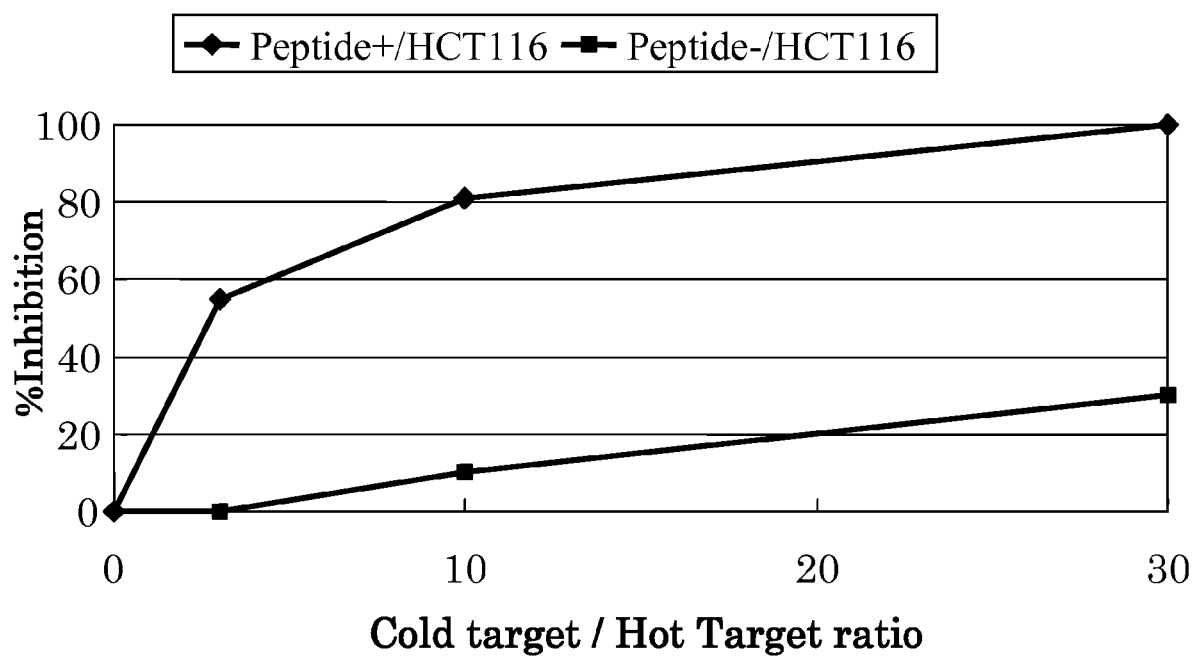
FIG. 43 depicts the result of cold target inhibition assay. RNF43 CTL Clone specifically recognizes RNF 43 in a HLA-A2 restricted manner. HCT116 labeled with $Na_2{}^{51}CrO_4$ was prepared as a hot target, while RNF43 peptide-pulsed T2 (Peptide+) was used as a cold target (Inhibitors). E/T ratio was fixed to 20. The cytotoxic activity on HCT116 was inhibited by the addition of T2 pulsed with the identical peptide, while almost no inhibition was observed by the addition of TISI without peptide pulse.

A cold target inhibition assay was performed to confirm the specificity of RNF43-5-11 (9mer) CTL Clone. HCT116 cells labeled with $^{51}$Cr were used as a hot target, while T2 cells pulsed with RNF43-5 without $^{51}$Cr labeling were used as a cold target. Specific cell lysis of the HCT-116 cell target was significantly inhibited, when T2 pulsed with RNF43-5 was added in the assay at various ratios (FIG. 43).

INDUSTRIAL APPLICABILITY

The expression of novel human genes CXADRL1 and GCUD1 is markedly elevated in gastric cancer as compared to non-cancerous stomach tissues. On the other hand, the expression of novel human gene RNF43 is markedly elevated in colorectal cancers as compared to non-cancerous mucosal tissues. Accordingly, these genes may serve as a diagnostic marker of cancer and the proteins encoded thereby may be used in diagnostic assays of cancer.

The present inventors have also shown that the expression of novel protein CXADRL1, GCUD1, or RNF43 promotes cell growth whereas cell growth is suppressed by antisense oligonucleotides or small interfering RNAs corresponding to the CXADRL1, GCUD1, or RNF43 gene. These findings suggest that each of CXADRL1, GCUD1, and RNF43 proteins stimulate oncogenic activity. Thus, each of these novel oncoproteins is a useful target for the development of anti-cancer pharmaceuticals. For example, agents that block the expression of CXADRL1, GCUD1, or RNF43, or prevent its activity may find therapeutic utility as anti-cancer agents, particularly anti-cancer agents for the treatment of gastric and colorectal cancers. Examples of such agents include antisense oligonucleotides, small interfering RNAs, and antibodies that recognize CXADRL1, GCUD1, or RNF43.

Furthermore, the present inventors have shown that CXADRL1 interacts with AIP1. It is expected that the cell proliferating activity of CXADRL1 is regulated by its binding to AIP1. Thus, agents that inhibit the activity of the formation of a complex composed of CXADRL1 and AIP1 may also find utility in the treatment and prevention of cancer, specifically colorectal, lung, gastric, and liver cancers. Alternatively, the present inventors have shown that RNF43 interacts with NOTCH2 or STRIN. It is expected that the cell proliferating activity of RNF43 is regulated by its binding to NOTCH2 or STRIN. Thus, agents that inhibit the activity of the formation of a complex composed of RNF43 and NOTCH2 or STRIN may also find utility in the treatment and prevention of cancer, specifically colorectal, lung, gastric, and liver cancers.

The present inventions have also shown that the peptides, derived from the amino acid sequence of CXADRL1, GCUD1 or RNF43 protein, stimulate T cells and induce cytotoxic T cells. The peptides are useful as vaccine to induce anti-tumor immunity.

While the invention has been described in detail and with reference to specific embodiments thereof, it will be apparent to one skilled in the art that various changes and modifications can be made therein without departing from the spirit and scope of the invention.

The invention claimed is:

1. An isolated polynucleotide encoding a polypeptide comprising the amino acid sequence of SEQ ID NO: 6; or a polynucleotide comprising the nucleotide sequence from position 489 to 2840 of SEQ ID NO: 5, wherein the polypeptide encoded by the polynucleotide has a biological activity equivalent to a polypeptide consisting of the amino acid sequence of SEQ ID NO: 6.

2. An isolated polynucleotide encoding a polypeptide consisting of the amino acid sequence selected from the group consisting of SEQ ID NO: 80, 97, and 108.

3. An isolated vector comprising the polynucleotide of claim 1.

4. An isolated host cell harboring the polynucleotide of claim 1 or the vector of claim 3.

5. A method for producing a polypeptide, said method comprising the steps of:
   (a) culturing the host cell of claim 4;
   (b) allowing the host cell to express the polypeptide encoded by the polynucleotide of claim 1 or the vector of claim 3, and
   (c) collecting the expressed polypeptide.

6. A composition comprising
   a polynucleotide encoding a polypeptide comprising the amino acid sequence of SEQ ID NO: 6; or
   a polynucleotide comprising the nucleotide sequence from position 489 to 2840 of SEQ ID NO: 5.

7. A composition comprising a polynucleotide encoding a polypeptide consisting of the amino acid sequence selected from the group consisting of SEQ ID NO: 80, 97, and 108.

8. The composition of claim 6, wherein the polynucleotide is incorporated into an isolated expression vector.

* * * * *